US007615213B2

(12) United States Patent
Kasaian et al.

(10) Patent No.: US 7,615,213 B2
(45) Date of Patent: Nov. 10, 2009

(54) ANTIBODIES AGAINST HUMAN INTERLEUKIN-13 AND PHARMACEUTICAL COMPOSITIONS THEREOF

(75) Inventors: Marion T. Kasaian, Charlestown, MA (US); Lioudmila Tchistiakova, Andover, MA (US); Geertruida M. Veldman, Sudbury, MA (US); Kimberly Ann Marquette, Somerville, MA (US); Xiang-Yang Tan, Reading, MA (US); Debra D. Donaldson, Medford, MA (US); Laura Long Lin, Weston, MA (US); Tania Shane, Newton, MA (US); Amy Sze Pui Tam, Medford, MA (US); Eric Feyfant, Lexington, MA (US); Nancy L. Wood, Somerville, MA (US); Lori J. Fitz, Somerville, MA (US); Angela M. Widom, Acton, MA (US); Kevin D. Parris, Auburndale, MA (US); Samuel J. Goldman, Acton, MA (US); Jose W. Saldanha, Middlesex (GB)

(73) Assignee: Wyeth, Madison, NJ (US)

( * ) Notice: Subject to any disclaimer, the term of this patent is extended or adjusted under 35 U.S.C. 154(b) by 404 days.

(21) Appl. No.: 11/149,309

(22) Filed: Jun. 9, 2005

(65) Prior Publication Data

US 2006/0063228 A1    Mar. 23, 2006

Related U.S. Application Data

(60) Provisional application No. 60/578,473, filed on Jun. 9, 2004, provisional application No. 60/581,375, filed on Jun. 22, 2004, provisional application No. 60/578,736, filed on Jun. 9, 2004.

(51) Int. Cl.
    *A61K 39/395* (2006.01)
(52) U.S. Cl. ............. 424/133.1; 424/145.1; 530/387.3; 530/388.23
(58) Field of Classification Search ....................... None
    See application file for complete search history.

(56) References Cited

U.S. PATENT DOCUMENTS

| 5,011,778 | A | | 4/1991 | Newman et al. |
| 5,225,539 | A | | 7/1993 | Winter et al. |
| 5,246,701 | A | | 9/1993 | Dugas et al. |
| 5,359,037 | A | | 10/1994 | Wallach et al. |
| 5,585,089 | A | | 12/1996 | Queen et al. |
| 5,596,072 | A | | 1/1997 | Culpeper et al. |
| 5,599,905 | A | | 2/1997 | Mosley et al. |
| 5,624,821 | A | | 4/1997 | Winter et al. |
| 5,648,260 | A | * | 7/1997 | Winter et al. ............. 435/252.3 |
| 5,652,123 | A | | 7/1997 | Caput et al. |
| 5,677,165 | A | | 10/1997 | de Boer et al. |
| 5,693,761 | A | | 12/1997 | Queen et al. |
| 5,693,762 | A | | 12/1997 | Queen et al. |
| 5,696,234 | A | | 12/1997 | Zurzwski et al. |
| 5,705,154 | A | | 1/1998 | Dalie et al. |
| 5,710,023 | A | | 1/1998 | Collins et al. |
| 5,717,072 | A | | 2/1998 | Mosley et al. |
| 5,747,037 | A | | 5/1998 | Noelle et al. |
| 5,783,181 | A | | 7/1998 | Browne et al. |
| 5,859,205 | A | * | 1/1999 | Adair et al. ............. 530/387.3 |
| 6,140,047 | A | | 10/2000 | Duff et al. |
| 6,143,871 | A | | 11/2000 | Bonnefoy et al. |
| 6,180,370 | B1 | | 1/2001 | Queen et al. |
| 6,214,559 | B1 | | 4/2001 | Collins et al. |
| 6,248,714 | B1 | | 6/2001 | Collins et al. |
| 6,268,480 | B1 | | 7/2001 | Collins et al. |
| 6,407,213 | B1 | | 6/2002 | Carter et al. |
| 6,632,927 | B2 | | 10/2003 | Adair et al. |
| 6,664,227 | B1 | | 12/2003 | Wynn et al. |
| 6,703,360 | B2 | | 3/2004 | McCall et al. |
| 6,746,838 | B1 | | 6/2004 | Choo et al. |
| 6,811,780 | B2 | | 11/2004 | Furfine et al. |
| 6,911,530 | B1 | | 6/2005 | Willson et al. |
| 7,078,494 | B1 | | 7/2006 | Collins et al. |
| 7,282,206 | B2 | | 10/2007 | Wynn et al. |
| 2002/0136719 | A1 | | 9/2002 | Shenoy et al. |
| 2003/0013851 | A1 | | 1/2003 | Powes et al. |
| 2003/0023555 | A1 | | 1/2003 | Rees |
| 2003/0031666 | A1 | | 2/2003 | Debinski et al. |
| 2003/0040606 | A1 | | 2/2003 | Leung |
| 2003/0166871 | A1 | | 9/2003 | Barbas et al. |
| 2003/0175898 | A1 | | 9/2003 | Pantelidis |
| 2003/0235555 | A1 | | 12/2003 | Shealey et al. |
| 2004/0023449 | A1 | | 2/2004 | Hsu et al. |
| 2004/0142372 | A1 | | 7/2004 | McCall et al. |

(Continued)

FOREIGN PATENT DOCUMENTS

EP          0 506 574       11/1995

(Continued)

OTHER PUBLICATIONS

Eduardo Padlan, Mol Immunol. Feb. 1994;31(3):169-217.*

(Continued)

*Primary Examiner*—Ram R Shukla
*Assistant Examiner*—Zachary Skelding
(74) *Attorney, Agent, or Firm*—Lando & Anastasi, LLP

(57) ABSTRACT

This application relates to antibodies, e.g., humanized antibodies, and antigen-binding fragments thereof, that bind to interleukin-13 (IL-13), in particular, human IL-13, and their uses in regulating immune responses mediated by IL-13. The antibodies disclosed herein are useful in diagnosing, preventing, and/or treating a subject, e.g., a human patient, one or more IL-13-associated disorders, e.g., respiratory disorders (e.g., asthma); atopic disorders (e.g., allergic rhinitis); inflammatory and/or autoimmune conditions of the skin (e.g., atopic dermatitis), and gastrointestinal organs (e.g., inflammatory bowel diseases (IBD)), as well as fibrotic and cancerous disorders.

85 Claims, 37 Drawing Sheets

U.S. PATENT DOCUMENTS

| | | | |
|---|---|---|---|
| 2004/0234499 A1 | 11/2004 | Shealy et al. | |
| 2004/0248260 A1 | 12/2004 | Heavner et al. | |
| 2005/0019260 A1 | 1/2005 | Meeusen et al. | |
| 2005/0028496 A1 | 2/2005 | Sabbadini et al. | |
| 2005/0032175 A1 | 2/2005 | Stahl et al. | |
| 2005/0058645 A1 | 3/2005 | Dunlop et al. | |
| 2005/0065327 A1* | 3/2005 | Monk et al. | 530/388.23 |
| 2005/0096268 A1 | 5/2005 | Wynn et al. | |
| 2005/0142105 A1 | 6/2005 | Puri et al. | |
| 2005/0154192 A1 | 7/2005 | Shirakzwa et al. | |
| 2005/0164323 A1 | 7/2005 | Chaudhary et al. | |
| 2005/0186146 A1 | 8/2005 | Gong et al. | |
| 2005/0260216 A1 | 11/2005 | Ashman et al. | |
| 2005/0266005 A1 | 12/2005 | Heavner et al. | |
| 2005/0277126 A1 | 12/2005 | Collins et al. | |
| 2005/0282216 A1 | 12/2005 | Caput et al. | |
| 2006/0024306 A1 | 2/2006 | Strober et al. | |
| 2006/0073148 A1 | 4/2006 | Tchistiakova et al. | |
| 2007/0048785 A1 | 3/2007 | Lin et al. | |

FOREIGN PATENT DOCUMENTS

| | | |
|---|---|---|
| EP | 0812913 | 12/1997 |
| EP | 0 876 482 B1 | 11/1998 |
| EP | 1 176 140 | 1/2002 |
| EP | 1 141 286 B1 | 10/2006 |
| WO | WO 89/04838 | 6/1989 |
| WO | WO 91/09059 | 6/1991 |
| WO | WO 93/15766 | 8/1993 |
| WO | WO 94/04680 | 3/1994 |
| WO | WO 94/14975 | 7/1994 |
| WO | WO 95/14780 | 6/1995 |
| WO | WO 97/15663 | 5/1997 |
| WO | WO 97/20926 | 6/1997 |
| WO | WO 97/29131 | 8/1997 |
| WO | WO 97/31946 | 9/1997 |
| WO | WO 97/33913 | 9/1997 |
| WO | WO 97/47741 | 12/1997 |
| WO | WO 97/47742 | 12/1997 |
| WO | WO 98/10638 | 3/1998 |
| WO | WO 98/30240 | 8/1998 |
| WO | WO 99/29888 | 6/1999 |
| WO | WO 00/36103 | 6/2000 |
| WO | 00/40264 | 7/2000 |
| WO | WO 00/64944 | 11/2000 |
| WO | WO 00/78336 | 12/2000 |
| WO | WO 01/23410 | 4/2001 |
| WO | WO 01/25282 | 4/2001 |
| WO | WO 01/62287 | 8/2001 |
| WO | 01/77332 | 10/2001 |
| WO | WO 01/92340 | 12/2001 |
| WO | WO 02/18445 | 3/2002 |
| WO | WO 02/055100 | 7/2002 |
| WO | WO 02/101629 | 12/2002 |
| WO | WO 03/034984 | 5/2003 |
| WO | WO 03/035847 | 5/2003 |
| WO | WO 03/086451 | 10/2003 |
| WO | 03/092610 | 11/2003 |
| WO | WO 04/001655 | 12/2003 |
| WO | WO 2004/039956 | 5/2004 |
| WO | WO 2004/047728 | 6/2004 |
| WO | WO 2004/069274 | 8/2004 |
| WO | WO 2005/007699 | 1/2005 |
| WO | WO 2005/009464 | 2/2005 |
| WO | WO 2005/016962 | 2/2005 |
| WO | WO 2005/019258 | 3/2005 |
| WO | WO 2005/042028 | 5/2005 |
| WO | WO 2005/062967 | 7/2005 |
| WO | WO 2005/062972 | 7/2005 |
| WO | WO 2005/079755 | 9/2005 |
| WO | WO 2005/081873 | 9/2005 |
| WO | WO 2005/091853 | 10/2005 |
| WO | WO 2005/091856 | 10/2005 |
| WO | WO 2005/121177 | 12/2005 |
| WO | WO 2006/003407 | 1/2006 |
| WO | WO 2006/085938 | 8/2006 |

OTHER PUBLICATIONS

Jefferies et al., Immunol Rev. Jun. 1998;163:59-76.*
Janeway et al., Immunobiology, 5th Ed., Garland Science, pp. 94-105 (2001).*
al Ghamdi et al., "IL-4 and IL-13 expression in chronic sinusitis: relationship with cellular infiltrate and effect of topical corticosteroid treatment," J. Otolaryngol. 26:160-166 (1997).
Aversa et al., "An interleukin 4 mutant protein inhibits both IL-4 or IL-13 induced human immunoglobulin G4 and IgE synthesis and B cell proliferation: support for a common component shared by IL-4 and IL-13 receptors," J. Exp. Med. 178:2213-18 (1993).
Bellanti, "Cytokines and allergic diseases: clinical aspects," Allergy Asthma Proc. 19:337-341 (1998).
Blundell et al., "High-Throughput Crystallography for Lead Discovery in Drug Design," Nature Reviews 11:45-54 (2002).
Bouma et al., "The Immunological and Genetic Basis of Inflammatory Bowel Disease," Nature Reviews 3:521-532 (2003).
Casolaro et al., "Biology and genetics of atopic disease," Curr. Opin. Immunol. 8:796-803 (1996).
Cocks et al., "IL-13 induces proliferation and differentiation of human B cells activated by the CD40 ligand," Int. Immunol. 5:657-663 (1993).
de Vries and Yssel, "Modulation of the human IgE response," Eur. Respir. J. Suppl. 22:58s-62s (1996).
de Vries, "Novel fundamental approaches to intervening in IgE-mediated allergic diseases," J. Invest. Dermatol. 102:141-144 (1994).
Doucet et al., "Interleukin (IL) 4 and IL-13 act on human lung fibroblasts. Implication in asthma," J. Clin. Invest. 101:2129-39 (1998).
Gabrielsson et al., "Increased frequencies of allergen-induced interleukin-13-producing cells in atopic individuals during the pollen season," Scand. J. Immunol. 48:429-35 (1998).
Ghaffar et al., "IL-13 mRNA and immunoreactivity in allergen-induced rhinitis: comparison with IL-4 expression and modulation by topical glucocorticoid therapy," Am. J. Respir. Cell. Mol. Biol. 17:17-24 (1997).
Gruenig et al., "Requirement of IL-13 independently of IL-4 in experimental asthma," Science 282:2261-63 (1998).
Grunewald et al., "An antagonistic IL-4 mutant prevents type I allergy in the mouse: inhibition of the IL-4/IL-13 receptor system completely abrogates humoral immune response to allergen and development of allergic symptoms in vivo," J. Immunol. 160:4004-09 (1998).
Hamid et al., "In vivo expression of IL-12 and IL-13 in atopic dermatitis," J. Allergy Clin. Immunol. 98:225-31 (1996).
Hilton et al., "Cloning and characterization of a binding subunit of the interleukin 13 receptor that is also a component of the interleukin 4 receptor," Proc. Natl. Acad. Sci. USA 93:497-501 (1996).
Huang et al., "IL-13 expression at the sites of allergen challenge in patients with asthma," J. Immunol. 155:2688-94 (1995).
Humbert et al., "Elevated expression of messenger ribonucleic acid encoding IL-13 in the bronchial mucosa of atopic and nonatopic subjects with asthma," J. Allergy Clin. Immunol. 99:657-665 (1997).
Kimata et al., "Involvement of interleukin (IL)-13, but not IL-4, in spontaneous IgE and IgG4 production in nephrotic syndrome," Eur. J. Immunol. 25:1497-1501 (1995).
Kotsimbos et al., "Interleukin-13 and interleukin-4 are coexpressed in atopic asthma," Proc. Assoc. Am. Physicians 108:368-373 (1996).
Kroegel et al., "Endobronchial secretion of interleukin-13 following local allergen challenge in atopic asthma: relationship to interleukin-4 and eosinophil counts," Eur. Resp. J. 9:899-904 (1996).
Maini et al., "Interleukin-13 receptors on human prostate carcinoma cell lines represent a novel target for a chimeric protein composed of IL-13 and a mutated form of *Pseudomonas* exotoxin," J. Urol. 158:948-953 (1997).

Marsh et al., "Linkage analysis of IL4 and other chromosome 5q31.1 markers and total serum immunoglobulin E concentrations," Science. 264:1152-56 (1994).

McKenzie et al., "Interleukin-13, a T-cell-derived cytokine that regulates human monocyte and B-cell function," Proc. Natl. Acad. Sci. USA 90:3735-39 (1993).

Mentik-Kane and Wynn, "Opposing roles for IL-13 and IL-13 receptor alpha 2 in health and disease," Immunol. Rev. 202:191-202 (2004).

Minty et al., "Interleukin-13 is a new human lymphokine regulating inflammatory and immune responses," Nature 362:248-250 (1993).

Moy et al., "Solution structure of human IL-13 and implication for receptor binding," J. Mol. Biol. 310:219-230 (2001).

Naseer et al., "Expression of IL-12 and IL-13 mRNA in asthma and their modulation in response to steroid therapy," Am. J. Respir. Crit. Care Med. 155:845-851 (1997).

Pawankar et al., "Nasal mast cells in perennial allergic rhinitics exhibit increased expression of the FcεRI, CD40L, IL-4, and IL-13, and can induce IgE synthesis in B cells," J. Clin. Invest. 99:1492-99 (1997).

Postma et al., "Genetic susceptibility to asthma—bronchial hyper-responsiveness coinherited with a major gene for atopy," N. Engl. J. Med. 333:894-900 (1995).

Punnonen and deVries, Oct. 1998, In: *Allergy and Allergic Diseases*, J.A. Denburg ed., Human Press Inc., Totowa, New Jersey, pp. 13-40.

Punnonen et al., "IL-13 induces proliferation, Ig isotype switching, and Ig synthesis by immature human fetal B cells," J. Immunol., 152:1094-1102 (1994).

Punnonen et al., "Interleukin 13 induces interleukin 4-independent IgG4 and IgE synthesis and CD23 expression by human B cells," Proc. Natl. Acad. Sci. USA 90:3730-34 (1993).

Punnonen et al., "The relative contribution of IL-4 and IL-13 to human IgE synthesis induced by activated $CD4^+$ or $CD8^+$ cells," J. Allergy Clin. Immunol. 100(6):792-801 (1997).

Shanafelt et al., "An immune cell-selective interleukin 4 agonist," Proc. Natl. Acad. Sci. USA 95:9454-58 (1998).

Van der Pouw Kraan et al., "The role of IL-13 in IgE synthesis by allergic asthma patients," Clin. Exp. Immunol. 111:129-135 (1998).

Warner, "Bronchial hyperresponsiveness, atopy, airway inflammation, and asthma," Pediatr. Allergy Immunol. 9:56-60 (1998).

Yssel et al., "The role of IgE in asthma," Clin. Exp. Allergy 28(Suppl. 5):104-109 (1998).

Zurawski et al., "Receptors for interleukin-13 and interleukin-4 are complex and share a novel component that functions in signal transduction," EMBO J. 12:2663-70 (1993).

Bouma et al., "The Immunological and Genetic Basis of Inflammatory Bowel Disease", Nature Reviews 3:521-532, Jul. 2003.

Ahlers et al., "A push-pull approach to maximize vaccine efficacy: Abrogating suppression with an IL-13 inhibitor while augmenting help with granulocyte macrophage colony-stimulating factor and CD40L," PNAS, vol. 99, No. 20, pp. 13020-13025, 2002.

Bancroft et al., "Gastrointestinal nematode expulsion in IL-4 knockout mice is IL-13 dependent," Eur. J. Immunol. vol. 30, pp. 2083-2091, 2000.

Blease et al., "Therapeutic Effect of IL-13 Immunoneutralization During Chronic Experimental Fungal Asthma," The Journal of Immunology, vol. 166, pp. 5219-5224, 2001.

Borish et al., "Interleukin-4 Receptor in Moderate Atopic Asthma," Am J Respir Crit Care Med, vol. 160, pp. 1816-1823, 1999.

Bost et al., "In vivo treatment with anti-interleukin-13 antibodies significantly reduces the humoral immune response against an oral immunogen in mice," Immunology, vol. 87, pp. 633-641, 1996.

Caput et al., "Cloning and Characterization of a Specific Interleukin (IL)-13 Binding Protein Structurally Related to the IL-5 Receptor alpha Chain," The Journal of Biological Chemistry, vol. 271, No. 28, pp. 16921-16926, 1996.

Carballido et al., "IL-4 Induces Human B Cell Maturation and IgE Synthesis in SCI D-hu Mice," The Journal of Immunology, vol. 155, pp. 4162-4170, 1995.

Chiaramonte et al., "An IL-13 inhibitor blocks the development of hepatic fibrosis during a T-helper type 2-dominated inflammatory response," J. Clin. Invest. vol. 104, pp. 777-785, 1999.

Chiaramonte et al., "IL-13 Is a Key Regulatory Cytokine for Th2 Cell-Mediated Pulmonary Granuloma Formation and IgE Responses Induced by Schistosoma mansoni Eggs," The Journal of Immunology, vol. 162, pp. 920-930, 1999.

Chiaramonte et al., "Regulation and Function of the Interleukin 13 Receptor alpha 2 During a T Helper Cell Type 2-dominant Immune Response," The Journal of Experimental Medicine, vol. 197, No. 6, pp. 687-701, 2003.

Chiaramonte et al., "Studies of Murine Schistosomiasis Reveal Interleukin-13 Blockade as a Treatment for Established and Progressive Liver Fibrosis," Hepatology, vol. 34, pp. 273-282, 2001.

Donaldson et al., "The Murine IL-13 Receptor a2: Molecular Cloning, Characterization, and Comparison with Murine IL-13 Receptor alpha 1," The Journal of Immunology, vol. 161, pp. 2317-2324, 1998.

Economides et al., "Cytokine traps: multi-component, high-affinity blockers of cytokine action," Nature Medicine vol. 9, No. 1, pp. 47-52, 2003.

Finkelman et al., "The role of IL-13 in helminth-induced inflammation and protective immunity against nematode infections," Current Opinion in Immunology, vol. 11, pp. 420-426, 1999.

Fish et al., "IgE Generation and Mast Cell Effector Function in Mice Deficient in IL-4 and IL-13," The Journal of Immunology, vol. 174, pp. 7716-7724, 2005.

Ford et al., "IL-13 and IFN-g: Interactions in Lung Inflammation," The Journal of Immunology, vol. 167, pp. 1769-1777, 2001.

Gruenig et al., "Roles of Interleukin-13 and Interferon-gama in Lung Inflammation," Chest, Mar. 2002;121(3 Suppl.): 88S.

Hart et al., "Preclinical efficacy and safety of pascolizumab (SB 240683): a humanized anti-interleukin-4 antibody with therapeutic potential in asthma," Clin Exp Immunol, vol. 130, pp. 93-100, 2002.

Heller et al., "Oxazolone Colitis, a Th2 Colitis Model Resembling Ulcerative Colitis, Is Mediated by IL-13-Producing NK-T Cells," Immunity, vol. 17 pp. 629-638, Nov. 2002.

Henderson et al., "Soluble IL-4 Receptor Inhibits Airway Inflammation Following Allergen Challenge in a Mouse Model of Asthma," The Journal of Immunology vol. 164, pp. 1086-1095, 2000.

Leigh et al., "Is Interleukin-13 Critical in Maintaining Airway Hyper-resposiveness in Allergen-challenged Mice?," Am. J. Respir. Crit. Care. Med., vol. 170, pp. 851-856, 2004.

Lentsch et al., "Regulation of Acute Lung Inflammatory Injury by Endogenous IL-13," The Journal of Immunology, vol. 162, pp. 1071-1076, 1999.

Li et al., "Effects of Th2 Cytokines on Chemokine Expression in the Lung: IL-13 Potently Induces Eotaxin Expression by Airway Epithelial Cells1," The Journal of Immunology, vol. 162, pp. 2477-2487, 1999.

Ma et al., "Turmor cells secreting IL-13 but not IL-13Ralpha2 fusion protein have reduced tumorigenicity in vivo," International Immunology, vol. 16, No. 7, pp. 1009-1017, 2004.

Mentink-Kane et al., "IL-13 receptor alpha 2 down-modulates granulomatous inflammation and prolongs host survival in schistosomiasis," PNAS, vol. 101, No. 2, pp. 586-590, 2004.

Morse et al. "Effects of IL-13 on airway responses in the guinea pig," Am. J. Physiol. Lung. Cell. Mol. Physiol., vol. 282, pp. 44-49, 2002.

Obiri et al., "Receptor for Interleukin 13," The Journal of Biological Chemistry, vol. 270, No. 15, pp. 8797-8804, 1995.

Padilla et al., "IL-13 Regulates the Immune Response to Inhaled Antigens," The Journal of Immunology, vol. 174, pp. 8097-8105, 2005.

Park et al., "Respiratory syncytial virus-induced airway hyper-responsiveness is independent of IL-13 compared with that induced by allergen,"J. Allergy Clin Immunol, vol. 112, pp. 1078-1087, 2003.

Park et al., "Unmasking immunosurveillance against a syngeneic colon cancer by elimination of CD4 NKT regulatory cells and IL-13," Int. J. Cancer, vol. 114, pp. 80-87, 2005.

Proust et al., "Persistence of bronchopulmonary hyper-reactivity and eosinophilic lung inflammation after anti-IL-5 or -IL-13 treatment in allergic BALB/c and IL-4Rα knockout nice," Clin Exp Allergy vol. 33, pp. 119-131, 2003.

Taube et al., "Mast Cells, FcεRI, and IL-13 Are Required for Development of Airway Hyperresponsiveness after Aerosolized Allergen Exposure in the Absence of Adjuvant," The Journal of Immunology, vol. 172, pp. 6398-6406, 2004.

Taube et al., "The Role of IL-13 in Established Allergic Airway Disease," The Journal of Immunology, vol. 169, pp. 6482-6489, 2002.

Tekkanat et al., "IL-13-Induced Airway Hyperreactivity During Respiratory Syncytial Virus Infection Is STAT6 Dependent," The Journal of Immunology, vol. 166, pp. 3542-3548, 2001.

Terabe et al., "NKT cell-mediated repression of tumor immunosurveillance by IL-13 and the IL-4R-STAT6 pathway," Nature Immunology, vol. 1, No. 6, pp. 515-520, 2000.

Tomkinson et al., "A Murine IL-4 Receptor Antagonist That Inhibits IL-4- and IL-13-Induced Responses Prevents Antigen-Induced Airway Eosinophilia and Airway Hyperresponsiveness," The Journal of Immunology, vol. 166, pp. 5792-5800, 2001.

Urban et al., "IL-13-Mediated Worm Expulsion Is B7 Independent and IFN-gama Sensitive," The Journal of Immunology, vol. 164, pp. 4250-4256, 2000.

Vita et al., "Characterization and Comparison of the Interleukin 13 Receptor with the Interleuking 4 receptor on Several Cell Types," The Journal of Biological Chemistry, vol. 270, No. 8, pp. 3512-3517, 1995.

Vogel, "Interleukin-13's Key Role in Asthma Shown," Science, vol. 282, p. 2168, 1998.

Walter et al., "Critical Role for IL-13 in the Development of Allergen-Induced Airway Hyperreactivity," The Journal of Immunology, vol. 167, pp. 4668-4675, 2001.

Webb et al., "Antigen-specific production of interleukin (IL)-13 and IL-5 cooperate to mediate IL-4Ralpha -independent airway hyper-reactivity," Eur. J. Immunol., vol. 33, pp. 3377-3385, 2003.

Wills-Karp et al., "Polymorphisms Not Foud in the IL-13 Gene Promotor," Science, vol. 284, p. 1431, 1999.

Wills-Karp et al., "Interleukin-13: Central Mediator of Allergic Asthma", Science, vol. 282, No. 5397, pp. 2258-2261, 18, 1998.

Wood et al., "Enhanced Interleukin (IL)-13 Responses in Mice Lacking IL-13 Receptor alpha 2," J. Exp. Med., vol. 197, No. 6, pp. 703-709, 2003.

Wood et al., "IL-21 eVects on human IgE production in response to IL-4 or IL-13," Cellular Immunology, vol. 231, pp. 133-145, 2004.

Zurawski et al., "The Primary Binding Subunit of the Human Interleukin-4 Receptor Is Also a Component of the Interleukin-13 Receptor," The Journal of Biological Chemistry, vol. 270, No. 23, pp. 13869-13878, 1995.

Andrews, A. L. et al., "Kinetic Analysis of the Interleukin -13 Receptor Complex," Journal of Biological Chemistry, 277 (48):46073-8 (2002).

Berger, R. et al., "IL-4 and IL-13 regulation of ICAm-1 expression and eosinophil recruitment in *Onchocera volvulus* keratitus," Investigative Ophthalmology and Visual Science, 43(9):2992-7 (2002).

Bree, A. et al., "Il-13 blockade reduces lung inflammation after *Ascaris Suum* challenge in Cynomolgus monkeys," Journal of Allergy and Clinical Immunology, 119(5):1251-7 (2007).

Cetre, C. et al., "Interleukin-13 and IgE production in rat experimental schistosomiasis," European Cytokine Network, 11(2):241-9 (2000).

Fichter-Feigl, S. et al., "IL-13 signaling through the IL-13-alpha2 receptor is involved in induction of TGF-β1 production and fibrosis," Nature Medicine, 12(1):99-106 (2006).

Hahn, C. et al., "Inhibition of the IL-4/IL-13 receptor system prevents allergic sensitization without affecting established allergy in a mouse model for allergic asthma," Journal of Allergy and Clinical Immunology, 111(6):1361-9 (2003).

Kasaian, M. et al., "Efficacy of IL-13 Neutralization in a sheep model of experimental asthma," American Journal of Respiratory Cell and Molecular Biology, 36:368-76 (2007).

Lee, S.H., et al., "Inhibitory effect of DA-9201, and extract of *Oryza sativa* L., on airway inflammation and bronchial hyperresponsiveness in mouse asthma model," Medicinal and Aromatic Plants Abstracts, 28(5):1148 (2006).

Li, X. et al., "The Chinese herbal medicine formula MSSM-002 suppresses allergic airway hyperreactivity and modulates TH1/TH2 responses in a murine model of allergic asthma," Journal of Allergy and Clinical Immunology, 106(4):660-8 (2000).

Tekkanat, K. et al., "IL-13-induced airway hyperreactivity during respiratory syncytial virus infection is STAT6 dependent," Journal of Immunology, 166(5):3542-8 (2001).

Vugmeyster, Y. et al., "Preclinical pharmacokinetics, interspecies scaling, and tissue distribution of humanized monoclonal anti-IL-13 neutralization mechanisms," International Immunopharmacology, 8(3):477-83 (2008).

Appeal Brief of Opposition to EP 1 141 286 B1, filed by Genentech, Inc. and received by the European Patent Office on Jul. 9, 2007.

Appeal Brief of Opposition to EP 1 141 286 B1, filed by George W. Schlich and received by the European Patent Office on Jul. 9, 2007.

Appeal Brief of Opposition to EP 1 141 286 B1, filed by UCB Pharma S.A. and received by the European Patent Office on Jul. 16, 2007.

Appeal Brief of Opposition to EP 1 141 286 B1, filed by AstraZeneca AB and received by the European Patent Office on Jul. 16, 2007.

Appeal Brief of Opposition to EP 1 141 286 B1, filed by Glaxo Group Limited and received by the European Patent Office on Jul. 19, 2007.

Proprietor's Brief in the Opposition of EP 1 141 286 B1, received by the European Patent Office on Jul. 7, 2008.

International Search Report in related International Application PCT/US99/29493, dated Apr. 25, 2000.

International Search Report in related International Application PCT/US05/21454, dated May 21, 2008.

International Search Report in related International Application PCT/US07/25418, dated Jul. 14, 2008.

Written Opinion of the Australian Patent Office (Application No. 200608368-7), dated Feb. 20, 2009 (4 pgs.).

Ohno S et al., Antigen-binding specificities of antibodies are primarily determined by seven residues of VH. Proc. Natl. Acad. Sci. USA. May 1985;82(9):2945-9.

International Search Report in related International Application PCT/US05/020160, dated Apr. 25, 2007.

International Search Report in related International Application PCT/US01/51339, dated Nov. 14, 2002.

International Search Report in related International Application PCT/US00/11612, dated Aug. 3, 2000.

Further Observations in the Opposition of EP 1 141 286 B1, received from the European Patent Office on Dec. 29, 2008.

\* cited by examiner

MALLLTTVIALTCLGGFASPGPVPPSTALRELIEELVNITQNQKA  25/45

PLCNGSMVWSINLTAGMYCAALESLINVSGCSAIEKTQRMLSGF  69/89

CPHKVSAGQFSSLHVRDTKIEVAQFVKDLLLHLKKLFREGRFN (SEQ ID NO: 31)  112/132

Fig. 11

☐ Major Ab-contact sites from crystal structure
■ ARG variant (R130Q)
<u>alpha helices</u>

```
                                                           CDR1
DP-54 hu ger   EVQLVESGGG LVQPGGSLRL SCAASGFTFS   SYWMSWVRQA PGKGLEWVAN
Murine 13.2    EVKLVESGGG LVKPGGSLKL SCAASGFTFI   SYAMSWVRQT PEKRLEWVAS
h13.2v1        EVKLVESGGG LVQPGGSLRL SCAASGFTFI   SYAMSWVRQA PGKGLEWVAS CDR3
DP-54 hu ger   IKQDGSEKYY VDSVKGRFTI SRDNAKNSLY   LQMNSLRAED TAVYYCARV.
Murine 13.2    I.SSGGNTYY PDSVKGRFTI SRDNARNTLY   LQMSSLRSED TAMYYCARLD
h13.2v1        I.SSGNTYY  PDSVKGRFTI SRDNAKNSLY   LQMNSLRAED TAVYYCARLD
                   CDR2

CDR3
DP-54 hu ger   RRGSGDS.WG QGTLVTVSS
Murine 13.2    GYYFGFAYWG QGTTVTVSS          *AMINO ACID CHANGES
h13.2v1        GYYFGFAYWG QGTLVTVSS              UNCHANGED
```

Figure 15

```
                    CDR1
DPK9 hu ger   DIQMTQSPSS LSASVGDRVT ITCRASQSIS SY...LNWY QQKPGKAPKL
Murine 13.2   DIVLTQSPAS LAVSLGQRAT ISCKASESVD NYGKSLMHWY QQKPGQSPKL
h13.2v1       DIQLTQSPSS LSASVGDRVT ITCKASESVD NYGKSLMHWY QQKPGKAPKL
                              CDR2
DPK9 hu ger   LIYAASSLQS GVPSRFSGSG SGTDFTLTIS SLQPEDFATY YCQQSYSTLL
Murine 13.2   LIYRASNLES GIPARFSGSG SRTDFTLTIN PVEADDVATY YCQQSNEDPW
h13.2v1       LIYRASNLES GVPSRFSGSG SRTDFTLTIS SLQPEDFATY YCQQSNEDPW
                                                           CDR3
CDR3
DPK9 hu ger   TFGGGTKVEI    (SEQ ID NO: 39)
Murine 13.2   TFGGGTKIEI K  (SEQ ID NO: 10)
h13.2v1       TFGGGTKVEI K  (SEQ ID NO: 11)
```

*AMINO ACID CHANGES

UNCHANGED

Fig. 16

```
                                                              CDR1
DP-54 hu ger   EVQLVESGGG LVQPGGSLRL SCAASGFTFS SYWMSWVRQA PGKGLEWVAN
Murine 13.2    EVKLVESGGG LVKPGGSLKL SCAASGFTFI SYAMSWVRQT PEKRLEWVAS
h13.2v2        EVQLVESGGG LVQPGGSLRL SCAASGFTFI SYAMSWVRQA PGKGLEWVAS CDR2
DP-54 hu ger   IKQDGSEKYY VDSVKGRFTI SRDNAKNSLY LQMNSLRAED TAVYYCARV.
Murine 13.2    I.SSGNTYY  PDSVKGRFTI SRDNARNILY LQMSSLRSED TAMYYCARLD
h13.2v2        I.SSGNTYY  PDSVKGRFTI SRDNAKNSLY LQMNSLRAED TAVYYCARLD
                                                                 CDR3

CDR3
DP-54 hu ger   RRGSGDS.WG QGTLVTVSS
Murine 13.2    GYYFGFAYWG QGTLVTVSS
h13.2v2        GYYFGFAYWG QGTLVTVSS
```

**\*AMINO ACID CHANGES**
UNCHANGED

Figure 17

|  | | | CDR1 | |
|---|---|---|---|---|
| DPK9 hu ger | DIQMTQSPSS | LSASVGDRVT | ITCRASQSIS SY....LNWY | QQKPGKAPKL |
| Murine 13.2 | DIVLTQSPAS | LAVSLGQRAT | ISCKASESVD NYGKSLMHWY | QQKPGQSPKL |
| h13.2v2 | DIQMTQSPSS | LSASVGDRVT | ITCKASESVD NYGKSLMHWY | QQKPGKAPKL |

|  | CDR2 | | | CDR3 |
|---|---|---|---|---|
| DPK9 hu ger | LIYAASSLQS | GVPSRFSGSG | SGTDFTLTIS | SLQPEDFATY YCQQSYSTLL |
| Murine 13.2 | LIYRASNLES | GIPARFSGSG | SRTDFTLTIN | PVEADDVATY YCQQSNEDPW |
| h13.2v2 | LIYRASNLES | GVPSRFSGSG | SGTDFTLTIS | SLQPEDFATY YCQQSNEDPW |

|  |  | |
|---|---|---|
| DPK9 hu ger | TFGGGTKVEI K | (SEQ ID NO: 39) |
| Murine 13.2 | TFGGGTKLEI K | (SEQ ID NO: 10) |
| h13.2v2 | TFGGGTKVEI K | (SEQ ID NO: 12) |

**\*AMINO ACID CHANGES**

UNCHANGED

Fig. 18

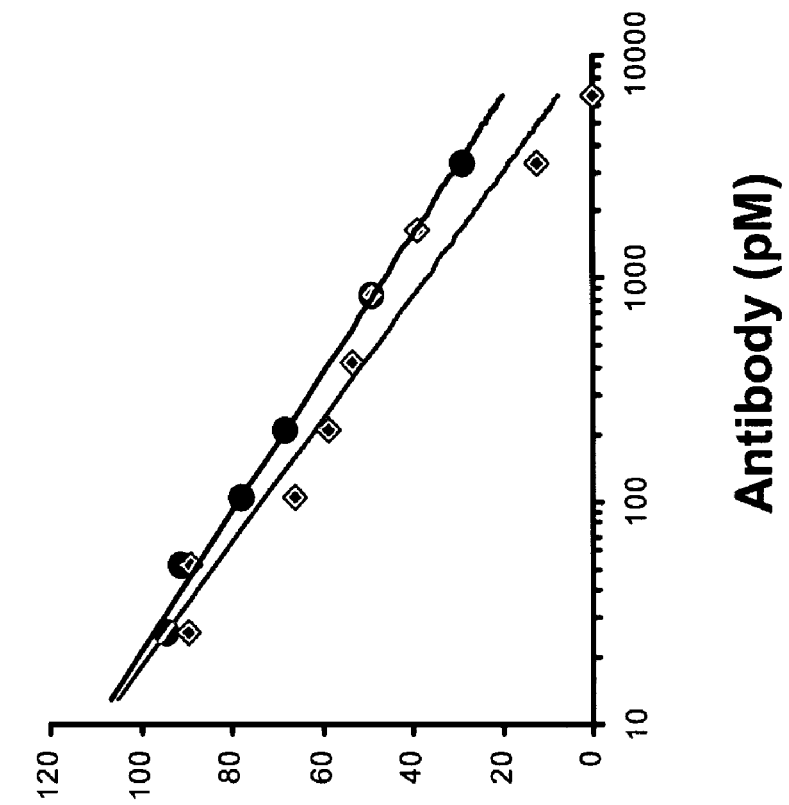
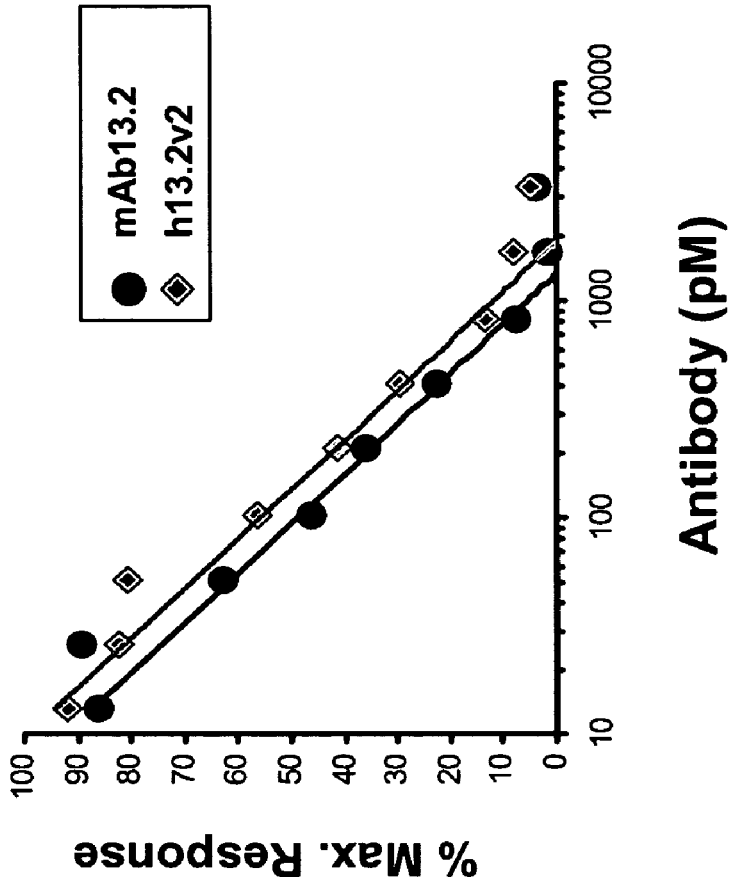
Figure 21A
Figure 21B

| VH3 | FW1 | CDR1 | FW2 | CDR2 | FW3 | |
|---|---|---|---|---|---|---|
| 3-07 | EVQLVESGGGLVQPGGSLRLSCAASGFTFS | S--YWMS | WVRQAPGKGLEWVA | NIKQ--DGSEKYYVDSVKG | RFTISRDNAKNSLYLQMNSLRAEDTAVYYCAR | (SEQ ID NO: 40) |
| 3-09 | EVQLVESGGGLVQPGRSLRLSCAASGFTFD | D--YAMH | WVRQAPGKGLEWVS | GISW--NSGSIGYADSVKG | RFTISRDNAKNSLYLQMNSLRAEDTALYYCAKD | (SEQ ID NO: 41) |
| 3-11* | QVQLVESGGGLVKPGGSLRLSCAASGFTFS | D--YYMS | WIRQAPGKGLEWVS | YISS-SGSTIYYADSVKG | RFTISRDNAKNSLYLQMNSLRAEDTAVYYCAR | (SEQ ID NO: 42) |
| 3-13 | EVQLVESGGGLVQPGGSLRLSCAASGFTFS | S--YDMH | WVRQATGKGLEWVS | AIG---TAGDTYYPGSVKG | RFTISRENAKNSLYLQMNSLRAGDTAVYYCAR | (SEQ ID NO: 43) |
| 3-15 | EVQLVESGGGLVKPGGSLRLSCAASGFTFS | N--AMMS | WVRQAPGKGLEWVG | RIKSKTDGGTTDYAAPVKG | RFTISRDDSKNTLYLQMNSLKTEDTAVYYCAR | (SEQ ID NO: 44) |
| 3-20 | EVQLVESGGGVVRPGGSLRLSCAASGFTFD | D--YGMS | WVRQAPGKGLEWVS | GINW--NGGSTGYADSVKG | RFTISRDNAKNSLYLQMNSLRAEDTALYHCAR | (SEQ ID NO: 45) |
| 3-21 | EVQLVESGGGLVKPGGSLRLSCAASGFTFS | S--YSMN | WVRQAPGKGLEWVS | SISS--SSSYIYYADSVKG | RFTISRDNAKNSLYLQMNSLRAEDTAVYYCAR | (SEQ ID NO: 46) |
| 3-23 | EVQLLESGGGLVQPGGSLRLSCAASGFTFS | S--YAMS | WVRQAPGKGLEWVS | AISG--SGGSTYYADSVKG | RFTISRDNSKNTLYLQMNSLRAEDTAVYYCAR | (SEQ ID NO: 47) |
| 3-30 | QVQLVESGGGVVQPGRSLRLSCAASGFTFS | S--YGMH | WVRQAPGKGLEWVA | VISY--DGSNKYYADSVKG | RFTISRDNSKNTLYLQMNSLRAEDTAVYYCAK | (SEQ ID NO: 48) |
| 3-30.3 | QVQLVESGGGVVQPGRSLRLSCAASGFTFS | S--YAMH | WVRQAPGKGLEWVA | VISY--DGGNKYYADSVKG | RFTISRDNSKNTLYLQMNSLRAEDTAVYYCAR | (SEQ ID NO: 49) |
| 3-30.5 | QVQLVESGGGVVQPGRSLRLSCAASGFTFS | S--YGMH | WVRQAPGKGLEWVA | VISY--DGSNKYYADSVKG | RFTISRDNSKNTLYLQMNSLRAEDTAVYYCAK | (SEQ ID NO: 50) |
| 3-33 | QVQLVESGGGVVQPGRSLRLSCAASGFTFS | S--YGMH | WVRQAPGKGLEWVA | VIWY--DGSNKYYADSVKG | RFTISRDNSKNTLYLQMNSLRAEDTAVYYCAR | (SEQ ID NO: 51) |
| 3-43 | EVQLVESGGVVVQPGGSLRLSCAASGFTFD | D--YTMH | WVRQAPGKGLEWVS | LISW--DGGSTYYADSVKG | RFTISRDNSKNSLRTEDTALYYCAKD | (SEQ ID NO: 52) |
| 3-48 | EVQLVESGGGLVQPGGSLRLSCAASGFTFS | S--YSMN | WVRQAPGKGLEWVS | YISS--SSSTIYYADSVKG | RFTISRDNAKNSLYLQMNSLRDEDTAVYYCAR | (SEQ ID NO: 53) |
| 3-49 | EVQLVESGGGLVQPGRSLRLSCTASGFTFG | D--YAMS | WFRQAPGKGLEWVG | FIRSKAYGGTTEYTASVKG | RFTISRDGSKSTAYLQMNSLRTKEDTAVYYCTR | (SEQ ID NO: 54) |
| 3-53 | EVQLVETGGGLIQPGGSLRLSCAASGFTVS | S--NYMS | WVRQAPGKGLEWVS | VIY---SGGSTYYADSVKG | RFTISRDNSKNTLYLQMNSLRAEDTAVYYCAR | (SEQ ID NO: 55) |
| 3-64 | EVQLVESGGGLVQPGGSLRLSCAASGFTFS | S--YAMH | WVRQAPGKGLEIVS | AISS--NGGSTYYANSVKG | RFTISRDNSKNTLYLQMNSLRAEDMAVYYCAR | (SEQ ID NO: 56) |
| 3-66 | EVQLVESGGGLVQPGGSLRLSCAASGFTVS | S--NYMS | WVRQAPGKGLEWVS | VIY---SGGSTYYADSVKG | RFTISRDNSKNTLYLQMNSLRAEDTAVYYCAR | (SEQ ID NO: 57) |
| 3-72 | EVQLVESGGGLVQPGGSLRISCAASGFTES | D--HYMD | WVRQAPGKGLEWVG | RTRNKANSYTTEYAASVKG | RFTISRDDSKNSLYLQMNSLKTEDTAVYYCAR | (SEQ ID NO: 58) |
| 3-73 | EVQLVESGGGLVQPGGSLKLSCAASGFTFS | G--SAMH | WVRQASGKGLEWVG | RIRSKANSYATAYAASVKG | RFTISRDDSKNTAVLQMNSLRAEDTAVYYCTR | (SEQ ID NO: 59) |
| 3-74 | EVQLVESGGGLVQPGGSLRLSCAASGFTFS | S--YWMH | WVRQAPGKGLVWVS | RINS--DGSSTYYADSVKG | RFTISRDNAKNTLYLQMNSLRAEDTAVYYCAR | (SEQ ID NO: 60) |
| 3-d | EVQLVESRGVLVQPGGSLRLSCAASGFTVS | S--NEMS | WVRQAPGKGLEWVS | SI----SGGSTYYADSRKG | RFTISRDNSKNTLHLQMNSLRAEDTAVYYCKK | (SEQ ID NO: 61) |
| DP-61 | EVQLVQSGGGLVQPGGSLRLSCAGSGFTFS | S--YAMH | WVRQAPGKGLEWVS | AI----GTGGGTYYADSVKG | RFTISRDNAKNSLYLQMNSLRAEDMAVYYCAR | (SEQ ID NO: 62) |
| mAb13.2 | EVKLVESGGGLVKPGGSLKLSCAASGFTFI | S--YAMS | WVRQTPEKRLEWVA | SI---SSGGNTYYPDSVKG | RFTISRDNARNILVLQMSSLRSEDTAMYYCAR | (SEQ ID NO: 63) |

Fig. 26

```
                         CDR1
DP-77 hu ger   EVQLVESGGG LVKPGGSLRL SCAASGFTFS          SYSMNWVRQA PGKGLEWVSS
Murine 13.2    EVKLVESGGG LVKPGGSLKL SCAASGFTFI          SYAMSWVRQT PEKRLEWVAS
h13.2v3        EVQLVESGGG LVKPGGSLRL SCAASGFTFI          SYAMSWVRQA PGKGLEWVSS CDR2
DP-77 hu ger   ISSSSSYIYY ADSVKGRFTI SRDNAKNSLY LQMNSLRAED TAVYYCAR
Murine 13.2    I.SSGGNTYY PDSVKGRFTI SRDNARNILY LQMSSLRSED TAMYYCARLD
h13.2v3        I.SSGGNTYY PDSVKGRFTI SRDNAKNSLY LQMNSLRAED TAVYYCARLD
                                                                   CDR3

CDR3
DP-77 hu ger   GYYFGFAYWG QGTTVTVSS
Murine 13.2
h13.2v3        GYYFGFAYWG QGTTVTVSS
```

*AMINO ACID CHANGES
UNCHANGED

Figure 27

```
                              CDR1
B1 hu ger    DIVLTQSPAS LAVSPGQRAT ITCRASESVS FLGINLIHWY QQKPGQPPKL
Murine 13.2  DIVLTQSPAS LAVSLGQRAT ISCKASESVD NYGKSLMHWY QQKPGQSPKL
h13.2v3      DIVLTQSPAS LAVSPGQRAT ITCKASESVD NYGKSLMHWY QQKPGQPPKL CDR2
B1 hu ger    LIYQASNKDT GVPARFSGSG SGTDFTLTIN PVEANDTANY YCLQSKNFPP
Murine 13.2  LIYRASNLES GIPARFSGSG SRTDFTLTIN PVEADDVATY YCQQSNEDPW
h13.2v3      LIYRASNLES GVPARFSGSG SGTDFTLTIN PVEANDTANY YCQQSNEDPW
                                                              CDR3

CDR3
B1 hu ger    TV
Murine 13.2  TFGGGTKLEI K
h13.2v3      TFGGGTKVEI K (SEQ ID NO: 65)
(SEQ ID NO: 10)
(SEQ ID NO: 35)
```

**\*AMINO ACID CHANGES**

UNCHANGED

Fig. 28

| RESIDUE | LINEAR SEQUENCE NUMBER | CHOTHIA STRUCTURE NUMBER | KABAT SEQUENCE NUMBER | RESIDUE | LINEAR SEQUENCE NUMBER | CHOTHIA STRUCTURE NUMBER | KABAT SEQUENCE NUMBER | RESIDUE | LINEAR SEQUENCE NUMBER | CHOTHIA STRUCTURE NUMBER | KABAT SEQUENCE NUMBER | RESIDUE | LINEAR SEQUENCE NUMBER | CHOTHIA STRUCTURE NUMBER | KABAT SEQUENCE NUMBER |
|---|---|---|---|---|---|---|---|---|---|---|---|---|---|---|---|
| E | 1 | 1 | 1 | A | 33 | 33 | 33 | G | 65 | 65 | 65 | R | 97 | 94 | 94 |
| V | 2 | 2 | 2 | M | 34 | 34 | 34 | R | 66 | 66 | 66 | L | 98 | 95 | 95 |
| K | 3 | 3 | 3 | S | 35 | 35 | 35 | F | 67 | 67 | 67 | D | 99 | 96 | 96 |
| L | 4 | 4 | 4 | W | 36 | 36 | 36 | T | 68 | 68 | 68 | G | 100 | 97 | 97 |
| V | 5 | 5 | 5 | V | 37 | 37 | 37 | I | 69 | 69 | 69 | Y | 101 | 98 | 98 |
| E | 6 | 6 | 6 | R | 38 | 38 | 38 | S | 70 | 70 | 70 | Y | 102 | 99 | 99 |
| S | 7 | 7 | 7 | Q | 39 | 39 | 39 | R | 71 | 71 | 71 | F | 103 | 100 | 100 |
| G | 8 | 8 | 8 | T | 40 | 40 | 40 | D | 72 | 72 | 72 | G | 104 | 100A | 100A |
| G | 9 | 9 | 9 | P | 41 | 41 | 41 | N | 73 | 73 | 73 | F | 105 | 100B | 100B |
| G | 10 | 10 | 10 | E | 42 | 42 | 42 | A | 74 | 74 | 74 | A | 106 | 101 | 101 |
| L | 11 | 11 | 11 | K | 43 | 43 | 43 | R | 75 | 75 | 75 | Y | 107 | 102 | 102 |
| V | 12 | 12 | 12 | R | 44 | 44 | 44 | N | 76 | 76 | 76 | W | 108 | 103 | 103 |
| K | 13 | 13 | 13 | L | 45 | 45 | 45 | I | 77 | 77 | 77 | G | 109 | 104 | 104 |
| P | 14 | 14 | 14 | E | 46 | 46 | 46 | L | 78 | 78 | 78 | Q | 110 | 105 | 105 |
| G | 15 | 15 | 15 | W | 47 | 47 | 47 | Y | 79 | 79 | 79 | G | 111 | 106 | 106 |
| G | 16 | 16 | 16 | V | 48 | 48 | 48 | L | 80 | 80 | 80 | T | 112 | 107 | 107 |
| S | 17 | 17 | 17 | A | 49 | 49 | 49 | Q | 81 | 81 | 81 | T | 113 | 108 | 108 |
| L | 18 | 18 | 18 | S | 50 | 50 | 50 | M | 82 | 82 | 82 | V | 114 | 109 | 109 |
| K | 19 | 19 | 19 | I | 51 | 51 | 51 | S | 83 | 82A | 82A | T | 115 | 110 | 110 |
| L | 20 | 20 | 20 | S | 52 | 52 | 52 | S | 84 | 82B | 82B | V | 116 | 111 | 111 |
| S | 21 | 21 | 21 | S | 53 | 53 | 53 | L | 85 | 82C | 82C | S | 117 | 112 | 112 |
| C | 22 | 22 | 22 | G | 54 | 54 | 54 | R | 86 | 83 | 83 | S | 118 | 113 | 113 |
| A | 23 | 23 | 23 | G | 55 | 55 | 55 | S | 87 | 84 | 84 | (SEQ ID NO: 14) | | | |
| A | 24 | 24 | 24 | N | 56 | 56 | 56 | E | 88 | 85 | 85 | | | | |
| S | 25 | 25 | 25 | T | 57 | 57 | 57 | D | 89 | 86 | 86 | | | | |
| G | 26 | 26 | 26 | Y | 58 | 58 | 58 | T | 90 | 87 | 87 | | | | |
| F | 27 | 27 | 27 | Y | 59 | 59 | 59 | A | 91 | 88 | 88 | | | | |
| T | 28 | 28 | 28 | P | 60 | 60 | 60 | M | 92 | 89 | 89 | | | | |
| F | 29 | 29 | 29 | D | 61 | 61 | 61 | Y | 93 | 90 | 90 | | | | |
| I | 30 | 30 | 30 | S | 62 | 62 | 62 | Y | 94 | 91 | 91 | | | | |
| S | 31 | 31 | 31 | V | 63 | 63 | 63 | C | 95 | 92 | 92 | | | | |
| Y | 32 | 32 | 32 | K | 64 | 64 | 64 | A | 96 | 93 | 93 | | | | |

Numbering of mAb13.2 Variable Heavy Chain According to Different Schemes

Fig. 29

| RESIDUE | LINEAR SEQUENCE NUMBER | CHOTHIA STRUCTURE NUMBER | KABAT SEQUENCE NUMBER | RESIDUE | LINEAR SEQUENCE NUMBER | CHOTHIA STRUCTURE NUMBER | KABAT SEQUENCE NUMBER | RESIDUE | LINEAR SEQUENCE NUMBER | CHOTHIA STRUCTURE NUMBER | KABAT SEQUENCE NUMBER | RESIDUE | LINEAR SEQUENCE NUMBER | CHOTHIA STRUCTURE NUMBER | KABAT SEQUENCE NUMBER |
|---|---|---|---|---|---|---|---|---|---|---|---|---|---|---|---|
| D | 1 | 1 | 1 | G | 33 | 30C | 29 | R | 65 | 61 | 61 | E | 97 | 93 | 93 |
| I | 2 | 2 | 2 | K | 34 | 30D | 30 | F | 66 | 62 | 62 | D | 98 | 94 | 94 |
| V | 3 | 3 | 3 | S | 35 | 31 | 31 | S | 67 | 63 | 63 | P | 99 | 95 | 95 |
| L | 4 | 4 | 4 | L | 36 | 32 | 32 | G | 68 | 64 | 64 | W | 100 | 96 | 96 |
| T | 5 | 5 | 5 | M | 37 | 33 | 33 | S | 69 | 65 | 65 | T | 101 | 97 | 97 |
| Q | 6 | 6 | 6 | H | 38 | 34 | 34 | G | 70 | 66 | 66 | F | 102 | 98 | 98 |
| S | 7 | 7 | 7 | W | 39 | 35 | 35 | S | 71 | 67 | 67 | G | 103 | 99 | 99 |
| P | 8 | 8 | 8 | Y | 40 | 36 | 36 | R | 72 | 68 | 68 | G | 104 | 100 | 100 |
| A | 9 | 9 | 9 | Q | 41 | 37 | 37 | T | 73 | 69 | 69 | G | 105 | 101 | 101 |
| S | 10 | 10 | 10 | Q | 42 | 38 | 38 | D | 74 | 70 | 70 | T | 106 | 102 | 102 |
| L | 11 | 11 | 11 | K | 43 | 39 | 39 | F | 75 | 71 | 71 | K | 107 | 103 | 103 |
| A | 12 | 12 | 12 | P | 44 | 40 | 40 | T | 76 | 72 | 72 | L | 108 | 104 | 104 |
| V | 13 | 13 | 13 | G | 45 | 41 | 41 | L | 77 | 73 | 73 | E | 109 | 105 | 105 |
| S | 14 | 14 | 14 | Q | 46 | 42 | 42 | T | 78 | 74 | 74 | I | 110 | 106 | 106 |
| L | 15 | 15 | 15 | S | 47 | 43 | 43 | I | 79 | 75 | 75 | K | 111 | 107 | 107 |
| G | 16 | 16 | 16 | P | 48 | 44 | 44 | N | 80 | 76 | 76 | | | | |
| Q | 17 | 17 | 17 | K | 49 | 45 | 45 | P | 81 | 77 | 77 | (SEQ ID NO: 10) | | | |
| R | 18 | 18 | 18 | L | 50 | 46 | 46 | V | 82 | 78 | 78 | | | | |
| A | 19 | 19 | 19 | L | 51 | 47 | 47 | E | 83 | 79 | 79 | | | | |
| T | 20 | 20 | 20 | I | 52 | 48 | 48 | A | 84 | 80 | 80 | | | | |
| I | 21 | 21 | 21 | Y | 53 | 49 | 49 | D | 85 | 81 | 81 | | | | |
| S | 22 | 22 | 22 | R | 54 | 50 | 50 | D | 86 | 82 | 82 | | | | |
| C | 23 | 23 | 23 | A | 55 | 51 | 51 | V | 87 | 83 | 83 | | | | |
| K | 24 | 24 | 24 | S | 56 | 52 | 52 | A | 88 | 84 | 84 | | | | |
| A | 25 | 25 | 25 | N | 57 | 53 | 53 | T | 89 | 85 | 85 | | | | |
| S | 26 | 26 | 26 | L | 58 | 54 | 54 | Y | 90 | 86 | 86 | | | | |
| E | 27 | 27 | 27 | E | 59 | 55 | 55 | Y | 91 | 87 | 87 | | | | |
| S | 28 | 28 | 27A | S | 60 | 56 | 56 | C | 92 | 88 | 88 | | | | |
| V | 29 | 29 | 27B | G | 61 | 57 | 57 | Q | 93 | 89 | 89 | | | | |
| D | 30 | 30 | 27C | I | 62 | 58 | 58 | Q | 94 | 90 | 90 | | | | |
| N | 31 | 30A | 27D | P | 63 | 59 | 59 | S | 95 | 91 | 91 | | | | |
| Y | 32 | 30B | 28 | A | 64 | 60 | 60 | N | 96 | 92 | 92 | | | | |

Numbering of mAb13.2 Variable Light Chain According to Different Schemes

SEQUENCE LISTING

<160> NUMBER OF SEQ ID NOS: 37

<210> SEQ ID NO 1
<211> LENGTH: 333
<212> TYPE: DNA
<213> ORGANISM: Mus musculus

<400> SEQUENCE: 1

```
gacattgtgc tgacccaatc tccagcttct ttggctgtgt ctctagggca gagggccacc    60
atatcctgca aagccagtga agtgttgat  aattatggca aaagtttaat gcactggtac   120
cagcagaaac caggacagtc acccaaactc ctcatctatc gtgcatccaa cctagaatct   180
gggatccctg ccaggttcag tggcagtggg tctaggacag acttcaccct caccattaat   240
cctgtggagg ctgatgatgt tgcaacctat tactgtcagc aaagtaatga ggatccgtgg   300
acgttcggtg gaggcaccaa gctggaaatc aaa                                333
```

<210> SEQ ID NO 2
<211> LENGTH: 333
<212> TYPE: DNA
<213> ORGANISM: Mus musculus

<400> SEQUENCE: 2

```
gacattgtgc tgacccaatc tccagcttct ttggctgtgt ctctagggca gagggccacc    60
atatcctgca aagccagtga agtgttgat  aattatggca aaagtttaat gcactggtac   120
cagcagaaac caggacagtc acccaaactc ctcatctatc gtgcatccaa cctagaatct   180
gggatccctg ccaggttcag tggcagtggg tctaggacag acttcaccct caccattaat   240
cctgtggagg ctgatgatgt tgcaacctat tactgtcagc aaagtaatga ggatccgtgg   300
acgttcggtg gaggcaccaa gctggaaatc aaa                                333
```

<210> SEQ ID NO 3
<211> LENGTH: 333
<212> TYPE: DNA
<213> ORGANISM: Artificial
<220> FEATURE:
<223> OTHER INFORMATION: partially humanized antibody light chain

<400> SEQUENCE: 3

```
gacatccagc tgacccagtc tccatcctcc ctgtctgcat ctgtgggaga cagagtcacc    60
atcacttgca aagccagtga agtgttgat  aattatggca aaagtctgat gcactggtat   120
cagcagaaac cagggaaagc tcctaagctc ctgatctatc gtgcatccaa cctggaatct   180
ggcgtcccat caaggttcag tggcagtgga tctcgcacag atttcactct caccatcagc   240
agtctgcaac ctgaagattt tgcaacttac tactgtcagc aaagtaatga ggatccctgg   300
accttcggcg agggaccaa  ggtagagatc aaa                                333
```

<210> SEQ ID NO 4
<211> LENGTH: 333
<212> TYPE: DNA
<213> ORGANISM: Artificial
<220> FEATURE:
<223> OTHER INFORMATION: fully humanized antibody light chain

<400> SEQUENCE: 4

```
gacatccaga tgacccagtc tccatcctcc ctgtctgcat ctgtgggaga cagagtcacc    60
atcacttgca aagccagtga agtgttgat  aattatggca aaagtctgat gcactggtat   120
```

```
cagcagaaac cagggaaagc tcctaagctc ctgatctatc gtgcatccaa cctggaatct    180
ggcgtcccat caaggttcag tggcagtgga tctggcacag atttcactct caccatcagc    240
agtctgcaac tgaagatttt gcaacttac tactgtcagc aaagtaatga ggatccctgg    300
accttcggcg agggaccaa ggtagagatc aaa                                  333

<210> SEQ ID NO 5
<211> LENGTH: 351
<212> TYPE: DNA
<213> ORGANISM: Mus musculus

<400> SEQUENCE: 5
gaagtgaagc tggtggagtc tggggggaggc ttagtgaaac ctggagggtc cctgaaactc    60
tcctgtgcag cctctggatt cactttcatt agctatgcca tgtcttgggt tcgtcagact    120
ccagagaaga ggctggagtg ggtcgcatcc attagtagtg gtggtaacac ctactatcca    180
gacagtgtga agggccgatt caccatctcc agagataatg ccaggaacat cctataccctg   240 caaatgagca gtctgaggtc tgaggacacg gccatgtatt actgtgcacg acttgatggt    300
tactactttg gatttgctta ctggggccaa gggactctgg tcgctgtctc t             351

<210> SEQ ID NO 6
<211> LENGTH: 351
<212> TYPE: DNA
<213> ORGANISM: Mus musculus

<400> SEQUENCE: 6
gaagtgaagc tggtggagtc tggggggaggc ttagtgaaac ctggagggtc cctgaaactc    60
tcctgtgcag cctctggatt cactttcatt agctatgcca tgtcttgggt tcgtcagact    120
ccagagaaga ggctggagtg ggtcgcatcc attagtagtg gtggtaacac ctactatcca    180
gacagtgtga agggccgatt caccatctcc agagataatg ccaggaacat cctataccctg   240 caaatgagca gtctgaggtc tgaggacacg gccatgtatt actgtgcacg acttgatggt    300
tactactttg gatttgctta ctggggccaa gggactctgg tcgctgtctc t             351

<210> SEQ ID NO 7
<211> LENGTH: 354
<212> TYPE: DNA
<213> ORGANISM: Artificial
<220> FEATURE:
<223> OTHER INFORMATION: partially humanized antibody heavy chain

<400> SEQUENCE: 7
gaggtcaagc tggtggagtc aggggggaggc ttagtgcaac ctggagggtc cctgagactc    60
tcctgtgcag cctctggatt cactttcatt agctatgcca tgtcttgggt tcgtcaggct    120
ccagggaagg ggctggagtg ggtcgcatcc attagtagtg gtggtaacac ctactatcca    180
gacagcgtga agggccgatt caccatctcc agagataatg ccaagaacag cctataccctg    240 caaatgaaca gtctgagggc tgaggacacg gccgtgtatt actgtgcacg acttgatggt    300
tactactttg gatttgctta ctggggccaa gggaccctgg tcaccgtctc ctca           354

<210> SEQ ID NO 8
<211> LENGTH: 354
<212> TYPE: DNA
<213> ORGANISM: Artificial
<220> FEATURE:
<223> OTHER INFORMATION: fully humanized antibody heavy chain
```

```
<400> SEQUENCE: 8
gaggtccagc tggtggagtc aggggaggc ttagtgcaac ctggagggtc cctgagactc        60
tcctgtgcag cctctggatt cactttcatt agctatgcca tgtcttgggt tcgtcaggct       120
ccagggaagg gctggagtg gtcgcatcc attagtagtg gtggtaacac ctactatcca         180
gacagcgtga agggccgatt caccatctcc agagataatg ccaagaacag cctatacctg       240
caaatgaaca gtctgagggc tgaggacacg gccgtgtatt actgtgcacg acttgatggt       300
tactactttg gatttgctta ctggggccaa gggaccctgg tcaccgtctc ctca             354
```

<210> SEQ ID NO 9
<211> LENGTH: 111
<212> TYPE: PRT
<213> ORGANISM: Mus musculus

<400> SEQUENCE: 9

Asp Ile Val Leu Thr Gln Ser Pro Ala Ser Leu Ala Val Ser Leu Gly
1               5                   10                  15

Gln Arg Ala Thr Ile Ser Cys Lys Ala Ser Glu Ser Val Asp Asn Tyr
            20                  25                  30

Gly Lys Ser Leu Met His Trp Tyr Gln Gln Lys Pro Gly Gln Ser Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 10
<211> LENGTH: 111
<212> TYPE: PRT
<213> ORGANISM: Mus musculus

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Lys Ala Ser Glu Ser Val Asp Asn Tyr
            20                  25                  30

Gly Lys Ser Leu Met His Trp Tyr Gln Gln Lys Pro Gly Gln Ser Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 11
<211> LENGTH: 111
<212> TYPE: PRT
<213> ORGANISM: Artificial
<220> FEATURE:
<223> OTHER INFORMATION: partially humanized antibody light chain

```
<400> SEQUENCE: 11

Asp Ile Gln Leu Thr Gln Ser Pro Ser Ser Leu Ser Ala Ser Val Gly
1               5                   10                  15

Asp Arg Val Thr Ile Thr Cys Lys Ala Ser Glu Ser Val Asp Asn Tyr
            20                  25                  30

Gly Lys Ser Leu Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 12
<211> LENGTH: 111
<212> TYPE: PRT
<213> ORGANISM: Artificial
<220> FEATURE:
<223> OTHER INFORMATION: fully humanized antibody light chain

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Ser Val Asp Asn Tyr
            20                  25                  30

Gly Lys Ser Leu Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 13
<211> LENGTH: 118
<212> TYPE: PRT
<213> ORGANISM: Mus musculus

<400> SEQUENCE: 13

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ile Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Asn Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
```

-continued

```
                85                  90                  95
Arg Leu Asp Gly Tyr Tyr Phe Gly Phe Ala Tyr Trp Gly Gln Gly Thr
            100                 105                 110

Thr Val Thr Val Ser Ser
        115

<210> SEQ ID NO 14
<211> LENGTH: 118
<212> TYPE: PRT
<213> ORGANISM: Mus musculus

<400> SEQUENCE: 14

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ile Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Asn Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Leu Asp Gly Tyr Tyr Phe Gly Phe Ala Tyr Trp Gly Gln Gly Thr
            100                 105                 110

Thr Val Thr Val Ser Ser
        115

<210> SEQ ID NO 15
<211> LENGTH: 118
<212> TYPE: PRT
<213> ORGANISM: Artificial
<220> FEATURE:
<223> OTHER INFORMATION: partially humanized antibody heavy chain

<400> SEQUENCE: 15

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ile Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Asn Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Leu Asp Gly Tyr Tyr Phe Gly Phe Ala Tyr Trp Gly Gln Gly Thr
            100                 105                 110

Leu Val Thr Val Ser Ser
        115

<210> SEQ ID NO 16
<211> LENGTH: 118
<212> TYPE: PRT
<213> ORGANISM: Artificial
```

```
<220> FEATURE:
<223> OTHER INFORMATION: fully humanized antibody heavy chain

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ile Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Asn Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Leu Asp Gly Tyr Tyr Phe Gly Phe Ala Tyr Trp Gly Gln Gly Thr
            100                 105                 110

Leu Val Thr Val Ser Ser
        115

<210> SEQ ID NO 17
<211> LENGTH: 329
<212> TYPE: PRT
<213> ORGANISM: Homo sapiens
<220> FEATURE:
<221> NAME/KEY: MISC_FEATURE
<223> OTHER INFORMATION: The "S" in position #1 represents amino acid
      residue #119 when the sequence follows residue #118 of, e.g., SEQ
      ID NOs:15 or 16. In this representation of the sequence, mutated
      amino acids are at residue #s 234 and 237 [instead of 116 and 119,
      respectively].
<220> FEATURE:
<221> NAME/KEY: MISC_FEATURE
<223> OTHER INFORMATION: "S" at 1 (as shown) - L116A and G119A "S" at
      119 -- L234A and G237A
<220> FEATURE:
<221> NAME/KEY: MUTAGEN
<222> LOCATION: (116)..(116)
<220> FEATURE:
<221> NAME/KEY: MUTAGEN
<222> LOCATION: (119)..(119)

<400> SEQUENCE: 17

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Ala Leu Gly Ala Pro Ser Val Phe Leu Phe Pro Pro Lys
        115                 120                 125

Pro Lys Asp Thr Leu Met Ile Ser Arg Thr Pro Glu Val Thr Cys Val
```

```
                130                 135                 140
Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
                195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
                275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 18
<211> LENGTH: 107
<212> TYPE: PRT
<213> ORGANISM: Homo sapiens
<220> FEATURE:
<221> NAME/KEY: MISC_FEATURE
<223> OTHER INFORMATION: The "R" in position #1 represents amino acid
      residue #112 when the sequence follows residue #111 of, e.g., SEQ
      ID NOs:11 or 12.

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 19
<211> LENGTH: 15
<212> TYPE: PRT
<213> ORGANISM: Mus musculus
<220> FEATURE:
<221> NAME/KEY: MISC_FEATURE
```

```
<223> OTHER INFORMATION: This fragment corresponds to residues 24-38
      (linear) of, e.g., Figure 30.

<400> SEQUENCE: 19

Lys Ala Ser Glu Ser Val Asp Asn Tyr Gly Lys Ser Leu Met His
1               5                   10                  15

<210> SEQ ID NO 20
<211> LENGTH: 7
<212> TYPE: PRT
<213> ORGANISM: Mus musculus
<220> FEATURE:
<221> NAME/KEY: MISC_FEATURE
<223> OTHER INFORMATION: This fragment corresponds to residues 54-60
      (linear) of, e.g., Figure 30.

<400> SEQUENCE: 20

Arg Ala Ser Asn Leu Glu Ser
1               5

<210> SEQ ID NO 21
<211> LENGTH: 9
<212> TYPE: PRT
<213> ORGANISM: Mus musculus
<220> FEATURE:
<221> NAME/KEY: MISC_FEATURE
<223> OTHER INFORMATION: This fragment corresponds to residues 93-101
      (linear) of, e.g., Figure 30.

<400> SEQUENCE: 21

Gln Gln Ser Asn Glu Asp Pro Trp Thr
1               5

<210> SEQ ID NO 22
<211> LENGTH: 6
<212> TYPE: PRT
<213> ORGANISM: Mus musculus
<220> FEATURE:
<221> NAME/KEY: MISC_FEATURE
<223> OTHER INFORMATION: This fragment corresponds to residues 30-35
      (linear) of, e.g., Figure 29.

<400> SEQUENCE: 22

Ile Ser Tyr Ala Met Ser
1               5

<210> SEQ ID NO 23
<211> LENGTH: 16
<212> TYPE: PRT
<213> ORGANISM: Mus musculus
<220> FEATURE:
<221> NAME/KEY: MISC_FEATURE
<223> OTHER INFORMATION: This fragment corresponds to residues 50-65
      (linear) of, e.g., Figure 29.

<400> SEQUENCE: 23

Ser Ile Ser Ser Gly Gly Asn Thr Tyr Tyr Pro Asp Ser Val Lys Gly
1               5                   10                  15

<210> SEQ ID NO 24
<211> LENGTH: 10
<212> TYPE: PRT
<213> ORGANISM: Mus musculus
<220> FEATURE:
<221> NAME/KEY: MISC_FEATURE
<223> OTHER INFORMATION: This fragment corresponds to residues 98-107
      (linear) of, e.g., Figure 29.

<400> SEQUENCE: 24
```

```
Leu Asp Gly Tyr Tyr Phe Gly Phe Ala Tyr
1               5                   10

<210> SEQ ID NO 25
<211> LENGTH: 15
<212> TYPE: PRT
<213> ORGANISM: Artificial
<220> FEATURE:
<223> OTHER INFORMATION: minimum core CDR sequence
<220> FEATURE:
<221> NAME/KEY: MISC_FEATURE
<223> OTHER INFORMATION: This fragment corresponds to residues 24-38
      (linear) of, e.g., Figure 30; also corresponds to SEQ ID NO:19.
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid

<400> SEQUENCE: 25

Xaa Xaa Xaa Xaa Xaa Xaa Xaa Asn Tyr Xaa Lys Xaa Xaa Xaa Xaa
1               5                   10                  15

<210> SEQ ID NO 26
<211> LENGTH: 7
<212> TYPE: PRT
<213> ORGANISM: Artificial
<220> FEATURE:
<223> OTHER INFORMATION: minimum core CDR sequence
<220> FEATURE:
<221> NAME/KEY: MISC_FEATURE
<223> OTHER INFORMATION: This fragment corresponds to residues 54-60
      (linear) of, e.g., Figure 30; also corresponds to SEQ ID NO:20.
<220> FEATURE:
<221> NAME/KEY: misc_feature
<222> LOCATION: (2)..(7)
<223> OTHER INFORMATION: Xaa can be any naturally occurring amino acid

<400> SEQUENCE: 26

Arg Xaa Xaa Xaa Xaa Xaa Xaa
1               5

<210> SEQ ID NO 27
<211> LENGTH: 9
<212> TYPE: PRT
<213> ORGANISM: Artificial
<220> FEATURE:
<223> OTHER INFORMATION: minimum core CDR sequence
<220> FEATURE:
<221> NAME/KEY: MISC_FEATURE
<223> OTHER INFORMATION: This fragment corresponds to residues 93-101
      of, e.g., Figure 30; also corresponds to SEQ ID NO:21.
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
```

```
<222> LOCATION: (9)..(9)
<223> OTHER INFORMATION: Xaa can be any naturally occurring amino acid

<400> SEQUENCE: 27

Xaa Xaa Xaa Asn Xaa Asp Xaa Trp Xaa
1               5

<210> SEQ ID NO 28
<211> LENGTH: 6
<212> TYPE: PRT
<213> ORGANISM: Artificial
<220> FEATURE:
<223> OTHER INFORMATION: minimum core CDR sequence
<220> FEATURE:
<221> NAME/KEY: MISC_FEATURE
<223> OTHER INFORMATION: This fragment corresponds to residues 30-35 of,
      e.g., Figure 29; also corresponds to SEQ ID NO:22.
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 28

Ile Ser Xaa Ala Xaa Xaa
1               5

<210> SEQ ID NO 29
<211> LENGTH: 16
<212> TYPE: PRT
<213> ORGANISM: Artificial
<220> FEATURE:
<223> OTHER INFORMATION: minimum core CDR sequence
<220> FEATURE:
<221> NAME/KEY: MISC_FEATURE
<223> OTHER INFORMATION: This fragment corresponds to residues 50-65
      (linear) of, e.g., Figure 29; also corresponds to SEQ ID NO:23.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (11)..(16)
<223> OTHER INFORMATION: Xaa can be any naturally occurring amino acid

<400> SEQUENCE: 29

Ser Xaa Ser Ser Xaa Xaa Xaa Xaa Tyr Xaa Xaa Xaa Xaa Xaa Xaa
1               5                   10                  15

<210> SEQ ID NO 30
<211> LENGTH: 10
<212> TYPE: PRT
<213> ORGANISM: Artificial
<220> FEATURE:
<223> OTHER INFORMATION: minimum core CDR sequence
<220> FEATURE:
<221> NAME/KEY: MISC_FEATURE
<223> OTHER INFORMATION: This fragment corresponds to residues 98-107
      (linear) of, e.g., Figure 29; also corresponds to SEQ ID NO:24.
<220> FEATURE:
<221> NAME/KEY: misc_feature
<222> LOCATION: (7)..(10)
<223> OTHER INFORMATION: Xaa can be any naturally occurring amino acid

<400> SEQUENCE: 30
```

Leu Asp Gly Tyr Tyr Phe Xaa Xaa Xaa Xaa
1               5                   10

<210> SEQ ID NO 31
<211> LENGTH: 132
<212> TYPE: PRT
<213> ORGANISM: Homo sapiens

<400> SEQUENCE: 31

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130

<210> SEQ ID NO 32
<211> LENGTH: 113
<212> TYPE: PRT
<213> ORGANISM: Homo sapiens

<400> SEQUENCE: 32

Pro Gly Pro Val Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Arg Phe
            100                 105                 110

Asn

<210> SEQ ID NO 33
<211> LENGTH: 333
<212> TYPE: DNA
<213> ORGANISM: Artificial
<220> FEATURE:
<223> OTHER INFORMATION: fully humanized antibody light chain

<400> SEQUENCE: 33

```
gacatcgtgc tcactcagtc tccagcttct ttggctgtgt ctccagggca gagggccacc      60
ataacctgca aagccagtga aagtgttgat aattatggca aaagtttaat gcactggtac     120
cagcagaaac caggacagcc acccaaactc ctcatctatc gtgcatccaa cctagaatct     180
ggggtccctg ccaggttcag tggcagtggg tctgggacag acttcaccct caccattaat     240
cctgtggagg ctaatgatac tgcaaactat tactgtcagc aaagtaatga ggatccgtgg     300
acgttcggtg gagggaccaa ggtggaaata aaa                                  333
```

<210> SEQ ID NO 34
<211> LENGTH: 354
<212> TYPE: DNA
<213> ORGANISM: Artificial
<220> FEATURE:
<223> OTHER INFORMATION: fully humanized antibody heavy chain

<400> SEQUENCE: 34

```
gaggtccagc tggtggagtc agggggaggc ttagtgaaac ctggagggtc cctgagactc      60
tcctgtgcag cctctggatt cactttcatt agctatgcca tgtcttgggt tcgtcaggct     120
ccagggaagg ggctggagtg ggtctcatcc attagtagtg gtggtaacac ctactatcca     180
gacagtgtga agggccgatt caccatctcc agagataatg ccaagaacag cctatacctg     240
caaatgaaca gtctgagggc tgaggacacg gccgtgtatt actgtgcacg acttgatggt     300
tactactttg gatttgctta ctggggccaa gggaccacgg tcaccgtctc ctca           354
```

<210> SEQ ID NO 35
<211> LENGTH: 111
<212> TYPE: PRT
<213> ORGANISM: Artificial
<220> FEATURE:
<223> OTHER INFORMATION: fully humanized antibody light chain

<400> SEQUENCE: 35

Asp Ile Val Leu Thr Gln Ser Pro Ala Ser Leu Ala Val Ser Pro Gly
1               5                   10                  15

Gln Arg Ala Thr Ile Thr Cys Lys Ala Ser Glu Ser Val Asp Asn Tyr
            20                  25                  30

Gly Lys Ser Leu Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 36
<211> LENGTH: 118
<212> TYPE: PRT
<213> ORGANISM: Artificial
<220> FEATURE:
<223> OTHER INFORMATION: fully humanized antibody heavy chain

<400> SEQUENCE: 36

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ile Ser Tyr
                20                  25                  30

Ala Met Ser Trp Val Arg Gln Ala Pro Gly Lys Gly Leu Glu Trp Val
            35                  40                  45

Ser Ser Ile Ser Ser Gly Gly Asn Thr Tyr Tyr Pro Asp Ser Val Lys
 50                      55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                85                  90                  95

Arg Leu Asp Gly Tyr Tyr Phe Gly Phe Ala Tyr Trp Gly Gln Gly Thr
            100                 105                 110

Thr Val Thr Val Ser Ser
            115

<210> SEQ ID NO 37
<211> LENGTH: 427
<212> TYPE: PRT
<213> ORGANISM: Homo sapiens

<400> SEQUENCE: 37

Met Glu Trp Pro Ala Arg Leu Cys Gly Leu Trp Ala Leu Leu Leu Cys
 1               5                  10                  15

Ala Gly Gly Gly Gly Gly Gly Ala Ala Pro Thr Glu Thr Gln
                20                  25                  30

Pro Pro Val Thr Asn Leu Ser Val Ser Val Glu Asn Leu Cys Thr Val
            35                  40                  45

Ile Trp Thr Trp Asn Pro Pro Glu Gly Ala Ser Ser Asn Cys Ser Leu
 50                      55                  60

Trp Tyr Phe Ser His Phe Gly Asp Lys Gln Asp Lys Lys Ile Ala Pro
 65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
            115                 120                 125

Val Thr Glu Leu Gln Cys Ile Trp His Asn Leu Ser Tyr Met Lys Cys
            130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
            195                 200                 205

Asn Ala Gly Lys Ile Lys Pro Ser Phe Asn Ile Val Pro Leu Thr Ser
            210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270
```

```
Asn Val Phe Tyr Val Gln Glu Ala Lys Cys Glu Asn Pro Glu Phe Glu
            275                 280                 285

Arg Asn Val Glu Asn Thr Ser Cys Phe Met Val Pro Gly Val Leu Pro
        290                 295                 300

Asp Thr Leu Asn Thr Val Arg Ile Arg Val Lys Thr Asn Lys Leu Cys
305                     310                 315                 320

Tyr Glu Asp Asp Lys Leu Trp Ser Asn Trp Ser Gln Glu Met Ser Ile
                325                 330                 335

Gly Lys Lys Arg Asn Ser Thr Leu Tyr Ile Thr Met Leu Leu Ile Val
            340                 345                 350

Pro Val Ile Val Ala Gly Ala Ile Ile Val Leu Leu Leu Tyr Leu Lys
            355                 360                 365

Arg Leu Lys Ile Ile Ile Phe Pro Pro Ile Pro Asp Pro Gly Lys Ile
        370                 375                 380

Phe Lys Glu Met Phe Gly Asp Gln Asn Asp Asp Thr Leu His Trp Lys
385                     390                 395                 400

Lys Tyr Asp Ile Tyr Glu Lys Gln Thr Lys Glu Glu Thr Asp Ser Val
                405                 410                 415

Val Leu Ile Glu Asn Leu Lys Lys Ala Ser Gln
            420                 425
```

ANTIBODIES AGAINST HUMAN INTERLEUKIN-13 AND PHARMACEUTICAL COMPOSITIONS THEREOF

CROSS-REFERENCE TO RELATED APPLICATIONS

This application claims priority to U.S. Patent Application Ser. No. 60/578,473, filed on Jun. 9, 2004, Ser. No. 60/581,375, filed on Jun. 22, 2004, and Ser. No. 60/578,736, filed on Jun. 9, 2004. The entire contents of all of which are hereby incorporated by reference. U.S. patent application Ser. No. 11/149,025, filed on Jun. 9, 2005, and PCT/US2005/020160, filed on Jun. 9, 2005, are also incorporated by reference.

SEQUENCE LISTING

This application incorporates by reference the sequence listing file titled 16158-048001.txt on CD-ROM copy 1.

FIELD OF THE INVENTION

This application relates to antibodies, e.g., humanized antibodies, and antigen-binding fragments thereof, that bind to interleukin-13 (IL-13), in particular, human IL-13, and their uses in regulating immune responses mediated by IL-13. The antibodies disclosed herein are useful in diagnosing, preventing, and/or treating a subject, e.g., a human patient, one or more IL-13-associated disorders, e.g., respiratory disorders (e.g., asthma); atopic disorders (e.g., allergic rhinitis); inflammatory and/or autoimmune conditions of the skin (e.g., atopic dermatitis), and gastrointestinal organs (e.g., inflammatory bowel diseases (IBD)), as well as fibrotic and cancerous disorders.

BACKGROUND OF THE INVENTION

Interleukin-13 (IL-13) is a cytokine secreted by T lymphocytes and mast cells (McKenzie et al. (1993) *Proc. Natl. Acad. Sci. USA* 90:3735-39; Bost et al. (1996) *Immunology* 87:663-41). IL-13 shares several biological activities with IL-4. For example, either IL-4 or IL-13 can cause IgE isotype switching in B cells (Tomkinson et al. (2001) *J. Immunol.* 166:5792-5800). Additionally, increased levels of cell surface CD23 and serum CD23 (sCD23) have been reported in asthmatic patients (Sanchez-Guererro et al. (1994) *Allergy* 49:587-92; DiLorenzo et al. (1999) *Allergy Asthma Proc.* 20:119-25). In addition, either IL-4 or IL-13 can upregulate the expression of MHC class II and the low-affinity IgE receptor (CD23) on B cells and monocytes, which results in enhanced antigen presentation and regulated macrophage function (Tomkinson et al., supra). Importantly, either IL-4 or IL-13 can increase the expression of VCAM-1 on endothelial cells, which facilitates preferential recruitment of eosinophils (and T cells) to the airway tissues (Tomkinson et al., supra). Either IL-4 or IL-13 can also increase airway mucus secretion, which can exacerbate airway responsiveness (Tomkinson et al., supra). These observations suggest that although IL-13 is not necessary for, or even capable of, inducing Th2 development, IL-13 may be a key player in the development of airway eosinophilia and AHR (Tomkinson et al., supra; Wills-Karp et al. (1998) *Science* 282:2258-61).

SUMMARY OF THE INVENTION

The present application provides, inter alia, IL-13 binding agents that are IL-13 antagonists, including antibodies and antigen-binding fragments thereof that bind to IL-13, in particular, human IL-13, with high affinity and specificity. The antibodies and antigen-binding fragments thereof of the present disclosure are also referred to herein as "anti-IL-13 antibodies" and "fragments thereof," respectively. In one embodiment, the anti-IL-13 antibody or fragment thereof reduces, neutralizes, and/or antagonizes at least one IL-13-associated activity. For example, the anti-IL-13 antibody or fragment thereof can bind to IL-13, e.g., an epitope of IL-13, and interfere with an interaction, e.g., binding, between IL-13 and an IL-13 receptor complex ("IL-13R"), e.g., a complex comprising IL-13 receptor al ("IL-13Rα1") and the interleukin-4 receptor alpha chain ("IL-4Rα"), or a subunit thereof (e.g., IL-13Rα1 or IL-4Rα, individually). Thus, the antibodies and fragments thereof described herein can be used to interfere with (e.g., inhibit, block or otherwise reduce) an interaction, e.g., binding, between IL-13 and an IL-13 receptor complex, or a subunit thereof, thereby interfering with the formation of a functional signaling complex.

In addition, we have shown that administration of a neutralizing anti-IL-13 antibody ameliorates, inter alia, antigen-induced lung inflammation, e.g., eosinophilia and bronchoconstriction, in nonhuman primates and sheep, respectively. Thus, IL-13 antagonists, e.g., neutralizing anti-IL-13 antibodies and fragments thereof, can be used to ameliorate at least one IL-13-associated activity in vivo, e.g., an inflammatory condition (e.g., lung inflammation). Additionally, neutralizing anti-IL-13 antibodies and fragments thereof, may be used to ameliorate the enhanced sensitivity of cells from atopic patients to IL-13. Accordingly, the antibodies or fragments thereof can be used, e.g., for the treatment of seasonal allergies, e.g., allergic rhinitis. The anti-IL-13 antibodies or fragments thereof (including those described herein) are useful in diagnosing, treating and/or preventing, in a subject, e.g., a human patient, one or more IL-13-associated disorders, e.g., respiratory disorders (e.g., asthma, including allergic and non-allergic asthma, chronic obstructive pulmonary disease (COPD)), as well as conditions involving airway inflammation, eosinophilia, fibrosis and excess mucus production (e.g., cystic fibrosis and pulmonary fibrosis); atopic disorders (e.g., allergic rhinitis); inflammatory and/or autoimmune conditions of, the skin (e.g., atopic dermatitis), gastrointestinal organs (e.g., inflammatory bowel diseases (IBD)), liver (e.g., cirrhosis); viral infections; scleroderma and fibrosis of other organs, such as liver fibrosis.

Accordingly, in one aspect, this application features an IL-13 binding agent such as an IL-13 antagonist. An IL-13 binding agent can be a protein, e.g., an antibody or an antigen-binding fragment thereof, a peptide, or a scaffold domain, that interacts with, e.g., binds to and/or neutralizes, IL-13, in particular, mammalian IL-13, e.g., human, sheep, or nonhuman primate IL-13. The antibody can be an isolated antibody. In one embodiment, the antibody or fragment thereof is a neutralizing antibody, e.g., it reduces and/or inhibits one or more IL-13-associated activities, including but not limited to, induction of CD23 expression; production of IgE by human B cells; phosphorylation of a transcription factor, e.g., STAT protein (e.g., STAT6 protein); antigen-induced eosinophilia in vivo; antigen-induced bronchoconstriction in vivo; or drug-induced airway hyperreactivity in vivo, among others.

The IL-13 antagonists described herein, e.g., anti-IL-13 antibodies or fragments thereof, can bind to IL-13 with high affinity, e.g., with a Kd less than $10^{-7}$ M, $10^{-8}$, $10^{-9}$, $10^{-10}$, $10^{-11}$ M or better. For example, the anti-IL-13 antibodies or fragments thereof can bind to IL-13 with an affinity between 50 and 500 pM, e.g., between 90 and 120 pM, e.g., between 95 and 105 pM. In other embodiments, the anti-IL-13 antibodies or fragments thereof can neutralize one or more IL-13-associated activities with an $IC_{50}$ of at least about 50 nM to 5 pM, typically about 100 to 250 pM or stronger. In other embodiments, the anti-IL-13 antibodies or fragments thereof associate with IL-13 with kinetics in the range of $10^3$ to $10^7$ $M^{-1}s^{-1}$, typically $10^4$ to $10^6$ $M^{-1}s^{-1}$. For example, the anti-IL-13 antibodies or fragments thereof may associate with IL-13 with kinetics in the range of $5 \times 10^4$ to $8 \times 10^6$ $M^{-1}s^{-1}$. In yet another embodiment, the anti-IL-13 antibodies or fragments thereof have dissociation kinetics in the range of $10^{-2}$ to $10^{-6}$ $s^{-1}$, typically $10^{-3}$ to $10^{-6}$ $s^{-1}$, e.g., slower than $5 \times 10^{-4}$ $s^{-1}$, e.g., 9, 8, $6 \times 10^{-5}$ $s^{-1}$. In one embodiment, the anti-IL-13 antibodies or fragments thereof bind to IL-13, e.g., human IL-13, with an affinity and/or kinetics similar to monoclonal antibody 13.2 ("mAb13.2"), or modified forms thereof, e.g., chimeric forms (e.g., "ch13.2"), or humanized forms thereof (e.g., "h13.2v1," "h13.2v2" or "h13.2v3"). The affinity and binding kinetics of the anti-IL-13 antibody or fragment thereof can be tested using, e.g., biosensor technology (BIA-CORE™ (see Example 1.2, below).

In one embodiment, the anti-IL-13 antibody or fragment thereof (e.g., a Fab, F(ab')$_2$, Fv, or a single chain Fv fragment) is a monoclonal antibody or an antibody with single specificity. The antibody or fragment thereof can also be a human, humanized, chimeric, or in vitro-generated antibody. In one embodiment, the anti-IL-13 antibody or fragment thereof is a humanized antibody. In one embodiment, the antibody is effectively human.

The heavy and light chains of the anti-IL-13 antibody can be full-length (e.g., an antibody can include at least one, and preferably two, complete heavy chains, and at least one, and preferably two, complete light chains) or can include an antigen-binding fragment (e.g., a Fab, F(ab')$_2$, Fv or a single chain Fv fragment). In yet other embodiments, the antibody has a heavy chain constant region chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 (e.g., human IgG1). In another embodiment, the antibody has a light chain constant region chosen from, e.g., the light chain constant regions of kappa or lambda, preferably kappa (e.g., human kappa). In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237 of SEQ ID NO:17 (e.g., residues 234 and 237 when the Serine at position no. 1 is shifted to residue no. 119 (following, e.g., 118 amino acids of VH chain); as shown in SEQ ID NO:17, with Serine at position no. 1, these same residues are nos. 116 and 119). In one embodiment, the anti-IL-13 antibody comprises the human IgG1 constant region shown as SEQ ID NO:17. In another embodiment, the anti-IL-13 antibody comprises the human kappa sequence shown as SEQ ID NO:18.

In another embodiment, the IL-13 antagonist, e.g., the anti-IL-13 antibody or fragment thereof, specifically binds to IL-13, in particular, mammalian, e.g., nonhuman primate, sheep, or human IL-13 (e.g., human IL-13 having an amino acid sequence of SEQ ID NO:31 (FIG. 11)), or mature human IL-13 sequence from about amino acids 20-132 of SEQ ID NO:31 (FIG. 11) (see also SEQ ID NO:32 for mature human IL-13 sequence numbering), or a sequence that is at least 85%, 90%, 95%, 99% or more identical thereto). In one embodiment, the anti-IL-13 antibody or fragment thereof binds to a variant of human IL-13, e.g., a variant of human IL-13 having a Glutamine (Q) instead of an Arginine (R) at position 130 of SEQ ID NO:31 (FIG. 11). In other embodiments, the antibody or fragment thereof specifically binds to a fragment of IL-13, e.g., a fragment of at least 10, 20, 50, 75, 100, 120, or 130 contiguous amino acids of the amino acid sequence set forth in SEQ ID NO:31, or a sequence that is at least 85%, 90%, 95%, 99% or more identical thereto. In one embodiment, the anti-IL-13 antibody or fragment thereof specifically binds to human IL-13 and does not cross-react with IL-13 from nonhuman species. In other embodiments, the anti-IL-13 antibody or fragment thereof binds to two or more forms of mammalian IL-13, e.g., human, sheep and/or nonhuman primate IL-13.

In one embodiment, the IL-13 antagonist, e.g., the anti-IL-13 antibody or fragment thereof, specifically binds to an epitope, e.g., a linear or a conformational epitope, of IL-13, e.g., in particular, mammalian, e.g., human IL-13. In one embodiment, the anti-IL-13 antibody or fragment thereof binds to an epitope comprising residues 81-93 and/or 114-132 of human IL-13 (SEQ ID NO:31), or a modified form thereof (e.g., a fragment or substituted (e.g., conservatively substituted) form thereof). In another embodiment, the anti-IL-13 antibody or fragment thereof specifically binds to an epitope of human IL-13 comprising one or more of the following amino acid residues: Glutamate at position 68 [49], Asparagine at position 72 [53], Glycine at position 88 [69], Proline at position 91 [72], Histidine at position 92 [73], Lysine at position 93 [74], and Arginine at position 105 [86] of SEQ ID NO:31 [position in mature sequence; SEQ ID NO:32], or a conserved amino acid substitution thereof.

In another embodiment, the IL-13 antagonist, e.g., the anti-IL-13 antibody or fragment thereof, binds to a complex chosen from, e.g., IL-13 and IL-13Rα1 ("IL-13/IL-13Rα1"); IL-13 and IL-4Rα ("IL-13/IL-4Rα"); and IL-13, IL-13Rα1, and IL-4Rα ("IL-13/IL-13Rα1/IL-4Rα"). In other embodiments, the IL-13 antagonist, e.g., the antibody or fragment thereof, binds to IL-13 and interferes with (e.g., inhibits, blocks or otherwise reduces) an interaction, e.g., binding, between IL-13 and an IL-13 receptor complex, e.g., a complex comprising IL-13Rα1 and IL-4Rα. In other embodiments, the IL-13 antagonist, e.g., the anti-IL-13 antibody or fragment thereof, binds to IL-13 and interferes with (e.g., inhibits, blocks or otherwise reduces) an interaction, e.g., binding, between IL-13 and a subunit of the IL-13 receptor complex, e.g., IL-13Rα1 or IL-4Rα, individually. In yet another embodiment, the IL-13 antagonist, e.g., the anti-IL-13 antibody or fragment thereof, binds to IL-13, and interferes with (e.g., inhibits, blocks or otherwise reduces) an interaction, e.g., binding, between IL-13/IL-13Rα1 and IL-4Rα. In another embodiment, the IL-13 antagonist, e.g., the anti-IL-13 antibody or fragment thereof, binds to IL-13 and interferes with (e.g., inhibits, blocks or otherwise reduces) an interaction, e.g., binding, between IL-13/IL-4Rα and IL-13Rα1. Typically, the anti-IL-13 antibody or fragment thereof interferes with (e.g., inhibits, blocks or otherwise reduces) an interaction, e.g., binding, of IL-13/IL-13Rα1 with IL-4Rα. Exemplary antibodies inhibit or prevent formation of the ternary complex, IL-13/IL-13Rα1/IL-4Rα.

Examples of IL-13 antibodies, that interfere with IL-13 binding to IL-13R (e.g., an IL-13 receptor complex), or a subunit thereof, include "mAb13.2" and modified, e.g., chimeric or humanized forms thereof. The amino acid and nucleotide sequences for the heavy chain variable region of mAb13.2 are set forth herein as SEQ ID NO:13 and SEQ ID NO:5, respectively. The amino acid and nucleotide sequences for the light chain variable region of mAb13.2 are set forth herein as SEQ ID NO:9 and SEQ ID NO:1, respectively. An exemplary chimeric form (e.g., a form comprising the heavy and light chain variable region of mAb13.2) is referred to herein as "ch13.2." The amino acid and nucleotide sequences for the heavy chain variable region of ch13.2 are set forth herein as SEQ ID NO:14 (e.g., FIG. 15) and SEQ ID NO:6, respectively. The amino acid and nucleotide sequences for the light chain variable region of ch13.2 are set forth herein as SEQ ID NO:10 (e.g., FIG. 16) and SEQ ID NO:2, respectively. A humanized form of mAb13.2, which is referred to herein as "h13.2v1," has amino acid and nucleotide sequences for the heavy chain variable region set forth herein as SEQ ID NO:15 (FIG. 15) and SEQ ID NO:7, respectively. The amino acid and nucleotide sequences for the light chain variable region of h13.2v1 are set forth herein as SEQ ID NO:11 (FIG. 16) and SEQ ID NO:3, respectively. Another humanized form of mAb13.2, which is referred to herein as "h13.2v2," has amino acid and nucleotide sequences for the heavy chain variable region set forth herein as SEQ ID NO:16 (FIG. 17) and SEQ ID NO:8, respectively. The amino acid and nucleotide sequences for the light chain variable region of h13.2v2 are set forth herein as SEQ ID NO:12 (FIG. 18) and SEQ ID NO:4, respectively. Another humanized form of mAb13.2, which is referred to herein as "h13.2v3," has amino acid and nucleotide sequences for the heavy chain variable region set forth herein as SEQ ID NO:36 (FIG. 27) and SEQ ID NO:34, respectively. The amino acid and nucleotide sequences for the light chain variable region of h13.2v3 are set forth herein as SEQ ID NO:35 (FIG. 28) and SEQ ID NO:33, respectively.

In one embodiment, the IL-13 antagonist, e.g., the antibody or fragment thereof, binds specifically to IL-13, e.g., human, nonhuman primate, or sheep IL-13, and competitively inhibits the binding of a second antibody to IL-13, e.g., to a target epitope on IL-13 (e.g., human, nonhuman primate, sheep IL-13). The second antibody can be an antibody chosen from, e.g., mAb13.2, ch13.2, h13.2v1, h13.2v2, and/or h13.2v3, as described herein.

In one embodiment, the IL-13 antibody or fragment thereof can confer a post-injection protective effect against exposure to *Ascaris* antigen in a sheep model at least six weeks after injection.

In another embodiment, the antibody or fragment thereof comprises at least one antigen-binding region, e.g., a variable region, from an antibody chosen from, e.g., mAb13.2, ch13.2, h13.2v1, h13.2v2, and/or h13.2v3. In yet another embodiment, the antibody or fragment thereof includes at least one, two, three or four variable regions from an antibody chosen from, e.g., mAb13.2, ch13.2, h13.2v1, h13.2v2, and/or h13.2v3, as described herein. In another embodiment, the antibody or fragment thereof includes at least one or two heavy chain variable regions from an antibody chosen from, e.g., mAb13.2, ch13.2, h13.2v1, h13.2v2 and/or h13.2v3, as described herein. In another embodiment, the antibody or fragment thereof includes at least one or two light chain variable regions from an antibody chosen from, e.g., mAb13.2, ch13.2, h13.2v1, h13.2v2, and/or h13.2v3, as described herein. In yet another embodiment, the antibody or fragment thereof includes at least one, two, or three complementarity determining regions (CDRs) from a heavy chain variable region of an antibody chosen from, e.g., mAb13.2, ch13.2, h13.2v1, h13.2v2, and/or h13.2v3, as described herein, or at least particularly the amino acids from those CDRs that contact IL-13. In yet another embodiment, the antibody or fragment thereof includes at least one, two, or three CDRs from a light chain variable region of an antibody chosen from, e.g., mAb13.2, ch13.2, h13.2v1, h13.2v2, and/or h13.2v3, as described herein, or at least includes the amino acids from those CDRs that contact IL-13. In yet another embodiment, the antibody or fragment thereof includes at least one, two, three, four, five, or six CDRs from the heavy and light chain variable regions of an antibody chosen from, e.g., mAb13.2, ch13.2, h13.2v1, h13.2v2, and/or h13.2v3, as described herein.

In one preferred embodiment, the protein includes all six CDR's from mAb13.2, ch13.2, h13.2v1, h13.2v2, and/or h13.2v3 or closely related CDRs, e.g., CDRs which are identical or which have at least one amino acid alteration, but not more than two, three or four alterations (e.g., substitutions, deletions, or insertions, e.g., conservative substitutions). Optionally, the protein may include any CDR described herein.

In yet another embodiment, the antibody or fragment thereof includes at least one, two, or three Chothia hypervariable loops from a heavy chain variable region of an antibody chosen from, e.g., mAb13.2, ch13.2, h13.2v1, h13.2v2, and/or h13.2v3, as described herein, or at least particularly the amino acids from those hypervariable loops that contact IL-13. In yet another embodiment, the antibody or fragment thereof includes at least one, two, or three hypervariable loops from a light chain variable region of an antibody chosen from, e.g., mAb13.2, ch13.2, h13.2v1, h13.2v2, and/or h13.2v3, as described herein, or at least includes the amino acids from those hypervariable loops that contact IL-13. In yet another embodiment, the antibody or fragment thereof includes at least one, two, three, four, five, or six hypervariable loops from the heavy and light chain variable regions of an antibody chosen from, e.g., mAb13.2, ch13.2, h13.2v1, h13.2v2, and/or h13.2v3, as described herein.

In one preferred embodiment, the protein includes all six hypervariable loop's from mAb13.2, ch13.2, h13.2v1, h13.2v2, and/or h13.2v3 or closely related hypervariable loops, e.g., hypervariable loops which are identical or which have at least one amino acid alteration, but not more than two, three or four alterations (e.g., substitutions, deletions, or insertions, e.g., conservative substitutions). Optionally, the protein may include any hypervariable loop described herein.

In still another example, the protein includes at least one, two, or three hypervariable loops that have the same canonical structures as the corresponding hypervariable loop of mAb13.2, ch13.2, h13.2v1, h13.2v2, and/or h13.2v3, e.g., the same canonical structures as at least loop 1 and/or loop 2 of the heavy and/or light chain variable domains of mAb13.2, ch13.2, h13.2v1, h13.2v2, and/or h13.2v3. See, e.g., Chothia et al. (1992) *J. Mol. Biol.* 227:799-817; Tomlinson et al. (1992) *J. Mol. Biol.* 227:776-798 for descriptions of hypervariable loop canonical structures. These structures can be determined by inspection of the tables described in these references.

In one embodiment, the light or the heavy chain variable framework (e.g., the region encompassing at least FR1, FR2, FR3, and optionally FR4) can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, a human consensus sequence, or a human antibody described herein; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VH segment of a human germline gene, e.g., DP-54 or DPK9. In one embodiment, the heavy chain variable region includes human residues or human consensus sequence residues at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering).

In one embodiment, the protein includes at least one non-human CDR, e.g., a murine CDR, e.g., a CDR from mAb13.2, or a mutant thereof, and at least one framework which differs from a framework of mAb13.2 by at least one amino acid, e.g., at least 5, 8, 10, 12, 15, or 18 amino acids. For example, the proteins include one, two, three, four, five, or six such non-human CDR's and includes at least one amino acid difference in at least three of HC FR1, HC FR2, HC FR3, LC FR1, LC FR2, and LC FR3.

In one embodiment, the heavy or light chain variable domain of the antibody includes an amino acid sequence, which is at least 80%, 85%, 90%, 92%, 95%, 97%, 98%, 99% or higher identical to a variable region of an antibody described herein, e.g., mAb13.2, ch13.2, h13.2v1, h13.2v2, and/or h13.2v3; or which differs at at least 1 or 5 residues, but less than 40, 30, 20, or 10 residues, from a variable region of an antibody described herein, e.g., mAb13.2, ch13.2, h13.2v1, h13.2v2, and/or h13.2v3.

In one embodiment, one or both of the variable domains include amino acid positions in the framework region that are variously derived from both a non-human antibody (e.g., a murine antibody such as mAb13.2) and a human antibody or germline sequence. For example, the variable domain will include a number of positions at which the amino acid residue is identical to both the non-human antibody and the human antibody (or human germline sequence) because the two are identical at that position. Of the remaining framework positions where the non-human and human differ, at least 50, 60, 70, 80, or 90% of the positions of the variable domain are preferably identical to the human antibody (or human germline sequence) rather than the non-human. For example, none, or at least one, two, three, or four of such remaining framework position may be identical to the non-human antibody rather than to the human. For example, in HC FR1, one or two such positions can be non-human; in HC FR2, one or two such positions can be non-human; in FR3, one, two, three, or four such positions can be non-human; in LC FR1, one, two, three, or four such positions can be non-human; in LC FR2, one or two such positions can be non-human; in LC FR3, one or two such positions can be non-human.

In one embodiment, the heavy or light chain variable region of the protein includes an amino acid sequence encoded by a nucleic acid sequence described herein or a nucleic acid that hybridizes to a nucleic acid sequence described herein (e.g., a specific nucleic acid sequence or a nucleic acid sequence that encodes an amino acid sequence described herein) or its complement, e.g., under low stringency, medium stringency, high stringency, or very high stringency conditions, or other hybridization condition described herein.

In another embodiment, the antibody or fragment thereof comprises at least one, two, three, or four antigen-binding regions, e.g., variable regions, having an amino acid sequence as set forth in Table 3 (SEQ ID NOs:13, 14, 15, 16, or 36 for VH, and/or SEQ ID NOs:9, 10, 11, 12, or 35 for VL), or a sequence substantially identical thereto (e.g., a sequence at least about 85%, 90%, 95%, 99% or more identical thereto, or which differs by no more than 1, 2, 5, 10, or 15 amino acid residues from SEQ ID NOs:9, 10, 11, 12, 13, 14, 15, 16, 35, or 36). In another embodiment, the antibody includes a VH and/or VL domain encoded by a nucleic acid having a nucleotide sequence as set forth in Table 2 (SEQ ID NOs:5, 6, 7, 8, or 34 for VH, and/or SEQ ID NOs:1, 2, 3, 4, or 33 for VL), or a sequence substantially identical thereto (e.g., a sequence at least about 85%, 90%, 95%, 99% or more identical thereto, or which differs by no more than 3, 6, 15, 30, or 45 nucleotides from SEQ ID NOs:1, 2, 3, 4, 5, 6, 7, 8, 33, or 34). In yet another embodiment, the antibody or fragment thereof comprises at least one, two, or three CDRs from a heavy chain variable region having an amino acid sequence as set forth in Table 1 (SEQ ID NOs:22, 23, or 24 for VH CDRs 1-3, respectively), or a sequence substantially homologous thereto (e.g., a sequence at least about 85%, 90%, 95%, 99% or more identical thereto, and/or having one or more substitutions, e.g., conserved substitutions). In yet another embodiment, the antibody or fragment thereof comprises at least one, two, or three CDRs from a light chain variable region having an amino acid sequence as set forth in Table 1 (SEQ ID NOs:19, 20, or 21 for VL CDRs 1-3, respectively), or a sequence substantially homologous thereto (e.g., a sequence at least about 85%, 90%, 95%, 99% or more identical thereto, and/or having one or more substitutions, e.g., conserved substitutions). In yet another embodiment, the antibody or fragment thereof comprises at least one, two, three, four, five or six CDRs from heavy and light chain variable regions having an amino acid sequence as set forth in Table 1 (SEQ ID NOs:22, 23, 24 for VH CDRs 1-3, respectively; and SEQ ID NO:19, 20, or 21 for VL CDRs 1-3, respectively), or a sequence substantially homologous thereto (e.g., a sequence at least about 85%, 90%, 95%, 99% or more identical thereto, and/or having one or more substitutions, e.g., conserved substitutions).

In yet another embodiment, the antibody or fragment thereof comprises at least one, two, or three Chothia hypervariable loops from a heavy chain variable region having an amino acid sequence of VH Chothia hypervariable loops 1-3, respectively, or a sequence substantially homologous thereto (e.g., a sequence at least about 85%, 90%, 95%, 99% or more identical thereto, and/or having one or more substitutions, e.g., conserved substitutions). In yet another embodiment, the antibody or fragment thereof comprises at least one, two, or three Chothia hypervariable loops from a light chain variable region having an amino acid sequence of Chothia hypervariable loops 1-3, respectively, or a sequence substantially homologous thereto (e.g., a sequence at least about 85%, 90%, 95%, 99% or more identical thereto, and/or having one or more substitutions, e.g., conserved substitutions).

In another embodiment, the anti-IL-13 antibody or fragment thereof comprises a human IgG1 constant region having an amino acid sequence as set forth in SEQ ID NO:17 or a sequence substantially homologous thereto (e.g., a sequence at least about 85%, 90%, 95%, 99% or more identical thereto, or which differs by no more than 1, 2, 5, 10, 50, or 100 amino acid residues from SEQ ID NO:17), or at corresponding positions. In another embodiment, the anti-IL-13 antibody comprises a human kappa constant chain having an amino acid sequence as set forth in SEQ ID NO:18 or a sequence substantially homologous thereto (e.g., a sequence at least about 85%, 90%, 95%, 99% or more identical thereto, or which differs by no more than 1, 2, 5, 10, 20, or 50 amino acid residues from SEQ ID NO:18). In yet another embodiment, the antibody or fragment thereof comprises a human IgG1 constant region and a human kappa constant chain, e.g., as described herein.

In yet another embodiment, the anti-IL-13 antibody or fragment thereof comprises a heavy chain variable domain that contacts IL-13, typically human IL-13, via hydrogen bonds at at least one, two, three or four residues chosen from, e.g., Serine 50 (CDR2), Serine 53 (CDR2), Tyrosine 101 (CDR3), Tyrosine 102 (CDR3), or a conservative substitution thereof, of the heavy chain variable region shown in FIG. 29 according to the linear sequence numbering scheme (see also, e.g., FIG. 17), or at positions that correspond to such amino acid residues in the heavy chain variable domain. In one embodiment, the antibody or fragment thereof comprises a heavy chain variable region that contacts IL-13, typically human IL-13, via van der Waals forces at at least one, two, three, four, five, six, seven, eight, nine, ten, eleven, twelve, thirteen, or fourteen residues chosen from, e.g., Isoleucine 30, Serine 31 (CDR1), Alanine 33 (CDR1), Tryptophan 47, Serine 50 (CDR2), Serine 52 (CDR2), Serine 53 (CDR2), Tyrosine 58 (CDR2), Leucine 98 (CDR3), Aspartate 99 (CDR3), Glycine 100 (CDR3), Tyrosine 101 (CDR3), Tyrosine 102 (CDR3), Phenylalanine 103 (CDR3), or a conservative substitution thereof, of the heavy chain variable region shown in FIG. 29 according to the linear sequence numbering scheme (see also, e.g., FIG. 17), or at positions that correspond to such amino acid residues in the heavy chain variable domain. In another embodiment, the antibody or fragment thereof comprises a heavy chain variable region that contacts IL-13, typically human IL-13, via hydrogen bonds at at least one, two, three or four residues chosen from, e.g., Serine 50 (CDR2), Serine 53 (CDR2), Tyrosine 101 (CDR3), Tyrosine 102 (CDR3), or a conservative substitution thereof, and via van der Waals forces at at least one, two, three, four, five, six, seven, eight, nine, ten, eleven, twelve, thirteen, or fourteen residues chosen from, e.g., Isoleucine 30, Serine 31 (CDR1), Alanine 33 (CDR1), Tryptophan 47, Serine 50 (CDR2), Serine 52 (CDR2), Serine 53 (CDR2), Tyrosine 58 (CDR2), Leucine 98 (CDR3), Aspartate 99 (CDR3), Glycine 100 (CDR3), Tyrosine 101 (CDR3), Tyrosine 102 (CDR3), Phenylalanine 103 (CDR3), or a conservative substitution thereof, of the heavy chain variable region shown in FIG. 29 according to the linear sequence numbering scheme (see also, e.g., FIG. 17), or at positions that correspond to such amino acid residues in the heavy chain variable domain.

In another embodiment, the anti-IL-13 antibody or fragment thereof comprises a light chain variable region that contacts IL-13, typically human IL-13, via hydrogen bonds at at least one, two, three, four or five residues chosen from, e.g., Asparagine 31 (CDR1), Tyrosine 32 (CDR1), Lysine 34 (CDR1), Asparagine 96 (CDR3), Aspartate 98 (CDR3), or a conservative substitution thereof, of the light chain variable region shown in FIG. 30 according to the linear sequence numbering scheme (see also, e.g., FIG. 18). In yet another embodiment, the anti-IL-13 antibody or fragment thereof comprises a light chain variable region that contacts IL-13, typically human IL-13, via van der Waals forces at at least one, two, three, four, five, six, or seven residues chosen from, e.g., Asparagine 31 (CDR1), Tyrosine 32 (CDR1), Lysine 34 (CDR1), Arginine 54 (CDR2), Asparagine 96 (CDR3), Aspartate 98 (CDR3), Tryptophan 100 (CDR3), or a conservative substitution thereof, of the light chain variable region shown in FIG. 30 according to the linear sequence numbering scheme (see also, e.g., FIG. 18). In another embodiment, the antibody or fragment thereof comprises a light chain variable region that contacts IL-13, typically human IL-13, via hydrogen bonds at at least one, two, three, four or five residues chosen from, e.g., Asparagine 31 (CDR1), Tyrosine 32 (CDR1), Lysine 34 (CDR1), Asparagine 96 (CDR3), Aspartate 98 (CDR3), or a conservative substitution thereof, of the light chain variable region, and via van der Waals forces at at least one, two, three, four, five, six, or seven residues chosen from, e.g., Asparagine 31 (CDR1), Tyrosine 32 (CDR1), Lysine 34 (CDR1), Arginine 54 (CDR2), Asparagine 96 (CDR3), Aspartate 98 (CDR3), Tryptophan 100 (CDR3), or a conservative substitution thereof, of the light chain variable region shown in FIG. 30 according to the linear sequence numbering scheme (see also, e.g., FIG. 18).

In another embodiment, the anti-IL-13 antibody or fragment thereof comprises heavy and light chain variable regions that contact IL-13, e.g., human IL-13, via hydrogen bonds as described herein. In yet another embodiment, the anti-IL-13 antibody or fragment thereof comprises heavy and light chain variable regions that contact IL-13, e.g., human IL-13, via van der Waals forces as described herein. In one embodiment, the anti-IL-13 antibody or fragment thereof comprises heavy and light chain variable regions that contact IL-13, e.g., human IL-13, via hydrogen bonds and van der Waals forces as described herein.

In yet another embodiment, the IL-13 antagonist, e.g., anti-IL-13 antibody or fragment thereof, comprises a heavy chain variable region having one or more mutations at positions 13, 19, 40, 42, 44, 75, 77, 83, 87, 92, or 113 of SEQ ID NO:14. In another embodiment, the heavy chain variable region of the anti-IL-13 antibody or fragment thereof further comprises a mutation at position 3 of SEQ ID NO:14. In one embodiment, the heavy chain variable region of the anti-IL-13 antibody or fragment thereof comprises one or more of the following substitutions: Lysine replaced by Glutamine at position 3, Lysine replaced by Glutamine at position 13, Lysine replaced by Arginine at position 19, Threonine replaced by Alanine at position 40, Glutamate replaced by Glycine at position 42, Arginine replaced by Glycine at position 44, Arginine replaced by Lysine at position 75, Isoleucine replaced by Serine at position 77, Serine replaced by Asparagine at position 83, Serine replaced by Alanine at position 87, Methionine replaced by Valine at position 92, or Threonine replaced by Leucine at position 113 of SEQ ID NO:14.

In another embodiment, the IL-13 antagonist, e.g., anti-IL-13 antibody or fragment thereof, comprises a light chain variable region having one or more mutations at positions 3, 9, 12, 13, 15, 17, 19, 22, 46, 47, 62, 64, 80, 81, 82, 83, 84, 85, 87, or 108 of SEQ ID NO:10. In another embodiment, the light chain variable region of the anti-IL-13 antibody, or fragment thereof, further comprises one or more mutations at positions 4 or 72 of SEQ ID NO:10. In one embodiment, the light chain variable region of the anti-IL-13 antibody or fragment thereof comprises one or more of the following substitutions: Valine replaced by Glutamine at position 3, Leucine replaced by Methionine at position 4, Alanine replaced by Serine at position 9, Alanine replaced by Serine at position 12, Valine replaced by Alanine at position 13, Leucine replaced by Valine at position 15, Glutamine replaced by Aspartate at position 17, Alanine replaced by Valine at position 19, Serine replaced by Threonine at position 22, Glutamine replaced by Lysine at position 46, Serine replaced by Alanine at position 47, Isoleucine replaced by Valine at position 62, Alanine replaced by Serine at position 64, Arginine replaced by Glycine at position 72, Asparagine replaced by Serine at position 80, Proline replaced by Serine at position 81, Valine replaced by Leucine at position 82, Glutamate replaced by Glutamine at position 83, Alanine replaced by Proline at position 84, Aspartate replaced by Glutamate at position 85, Valine replaced by Phenylalanine at position 87, or Leucine replaced by Valine at position 108 of SEQ ID NO:10.

In another embodiment, the antibody or antigen binding fragment thereof includes one or more CDRs that has a backbone conformation of a CDR described in Table 10 (of application Ser. No. 11/149,025)± a root mean square deviation (RMSD) of not more than 1.5, 1.2, 1.1, or 1.0 Angstroms, Table 11 (of application Ser. No. 11/149,025)± an RMSD of not more than 1.5, 1.2, 1.1, or 1.0 Angstroms, or Table 12 (of application Ser. No. 11/149,025)± an RMSD of not more than 1.5, 1.2, 1.1, or 1.0 Angstroms. For example, one, two, or three of the CDRs of the heavy chain variable domain (e.g., particularly in CDR3, or in at least two CDRs, e.g., CDR1 and CDR3, CDR2 and CDR3, or in all three CDRs) have an RMSD of not more than 1.5, 1.2, 1.1, or 1.0 Angstroms relative to those structures. For example, one, two, or three of the CDRs of the light chain variable domain (e.g., particularly in CDR1, or in at least two CDRs, e.g., CDR1 and CDR3, CDR1 and CDR2, or in all three CDRs) have an RMSD of not more than 1.5, 1.2, 1.1, or 1.0 Angstroms relative to those structures. In embodiment, the antibody or antigen binding fragment thereof includes a variable domain that, as a whole, has a backbone conformation of a CDR described in Table 10 (of application Ser. No. 11/149,025)± a root mean square deviation (RMSD) of not more than 1.5, 1.2, 1.1, or 1.0 Angstroms, Table 11 (of application Ser. No. 11/149,025)± an RMSD of not more than 1.5, 1.2, 1.1, or 1.0 Angstroms, or Table 12 (of application Ser. No. 11/149,025)± an RMSD of not more than 1.5, 1.2, 1.1, or 1.0 Angstroms. The variable domain can also be at least at least 70%, 80%, 85%, 87%, 90%, 92%, 93%, 95%, 96%, 97%, 98%, or 99% identical to an antibody described herein, e.g., in the CDR region and/or framework regions.

In yet another embodiment, the IL-13 antagonist, e.g., anti-IL-13 antibody or fragment thereof, comprises a heavy chain variable region having one or more mutations at positions 3, 13, 19, 40, 42, 44, 75, 77, 83, 87, 92, or 113 of SEQ ID NO:14 (e.g., the mutations as described herein), and a light chain variable region having one or more mutations at positions 3, 4, 9, 12, 13, 15, 17, 19, 22, 46, 47, 62, 64, 72, 80, 81, 82, 83, 84, 85, 87, or 108 of SEQ ID NO:10 (e.g., the mutations as described herein).

The IL-13 antagonist, e.g., anti-IL-13 antibody or fragment thereof described herein, can be derivatized or linked to another functional molecule, e.g., another peptide or protein (e.g., an Fab fragment). For example, the fusion protein or an antibody, or antigen-binding portion, can be functionally linked (e.g., by chemical coupling, genetic fusion, noncovalent association or otherwise) to one or more other molecular entities, such as an antibody (e.g., a bispecific or a multispecific antibody), toxins, radioisotopes, cytotoxic or cytostatic agents, among others.

In yet another embodiment, the IL-13 antagonist, e.g., the anti-IL-13 antibody or fragment thereof described herein, or a pharmaceutical composition thereof, is administered alone or in combination therapy, i.e., combined with other agents, e.g., therapeutic agents, which are useful for treating IL-13-associated disorders. Examples of IL-13-associated disorders include, but are not limited to, disorders chosen from one or more of: respiratory disorders, e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis; atopic disorders, e.g., resulting from an increased sensitivity to IL-13, (e.g., atopic dermatitis, urticaria, eczema, allergic rhinitis, and allergic enterogastritis); inflammatory and/or autoimmune conditions of, the skin (e.g., atopic dermatitis), gastrointestinal organs (e.g., inflammatory bowel diseases (IBD), such as ulcerative colitis and/or Crohn's disease), liver (e.g., cirrhosis, hepatocellular carcinoma), and scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus); and suppression of expression of protective type 1 immune responses, (e.g., during vaccination), as described herein.

The combination therapy can include one or more IL-13 antagonists, e.g., anti-IL-13 antibodies or fragments thereof, coformulated with, and/or coadministered with, one or more additional therapeutic agents, e.g., one or more cytokine and growth factor inhibitors, immunosuppressants, anti-inflammatory agents (e.g., systemic anti-inflammatory agents), metabolic inhibitors, enzyme inhibitors, and/or cytotoxic or cytostatic agents, as described in more herein.

Examples of preferred additional therapeutic agents that can be coadministered and/or coformulated with one or more IL-13 antagonists, e.g., anti-IL-13 antibodies or fragments thereof, include, but are not limited to, one or more of: inhaled steroids; beta-agonists, e.g., short-acting or long-acting beta-agonists; antagonists of leukotrienes or leukotriene receptors; combination drugs such as ADVAIR®; IgE inhibitors, e.g., anti-IgE antibodies (e.g., XOLAIR®); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; and antihistamines. Such combinations can be used to treat asthma and other respiratory disorders. Additional examples of therapeutic agents that can be coadministered and/or coformulated with one or more anti-IL-13 antibodies or fragments thereof include one or more of: TNF antagonists (e.g., a soluble fragment of a TNF receptor, e.g., p55 or p75 human TNF receptor or derivatives thereof, e.g., 75 kd TNFR-IgG (75 kD TNF receptor-IgG fusion protein, ENBREL™)); TNF enzyme antagonists, e.g., TNFα converting enzyme (TACE) inhibitors; muscarinic receptor antagonists; TGF-β antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, Mk-2 and NFκB inhibitors, among others.

In another aspect, this application provides compositions, e.g., pharmaceutical compositions that include a pharmaceutically acceptable carrier and at least one IL-13 antagonist, e.g., anti-IL-13 antibody or fragment thereof described herein. In one embodiment, the compositions, e.g., pharmaceutical compositions, comprise a combination of two or more one of the aforesaid IL-13 antagonists, e.g., anti-IL-13 antibodies or fragments thereof. Combinations of the IL-13 antagonist, e.g., the anti-IL-13 antibody or fragment thereof, and a drug, e.g., a therapeutic agent (e.g., one or more cytokine and growth factor inhibitors, immunosuppressants, anti-inflammatory agents (e.g., systemic anti-inflammatory agents), metabolic inhibitors, enzyme inhibitors, and/or cytotoxic or cytostatic agents, as described herein) are also within the scope of the invention.

This application also features nucleic acids comprising nucleotide sequences that encode heavy and light chain variable regions of the anti-IL-13 antibodies, and fragments thereof, as described herein. For example, the application features a first and second nucleic acid encoding heavy and light chain variable regions, respectively, of an anti-IL-13 antibody chosen from one or more of, e.g., mAb13.2, ch13.2, h13.2v1, h13.2v2, and/or h13.2v3, as described herein.

In another aspect, the application features host cells and vectors containing the nucleic acids described herein.

The epitope of IL-13, e.g., human IL-13, recognized by one or more of, e.g., mAb13.2, ch13.2, h13.2v1, h13.2v2, and/or h13.2v3, is featured. In one embodiment, the anti-IL-13 antibody or fragment thereof binds to an epitope comprising residues 81-93 and/or 114-132 of human IL-13 (SEQ ID NO:31), or a modified form thereof (e.g., a fragment or substituted (e.g., conservatively substituted) form thereof). In one embodiment, the epitope of human IL-13 comprises one or more of: Glutamate at position 49, Asparagine at position 53, Glycine at position 69, Proline at position 72, Histidine at position 73, Lysine at position 74, and Arginine at position 86 of SEQ ID NO:32, or a conserved amino acid substitution thereof.

In another aspect, this application features a method of modulating, e.g., interfering with (e.g., inhibiting, blocking or otherwise reducing), an interaction, e.g., binding, between IL-13 and a cognate IL-13 binding protein, e.g., an IL-13 receptor complex, e.g., a complex comprising IL-13Rα1 and IL-4Rα, or a subunit thereof. The modulating can be effected in vivo or in vitro. In other embodiments, the IL-13 antagonist, e.g., the anti-IL-13 antibody or fragment thereof, binds to IL-13, and interferes with (e.g., inhibits, blocks or otherwise reduces) an interaction, e.g., binding, between IL-13 and a subunit of the IL-13 receptor complex, e.g., IL-13Rα1 or IL-4Rα, individually. In yet another embodiment, the IL-13 antagonist, e.g., the anti-IL-13 antibody or fragment thereof, binds to IL-13, and interferes with (e.g., inhibits, blocks or otherwise reduces) an interaction, e.g., binding, between IL-13/IL-13Rα1 and IL-4Rα. In another embodiment, the IL-13 antagonist, e.g., the anti-IL-13 antibody or fragment thereof, binds to IL-13, and interferes with (e.g., inhibits, blocks or otherwise reduces) an interaction, e.g., binding, between IL-13/IL-4Rα and IL-13Rα1. Typically, the anti-IL-13 antibody or fragment thereof interferes with (e.g., inhibits, blocks or otherwise reduces) an interaction, e.g., binding, of IL-13/IL-13Rα1 with IL-4Rα.

The subject method can be used on cells in vitro (e.g., in a cell-free system), in culture, e.g. in vitro or ex vivo. For example, IL-13 receptor-expressing cells can be cultured in vitro in culture medium and the contacting step can be effected by adding one or more anti-IL-13 antibodies or fragments thereof, e.g., anti-IL-13 antibodies or fragments thereof as described herein, to the culture medium. Alternatively, the method can be performed on cells present in a subject, e.g., as part of an in vivo (e.g., therapeutic or prophylactic) protocol.

In another aspect, this application features a method of treating (e.g., curing, suppressing, ameliorating, delaying or preventing the onset of, or preventing recurrence or relapse of) or preventing an IL-13-associated disorder, in a subject. The method includes: administering to the subject an IL-13 binding agent (particularly an antagonist), e.g., an anti-IL-13 antibody or fragment thereof as described herein, in an amount sufficient to treat or prevent the IL-13-associated disorder. The IL-13 antagonist, e.g., the anti-IL-13 antibody or fragment thereof, can be administered to the subject, alone or in combination with other therapeutic modalities as described herein. In one embodiment, the subject is a mammal, e.g., a human suffering from one or more IL-13-associated disorders, including, e.g., respiratory disorders (e.g., asthma (e.g., allergic and nonallergic asthma), chronic obstructive pulmonary disease (COPD), and other conditions involving airway inflammation, eosinophilia, fibrosis and excess mucus production; atopic disorders (e.g., atopic dermatitis and allergic rhinitis); inflammatory and/or autoimmune conditions of, the skin, gastrointestinal organs (e.g., inflammatory bowel diseases (IBD), such as ulcerative colitis and/or Crohn's disease), and liver (e.g., cirrhosis, fibrosis); scleroderma; tumors or cancers, e.g., Hodgkin's lymphoma as described herein. Accordingly, the disclosure includes the use of an IL-13 binding agent (such as an anti-IL-13 antibody or fragment thereof described herein) for a treatment described herein and the use of an IL-13 binding agent (such as an anti-IL-13 antibody or fragment thereof described herein) for preparing a medicament for a treatment described herein.

Examples of IL-13-associated disorders include, but are not limited to, a disorder chosen from one or more of: respiratory disorders, e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis; atopic disorders, e.g., resulting from an increased sensitivity to IL-13 (e.g., atopic dermatitis, urticaria, eczema, allergic rhinitis, and allergic enterogastritis); inflammatory and/or autoimmune conditions of, the skin (e.g., atopic dermatitis), gastrointestinal organs (e.g., inflammatory bowel diseases (IBD), such as ulcerative colitis and/or Crohn's disease), liver (e.g., cirrhosis, hepatocellular carcinoma), and scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus); and suppression of expression of protective type 1 immune responses, (e.g., during vaccination), as described herein.

In other embodiments, this application provides a method of treating (e.g., reducing, ameliorating) or preventing one or more symptoms associated with a respiratory disorder, e.g., asthma (e.g., allergic and nonallergic asthma); allergies; chronic obstructive pulmonary disease (COPD); a condition involving airway inflammation, eosinophilia, fibrosis and excess mucus production, e.g., cystic fibrosis and pulmonary fibrosis. For example, symptoms of asthma include, but are not limited to, wheezing, shortness of breath, bronchoconstriction, airway hyperreactivity, decreased lung capacity, fibrosis, airway inflammation, and mucus production. The method comprises administering to the subject an IL-13 antagonist, e.g., an IL-13 antibody or a fragment thereof, in an amount sufficient to treat (e.g., reduce, ameliorate) or prevent one or more symptoms. The IL-13 antibody can be administered therapeutically or prophylactically, or both. The IL-13 antagonist, e.g., the anti-IL-13 antibody, or fragment thereof, can be administered to the subject, alone or in combination with other therapeutic modalities as described herein. Preferably, the subject is a mammal, e.g., a human suffering from an IL-13-associated disorder as described herein.

In another aspect, this application provides a method for detecting the presence of IL-13 in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with the anti-IL-13 antibody or fragment thereof as described herein; and (ii) detecting formation of a complex between the anti-IL-13 antibody or fragment thereof, and the sample or the control sample, wherein a statistically significant change in the formation of the complex in the sample relative to the control sample is indicative of the presence of the IL-13 in the sample.

In yet another aspect, this application provides a method for detecting the presence of IL-13 in vivo (e.g., in vivo imaging in a subject). The subject method can be used to diagnose a disorder, e.g., an IL-13-associated disorder. The method includes: (i) administering the anti-IL-13 antibody or fragment thereof as described herein to a subject or a control subject under conditions that allow binding of the antibody or fragment to IL-13; and (ii) detecting formation of a complex between the antibody or fragment and IL-13, wherein a statistically significant change in the formation of the complex in the subject relative to the control subject is indicative of the presence of IL-13.

Preferably, the antibody or fragment thereof is directly or indirectly labeled with a detectable substance to facilitate detection of the bound or unbound antibody. Suitable detectable substances include various enzymes, prosthetic groups, fluorescent materials, luminescent materials and radioactive materials.

Methods for delivering or targeting an agent, e.g., a therapeutic or a cytotoxic agent, to an IL-13-expressing cell in vivo are also disclosed.

Kits comprising the IL-13 antagonists described herein, e.g., the anti-IL-13 antibodies or fragment thereof, for therapeutic and diagnostic uses are also within the scope of the application.

In another aspect, this application provides methods for providing an antibody that includes a heavy chain variable domain and a light chain variable domain. The methods include preparing an antibody (or a nucleic acid encoding such an antibody) by using one or more framework regions from DP-54 and DPK-9 or framework regions at least 75, 80, 82, 85, 88, 90, 92, 94, 95, 96, 97, or 98% identical to one or more framework regions of DP-54 and DPK-9. In one embodiment, the method includes engineering CDRs or portions of CDRs from a non-human antibody into the context of a variable domain that includes DP-54 and DPK-9 frameworks in the heavy chain variable domain and the light chain variable domain, respectively, or a variable domain that includes framework regions at least 75, 80, 82, 85, 88, 90, 92, 94, 95, 96, 97, or 98% identical to one or more framework regions of DP-54 and DPK-9. Nucleic acids that include sequences encoding protein chains that include such variable domains can be expressed in mammalian cells, e.g., tissue culture cells.

In a related aspect, the application features an antibody, e.g., an artificial antibody, that includes a heavy chain variable domain and a light chain variable domain, wherein the heavy chain variable domain includes using one or more framework regions from DP-54 or framework regions at least 75, 80, 82, 85, 88, 90, 92, 94, 95, 96, 97, or 98% identical to one or more framework regions of DP-54, and the light chain variable domain includes using one or more framework regions from DPK-9 or framework regions at least 75, 80, 82, 85, 88, 90, 92, 94, 95, 96, 97, or 98% identical to one or more framework regions of DPK-9. The one or more of the CDRs and/or hypervariable loops are generally non-human, e.g., from a non-human antibody such as a murine antibody. In one embodiment, the antibody binds to a human antigen, e.g., IL-13 or an antigen other than IL-13.

Other features and advantages will be apparent from the following detailed description and claims.

BRIEF DESCRIPTION OF THE DRAWINGS

FIG. 11: Human IL-13 sequence analysis showing mAb13.2 contact sites. The panel shows the amino acid sequence of human IL-13 (SEQ ID NO: 31), wherein the arrow indicates the signal peptide cleavage site, the four alpha helices are underlined, the antibody contact sites from the mAb13.2 Fab—IL-13 cocrystal structure are highlighted in light boxes, and the ARG-variant residue is highlighted in a dark box.

FIG. 15: Comparison of the human DP-54 germline gene (SEQ ID NO: 38) with the variable heavy (VH) chain amino acid sequences of a chimeric version of mAb13.2 (SEQ ID NO: 14) and a partially humanized version of mAb13.2 (h13.2v1) (SEQ ID NO: 15). The figure shows the complementarity determining regions (CDR) (boxed regions) and amino acid sequences of DP-54, the variable heavy region of a chimeric version of mAb13.2 (chimeric 13.2), and the variable heavy region of a partially humanized version of mAb13.2 (h13.2v1) as aligned and compared with SEQWEB™, wherein the amino acid substitutions made for the partially humanized version of mAb13.2 (h13.2v1) are indicated with shaded boxes and the residues left unchanged are underlined.

FIG. 16: Comparison of the human DPK9 germline gene (SEQ ID NO: 39) with the variable light (VL) chain amino acid sequences of a chimeric version of mAb13.2 (SEQ ID NO: 10) and a partially humanized version of mAb13.2 (h13.2v1) (SEQ ID NO: 11). The figure shows the complementarity determining regions (CDR) (boxed regions) and amino acid sequences of DPK-9, the variable light region of a chimeric version of mAb13.2 (chimeric 13.2), and the variable light region of a partially humanized version of mAb13.2 (h13.2v1) as aligned and compared with SEQWEB™, wherein the amino acid substitutions made for the partially humanized version of mAb13.2 (h13.2v1) are indicated with shaded boxes and the residues left unchanged are underlined.

FIG. 17: Comparison of the human DP-54 germline gene (SEQ ID NO: 38) with the variable heavy (VH) chain amino acid sequences of a chimeric version of mAb13.2 (SEQ ID NO: 14) and a fully humanized version of mAb13.2 (h13.2v2) (SEQ ID NO: 16). The figure shows the complementarity determining regions (CDR) (boxed regions) and amino acid sequences of DP-54, the variable heavy region of a chimeric version of mAb13.2 (chimeric 13.2), and the variable heavy region of a fully humanized version of mAb13.2 (h13.2v2) as aligned and compared with SEQWEB™, wherein the amino acid substitutions made for the fully humanized version of mAb13.2 (h13.2v2) are indicated with shaded boxes and the residues left unchanged are underlined.

FIG. 18: Comparison of the human DPK9 germline gene (SEQ ID NO: 39) with the variable light (VL) chain amino acid sequences of a chimeric version of mAb13.2 (SEQ ID NO: 10) and a fully humanized version of mAb13.2 (h13.2v2) (SEQ ID NO: 12). The figure shows the complementarity determining regions (CDR) (boxed regions) and amino acid sequences of DPK-9, the variable light region of a chimeric version of mAb13.2 (chimeric 13.2), and the variable light region of a fully humanized version of mAb13.2 (h13.2v2) as aligned and compared with SEQWEB™, wherein the amino acid substitutions made for the fully humanized version of mAb13.2 (h13.2v2) are indicated with shaded boxes and the residues left unchanged are underlined.

FIG. 20: Chimeric mAb13.2 (ch13.2), partially humanized mAB13.2 (h13.2v1), and fully humanized mAb13.2 (h13.2v2) can neutralize IL-13-mediated CD23 expression and IL-13-mediated phosphorylation of STAT6. (A) Shown is the percentage of monocytes that expressed cell surface CD23 (y-axis) after PBMCs isolated from a healthy donor were treated overnight with 1 ng/ml IL-13 and indicated concentrations (x-axis) of chimeric mAb13.2 (ch13.2; ♦), partially humanized mAb13.2 (h13.2v1;), or fully humanized mAb13.2 (h13.2v2; ●). (B) The percent of HT-29 cells that expressed phosphorylated STAT6 (y-axis) after incubation with IL-13 and indicated concentration (x-axis) of chimeric mAb13.2 (ch13.2; ♦), partially humanized mAb13.2 (h13.2v1;), or fully humanized mAb13.2 (h13.2v2; ●) as determined by flow cytometric analysis is depicted.

FIG. 21: The ability of fully humanized mAb13.2 (h13.2v2) to neutralize human IL-13 mediated CD23 expression is comparable to the ability of mAb13.2 to do the same. The number of gated monocytes that express cell surface CD23 after incubation with (A) recombinant human IL-13 or (B) native human IL-13 and increasing concentrations (x-axis) of mAb13.2 (●) or fully humanized mAb13.2 (h13.2v2; ♦) is presented as a percentage of the maximum number of monocytes that express cell surface CD23 after incubation with IL-13 alone (% Max. Response; y-axis).

Figures 22A, 22B:
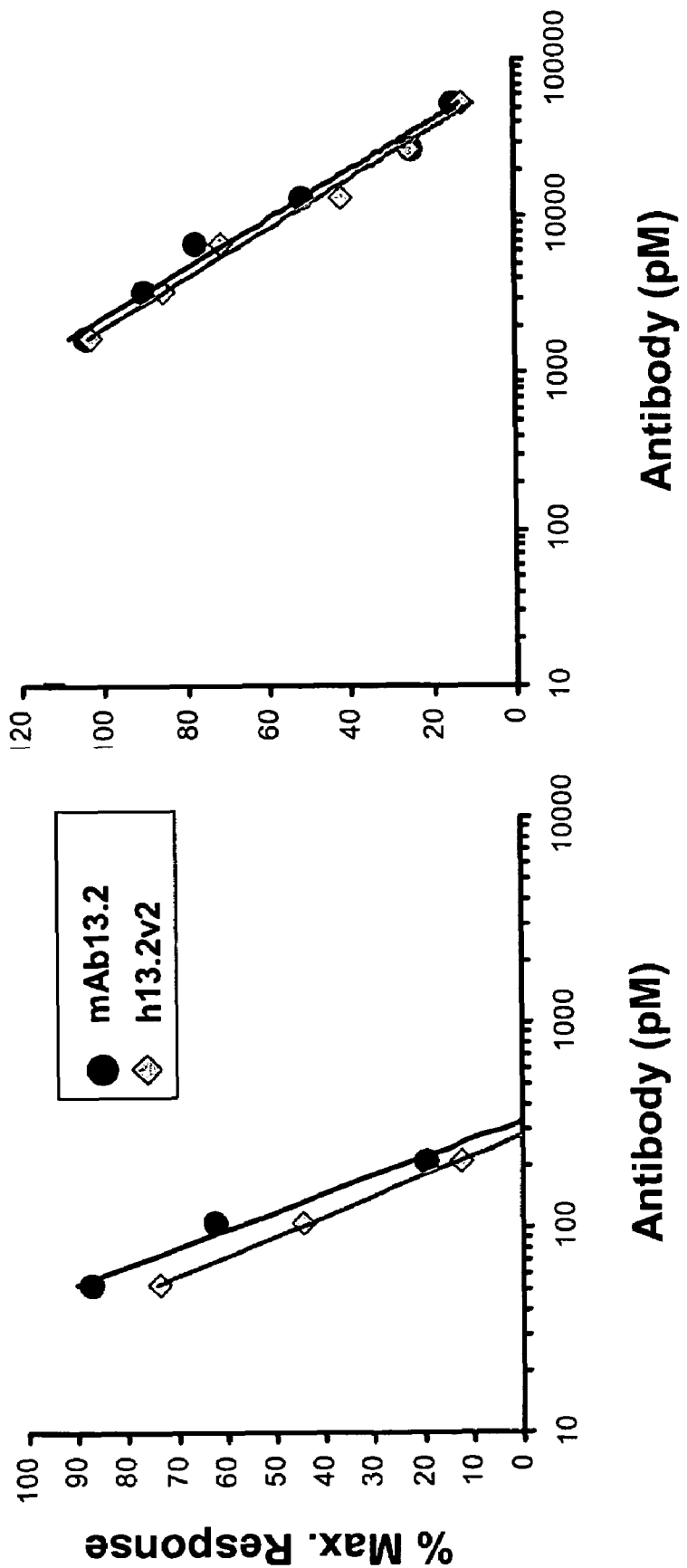

FIG. 22: The ability of fully humanized mAb13.2 (h13.2v2) to neutralize nonhuman primate or sheep IL-13-mediated CD23 expression is comparable to the ability of mAb13.2 to do the same. The number of gated monocytes that express cell surface CD23 after incubation with (A) recombinant nonhuman primate IL-13 (rec NHP IL-13) or (B) recombinant sheep IL-13 (rec Sheep IL-13) and increasing concentrations (x-axis) of mAb13.2 (●) or fully humanized mAb13.2 (h13.2v2; ♦) is presented as a percentage of the maximum number of monocytes that express cell surface CD23 after incubation with IL-13 alone (% Max. Response; y-axis).

Figure 23B:
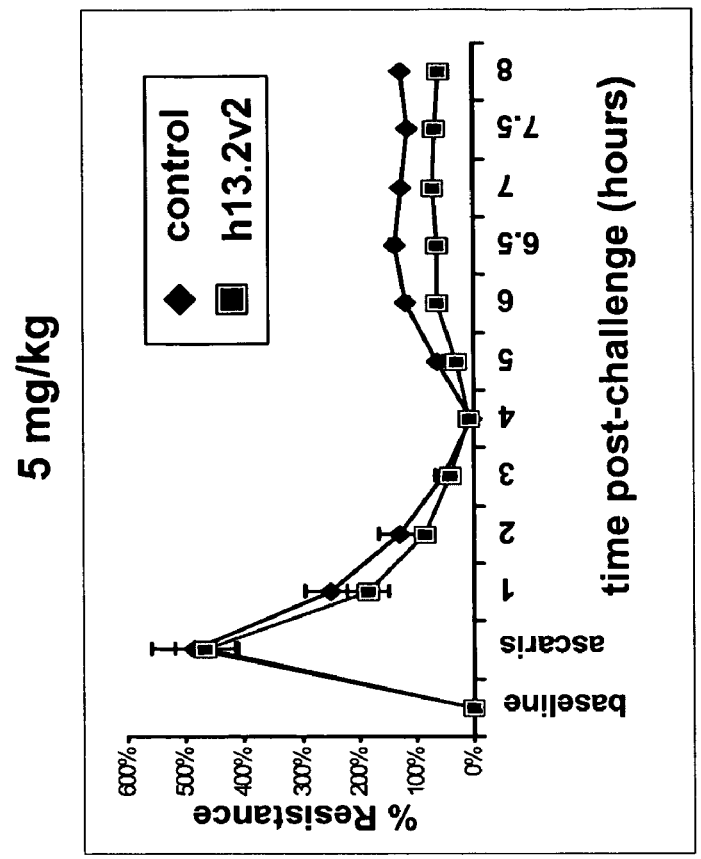
Figure 23A:
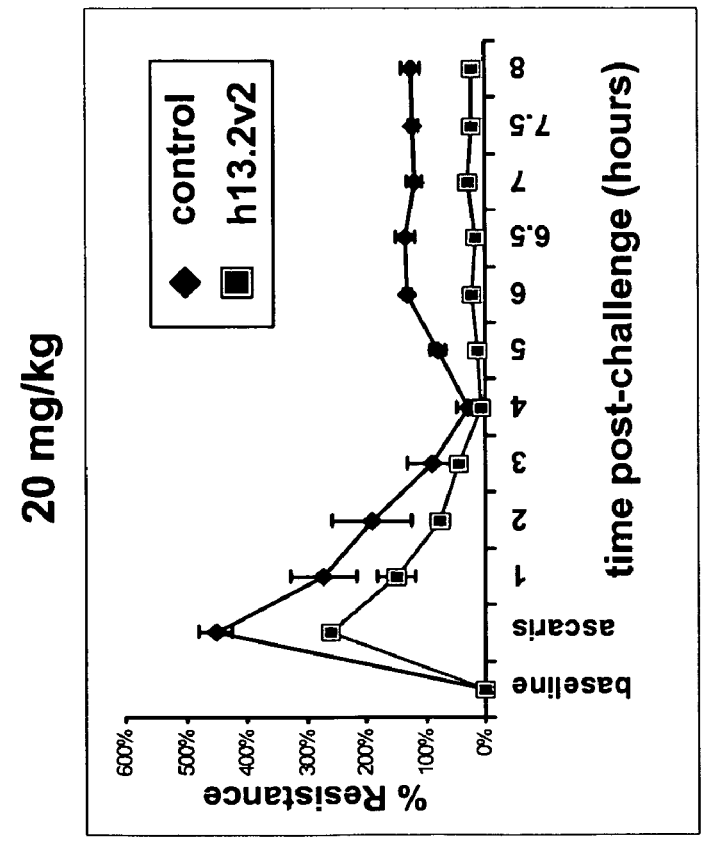

FIG. 23: Fully humanized mAb13.2 (h13.2v2) reduces late-phase bronchoconstriction in sheep. The percent airway resistance (y-axis) as measured 24 hours prior to *Ascaris suum* challenge (baseline), during challenge (*ascaris*), and for several hours after challenge (x-axis) is shown for sheep that were untreated (control; ♦) or prophylactically treated with fully humanized mAb13.2 (h13.2v2; ■) at a (A) 20 mg/kg or (B) 5 mg/kg dose. Data shown are mean ± s.d. for a sample size of three sheep per group.

Figures 24A, 24B:
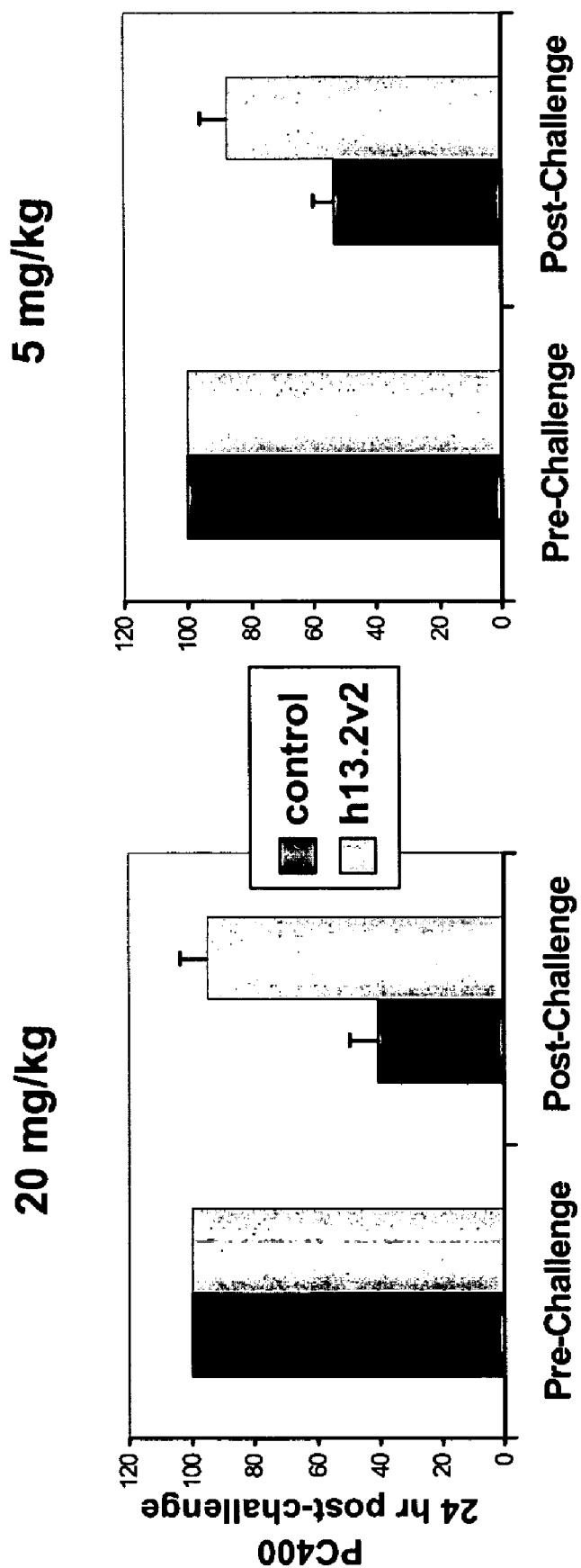

FIG. 24: Fully humanized mAb13.2 (h13.2v2) prevents airway hyperreactivity in sheep. The percent dose of carbachol required to elicit a given magnitude of response (PC400; y-axis) is shown for sheep prophylactically treated with (A) 20 mg/kg or (B) 5 mg/kg fully humanized mAb13.2 (h 13.2v2; ■) or sheep that remained untreated (control; ■) pre- and post-*Ascaris suum* challenge (x-axis). Data shown are mean ± s.d. for a sample size of three sheep per group.

Figure 25:
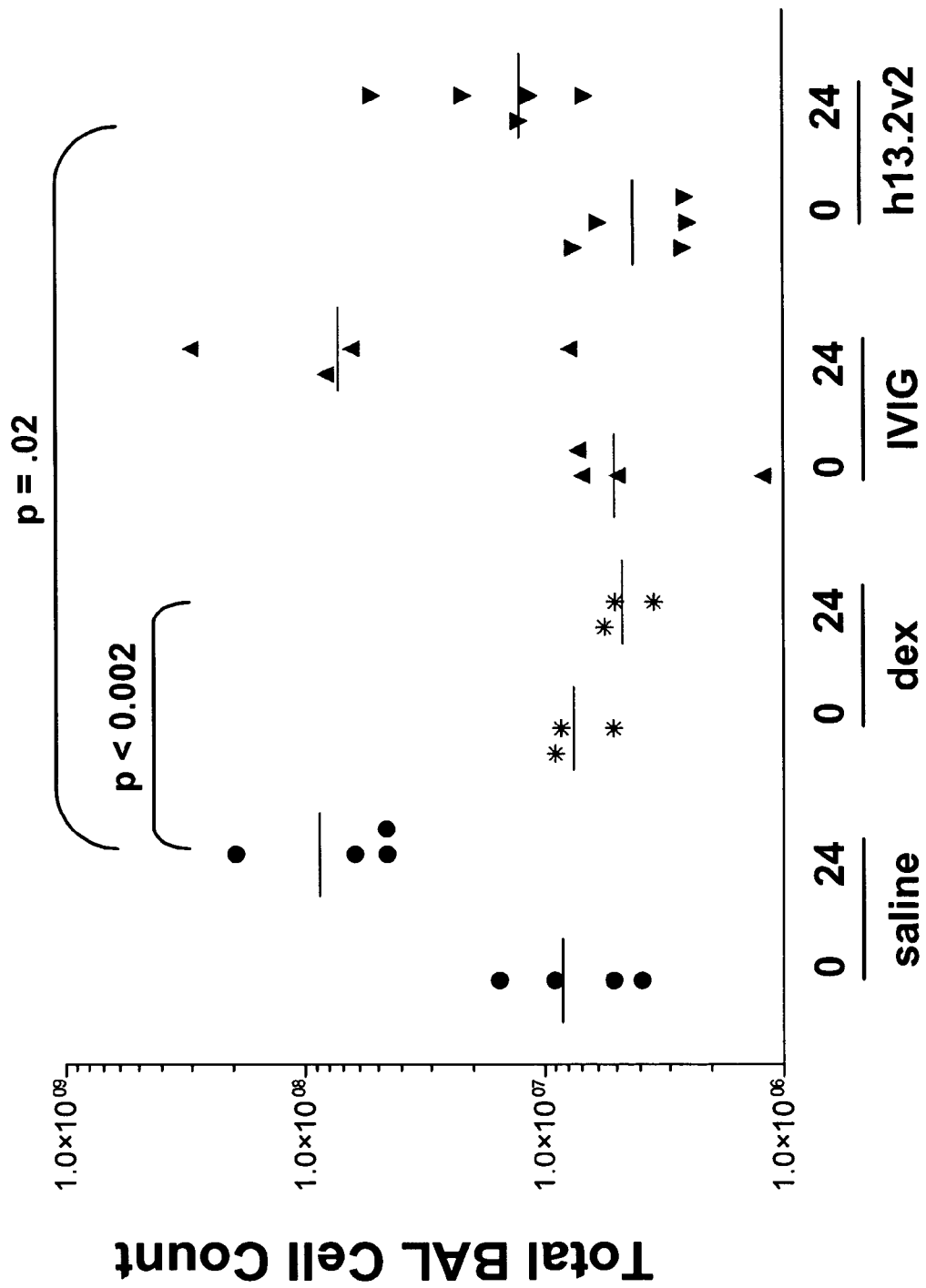

FIG. 25: Fully humanized mAb13.2 (h13.2v2) prevents antigen-induced lung inflammation in nonhuman primates. The figure shows the total number of cells found in bronchoalveolar lavage (BAL) samples (y-axis) taken prior to challenge (0) or 24 hours post-challenge (24) with *Ascaris suum* antigen from control cynomolgus monkeys treated intravenously with saline (●), positive control cynomolgus monkeys treated intramuscularly with 2 mg/kg dexamethasone (*), negative control cynomolgus monkeys pretreated with 8 mg/kg irrelevant human IgG (IVIG) (▲), or cynomolgus monkeys pretreated intravenously with fully humanized mAb13.2 (h13.2v2) (▼). A bar also depicts the mean number of cells found in BAL samples of each group. The p-values obtained using unpaired T-tests are also shown.

FIG. 26: Humanization of mAb13.2 may be based on sequence homology to other human germline genes in VH Group 3 of V-BASE. Shown is the alignment of the amino acid sequence of mAb13.2 (SEQ ID NO: 63) to human germline amino acid sequences within VH group 3 of the database, V-base (SEQ ID NOS 40-62, respectively in order of appearance). Bolded sequences are proposed as those to which humanization of mAb13.2 may be based.

FIG. 27: Comparison of the human DP-77 germline gene (SEQ ID NO: 64) with the variable heavy (VH) chain amino acid sequences of a chimeric version of mAb13.2 (SEQ ID NO: 14) and a fully humanized version of mAb13.2 (h13.2v3) (SEQ ID NO: 36). The figure shows the complementarity determining regions (CDR) (boxed regions) and amino acid sequences of DP-77, the variable heavy region of a chimeric version of mAb13.2 (chimeric 13.2), and the variable heavy region of a fully humanized version of mAb13.2 (h13.2v3) as aligned and compared with SEQWEB™, wherein the amino acid substitutions made for the fully humanized version of mAb13.2 (h13.2v3) are indicated with shaded boxes and the residues left unchanged are underlined.

FIG. 28: Comparison of the human B1 germline gene (SEQ ID NO: 65) with the variable light (VL) chain amino acid sequences of a chimeric version of mAb13.2 (SEQ ID NO: 10) and a fully humanized version of mAb13.2 (h13.2v3) (SEQ ID NO: 35). The figure shows the complementarity determining regions (CDR) (boxed regions) and amino acid sequences of B1, the variable light region of a chimeric version of mAb13.2 (chimeric 13.2), and the variable light region of a fully humanized version of mAb13.2 (h13.2v3) as aligned and compared with SEQWEB™, wherein the amino acid substitutions made for the fully humanized version of mAb13.2 (h13.2v3) are indicated with shaded boxes and the residues left unchanged are underlined.

FIG. 29: The number designation for each residue in the variable heavy chain amino acid sequence of monoclonal antibody mAb13.2 (SEQ ID NO: 14) according to various schemes. Shown is the number designation for each residue in the amino acid sequence of the variable heavy region of mAb13.2 according to a linear sequence numbering scheme, the Chothia structure numbering scheme, and the Kabat sequence numbering scheme.

FIG. 30: The number designation for each residue in the variable light chain amino acid sequence of monoclonal antibody mAb13.2 (SEQ ID NO: 10) according to various schemes. Shown is the number designation for each residue in the amino acid sequence of the variable light region of mAb13.2 according to a linear sequence numbering scheme, the Chothia structure numbering scheme, and the Kabat sequence numbering scheme.

FIG. 31: Titers of *Ascaris*-specific IgE at 8 weeks post-*Ascaris* challenge decreased in cynomolgus monkeys treated with anti-human IL-13 antibody (h13.2v2). The graphs depict the relative titers of *Ascaris*-specific IgE in cynomolgus monkeys (y-axis) before and 8 weeks following challenge with

*Ascaris suum* antigen. Pre-challenge values were normalized to "100." (A) Animals were treated intravenously with humanized anti-IL-13 antibody (h13.2v2). (B) Control animals were administered saline or irrelevant human IgG (IVIG) intravenously.

FIG. 32: Anti-IL-13 antibody (h13.2v2) prevented the increase in basophil sensitivity that follows in vivo allergen challenge. (A) Dose-dependent histamine release as a percentage of the maximum (y-axis) from blood of representative control and antibody-treated animals is depicted for animals before treatment and 24 hours and 8 weeks after *Ascaris* antigen challenge. (B) The total histamine release over the dose range shown in (a) was determined for each animal at each time point. The figure shows mean and standard error of normalized histamine release at each time point for the Control and anti-IL-13—treated groups. Pre=pre-antibody treatment. Time 0=24 hr post-antibody, pre-*Ascaris* lung challenge. The 24 hour, 8 week and 4 month time points refer to time post-*Ascaris* challenge.

Figure 33:
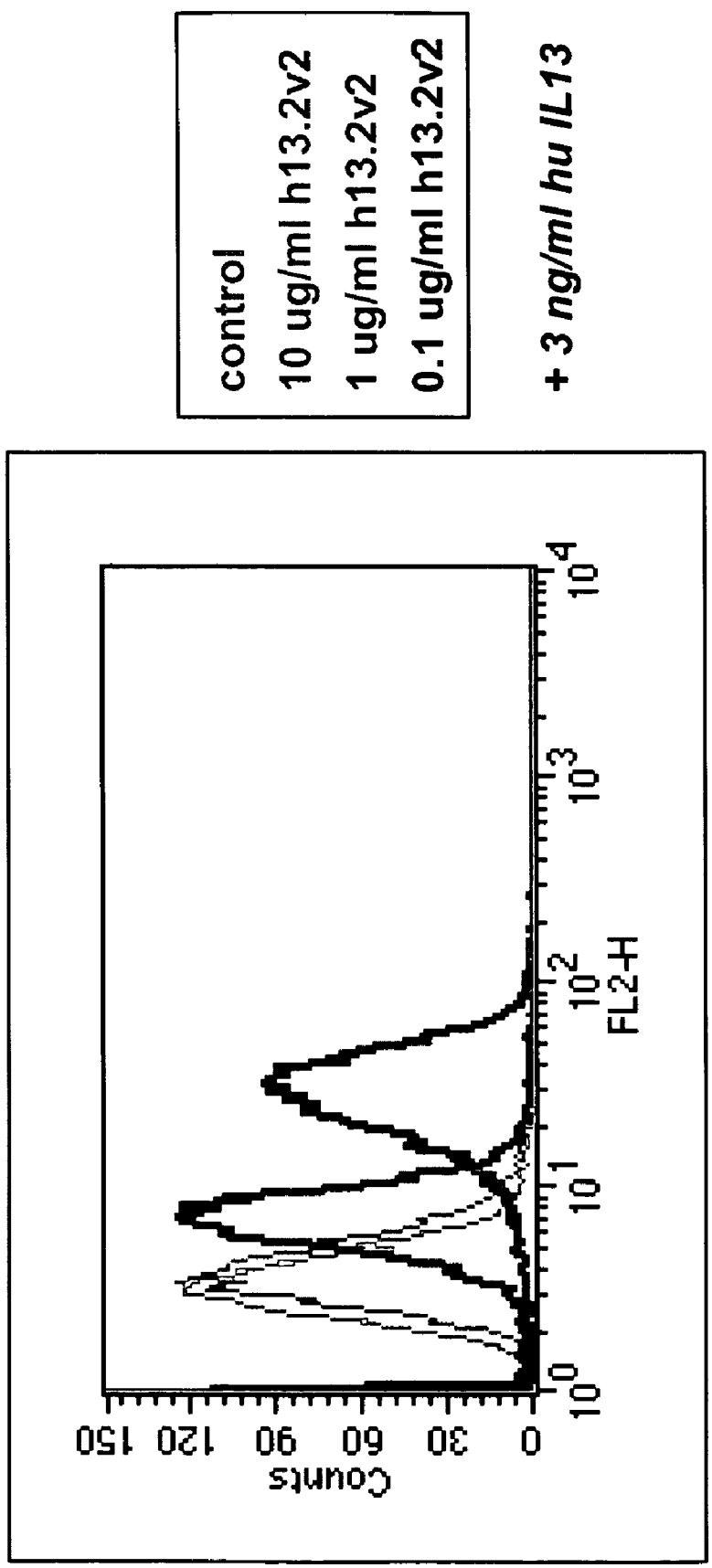

FIG. 33: Binding of biotinylated h13.2v2 to IL-13-loaded A375 cells. The histograms depict the number of A375 human melanoma cells (counts; y-axis) that demonstrated binding (fluorescence; x-axis) of biotinylated h13.2v2 (0.1 µg/ml, 1 µg/ml, or 10 µg/ml) following pre-incubation with 3 ng/ml human IL-13, as determined by flow cytometric analysis.

FIG. 34: The wild-type Fc revertant of h13.2v2 mediates ADCC in the presence of IL-13. (A) The percentage of Chromium-51 release (y-axis) of A375 human melanoma cells treated with the indicated concentration (x-axis) of h13.2v2 (L234A/G237A; ●) or its wild-type Fc revertant (O) is shown. (B) The percentage of Chromimum-51 released (y-axis) is shown for IL-13 loaded A375 cells treated with the wild-type Fc revertant of h13.2v2 in the presence or absence of IL-13.

Figures 35A, 35B:
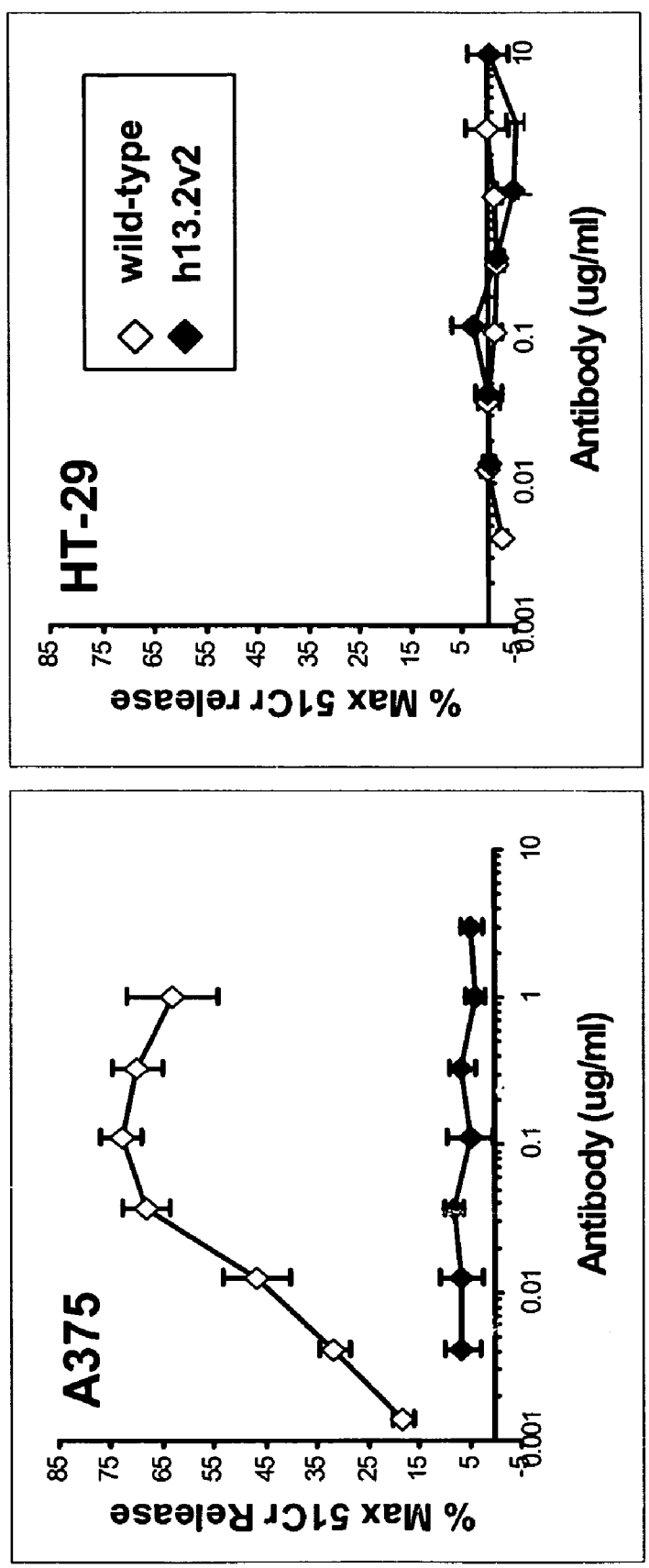

FIG. 35: The wild-type Fc revertant of h13.2v2 mediates ADCC of IL-13R$\alpha$2-expressing A375 cells, but not of IL-13R$\alpha$1-expressing HT-29 cells. (A) The percentage of Chromium-51 release (y-axis) of IL-13-loaded A375 human melanoma cells treated with the indicated concentration (x-axis) of h13.2v2 (L234A/G237A; ◆) or its wild-type Fc revertant (◇) is shown. (B) The percentage of Chromium-51 release (y-axis) of IL-13-loaded HT-29 human epithelial cells treated with the indicated concentration (x-axis) of h13.2v2 (L234A/G237A; ◆) or its wild-type Fc revertant (◇) is shown.

DETAILED DESCRIPTION

IL-13 binding agents, e.g., anti-IL13 antibodies and antigen-binding fragments thereof, pharmaceutical compositions thereof, nucleic acids encoding the aforesaid antibodies, as well as vectors and host cells containing the aforesaid nucleic acid sequences, are disclosed. Methods of producing the aforesaid antibodies, as well as methods for modulating one or more IL-13-associated activities using antibodies that bind to IL-13, e.g., human IL-13, and reduce or prevent it from binding to its receptor are also disclosed. Anti-IL-13 antibodies can be used to mitigate IL-13-mediated disorders, e.g., for treating respiratory disorders (e.g., asthma); atopic disorders (e.g., allergic rhinitis); inflammatory and/or autoimmune conditions of, the skin (e.g., atopic dermatitis), gastrointestinal organs (e.g., inflammatory bowel diseases (IBD)), as well as fibrotic and cancerous disorders. Anti-IL-13 antibodies can be used alone or in combination with other therapies used to treat the same or another disease, e.g., an allergic response.

It has been found, inter alia, that a reduction of IL-13 activity by using the antibodies described herein, which interfere with the formation of a functional IL-13 signaling complex, reduces airway inflammation in cynomolgus monkeys naturally allergic to *Ascaris suum* (Examples 1.4 and 3.5, below). In addition, the anti-human IL-13 antibodies described herein prevent late-phase bronchoconstriction in sheep naturally allergic to *Ascaris suum*, and prevent carbachol-induced airway hyperresponsiveness in sheep (Example 3.5, below). Accordingly, anti-IL-13 antibodies that neutralize one or more IL-13-associated activities may be used to reduce one or more IL-13-associated activities in vivo, e.g., to treat or prevent IL-13-mediated disorders (e.g., asthma, airway inflammation, eosinophilia, fibrosis, and excess mucus production).

Anti-Human IL-13 Antibodies

Antibodies that are capable of binding to, neutralizing and/or inhibiting one or more IL-13-associated activities, particularly the signaling activity of IL-13, are useful for treating IL-13-mediated diseases, such as allergic asthma, nonallergic asthma, and asthma-related pathologies, such as fibrosis, eosinophilia, and mucus production.

In one embodiment, the anti-IL13 antibodies disclosed herein are isolated or purified. An "isolated" or "purified" polypeptide or protein, e.g., an "isolated antibody," is purified to a state beyond that in which it exists in nature. For example, the "isolated" or "purified" polypeptide or protein, e.g., an "isolated antibody," refers to a protein that is separated from at least one component of cellular material or other contaminating proteins from the cell or tissue source from which the protein is derived, or separated from at least one component of the chemical precursors or other chemicals when chemically synthesized. For example, an isolated protein can be substantially free of other proteins, other cellular material, or chemical precursors. In some embodiments, the preparation of antibody protein having less than about 50% of non-antibody protein (also referred to herein as a "contaminating protein"), or of chemical precursors, is considered to be "substantially free." In other embodiments, 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, e.g., the culture medium represents less than about 30%, 20%, more preferably less than about 10%, and most preferably less than about 5% of the volume or mass of the protein preparation. Proteins or polypeptides referred to herein as "recombinant" are proteins or polypeptides produced by the expression of recombinant nucleic acids. Proteins can be purified by standard methods (including, e.g., ion exchange and affinity chromatography) to provide preparations in which a particular protein is at least 5, 10, 20, 25, 50, 75, 80, 90, 95, 98, 99% pure relative to other proteins or relative to other biologically active components.

The term "antibody" as used herein includes intact antibodies, fragments of antibodies, e.g., Fab, F(ab')$_2$ Fd, dAb and scFv fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced IL-13 binding and/or reduced FcR binding). Exemplary antibodies bind specifically to IL-13, and may, for example, interfere with the formation of a functional IL-13 signaling complex, and/or neutralize or inhibit one or more IL-13-associated activities.

The antibodies described herein can be effectively human. An "effectively human" antibody is an antibody that includes a sufficient number of human amino acid positions such that the antibody does not elicit an immunogenic response in a normal human. Preferably, the protein does not evoke a neutralizing antibody response, e.g., the human anti-murine antibody (HAMA) response. HAMA can be problematic in a number of circumstances, e.g., if the antibodies are desired to be administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain (VL) and a constant (C) domain (CL). Each heavy chain includes an N-terminal V domain (VH), three or four C domains (CHs), and a hinge region. The CH domain most proximal to VH is designated as CH1. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) *J. Mol. Biol.* 227:799-817; and Tomlinson et al. (1995) *EMBO J.* 14:4628-4638. Still another standard is the AbM definition used by Oxford Molecular's AbM antibody modelling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

Examples of binding fragments encompassed within the term "antigen-binding fragment" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-46), which consists of a VH domain; and (vi) an isolated complementarity determining region (CDR). Camelid antibodies, and camelized antibodies can also be used. Such antibodies, e.g., can include CDRs from just one of the variable domains described herein. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) *Science* 242:423-26; Huston et al. (1988) *Proc. Natl. Acad. Sci. U.S.A.* 85:5879-83). Such single chain antibodies are also intended to be encompassed within the term "antigen-binding fragment" of an antibody. These antibody fragments are obtained using conventional techniques known to those skilled in the art, and the fragments are evaluated for function in the same manner as are intact antibodies.

Antibody diversity, in a natural system, is created by the use of multiple germline genes encoding variable regions and a variety of somatic events. The somatic events include recombination of variable gene segments with diversity (D) and joining (J) gene segments to make a complete VH region, and the recombination of variable and joining gene segments to make a complete VL region. The recombination process itself can be imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies could be produced (Fundamental Immunology, 3rd ed. (1993), ed. Paul, Raven Press, New York, N.Y.). When other processes that contribute to antibody diversity (such as somatic mutation) are taken into account, it is thought that upwards of $10^{10}$ different antibodies could be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Thus, this disclosure provides, inter alia, antibodies, and antigen-binding fragments thereof, that bind to IL-13 and, e.g., interfere with the formation of a functional IL-13 signaling complex. The antigen-binding fragments described herein, e.g., structures containing a CDR, will generally be an antibody heavy or light chain sequence, or an active fragment thereof, in which the CDR is placed at a location corresponding to the CDR of naturally occurring VH and VL. The structures and locations of immunoglobulin variable domains may be determined as described in Sequences of Proteins of Immunological Interest, U.S. Department of Health and Human Services (1991), eds. Kabat et al.

Antibody molecules (including antigen-binding fragments) disclosed herein, i.e., antibody molecules that bind to IL-13 and interfere with the formation of a functional IL-13 signaling complex, include, but are not limited to, murine monoclonal antibody, mAb13.2, and its variants, specifically the chimeric variant ch13.2, the partially humanized variant h13.2v1, and the fully humanized variants h13.2v2 and h13.2v3. These antibody molecules may be useful in preventing or treating asthma (both allergic and nonallergic), as well as asthma-related pathologies. The amino acid sequences of the light chain variable regions of mAb13.2, ch13.2, h13.2v1, h13.2v2, and h13.2v3 are set forth in SEQ ID NOs:9, 10, 11, 12, and 35, respectively. The amino acid sequences of the heavy chain variable regions of mAb13.2, ch13.2, h13.2v1, h13.2v2, and h13.2v3 are set forth in SEQ ID NOs:13, 14, 15, 16, and 36, respectively. The amino acid sequences of the three complementarity determining regions (CDRs) in the variable light chains of mAb13.2, ch13.2, h13.2v1, h13.2v2, and h13.2v3 are set forth in SEQ ID NOs:19, 20, and 21. The amino acid sequences of the three CDRs in the variable heavy chains of mAb13.2, ch13.2, h13.2v1, h13.2v2, and h13.2v3 are set forth in SEQ ID NOs:22, 23, and 24.

As described above, the CDRs contain most of the residues responsible for specific interactions with the antigen, and are contained within the VH and VL domains, i.e., the heavy chain variable region and the light chain variable region, respectively. Exemplary antibodies include at least one CDR comprising an amino acid sequence selected from the amino acid sequences set forth in SEQ ID NOs:19-24, or selected residues, particularly IL-13 contact residues from such CDRs. Such antibodies may also bind to IL-13 and, e.g., interfere with the formation of a functional IL-13 signaling complex. The amino acid sequences of the active fragments of the CDRs, i.e., the minimum core CDR sequences, described herein are set forth in SEQ ID NOs:25-30, and are disclosed in Table 1. An antibody may include one or more CDRs of the VL chain as set forth in SEQ ID NOs:19-21 or SEQ ID NOs: 25-27. An antibody may include one or more CDRs of the VH chain as set forth in SEQ ID NOs:22-24 or SEQ ID NOs: 28-30. Additionally, an antibody may include one or more of the CDRs of the VL and VH chain has an amino acid sequence selected from the amino acid sequences set forth in SEQ ID NOs:19-30. As shown, X can be any amino acid, e.g., a non-cysteine amino acid, or an amino acid that is has a similar charge, hydrophobicity, and/or side chain length, as the amino acid at the corresponding position in the left hand column of Table 1.

TABLE 1

Exemplary CDRs

| CDR sequence | Minimum core CDR sequence |
|---|---|
| Light chain CDR1 (L1) | |
| SEQ ID NO: 19 24-KASESVDNYGKSLMH-38[1] | SEQ ID NO: 25 24-xxxxxxxNYxKxxxx-38 |
| Light chain CDR2 (L2) | |
| SEQ ID NO: 20 54-RASNLES-60 | SEQ ID NO: 26 54-Rxxxxxx-60 |
| Light chain CDR3 (L3) | |
| SEQ ID NO: 21 93-QQSNEDPWT-101 | SEQ ID NO: 27 93-xxxNxDxWx-101 |

TABLE 1-continued

Exemplary CDRs

| CDR sequence | Minimum core CDR sequence |
|---|---|
| Heavy chain CDR1 (H1) | |
| SEQ ID NO: 22 31-SYAMS-35[2] | SEQ ID NO: 28 |
| Heavy chain CDR2 (H2) | |
| SEQ ID NO: 23 50-SISSGGNTYYPDSVKG-65 | SEQ ID NO: 29 50-SxSSxxxxxYxxxxxx-65 |
| Heavy chain CDR3 (H3) | |
| SEQ ID NO: 24 98-LDGYYFGFAY-107 | SEQ ID NO: 30 98-LDGYYFxxxx-107 |

[1]Numbering for VL CDRs is according to a linear sequence numbering scheme as in FIG. 30.
[2]Numbering for VH CDRS is according to a linear sequence numbering scheme as in FIG. 29.

Also described above, an antigen-binding fragment may be an Fv fragment, which includes VH and VL domains. Thus, an Fv fragment of mAb13.3, ch13.2, h13.2v1, h13.2v2 or h13.2v3 may constitute an antibody described herein. It may bind to IL-13 and interfere with the formation of a functional IL-13 signaling complex. Other fragments include the Fv fragment, e.g., scFv fragments, Fab fragments, and F(ab')2 fragments of the mAb13.3, ch13.2, h13.2v1, h13.2v2, or h13.2v3 antibodies or of an antibody that includes one or more CDRs having an amino acid sequence selected from the amino acid sequences set forth in SEQ ID NOs: 19-30.

Such antibody molecules may be produced by methods known to those skilled in the art. For example, monoclonal antibodies may be produced by generation of hybridomas in accordance with known methods. Hybridomas formed in this manner are then screened using standard methods, such as enzyme-linked immunosorbent assay (ELISA) and surface plasmon resonance (Biacore™) analysis, to identify one or more hybridomas that produce an antibody that specifically binds with IL-13, interferes with the formation of a functional IL-13 signaling complex, and neutralizes one or more IL-13-associated activities. Recombinant IL-13, naturally occurring IL-13 (i.e., the processed mature form of IL-13), any variants thereof, and antigenic peptide fragments of IL-13 may be used as the immunogen.

An antigenic peptide fragment of IL-13 can comprise at least 7 continuous amino acid residues and encompasses an epitope such that an antibody raised against the peptide forms a specific immune complex with IL-13. Preferably, the antigenic peptide comprises at least 10 amino acid residues, more preferably at least 15 amino acid residues, even more preferably at least 20 amino acid residues, and most preferably at least 30 amino acid residues. Additionally, it is preferable that the antigenic peptide fragment of IL-13 comprises the IL-13 receptor-binding site or IL-4 receptor binding site.

As an alternative to preparing monoclonal antibody-secreting hybridomas, a monoclonal antibody may be identified and isolated by screening a recombinant combinatorial immunoglobulin library (e.g., an antibody phage display library) with IL-13, including variants and/or portions thereof, to thereby isolate immunoglobulin library members that bind to IL-13. Techniques and commercially available kits for generating and screening phage display libraries are known to those skilled in the art. Additionally, examples of methods and reagents particularly amenable for use in generating and screening antibody display include those described in U.S. Pat. Nos. 5,658,727, 5,667,988, and 5,885,793.

Polyclonal sera and antibodies described herein may be produced by immunizing a suitable subject with IL-13, its variants and/or portions thereof. The antibody titer in the immunized subject may be monitored over time by standard techniques, such as an Enzyme Linked immunosorbent Assay (ELISA), using immobilized IL-13 or other marker proteins (e.g., FLAG). Antibodies may be isolated from an animal or culture media. A variety of methods can be used to purify antibodies including well-known techniques, such as use of protein A chromatography to obtain an IgG fraction.

Certain embodiments comprise the VH and/or VL domain of the Fv fragment of mAb13.2, ch13.2, h13.2v1, h13.2v2 or h13.2v3. Fragments of antibodies e.g., Fab, F(ab')2, Fd, and dAb fragments, may be produced by cleavage of the antibodies or by recombinant engineering. For example, immunologically active Fab and F(ab')2 fragments may be generated by treating the antibodies with an enzyme such as pepsin.

Further embodiments comprise one or more complementarity determining regions (CDRs) of any of these VH and VL domains, as set forth in SEQ ID NOs:19-30. One embodiment comprises an H3 fragment of the VH domain of mAb13.2, ch13.2, h13.2v1, h13.2v2, or h13.2v3.

The VH and VL domains described herein, in certain embodiments, can be germlined, i.e., the framework regions (FRs) of these domains may be changed using conventional molecular biology techniques to match human germline genes or the consensus amino acid sequences of human germline gene products, at one or more positions (e.g., at at least 70, 80, 85, 90, 95, 97, 98, or 99% of framework positions). In other embodiments, the framework sequences remain diverged from the germline.

Human germline sequences, for example, are disclosed in Tomlinson, I. A. et al. (1992) *J. Mol. Biol.* 227:776-798; Cook, G. P. et al. (1995) *Immunol. Today* Vol. 16 (5): 237-242; Chothia, D. et al. (1992) *J. Mol. Biol.* 227:799-817; and Tomlinson et al. (1995) *EMBO J.* 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

Additionally, chimeric, humanized, and single-chain antibodies described herein, comprising both human and nonhuman portions, may be produced using standard recombinant DNA techniques, as described in more detail in the Examples. Humanized antibodies may also be produced using transgenic mice that express human heavy and light chain genes, but are incapable of expressing the endogenous mouse immunoglobulin heavy and light chain genes.

Additionally, the antibodies described herein also include those that bind to IL-13, interfere with the formation of a functional IL-13 signaling complex, and have mutations in the constant regions of the heavy and light chains. It is sometimes desirable to mutate and inactivate certain fragments of the constant region. For example, mutations in the heavy constant region can be made to produce antibodies with reduced binding to the Fc receptor (FcR) and/or complement; such mutations are well known in the art. An example of such a mutation to the amino sequence of the constant region of the heavy chain of IgG is provided in SEQ ID NO:17. Certain active fragments of the CL and CH subunits (e.g., CH1) are covalently link to each other. A further aspect provides a method for obtaining an antibody antigen-binding domain specific for domain of IL-13 that aids formation of a functional IL-13 signaling complex.

Exemplary antibodies can include sequences of VL chains as set forth in SEQ ID NOs:9, 10, 11, 12, or 35, and/or of VH chains as set forth in and SEQ ID NOs: 13, 14, 15, 16, or 36, but also can include variants of these sequences that retain antigen-binding ability. Such variants may be derived from the provided sequences using techniques well known in the art. Amino acid substitutions, deletions, or additions, can be made in either the FRs or in the CDRs. While changes in the framework regions are usually designed to improve stability and reduce immunogenicity of the antibody, changes in the CDRs are usually designed to increase affinity of the antibody for its target. Such affinity-increasing changes are typically determined empirically by altering the CDR region and testing the antibody. Such alterations can be made according to the methods described in Antibody Engineering, 2nd. ed. (1995), ed. Borrebaeck, Oxford University Press.

An exemplary method for making a VH domain, which is an amino acid sequence variant of a VH domain set out herein, comprises a step of adding, deleting, substituting or inserting one or more amino acids in the amino acid sequence of the presently disclosed VH domain, optionally combining the VH domain thus provided with one or more VL domains, and testing the VH domain or VH/VL combination or combinations for specific binding to IL-13, and (preferably) testing the ability of such antigen-binding domain to modulate one or more IL-13-associated activities. The VL domain may have an amino acid sequence that is substantially as set out herein. An analogous method may be employed in which one or more sequence variants of a VL domain disclosed herein are combined with one or more VH domains.

A further aspect of the invention provides a method of preparing an antigen-binding fragment that specifically binds to IL-13. The method comprises: (a) providing a starting repertoire of nucleic acids encoding a VH domain that either includes a CDR3 to be replaced or lacks a CDR3 encoding region; (b) combining the repertoire with a donor nucleic acid encoding a donor CDR comprising an active fragment of SEQ ID NO:24, e.g., a donor nucleic acid encoding the amino acid sequence set forth in SEQ ID NO:30, such that the donor nucleic acid is inserted into the CDR3 region in the repertoire so as to provide a product repertoire of nucleic acids encoding a VH domain; (c) expressing the nucleic acids of the product repertoire; (d) selecting a specific antibody or antigen-binding fragment specific for IL-13; and (e) recovering the specific antibody or antigen-binding fragment or nucleic acid encoding it.

In another embodiment, an analogous method may be employed in which a VL CDR3 (i.e., L3) described herein is combined with a repertoire of nucleic acids encoding a VL domain, which either includes a CDR3 to be replaced or lacks a CDR3-encoding region. A coding sequence of a CDR described herein (e.g., CDR3) may be introduced into a repertoire of variable domains lacking a CDR (e.g., CDR3), using recombinant DNA technology. For example, Marks et al. (*Bio/Technology* (1992) 10:779-83) describes methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. The repertoire may be combined with a CDR3 of a particular antibody. Using analogous techniques, the CDR3-derived sequences may be shuffled with repertoires of VH or VL domains lacking a CDR3, and the shuffled complete VH or VL domains combined with a cognate VL or VH domain to provide specific antigen-binding fragments. The repertoire may then be displayed in a suitable host system such as the phage display system of WO 92/01047, so that suitable antigen-binding fragments can be selected. Analogous shuffling or combinatorial techniques are also disclosed by Stemmer (*Nature* (1994) 370:389-91). A further alternative is to generate altered VH or VL regions using random mutagenesis of one or more selected VH and/or VL genes to generate mutations within the entire variable domain. See, e.g., Gram et al. *Proc. Nat. Acad. Sci. U.S.A.* (1992) 89:3576-80.

Another method that may be used is to direct mutagenesis to CDR regions of VH or VL genes. Such techniques are disclosed by, e.g., Barbas et al. (*Proc. Nat. Acad. Sci. U.S.A.* (1994) 91:3809-13) and Schier et al. (*J. Mol. Biol.* (1996) 263:551-67). Similarly, one or more, or all three CDRs may be grafted into a repertoire of VH or VL domains, or even some other scaffold (such as a fibronectin domain). The resulting protein is evaluated for ability to bind to IL-13.

In one embodiment, a binding protein that binds to a target is modified, e.g., by mutagenesis, to provide a pool of modified binding proteins. The modified binding proteins are then evaluated to identify one or more altered binding proteins which have altered functional properties (e.g., improved binding, improved stability, lengthened stability in vivo). In one implementation, display library technology is used to select or screen the pool of modified binding proteins. Higher affinity binding proteins are then identified from the second library, e.g., by using higher stringency or more competitive binding and washing conditions. Other screening techniques can also be used.

In some embodiments, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particular within 10, 5, or 3 amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, an antibody or fragment thereof has CDR sequences that differ only insubstantially from those of the antibodies described herein. Insubstantial differences include minor amino acid changes, such as substitutions of 1 or 2 out of any of typically 5-7 amino acids in the sequence of a CDR, e.g., a Chothia or Kabat CDR. Typically an amino acid is substituted by a related amino acid having similar charge, hydrophobic, or stereochemical characteristics. Such substitutions would be within the ordinary skills of an artisan. Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) *J. Immunol.* 147:2657-62; Morgan et al. (1995) *Immunology* 86:319-24), or changing the species from which the constant region is derived. Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. In the IgG1 or IgG2 heavy chain, for example, such mutations may be made to resemble the amino acid sequence set forth in SEQ ID NO:17. Antibodies may also have mutations that stabilize the disulfide bond between the two heavy chains of an immunoglobulin, such as mutations in the hinge region of IgG4, as disclosed in the art (e.g., Angal et al. (1993) *Mol. Immunol.* 30:105-08).

The IL-13 binding proteins can be in the form of intact antibodies, fragments of antibodies, e.g., Fab, F(ab')2, Fd, dAb, and scFv fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced IL 13 binding and/or reduced FcR binding).

In some embodiments, a substantial portion of an immunoglobulin variable domain can comprise at least one of the CDR regions and, optionally, their intervening framework regions from the variable regions as set out herein. The portion will also include at least about 50, 60, 70, 80, 85, 87, 88, 90, 92, 94, 95, 96, 97, 98% of either or both of FR1 and FR4. For example, the portion which may be contiguous or non-contiguous may include the C-terminal 50% of FR1 and the N-terminal 50% of FR4. Additional residues at the N-terminal or C-terminal end of the substantial part of the variable domain may be those not normally associated with naturally occurring variable domain regions. For example, construction of specific antigen-binding fragments made by recombinant DNA techniques may result in the introduction of N- or C-terminal residues encoded by linkers introduced to facilitate cloning or other manipulation steps. Other manipulation steps include the introduction of linkers to join variable domains described herein to further protein sequences, including immunoglobulin heavy chains, other variable domains (e.g., in the production of diabodies) or protein labels as discussed in more detail below.

Although the embodiments illustrated in the Examples comprise a "matching" pair of VH and VL domains, the invention also encompasses binding fragments containing a single variable domain derived from either VH or VL domain sequences, especially VH domains. In the case of either of the single-chain specific binding domains, these domains may be used to screen for complementary domains capable of forming a two-domain specific antigen-binding domain capable of binding IL-13. This may be achieved by phage display screening methods using the so-called hierarchical dual combinatorial approach (as disclosed in, e.g., WO 92/01047) in which an individual colony containing either an H or L chain clone is used to infect a complete library of clones encoding the other chain (L or H) and the resulting two-chain specific antigen-binding domain is selected in accordance with phage display techniques such as those described in that reference. This technique is also disclosed in Marks et al., supra. Antibodies can be conjugated by chemical methods with radionuclides, drugs, macromolecules, or other agents, or can be made as fusion proteins comprising one or more CDRs described herein.

An antibody fusion protein contains a VH-VL pair where one of these chains (usually VH) and another protein are synthesized as a single polypeptide chain. These types of products differ from antibodies in that they generally have an additional functional element: e.g., the active moiety of a small molecule or the principal molecular structural feature of the conjugated or fused macromolecule.

In addition to the changes to the amino acid sequence outlined above, the antibodies can be glycosylated, pegylated, or linked to albumin or a nonproteinaceous polymer. For instance, the presently disclosed antibodies may be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or U.S. Pat. No. 4,179,337. The antibodies are chemically modified by covalent conjugation to a polymer to increase their circulating half-life, for example. Exemplary polymers, and methods to attach them to peptides, are also shown in U.S. Pat. Nos. 4,766,106; 4,179,337; 4,495,285; and 4,609,546.

In other embodiments, the antibody may be modified to have an altered glycosylation pattern (e.g., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston ((1981) *CRC Crit. Rev. Biochem.* 22:259-306). Removal of any carbohydrate moieties present on the antibodies may be accomplished chemically or enzymatically as described in the art (Hakimuddin et al. (1987) *Arch. Biochem. Biophys.* 259:52; Edge et al. (1981) *Anal. Biochem.* 118:131; and Thotakura et al. (1987) *Meth. Enzymol.* 138: 350). See, e.g., U.S. Pat. No. 5,869,046 for a modification that increases in vivo half life by providing a salvage receptor binding epitope.

Antibodies described herein may also be tagged with a detectable or functional label. Detectable labels include radiolabels such as $^{131}$I or $^{99}$Tc, which may be attached to antibodies described herein using conventional chemistry known in the art. Labels also include enzyme labels such as horseradish peroxidase or alkaline phosphatase. Labels further include chemical moieties such as biotin, which may be detected via binding to a specific cognate detectable moiety, e.g., labeled avidin.

The binding characteristics of an antibody disclosed herein may be measured by any suitable methods, including the following methods: Biacore analysis, Enzyme Linked Immunosorbent Assay (ELISA), x-ray crystallography, sequence analysis and scanning mutagenesis as described in the Examples below, and other methods that are well known in the art. The ability of an antibody described herein to neutralize and/or inhibit one or more IL-13-associated activities may be measured by the following methods: assays for measuring the proliferation of an IL-13 dependent cell line, e.g. TFI; assays for measuring the expression of IL-13-mediated polypeptides, e.g., flow cytometric analysis of the expression of CD23; assays measuring the activity of downstream signaling molecules, e.g., STAT6; assays testing the efficiency of an antibody described herein to prevent asthma in a relevant animal model, e.g., the cynomolgus monkey; as described in the Examples below, and other assays that are well known in the art.

The binding interaction of a protein of interest and a target (e.g., IL-13) can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant (Kd), and kinetic parameters, including Kon and Koff, for the binding of a biomolecule to a target. Such data can be used to compare different biomolecules. For example, proteins encoded by nucleic acid selected from a library of diversity strands can be compared to identify individuals that have high affinity for the target or that have a slow Koff. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow Koff. This information can be combined with structural modeling (e.g., using homology modeling, energy minimization, or structure determination by x-ray crystallography or NMR). As a result, an understanding of the physical interaction between the protein and its target can be formulated and used to guide other design processes.

In a further aspect, this disclosure provides a method of selecting antibodies capable of binding IL-13 and neutralizing and/or inhibiting one or more IL-13-associated activities. The method comprises: a) contracting a plurality of antibodies or antigen binding fragments with IL-13; b) choosing antibodies or antigen binding fragments that bind to IL-13; c) testing the ability of chosen antibodies or antigen binding fragments to prevent IL-13 from binding to the IL-13 receptor; and d) selecting one or more antibodies or antigen binding fragments capable of preventing IL-13 from binding to its receptor. One or more antibodies can be further modified if desired. One or more such antibodies can be formulated, e.g., as a pharmaceutical composition.

The anti-IL-13 antibodies disclosed herein are also useful for isolating, purifying, and/or detecting IL-13 in supernatant, cellular lysate, or on the cell surface. Antibodies disclosed herein can be used diagnostically to monitor IL-13 protein levels as part of a clinical testing procedure. Additionally, antibodies disclosed herein can be used in treatments requiring the neutralization and/or inhibition of one or more IL-13-associated activities, e.g. allergic or nonallergic asthma, and related pathologies. The present disclosure also provides novel isolated and purified polynucleotides and polypeptides related to novel antibodies directed against human IL-13. The genes, polynucleotides, proteins, and polypeptides disclosed herein include, but are not limited to, a murine antibody to IL-13 (mAb13.2) and variants thereof.

Anti-IL-13 Antibody Polynucleotides and Polypeptides

For example, the disclosure provides purified and isolated polynucleotides encoding the variable region of a murine antibody to IL-13 that modulates one or more IL-13-associated activities (e.g., neutralizes IL-13 bioactivity) (mAb13.2), a chimeric version of mAb13.2 (ch13.2), a partially humanized version of mAb13.2 (h13.2v1) and two fully humanized versions of mAb13.2 (h13.2v2 and h13.2v3).

The nucleotide sequences can include those that encode the light chain variable regions of mAb13.2, ch13.2, h13.2v1, h13.2v2, and h13.2v3 and are set forth in SEQ ID NO:1, SEQ ID NO:2, SEQ ID NO:3, SEQ ID NO:4, and SEQ ID NO:33, respectively. The nucleotide sequences can also include those that encode the heavy chain variable regions of mAb13.2, ch13.2, h13.2v1, h13.2v2, and h13.3v3 and are set forth in SEQ ID NO:5, SEQ ID NO:6, SEQ ID NO:7, SEQ ID NO:8, and SEQ ID NO:34, respectively. The polynucleotides can also include polynucleotides that hybridize under stringent conditions to any of the sequences set forth in SEQ ID NOs: 1-8, 33, and 34, or complements thereof, and/or that encode polypeptides that retain substantial biological activity (i.e., active fragments) of the variable regions encoded by these sequences. The polynucleotides can also include continuous portions of the any of the sequences set forth in SEQ ID NOs:1-8, 33, and 34, comprising at least 21 consecutive nucleotides. Table 2 summarizes the SEQ ID NOs for the nucleotide sequences of several exemplary polynucleotides.

TABLE 2

| | Sequence Identification Numbers (SEQ ID NOs) of Polynucleotides of the Invention | | | | |
|---|---|---|---|---|---|
| | mAB13.2 | ch13.2 | h13.2v1 | h13.2v2 | h13.2v3 |
| VL region | SEQ ID NO: 1 | SEQ ID NO: 2 | SEQ ID NO: 3 | SEQ ID NO: 4 | SEQ ID NO: 33 |
| VH region | SEQ ID NO: 5 | SEQ ID NO: 6 | SEQ ID NO: 7 | SEQ ID NO: 8 | SEQ ID NO: 34 |

The amino acid sequences of the light chain variable regions of mAb13.2, ch13.2, h13.2v1, h13.2v2, and h13.2v3 are set forth in SEQ ID NOs:9, 10, 11, 12, and 35, respectively. The amino acid sequences of the heavy chain variable regions of mAb13.2, ch13.2, h13.2v1, h13.2v2, and h13.2v3 are set forth in SEQ ID NOs:13, 14, 15, 16, and 36, respectively. Polypeptides disclosed herein also include continuous portions of any of the sequences set forth in SEQ ID NOs:9-16, 35, and 36 comprising at least 4 consecutive amino acids and that retain substantial biological activity (i.e., active fragments) of these variable regions. Preferably, polypeptides of the present application include continuous portions of any of the sequences set forth in SEQ ID NOs:9-16, 35, and 36 comprising 5-7 amino acids. More preferred polypeptides of the present application include any continuous portion of the any of sequences set forth in SEQ ID NOs:9 and 13, SEQ ID NOs:10 and 14, SEQ ID NOs:11 and 15, SEQ ID NOs:12 and 16, and SEQ ID NOs:35 and 36 that retains substantial biological activity of mAb13.2, ch13.2, h13.2v1, h13.2v2, and h13.2v3, respectively. Polynucleotides disclosed herein also include, in addition to those polynucleotides described above, polynucleotides that encode any of the amino acid sequences set forth in SEQ ID NOs:9-16, 35 and 36, or a continuous portion thereof, and that differ from the polynucleotides described above only due to the well-known degeneracy of the genetic code. Table 3 summarizes the SEQ ID NOs for the amino acid sequences of several of the polypeptides disclosed herein. For example, Table 3 summarizes the SEQ ID NOs for the amino acid sequences for variable light chains (VL), variable heavy chains (VH), constant heavy chains (CH), constant light chains (CL), CDR1s of the variable light chains (L1), CDR2s of the variable light chains (L2), CDR3s of the variable light chains (L3), CDR1s of the variable heavy chains (H1), CDR2s of the variable heavy chains (H2), and CDR3s of the variable heavy chains (H3) of the antibodies mAb13.2, ch13.2, h13.2v1, h13.2v2 and h13.2v3.

TABLE 3

| | Sequence ID Numbers (SEQ ID NOs) of exemplary polypeptides | | | | |
|---|---|---|---|---|---|
| | mAb13.2 | ch13.2 | h13.2v1 | h13.2v2 | h13.2v3 |
| VL | SEQ ID NO: 9 | SEQ ID NO: 10 | SEQ ID NO: 11 | SEQ ID NO: 12 | SEQ ID NO: 35 |
| VH | SEQ ID NO: 13 | SEQ ID NO: 14 | SEQ ID NO: 15 | SEQ ID NO: 16 | SEQ ID NO: 36 |
| CH | | SEQ ID NO: 17 | SEQ ID NO: 17 | SEQ ID NO: 17 | SEQ ID NO: 17 |
| CL | | SEQ ID NO: 18 | SEQ ID NO: 18 | SEQ ID NO: 18 | SEQ ID NO: 18 |
| L1 | SEQ ID NO: 19 | SEQ ID NO: 19 | SEQ ID NO: 19 | SEQ ID NO: 19 | SEQ ID NO: 19 |
| L2 | SEQ ID NO: 20 | SEQ ID NO: 20 | SEQ ID NO: 20 | SEQ ID NO: 20 | SEQ ID NO: 20 |
| L3 | SEQ ID NO: 21 | SEQ ID NO: 21 | SEQ ID NO: 21 | SEQ ID NO: 21 | SEQ ID NO: 21 |
| H1 | SEQ ID NO: 22 | SEQ ID NO: 22 | SEQ ID NO: 22 | SEQ ID NO: 22 | SEQ ID NO: 22 |

TABLE 3-continued

Sequence ID Numbers (SEQ ID NOs) of exemplary polypeptides

|    | mAb13.2       | ch13.2        | h13.2v1       | h13.2v2       | h13.2v3       |
|----|---------------|---------------|---------------|---------------|---------------|
| H2 | SEQ ID NO: 23 | SEQ ID NO: 23 | SEQ ID NO: 23 | SEQ ID NO: 23 | SEQ ID NO: 23 |
| H3 | SEQ ID NO: 24 | SEQ ID NO: 24 | SEQ ID NO: 24 | SEQ ID NO: 24 | SEQ ID NO: 24 |

The isolated polynucleotides disclosed herein may be used as hybridization probes and primers to identify and isolate nucleic acids having sequences identical to or similar to those encoding the disclosed polynucleotides. Hybridization methods for identifying and isolating nucleic acids include polymerase chain reaction (PCR), Southern hybridization, in situ hybridization and Northern hybridization, and are well known to those skilled in the art.

Hybridization reactions can be performed under conditions of different stringency. The stringency of a hybridization reaction includes the difficulty with which any two nucleic acid molecules will hybridize to one another. Preferably, each hybridizing polynucleotide hybridizes to its corresponding polynucleotide under reduced stringency conditions, more preferably stringent conditions, and most preferably highly stringent conditions. Examples of stringency conditions are shown in Table 4 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 4

| Stringency Condition | Poly- nucleotide Hybrid | Hybrid Length (bp)[1] | Hybridization Temperature and Buffer[2] | Wash Temperature and Buffer[2] |
|---|---|---|---|---|
| A | DNA:DNA | >50 | 65° C.; 1X SSC -or- 42° C.; 1X SSC, 50% formamide | 65° C.; 0.3X SSC |
| B | DNA:DNA | <50 | $T_B$*; 1X SSC | $T_B$*; 1X SSC |
| C | DNA:RNA | >50 | 67° C.; 1X SSC -or- 45° C.; 1X SSC, 50% formamide | 67° C.; 0.3X SSC |
| D | DNA:RNA | <50 | $T_D$*; 1X SSC | $T_D$*; 1X SSC |
| E | RNA:RNA | >50 | 70° C.; 1X SSC -or- 50° C.; 1X SSC, 50% formamide | 70° C.; 0.3X SSC |
| F | RNA:RNA | <50 | $T_F$*; 1X SSC | $T_F$*; 1X SSC |
| G | DNA:DNA | >50 | 65° C.; 4X SSC -or- 42° C.; 4X SSC, 50% formamide | 65° C.; 1X SSC |
| H | DNA:DNA | <50 | $T_H$*; 4X SSC | $T_H$*; 4X SSC |
| I | DNA:RNA | >50 | 67° C.; 4X SSC -or- 45° C.; 4X SSC, 50% formamide | 67° C.; 1X SSC |
| J | DNA:RNA | <50 | $T_J$*; 4X SSC | $T_J$*; 4X SSC |
| K | RNA:RNA | >50 | 70° C.; 4X SSC -or- 50° C.; 4X SSC, 50% formamide | 67° C.; 1X SSC |
| L | RNA:RNA | <50 | $T_L$*; 2X SSC | $T_L$*; 2X SSC |
| M | DNA:DNA | >50 | 50° C.; 4X SSC -or- 40° C.; 6X SSC, 50% formamide | 50° C.; 2X SSC |
| N | DNA:DNA | <50 | $T_N$*; 6X SSC | $T_N$*; 6X SSC |
| O | DNA:RNA | >50 | 55° C.; 4X SSC -or- 42° C.; 6X SSC, 50% formamide | 55° C.; 2X SSC |
| P | DNA:RNA | <50 | $T_P$*; 6X SSC | $T_P$*; 6X SSC |
| Q | RNA:RNA | >50 | 60° C.; 4X SSC -or- 45° C.; 6X SSC, 50% formamide | 60° C.; 2X SSC |
| R | RNA:RNA | <50 | $T_R$*; 4X SSC | $T_R$*; 4X SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[2]SSPE (1xSSPE is 0.15 M NaCl, 10 mM NaH$_2$PO$_4$, and 1.25 mM EDTA, pH 7.4) can be substituted for SSC (1xSSC is 0.15 M NaCl and 15 mM sodium citrate) in the hybridization and wash buffers; washes are performed for 15 min after hybridization is complete.
$T_B$*–$T_R$*: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6 (log$_{10}$Na$^+$) + 0.41 (% G + C) − (600/N), where N is the number of bases in the hybrid, and Na$^+$ is the concentration of sodium ions in the hybridization buffer (Na$^+$ for 1X SSC = 0.165 M). Additional examples of stringency conditions for polynucleotide hybridization are provided in Sambrook et al., Molecular Cloning: A Laboratory Manual, Chs. 9 & 11, Cold Spring Harbor Laboratory Press, Cold Spring Harbor, NY (1989), and Ausubel et al., eds., Current Protocols in Molecular Biology, sects. 2.10 & 6.3–6.4, John Wiley & Sons, Inc. (1995), herein incorporated by reference.

The isolated polynucleotides disclosed herein may be used as hybridization probes and primers to identify and isolate DNA having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least 90% sequence identity (more preferably, at least 95% identity; most preferably, at least 99% identity) with the disclosed polynucleotides.

The isolated polynucleotides disclosed herein may also be used as hybridization probes and primers to identify and isolate DNAs having sequences encoding polypeptides homologous to the disclosed polynucleotides. These homologs are polynucleotides and polypeptides isolated from a different species than that of the disclosed polypeptides and polynucleotides, or within the same species, but with significant sequence similarity to the disclosed polynucleotides and polypeptides. Preferably, polynucleotide homologs have at least 50%, 70%, 75%, 80%, 85%, 87%, 89%, 90%, 91%, 92%, 93%, 94%, 95%, 96%, 97%, 98%, or 99%, sequence with the disclosed polynucleotides The isolated polynucleotides disclosed herein may also be used as hybridization probes and primers to identify cells and tissues that express the antibodies and the conditions under which they are expressed.

The isolated polynucleotides disclosed herein may be operably linked to an expression control sequence for recombinant production of the polypeptides described herein. A polynucleotide can be operably linked to a nucleotide sequence encoding a constant region, e.g., a constant region of one of the various antibody isotypes. For example, a polynucleotide that encodes a light chain variable region disclosed herein (e.g., any one of those set forth in SEQ ID NOs:1-4, and 33) may be operably linked to a nucleotide sequence that encodes the constant region (or derivatives thereof) of either a kappa light chain (e.g., as set forth in SEQ ID NO:18) or lambda light chain, such that the expression of the linked nucleotides will result in a full kappa or lambda light chain with a variable region that specifically binds to IL-13, interferes with the formation of a functional IL-13 signaling complex, and neutralizes one or more IL-13-associated activities. Similarly, a polynucleotide that encodes a heavy chain variable region disclosed herein (e.g., any of those set forth in SEQ ID NOs:5-8, and 34) may be operably linked to a nucleotide sequence that encodes the constant region of a heavy chain isotype (or derivatives thereof), e.g., IgM, IgD, IgE, IgG and IgA. General methods of expressing recombinant proteins are well known in the art. Such recombinant proteins may be expressed in soluble form for use in treatment of disorders resulting from IL-13-mediated signaling (e.g., allergic and nonallergic asthma).

The recombinant expression vectors disclosed herein may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017). For example, typically the selectable marker gene confers resistance to a drug, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

A number of cell lines are suitable host cells for recombinant expression. Mammalian host cell lines include, for example, COS cells, CHO cells, 293T cells, A431 cells, 3T3 cells, CV-1 cells, HeLa cells, L cells, BHK21 cells, HL-60 cells, U937 cells, HaK cells, Jurkat cells, as well as cell strains derived from in vitro culture of primary tissue and primary explants.

Alternatively, it may be possible to recombinantly produce polypeptides in lower eukaryotes such as yeast (e.g., *Saccharomyces, Pichia, Kluyveromyces* strains, and *Candida* strains) or in prokaryotes (e.g., *Escherichia coli, Bacillus subtilis*, and *Salmonella typhimurium*). Polypeptides made in yeast or bacteria can be modified, e.g., glycosylation of appropriate sites Polypeptides can also be produced in animal cells, e.g., insect or mammalian cells. For example, a sequence encoding the polypeptide can be inserted into an insect expression vector, such as a baculovirus vector, and used in an insect cell expression system (e.g., the MAXBAC® kit, Invitrogen, Carlsbad, Calif.).

The polypeptides disclosed herein may then be purified from culture medium or cell extracts using known purification processes, such as gel filtration and ion exchange chromatography. Purification may also include affinity chromatography with agents known to bind the polypeptides disclosed herein.

Alternatively, the polypeptides disclosed herein may also be recombinantly expressed in a form that facilitates purification. For example, the polypeptides may be expressed as fusions with proteins such as maltose-binding protein (MBP), glutathione-S-transferase (GST), or thioredoxin (TRX) or as fusions to hexa-histidine, penta-histidine, or small epitope tags, e.g., the FLAG epitope.

The polypeptides disclosed herein also encompass molecules that are structurally different from the disclosed polypeptides (e.g., which have a slightly altered sequence), but which have substantially the same biochemical properties as the disclosed polypeptides (e.g., are changed only in functionally nonessential amino acid residues). Such molecules include naturally occurring allelic variants and deliberately engineered variants containing alterations, substitutions, replacements, insertions, or deletions. Techniques for such alterations, substitutions, replacements, insertions, or deletions are well known to those skilled in the art.

IL-13 Binding Agents

Also provided are binding agents, other than binding agents that are antibodies and fragments thereof, that bind to IL-13, particularly binding agents that compete with mAb13.2 and other antibodies described herein for binding to IL-13. For example, the binding agents can bind to the same epitope or an overlapping epitope as mAb13.2 on IL-13. The binding agents preferably inhibit or neutralize IL-13 activity. For example, the binding agents inhibit binding of IL-13 to IL-4Rα, and, e.g., does not prevent binding of IL-13 to IL-13Rα1. Such binding agents can be used in the methods described herein, e.g., the methods of treating and preventing disorders. All embodiments described herein can be adapted for use with IL-13 binding agents.

Binding agents can be identified by a number of means, including modifying a variable domain described herein or grafting one or more CDRs of a variable domain described herein onto another scaffold. Binding agents can also be identified from diverse libraries, e.g., by screening. One method for screening protein libraries uses phage display. Particular regions of a protein are varied and proteins that interact with IL-13 are identified, e.g., by retention on a solid support or by other physical association. To identify particular binding agents that bind to the same epitope or an overlapping epitope as mAb13.2 on IL-13, binding agents can be eluted by adding mAb13.2 (or related antibody), or binding agents can be evaluated in competition experiments with mAb13.2 (or related antibody). It is also possible to deplete the library of agents that bind to other epitopes by contacting the library to a complex that contains IL-13 and mAb13.2 (or related antibody). The depleted library can then be contacted to IL-13 to obtain a binding agent that binds to IL-13 but not to IL-13 when it is bound by mAb13.2. It is also possible to use peptides from IL-13 that contain the mAb13.2 epitope as a target.

Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; WO 94/05781; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Rebar et al. (1996) *Methods*

*Enzymol.* 267:129-49; and Barbas et al. (1991) *PNAS* 88:7978-7982. Yeast surface display is described, e.g., in Boder and Wittrup (1997) *Nat. Biotechnol.* 15:553-557. Another form of display is ribosome display. See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30. and Schaffitzel et al. (1999) *J Immunol Methods.* 231(1-2):119-35.

Binding agents that bind to IL-13 can have structural features of one scaffold proteins, e.g., a folded domain. An exemplary scaffold domain, based on an antibody, is a "minibody" scaffold has been designed by deleting three beta strands from a heavy chain variable domain of a monoclonal antibody (Tramontano et al., 1994, J. Mol. Recognit. 7:9; and Martin et al., 1994, The EMBO Journal 13, pp. 5303-5309). This domain includes 61 residues and can be used to present two hypervariable loops, e.g., one or more hypervariable loops of a variable domain described herein or a variant described herein. In another approach, the binding agent includes a scaffold domain that is a V-like domain (Coia et al. WO 99/45110). V-like domains refer to a domain that has similar structural features to the variable heavy (VH) or variable light (VL) domains of antibodies. Another scaffold domain is derived from tendamistatin, a 74 residue, six-strand beta sheet sandwich held together by two disulfide bonds (McConnell and Hoess, 1995, *J. Mol. Biol.* 250:460). This parent protein includes three loops. The loops can be modified (e.g., using CDRs or hypervariable loops described herein) or varied, e.g., to select domains that bind to IL-13. WO 00/60070 describes a β-sandwich structure derived from the naturally occurring extracellular domain of CTLA-4 is used as a scaffold Still another scaffold domain for an IL-13 binding agent is a domain based on the fibronectin type III domain or related fibronectin-like proteins. The overall fold of the fibronectin type III (Fn3) domain is closely related to that of the smallest functional antibody fragment, the variable region of the antibody heavy chain. Fn3 is a β-sandwich similar to that of the antibody VH domain, except that Fn3 has seven β-strands instead of nine. There are three loops at the end of Fn3; the positions of BC, DE and FG loops approximately correspond to those of CDR1, 2 and 3 of the VH domain of an antibody. Fn3 is advantageous because it does not have disulfide bonds. Therefore, Fn3 is stable under reducing conditions, unlike antibodies and their fragments (see WO 98/56915; WO 01/64942; WO 00/34784). An Fn3 domain can be modified (e.g., using CDRs or hypervariable loops described herein) or varied, e.g., to select domains that bind to IL-13.

Still other exemplary scaffold domains include: T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). US 20040009530 describes examples of some alternative scaffolds.

Examples of small scaffold domains include: Kunitz domains (58 amino acids, 3 disulfide bonds), *Cucurbida maxima* trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fungal carbohydrate-binding domains (35 amino acids, 2 disulfide bonds), endothelin domains (18 amino acids, 2 disulfide bonds), and Streptococcal G IgG-binding domain (35 amino acids, no disulfide bonds). Examples of small intracellular scaffold domains include SH2, SH3, and EVH domains. Generally, any modular domain, intracellular or extracellular, can be used.

Exemplary criteria for evaluating a scaffold domain can include: (1) amino acid sequence, (2) sequences of several homologous domains, (3) 3-dimensional structure, and/or (4) stability data over a range of pH, temperature, salinity, organic solvent, oxidant concentration. In one embodiment, the scaffold domain is a small, stable protein domains, e.g., a protein of less than 100, 70, 50, 40 or 30 amino acids. The domain may include one or more disulfide bonds or may chelate a metal, e.g., zinc.

Still other binding agents are based on peptides, e.g., proteins with an amino acid sequence that are less than 30, 25, 24, 20, 18, 15 or 12 amino acids. Peptides can be incorporated in a larger protein, but typically a region that can independently bind to IL-13, e.g., to an epitope described herein. Peptides can be identified by phage display. See, e.g., An IL-13 binding agent may include non-peptide linkages and other chemical modification. For example, part or all of the binding agent may be synthesized as a peptidomimetic, e.g., a peptoid (see, e.g., Simon et al. (1992) Proc. Natl. Acad. Sci. USA 89:9367-71 and Horwell (1995) Trends Biotechnol. 13:132-4). A binding agent may include one or more (e.g., all) non-hydrolyzable bonds. Many non-hydrolyzable peptide bonds are known in the art, along with procedures for synthesis of peptides containing such bonds. Exemplary non-hydrolyzable bonds include —[$CH_2NH$]— reduced amide peptide bonds, —[$COCH_2$]— ketomethylene peptide bonds, —[CH(CN)NH]— (cyanomethylene)amino peptide bonds, —[$CH_2CH(OH)$]— hydroxyethylene peptide bonds, —[$CH_2O$]— peptide bonds, and —[$CH_2S$]— thiomethylene peptide bonds (see e.g., U.S. Pat. No. 6,172,043).

Pharmaceutical Composition, Dosages and Modes of Administration

Anti-IL-13 antibodies (or other IL-13 binding agent) can be incorporated into a pharmaceutical composition, e.g., by combination with a pharmaceutically acceptable carrier. Such a composition may also contain, e.g., various diluents, fillers, salts, buffers, stabilizers, solubilizers, and other materials well known in the art. The term "pharmaceutically acceptable" means a nontoxic material that does not interfere with the effectiveness of the biological activity of the active ingredient(s). The characteristics of the carrier can depend on the route of administration.

The pharmaceutical compositions may also contain other factors, such as, but not limited to, other anti-cytokine antibodies or other anti-inflammatory agents as described in more detail below. Such additional factors and/or agents may be included in the pharmaceutical composition to produce a synergistic effect with an antibody described herein. For example, in the treatment of allergic asthma, a pharmaceutical composition may also include, e.g., anti-IL-4 antibodies or drugs known to reduce an allergic response.

In one embodiment, the pharmaceutical composition includes the anti-IL-13 antibody as the sole biologic (e.g., the sole protein component) or as the sole biologically active ingredient. For example, the composition can include less than 25, 20, 15, 10, 5, 3, 2, 1, 0.4, or 0.1% other protein components on a w/w basis.

The pharmaceutical compositions may be in the form of a liposome in which an antibody is combined, in addition to other pharmaceutically acceptable carriers, with amphipathic agents such as lipids that exist in aggregated form as micelles, insoluble monolayers, liquid crystals, or lamellar layers while in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing an exemplary method of treatment or use described herein, a therapeutically effective amount of antibody that binds to IL-13 and interferes with the formation of a functional IL-13 signaling complex (and, e.g., neutralizes or inhibits one or more IL-13-associated activities), can be administered to a subject, e.g., mammal (e.g., a human). An antibody may be administered in accordance with the methods described either alone or in combination with other therapies such as treatments employing cytokines, lymphokines or other hematopoietic factors, or anti-inflammatory agents. When coadministered with one or more agents, the antibody may be administered either simultaneously with the second agent, or separately, e.g., sequentially. If administered separately, e.g., sequentially, the attending physician will decide on the appropriate sequence of administering the antibody in combination with other agents.

Administration of a pharmaceutical composition (e.g., a pharmaceutical composition containing an antibody that binds to IL-13) can be carried out in a variety of conventional ways, such as oral ingestion, inhalation, or cutaneous, subcutaneous, or intravenous injection. Subcutaneous administration to the patient is preferred.

When a therapeutically effective amount of an antibody that binds to IL-13 and interferes with the formation of a functional IL-13 signaling complex is administered orally, the binding agent will be in the form of a tablet, capsule, powder, solution or elixir. When administered in tablet form, a pharmaceutical composition may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the binding agent, and preferably from about 1 to 50% the binding agent.

When a therapeutically effective amount of an antibody that binds to IL-13 is administered by intravenous, cutaneous, or subcutaneous injection, the binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. A pharmaceutical composition may also contain stabilizers, preservatives, buffers, antioxidants, or other additive known to those of skill in the art.

The amount of an antibody (or other IL-13 binding agent) in the pharmaceutical composition can depend upon the nature and severity of the condition being treated, and on the nature of prior treatments that the patient has undergone. Ultimately, the attending physician will decide the amount of antibody with which to treat each individual patient. Initially, the attending physician will administer low doses of antibody and observe the patient's response. Larger doses of antibody may be administered until the optimal therapeutic effect is obtained for the patient, and at that point the dosage is not generally increased further. For example, doses in the range of 0.1-50 mg/kg, 0.5-50 mg/kg, 1-100 mg/kg, 0.5-25 mg/kg, 0.1-15 mg/kg, or 1-8 mg/kg of body weight can be administered. The pharmaceutical composition can be administered to normal patients or patients who do not show symptoms, e.g., in a prophylactic mode.

Inhalation

A composition that includes an IL-13 antibody or fragment thereof can be formulated for inhalation or other mode of pulmonary delivery. Accordingly, the compounds described herein can be administered by inhalation to pulmonary tissue. The term "pulmonary tissue" as used herein refers to any tissue of the respiratory tract and includes both the upper and lower respiratory tract, except where otherwise indicated. An IL-13 antibody or fragment thereof can be administered in combination with one or more of the existing modalities for treating pulmonary diseases.

In one example, the compound is formulated for a nebulizer. In one embodiment, the compound can be stored in a lyophilized form (e.g., at room temperature) and reconstituted in solution prior to inhalation.

It is also possible to formulate the compound for inhalation using a medical device, e.g., an inhaler (see, e.g., U.S. Pat. No. 6,102,035 (a powder inhaler) and U.S. Pat. No. 6,012,454 (a dry powder inhaler). The inhaler can include separate compartments for the active compound at a pH suitable for storage and another compartment for a neutralizing buffer, and a mechanism for combining the compound with a neutralizing buffer immediately prior to atomization. In one embodiment, the inhaler is a metered dose inhaler.

The three common systems used to deliver drugs locally to the pulmonary air passages include dry powder inhalers (DPIs), metered dose inhalers (MDIs) and nebulizers. MDIs, used in the most popular method of inhalation administration, may be used to deliver medicaments in a solubilized form or as a dispersion. Typically MDIs comprise a Freon or other relatively high vapor pressure propellant that forces aerosolized medication into the respiratory tract upon activation of the device. Unlike MDIs, DPIs generally rely entirely on the inspiratory efforts of the patient to introduce a medicament in a dry powder form to the lungs. Nebulizers form a medicament aerosol to be inhaled by imparting energy to a liquid solution. Direct pulmonary delivery of drugs during liquid ventilation or pulmonary lavage using a fluorochemical medium has also been explored. These and other methods can be used to deliver an IL-13 antibody or fragment thereof. In one embodiment, the IL-13 antibody or fragment thereof is associated with a polymer, e.g., a polymer that stabilizes or increases half-life of the compound.

For example, for administration by inhalation, an IL-13 antibody or fragment thereof is delivered in the form of an aerosol spray from a pressured container or dispenser that contains a suitable propellant or a nebulizer. The compound may be in the form of a dry particle or a liquid. Particles that include the compound can be prepared, e.g., by spray drying, by drying an aqueous solution of the IL-13 antibody or fragment thereof with a charge neutralizing agent and then creating particles from the dried powder, or by drying an aqueous solution in an organic modifier and then creating particles from the dried powder.

The compound may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges for use in an inhaler or insufflator may be formulated containing a powder mix of an IL-13 antibody or fragment thereof and a suitable powder base such as lactose or starch, if the particle is a formulated particle. In addition to the formulated or unformulated compound, other materials such as 100% DPPC or other surfactants can be mixed with the IL-13 antibody or fragment thereof to promote the delivery and dispersion of formulated or unformulated compound. Methods of preparing dry particles are described, for example, in PCT Publication WO 02/32406.

An IL-13 antibody or fragment thereof can be formulated for aerosol delivery, e.g., as dry aerosol particles, such that when administered it can be rapidly absorbed and can produce a rapid local or systemic therapeutic result. Administration can be tailored to provide detectable activity within 2 minutes, 5 minutes, 1 hour, or 3 hours of administration. In some embodiments, the peak activity can be achieved even more quickly, e.g., within 30 minutes or even within 10 minutes. An IL-13 antibody or fragment thereof can be formulated for longer biological half-life (e.g., by association with a polymer such as PEG) and can be used as an alternative to other modes of administration, e.g., such that the compound enters the circulation from the lungs and is distributed to other organs or to a particular target organ.

In one embodiment, the IL-13 antibody or fragment thereof is delivered in an amount such that at least 5% of the mass of the polypeptide is delivered to the lower respiratory tract or the deep lung. Deep lung has an extremely rich capillary network. The respiratory membrane separating the capillary lumen from the alveolar air space is very thin and extremely permeable. In addition, the liquid layer lining the alveolar surface is rich in lung surfactants. In other embodiments, at least 2%, 3%, 5%, 10%, 20%, 30%, 40%, 50%, 60%, 70%, or 80% of the composition of an IL-13 antibody or fragment thereof is delivered to the lower respiratory tract or to the deep lung. Delivery to either or both of these tissues results in efficient absorption of the compound and high bioavailability. In one embodiment, the compound is provided in a metered dose using, e.g., an inhaler or nebulizer. For example, the compound is delivered in a dosage unit form of at least about 0.02, 0.1, 0.5, 1, 1.5, 2, 5, 10, 20, 40, or 50 mg/puff or more. The percent bioavailability can be calculated as follows: the percent bioavailability=(AUCnoninvasive/AUCi.v. or s.c.)×(dosei.v. or s.c./dosenoninvasive)×100.

Although not necessary, delivery enhancers such as surfactants can be used to further enhance pulmonary delivery. A "surfactant" as used herein refers to a compound having hydrophilic and lipophilic moieties that promote absorption of a drug by interacting with an interface between two immiscible phases. Surfactants are useful with dry particles for several reasons, e.g., reduction of particle agglomeration, reduction of macrophage phagocytosis, etc. When coupled with lung surfactant, a more efficient absorption of the compound can be achieved because surfactants, such as DPPC, will greatly facilitate diffusion of the compound. Surfactants are well known in the art and include, but are not limited to, phosphoglycerides, e.g., phosphatidylcholines, L-alpha-phosphatidylcholine dipalmitoyl (DPPC) and diphosphatidyl glycerol (DPPG); hexadecanol; fatty acids; polyethylene glycol (PEG); polyoxyethylene-9-; auryl ether; palmitic acid; oleic acid; sorbitan trioleate (SPAN™ 85); glycocholate; surfactin; poloxomer; sorbitan fatty acid ester; sorbitan trioleate; tyloxapol; and phospholipids.

Stabilization and Retention

In one embodiment, an IL-13 antibody or fragment thereof is physically associated with a moiety that improves its stabilization and/or retention in circulation, e.g., in blood, serum, lymph, bronchopulmonary or bronchoalveolar lavage, or other tissues, e.g., by at least 1.5, 2, 5, 10, or 50 fold. For example, an IL-13 antibody or fragment thereof can be associated with a polymer, e.g., a substantially nonantigenic polymer, such as polyalkylene oxides or polyethylene oxides. Suitable polymers will vary substantially by weight. Polymers having molecular number average weights ranging from about 200 to about 35,000 (or about 1,000 to about 15,000, or about 2,000 to about 12,500) can be used. For example, an IL-13 antibody or fragment thereof can be conjugated to a water-soluble polymer, e.g., hydrophilic polyvinyl polymers, e.g. polyvinylalcohol and polyvinylpyrrolidone. A nonlimiting list of such polymers includes polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

The molecular weight of the polymer can range up to about 500,000 Da, and preferably is at least about 20,000 Da, or at least about 30,000 Da, or at least about 40,000 Da. The molecular weight chosen can depend upon the effective size of the conjugate to be achieved, the nature (e.g., structure, such as linear or branched) of the polymer, and the degree of derivatization. A covalent bond can be used to attach an IL-13 antibody or fragment thereof to a polymer, for example, cross linking to the N-terminal amino group of the antibody and epsilon amino groups found on lysine residues of the antibody, as well as other amino, imino, carboxyl, sulfhydryl, hydroxyl or other hydrophilic groups. Functionalized PEG polymers that can be attached to an IL-13 antibody or fragment thereof are available, e.g., from Shearwater Polymers, Inc. (Huntsville, Ala.). The reaction conditions for coupling PEG and other polymers may vary depending on the IL-13 antibody or fragment thereof, the desired degree of PEGylation, and the polymer utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of an IL-13 antibody or fragment thereof and a polymer can be separated from the unreacted starting materials, e.g., by gel filtration or ion exchange chromatography, e.g., HPLC. Heterologous species of the conjugates are purified from one another in the same fashion. Resolution of different species (e.g. containing one or two PEG residues) is also possible due to the difference in the ionic properties of the unreacted amino acids (see, e.g., WO 96/34015).

Therapeutic and Prophylactic Uses of Anti-IL-13 Antibodies

In yet another aspect, this disclosure features a method for neutralizing and/or inhibiting one or more associated activities of IL-13 in vivo by administering an antibody that binds to and/or neutralizes IL-13, e.g., an antibody described herein in an amount sufficient to inhibit its activity. Such antibodies can also be administered to subjects for whom inhibition of an IL-13-mediated inflammatory response is required. These conditions include, e.g., airway inflammation, asthma, fibrosis, eosinophilia and increased mucus production.

We have shown that an antibody that binds IL-13 reduces airway inflammation in cynomolgus monkeys exposed to the allergen *Ascaris suum* (Example 3.6). We have also demonstrated upregulation by IL-13 of CD23 in human peripheral blood monocytes. Accordingly, antibodies disclosed herein that bind to IL-13, interfere with the formation of a functional IL-13 signaling complex, and may neutralize one or more IL-13-associated activities, can be used to reduce IL-13 mediated inflammation in vivo, e.g., for treating or preventing IL-13-associated pathologies, including asthma and/or its associated symptoms and/or atopic disorders (e.g., that result from increased sensitivity to IL-13).

Accordingly, the antibodies disclosed herein may be used to treat an IL-13-associated disorder, e.g., a disorder chosen from one or more of: respiratory disorders, e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis; atopic disorders, e.g., resulting from an increased sensitivity to IL-13, (e.g., atopic dermatitis, urticaria, eczema, allergic rhinitis, and allergic enterogastritis); inflammatory and/or autoimmune conditions of, the skin (e.g., atopic dermatitis), gastrointestinal organs (e.g., inflammatory bowel diseases (IBD), such as ulcerative colitis and/or Crohn's disease), liver (e.g., cirrhosis, hepatocellular carcinoma), and scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus); and suppression of expression of protective type 1 immune responses, (e.g., during vaccination), as described herein.

Respiratory Disorders

IL-13 antagonists (e.g., an IL-13 binding agent such as an antibody or antigen binding fragment described herein) can be used to treat or prevent respiratory disorders including, but are not limited to asthma (e.g., allergic and nonallergic asthma (e.g., due to infection, e.g., with respiratory syncytial virus (RSV), e.g., in younger children)); bronchitis (e.g., chronic bronchitis); chronic obstructive pulmonary disease (COPD) (e.g., emphysema (e.g., cigarette-induced emphysema); conditions involving airway inflammation, eosinophilia, fibrosis and excess mucus production, e.g., cystic fibrosis, pulmonary fibrosis, and allergic rhinitis.

Asthma can be triggered by myriad conditions, e.g., inhalation of an allergen, presence of an upper-respiratory or ear infection, etc. (Opperwall (2003) *Nurs. Clin. North Am.* 38:697-711). Allergic asthma is characterized by airway hyperresponsiveness (AHR) to a variety of specific and non-specific stimuli, elevated serum immunoglobulin E (IgE), excessive airway mucus production, edema, and bronchial epithelial injury (Wills-Karp, supra). Allergic asthma begins when the allergen provokes an immediate early airway response, which is frequently followed several hours later by a delayed late-phase airway response (LAR) (Henderson et al. (2000) *J. Immunol.* 164:1086-95). During LAR, there is an influx of eosinophils, lymphocytes, and macrophages throughout the airway wall and the bronchial fluid. (Henderson et al., supra). Lung eosinophilia is a hallmark of allergic asthma and is responsible for much of the damage to the respiratory epithelium (Li et al. (1999) *J. Immunol.* 162:2477-87).

$CD4^+$ T helper (Th) cells are important for the chronic inflammation associated with asthma (Henderson et al., supra). Several studies have shown that commitment of $CD4^+$ cells to type 2 T helper (Th2) cells and the subsequent production of type 2 cytokines (e.g., IL-4, IL-5, IL-10, and IL-13) are important in the allergic inflammatory response leading to AHR (Tomkinson et al. (2001) *J. Immunol.* 166: 5792-5800, and references cited therein). First, $CD4^+$ T cells have been shown to be necessary for allergy-induced asthma in murine models. Second, $CD4^+$ T cells producing type 2 cytokines undergo expansion not only in these animal models but also in patients with allergic asthma. Third, type 2 cytokine levels are increased in the airway tissues of animal models and asthmatics. Fourth, Th2 cytokines have been implicated as playing a central role in eosinophil recruitment in murine models of allergic asthma, and adoptively transferred Th2 cells have been correlated with increased levels of eotaxin (a potent eosinophil chemoattractant) in the lung as well as lung eosinophilia (Wills-Karp et al., supra; Li et al., supra).

The methods for treating or preventing asthma described herein include those for extrinsic asthma (also known as allergic asthma or atopic asthma), intrinsic asthma (also known as non-allergic asthma or non-atopic asthma) or combinations of both, which has been referred to as mixed asthma. Extrinsic or allergic asthma includes incidents caused by, or associated with, e.g., allergens, such as pollens, spores, grasses or weeds, pet danders, dust, mites, etc. As allergens and other irritants present themselves at varying points over the year, these types of incidents are also referred to as seasonal asthma. Also included in the group of extrinsic asthma is bronchial asthma and allergic bronchopulmonary aspergillosis.

Disorders that can be treated or alleviated by the agents described herein include those respiratory disorders and asthma caused by infectious agents, such as viruses (e.g., cold and flu viruses, respiratory syncytial virus (RSV), paramyxovirus, rhinovirus and influenza viruses. RSV, rhinovirus and influenza virus infections are common in children, and are one leading cause of respiratory tract illnesses in infants and young children. Children with viral bronchiolitis can develop chronic wheezing and asthma, which can be treated using the methods described herein. Also included are the asthma conditions which may be brought about in some asthmatics by exercise and/or cold air. The methods are useful for asthmas associated with smoke exposure (e.g., cigarette-induced and industrial smoke), as well as industrial and occupational exposures, such as smoke, ozone, noxious gases, sulfur dioxide, nitrous oxide, fumes, including isocyanates, from paint, plastics, polyurethanes, varnishes, etc., wood, plant or other organic dusts, etc. The methods are also useful for asthmatic incidents associated with food additives, preservatives or pharmacological agents. Also included are methods for treating, inhibiting or alleviating the types of asthma referred to as silent asthma or cough variant asthma.

The methods disclosed herein are also useful for treatment and alleviation of asthma associated with gastroesophageal reflux (GERD), which can stimulate bronchoconstriction. GERD, along with retained bodily secretions, suppressed cough, and exposure to allergens and irritants in the bedroom can contribute to asthmatic conditions and have been collectively referred to as nighttime asthma or nocturnal asthma. In methods of treatment, inhibition or alleviation of asthma associated with GERD, a pharmaceutically effective amount of the IL-13 antagonist can be used as described herein in combination with a pharmaceutically effective amount of an agent for treating GERD. These agents include, but are not limited to, proton pump inhibiting agents like PROTONIX® brand of delayed-release pantoprazole sodium tablets, PRILOSEC® brand omeprazole delayed release capsules, ACIPHEX® brand rebeprazole sodium delayed release tablets or PREVACID® brand delayed release lansoprazole capsules.

Atopic Disorders and Symptoms Thereof

"Atopic" refers to a group of diseases in which there is often an inherited tendency to develop an allergic reaction. Examples of atopic disorders include allergy, allergic rhinitis, atopic dermatitis, asthma and hay fever. Asthma is a phenotypically heterogeneous disorder associated with intermittent respiratory symptoms such as, e.g., bronchial hyperresponsiveness and reversible airflow obstruction. Immunohistopathologic features of asthma include, e.g., denudation of airway epithelium, collagen deposition beneath the basement membrane, edema, mast cell activation, and inflammatory cell infiltration (e.g., by neutrophils, eosinophils, and lymphocytes). Airway inflammation can further contribute to airway hyperresponsiveness, airflow limitation, acute bronchoconstriction, mucus plug formation, airway wall remodeling, and other respiratory symptoms. An IL-13 antagonist (e.g., an IL-13 binding agent such as an antibody or antigen binding fragment described herein) can be administered to ameliorate one or more of these symptoms.

Symptoms of allergic rhinitis (hay fever) include itchy, runny, sneezing, or stuffy nose, and itchy eyes. An IL-13 antagonist can be administered to ameliorate one or more of these symptoms. Atopic dermatitis is a chronic (long-lasting) disease that affects the skin. Information about atopic dermatitis is available, e.g., from NIH Publication No. 03-4272. In atopic dermatitis, the skin can become extremely itchy, leading to redness, swelling, cracking, weeping clear fluid, and finally, crusting and scaling. In many cases, there are periods of time when the disease is worse (called exacerbations or flares) followed by periods when the skin improves or clears up entirely (called remissions). Atopic dermatitis is often referred to as "eczema," which is a general term for the several types of inflammation of the skin. Atopic dermatitis is the most common of the many types of eczema. Examples of atopic dermatitis include: allergic contact eczema (dermatitis: a red, itchy, weepy reaction where the skin has come into contact with a substance that the immune system recognizes as foreign, such as poison ivy or certain preservatives in creams and lotions); contact eczema (a localized reaction that includes redness, itching, and burning where the skin has come into contact with an allergen (an allergy-causing substance) or with an irritant such as an acid, a cleaning agent, or other chemical); dyshidrotic eczema (irritation of the skin on the palms of hands and soles of the feet characterized by clear, deep blisters that itch and burn); neurodermatitis (scaly patches of the skin on the head, lower legs, wrists, or forearms caused by a localized itch (such as an insect bite) that become intensely irritated when scratched); nummular eczema (coin-shaped patches of irritated skin-most common on the arms, back, buttocks, and lower legs that may be crusted, scaling, and extremely itchy); seborrheic eczema (yellowish, oily, scaly patches of skin on the scalp, face, and occasionally other parts of the body). Additional particular symptoms include stasis dermatitis, atopic pleat (Dennie-Morgan fold), cheilitis, hyperlinear palms, hyperpigmented eyelids (eyelids that have become darker in color from inflammation or hay fever), ichthyosis, keratosis pilaris, lichenification, papules, and urticaria. An IL-13 antagonist (e.g., an IL-13 binding agent such as an antibody or antigen binding fragment described herein) can be administered to ameliorate one or more of these symptoms.

An exemplary method for treating allergic rhinitis or other allergic disorder can include initiating therapy with an IL-13 antagonist prior to exposure to an allergen, e.g., prior to seasonal exposure to an allergen, e.g., prior to allergen blooms. Such therapy can include one or more doses, e.g., doses at regular intervals.

Cancer

IL-13 and its receptors may be involved in the development of at least some types of cancer, e.g., a cancer derived from hematopoietic cells or a cancer derived from brain or neuronal cells (e.g., a glioblastoma). For example, blockade of the IL-13 signaling pathway, e.g., via use of a soluble IL-13 receptor or a STAT6-/- deficient mouse, leads to delayed tumor onset and/or growth of Hodgkins lymphoma cell lines or a metastatic mammary carcinoma, respectively (Trieu et al. (2004) *Cancer Res.* 64: 3271-75; Ostrand-Rosenberg et al. (2000) *J. Immunol.* 165: 6015-6019). Cancers that express IL-13Rα2 (Husain and Puri (2003) *J. Neurooncol.* 65:37-48; Mintz et al. (2003) *J. Neurooncol.* 64:117-23) can be specifically targeted by anti-IL-13 antibodies described herein. IL-13 antagonists, e.g., anti-IL-13 antibodies and fragments thereof, can be useful to inhibit cancer cell proliferation or other cancer cell activity. A cancer refers to one or more cells that has a loss of responsiveness to normal growth controls, and typically proliferates with reduced regulation relative to a corresponding normal cell.

Examples of cancers against which IL-13 antagonists (e.g., an IL-13 binding agent such as an antibody or antigen binding fragment described herein) can be used for treatment include leukemias, e.g., B-cell chronic lymphocytic leukemia, acute myelogenous leukemia, and human T-cell leukemia virus type 1 (HTLV-1) transformed T cells; lymphomas, e.g. T cell lymphoma, Hodgkin's lymphoma; glioblastomas; pancreatic cancers; renal cell carcinoma; ovarian carcinoma; and AIDS-Kaposi's sarcoma.

Fibrosis

IL-13 antagonists (e.g., an IL-13 binding agent such as an antibody or antigen binding fragment described herein) can also be useful in treating inflammation and fibrosis, e.g., fibrosis of the liver. IL-13 production has been correlated with the progression of liver inflammation (e.g., viral hepatitis) toward cirrhosis, and possibly, hepatocellular carcinoma (de Lalla et al. (2004) *J. Immunol.* 173:1417-1425). Fibrosis occurs, e.g., when normal tissue is replaced by scar tissue, often following inflammation. Hepatitis B and hepatitis C viruses both cause a fibrotic reaction in the liver, which can progress to cirrhosis. Cirrhosis, in turn, can evolve into severe complications such as liver failure or hepatocellular carcinoma. Blocking IL-13 activity using the IL-13 antagonists, e.g., anti-IL-13 antibodies, described herein can reduce inflammation and fibrosis, e.g., the inflammation, fibrosis, and cirrhosis associated with liver diseases, especially hepatitis B and C.

Inflammatory Bowel Disease

Inflammatory bowel disease (IBD) is the general name for diseases that cause inflammation of the intestines. Two examples of inflammatory bowel disease are Crohn's disease and ulcerative colitis. IL-13/STAT6 signaling has been found to be involved in inflammation-induced hypercontractivity of mouse smooth muscle, a model of inflammatory bowel disease (Akiho et al. (2002) *Am. J. Physiol. Gastrointest. Liver Physiol.* 282:G226-232). IL-13 antagonists (e.g., an IL-13 binding agent such as an antibody or antigen binding fragment described herein) can be useful in treating, preventing, or alleviating inflammatory bowel disease or one or more symptoms of inflammatory bowel disease.

In one embodiment, an antibody described herein, e.g., a pharmaceutical composition thereof, is administered in combination therapy, i.e., combined with other agents, e.g., therapeutic agents, that are useful for treating pathological conditions or disorders, such as allergic and inflammatory disorders. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more antibodies described herein, i.e., that bind to IL-13 and interfere with the formation of a functional IL-13 signaling complex, coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more anti-IL-13 antibodies described herein may be used in combination with two or more of the therapeutic agents described herein. Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-13/IL-13-receptor pathway, and thus are expected to enhance and/or synergize with the effects of the IL-13 antibodies.

Examples of preferred additional therapeutic agents that can be coadministered and/or coformulated with one or more IL-13 antagonists, e.g., anti-IL-13 antibodies or fragments thereof, include, but are not limited to, one or more of: inhaled steroids; beta-agonists, e.g., short-acting or long-acting beta-agonists; leukotriene antagonists or leukotriene receptor antagonists; combination drugs such as ADVAIR®; IgE inhibitors, e.g., anti-IgE antibodies (e.g., XOLAIR®); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; and antihistamines. Such combinations can be used to treat asthma and other respiratory disorders. Additional examples of therapeutic agents that can be coadministered and/or coformulated with one or more anti-IL-13 antibodies or fragments thereof include one or more of: TNF antagonists (e.g., a soluble fragment of a TNF receptor, e.g., p55 or p75 human TNF receptor or derivatives thereof, e.g., 75 kd TNFR-IgG (75 kD TNF receptor-IgG fusion protein, ENBREL™)); TNF enzyme antagonists, e.g., TNFα converting enzyme (TACE) inhibitors); muscarinic receptor antagonists; TGF-β antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, Mk-2 and NFκB inhibitors, among others.

It is also possible to provide kits for carrying out the combined administration of an IL-13 antibody with one or more other therapeutic compounds, or for using the anti-IL-13 antibodies as a research or therapeutic tool to determine the presence and/or level of IL-13 in a biological sample, such as an ELISA kit. In one embodiment, the kit comprises one or more anti-IL-13 antibody formulated in a pharmaceutical carrier, and at least one agent, e.g., a therapeutic agent, formulated as appropriate, in one or more separate pharmaceutical preparations.

Vaccine Formulations

IL-13 antagonists (e.g., an IL-13 binding agent such as an antibody or antigen binding fragment described herein) can be used to increase the efficacy of a vaccine formulation to immunize an subject. For example, an IL-13 antagonist can be administered before, during, and/or after an immunization to increase vaccine efficacy. In one embodiment, the vaccine formulation contains one or more IL-13 antagonists and an antigen, i.e., an immunogen. In another embodiment, the IL-13 antagonist and the immunogen are administered separately, e.g., within one hour, three hours, one day, or two days of each other.

Inhibition of IL-13 can improve the efficacy of, e.g., cellular vaccines, e.g., vaccines against diseases such as cancer and viral infection, e.g., retroviral infection, e.g., HIV infection. Induction of $CD8^+$ cytotoxic T lymphocytes (CTL) by vaccines is down modulated by $CD4^+$ T cells, likely through the cytokine IL-13. Inhibition of IL-13 has been shown to enhance vaccine induction of CTL response (Ahlers et al. (2002) *Proc. Natl. Acad. Sci. USA* 99:13020-10325). An IL 13 antagonist, e.g., anti-IL 13 antibody or fragment thereof, an antibody described herein, can be used in conjunction with a vaccine to increase vaccine efficacy. Cancer and viral infection (such as retroviral (e.g., HIV) infection) are exemplary disorders against which a cellular vaccine response can be effective. Vaccine efficacy is enhanced by blocking IL-13 signaling at the time of vaccination (Ahlers et al. (2002) *Proc. Nat. Acad. Sci. USA* 99:13020-25).

A vaccine formulation may be administered to a subject in the form of a pharmaceutical or therapeutic composition. Pharmaceutical compositions comprising the IL-13 antagonists described herein and an antigen may be manufactured by means of conventional mixing, dissolving, granulating, dragee-making, levigating, emulsifying, encapsulating, entrapping, or lyophilizing processes. Pharmaceutical compositions may be formulated in conventional manner using one or more pharmaceutically acceptable carriers, diluents, excipients, or auxiliaries that facilitate processing of the antigens and antagonists described herein into preparations which can be used pharmaceutically. Proper formulation is dependent upon the route of administration chosen. Systemic formulations include those designed for administration by injection, e.g. subcutaneous, intradermal, intramuscular, or intraperitoneal injection. For injection, the vaccine preparations may be formulated in aqueous solutions, preferably in physiologically compatible buffers such as Hanks's solution, Ringer's solution, phosphate buffered saline, or any other physiological saline buffer. The solution may contain formulatory agents such as suspending, stabilizing, and/or dispersing agents. Alternatively, the proteins may be in powder form for constitution with a suitable vehicle, e.g., sterile pyrogen-free water, before use.

An effective dose can be estimated initially using animal models. For example, a dose can be formulated in animal models to achieve an induction of an immune response using techniques that are well known in the art. Dosage amount and interval may be adjusted individually. For example, when used as a vaccine, the vaccine formulations may be administered in about 1 to 3 doses for a 1-36 week period. Preferably, 1 or 2 doses are administered at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized subject sufficient to protect the subject from an infection for at least 4 to 12 months. In general, the amount of the antigen present in a dose ranges from about 1 pg to about 100 mg per kg of host, typically from about 10 pg to about 1 mg, and preferably from about 100 pg to about 1 µg. Suitable dose range will vary with the route of injection and the size of the patient, but will typically range from about 0.1 mL to about 5 mL.

Methods for Diagnosing, Prognosing and Monitoring Disorders

Proteins that bind to IL-13, e.g., antibodies, described herein have in vitro and in vivo diagnostic, utilities. An exemplary method includes: (i) administering the IL-13 antibody to a subject; and (ii) detecting the IL-13 antibody in the subject. The detecting can include determining location of the IL-13 antibody in the subject. Another exemplary method includes contacting an IL-13 antibody to a sample, e.g., a sample from a subject.

In another aspect, the present invention provides a diagnostic method for detecting the presence of a IL-13, in vitro (e.g., a biological sample, such as tissue, biopsy) or in vivo (e.g., in vivo imaging in a subject). The method includes: (i) contacting a sample with IL-13 antibody; and (ii) detecting formation of a complex between the IL-13 antibody and the sample. The method can also include contacting a reference sample (e.g., a control sample) with the ligand, and determining the extent of formation of the complex between the ligand an the sample relative to the same for the reference sample. A change, e.g., a statistically significant change, in the formation of the complex in the sample or subject relative to the control sample or subject can be indicative of the presence of IL-13 in the sample.

The IL-13 antibody can be directly or indirectly labeled with a detectable substance to facilitate detection of the bound or unbound protein. Suitable detectable substances include various enzymes, prosthetic groups, fluorescent materials, luminescent materials, and radioactive materials.

Complex formation between the IL-13 antibody and IL-13 can be detected by measuring or visualizing either the ligand bound to the IL-13 or unbound ligand. Conventional detection assays can be used, e.g., an enzyme-linked immunosorbent assays (ELISA), a radioimmunoassay (RIA) or tissue immunohistochemistry. Further to labeling the IL-13 antibody, the presence of IL-13 can be assayed in a sample by a competition immunoassay utilizing standards labeled with a detectable substance and an unlabeled IL-13 antibody.

Methods for Diagnosing, Prognosing, and Monitoring the Progress of Asthma

It is also possible to diagnose, prognose, and/or monitor the progress of asthma and/or atopic disorders (e.g., resulting from increased sensitivity to IL-13) by measuring the level of IL-13 in a biological sample. In particular, the antibodies disclosed herein can be used in a method of distinguishing whether a patient is suffering from allergic or nonallergic asthma.

Such methods for diagnosing allergic and nonallergic asthma can include detecting an alteration (e.g., a decrease or increase) of IL-13 in a biological sample, e.g., serum, plasma, bronchoalveolar lavage fluid, sputum, etc. "Diagnostic" or "diagnosing" means identifying the presence or absence of a pathologic condition. Diagnostic methods involve detecting the presence of IL-13 by determining a test amount of IL-13 polypeptide in a biological sample, e.g., in bronchoalveolar lavage fluid, from a subject (human or nonhuman mammal), and comparing the test amount with a normal amount or range (i.e., an amount or range from an individual(s) known not to suffer from asthma) for the IL-13 polypeptide. While a particular diagnostic method may not provide a definitive diagnosis of asthma, it suffices if the method provides a positive indication that aids in diagnosis.

Methods for prognosing asthma and/or atopic disorders can include detecting upregulation of IL-13, at the mRNA or protein level. "Prognostic" or "prognosing" means predicting the probable development and/or severity of a pathologic condition. Prognostic methods involve determining the test amount of IL-13 in a biological sample from a subject, and comparing the test amount to a prognostic amount or range (i.e., an amount or range from individuals with varying severities of asthma) for IL-13. Various amounts of the IL-13 in a test sample are consistent with certain prognoses for asthma. The detection of an amount of IL-13 at a particular prognostic level provides a prognosis for the subject.

The present invention also provides methods for monitoring the course of asthma and/or atopic disorders by detecting the upregulation of IL-13. Monitoring methods involve determining the test amounts of IL-13 in biological samples taken from a subject at a first and second time, and comparing the amounts. A change in amount of IL-13 between the first and second time indicates a change in the course of asthma and/or atopic disorder, with a decrease in amount indicating remission of asthma, and an increase in amount indicating progression of asthma and/or atopic disorder. Such monitoring assays are also useful for evaluating the efficacy of a particular therapeutic intervention (e.g., disease attenuation and/or reversal) in patients being treated for asthma and/or atopic disorder.

Fluorophore- and chromophore-labeled protein ligands can be prepared. Since antibodies and other proteins absorb light having wavelengths up to about 310 nm, the fluorescent moieties should be selected to have substantial absorption at wavelengths above 310 nm, and preferably above 400 nm. A variety of suitable fluorescers and chromophores are described by Stryer (*Science* (1968) 162:526) and by Brand et al. (*Annual Rev. Biochem.* (1972) 41:843 868). The protein ligands can be labeled with fluorescent chromphore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein ligand can be used to detect the presence or localization of the IL-13 in a sample, e.g., using fluorescent microscopy (such as confocal or deconvolution microscopy).

Immunohistochemistry can be performed using the protein ligands described herein. For example, in the case of an antibody, the antibody can synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

The antibody (or other polypeptide or peptide) can be unlabeled at the time of binding. After binding and washing, the antibody is labeled in order to render it detectable.

The IL-13 antibody can also be immobilized on a protein array. The protein array can be used as a diagnostic tool, e.g., to screen medical samples (such as isolated cells, blood, sera, biopsies, and the like). The protein array can also include other ligands, e.g., that bind to IL-13 or to other target molecules.

Methods of producing polypeptide arrays are described, e.g., in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the protein ligands can be grown on a filter in an arrayed format. Polypeptide production is induced, and the expressed polypeptides are immobilized to the filter at the location of the cell.

A protein array can be contacted with a labeled target to determine the extent of binding of the target to each immobilized polypeptide from the diversity strand library. If the target is unlabeled, a sandwich method can be used, e.g., using a labeled probed, to detect binding of the unlabeled target.

Information about the extent of binding at each address of the array can be stored as a profile, e.g., in a computer database. The protein array can be produced in replicates and used to compare binding profiles, e.g., of a target and a non-target. Thus, protein arrays can be used to identify individual members of the diversity strand library that have desired binding properties with respect to one or more molecules.

The IL-13 antibody can be used to label cells, e.g., cells in a sample (e.g., a patient sample). The ligand is also attached (or attachable) to a fluorescent compound. The cells can then be sorted using fluorescent activated cell sorted (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the ligand from those cells not bound by the ligand. The separated cells can be cultured and/or characterized.

In still another embodiment, the invention provides a method for detecting the presence of a IL-13 within a subject in vivo. The method includes (i) administering to a subject (e.g., a patient having an IL-13 associated disorder) an anti-IL-13 antibody, conjugated to a detectable marker; (ii) exposing the subject to a means for detecting the detectable marker. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{33}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short range radiation emitters, such as isotopes detectable by short range detector probes can also be employed. The protein ligand can be labeled with such reagents using known techniques. For example, see Wensel and Meares (1983) *Radioimmunoimaging and Radioimmunotherapy*, Elsevier, N.Y. for techniques relating to the radiolabeling of antibodies and Colcher et al. (1986) *Meth. Enzymol.* 121: 802 816.

A radiolabeled ligand can also be used for in vitro diagnostic tests. The specific activity of a isotopically-labeled ligand depends upon the half life, the isotopic purity of the radioactive label, and how the label is incorporated into the antibody.

Procedures for labeling polypeptides with the radioactive isotopes (such as $^{14}$C, $^{3}$H, $^{35}$S, $^{99m}$Tc, $^{125}$I, $^{32}$P, $^{33}$P, and $^{131}$I) are generally known. See, e.g., U.S. Pat. No. 4,302,438; Goding, J. W. (Monoclonal antibodies: principles and practice: production and application of monoclonal antibodies in cell biology, biochemistry, and immunology 2nd ed. London; Orlando: Academic Press, 1986. pp 124 126) and the references cited therein; and A. R. Bradwell et al., "Developments in Antibody Imaging", Monoclonal Antibodies for Cancer Detection and Therapy, R. W. Baldwin et al., (eds.), pp 65 85 (Academic Press 1985).

IL-13 antibodies described herein can be conjugated to Magnetic Resonance Imaging (MRI) contrast agents. Some MRI techniques are summarized in EP-A-0 502 814.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{3+}$, $Mn^{2+}$, $Gd^{3+}$). Other agents can be in the form of particles, e.g., less than 10 mm to about 10 nm in diameter and having ferromagnetic, antiferromagnetic, or superparamagnetic properties.

The IL-13 antibodies can also be labeled with an indicating group containing the NMR active $^{19}$F atom, or a plurality of such atoms as described by Pykett ((1982) *Scientific American* 246:78-88) to locate and image IL-13 distribution.

Also within the scope described herein are kits comprising the protein ligand that binds to IL-13 and instructions for diagnostic use, e.g., the use of the IL-13 antibody (e.g., antibody or antigen-binding fragment thereof, or other polypeptide or peptide) to detect IL-13, in vitro, e.g., in a sample, e.g., a biopsy or cells from a patient having an IL-13 associated disorder, or in vivo, e.g., by imaging a subject. The kit can further contain a least one additional reagent, such as a label or additional diagnostic agent. For in vivo use the ligand can be formulated as a pharmaceutical composition.

Kits

An IL-13 antagonist, e.g., anti-IL-13 antibody or fragment thereof, can be provided in a kit, e.g., as a component of a kit. For example, the kit includes (a) an IL-13 antagonist, e.g., anti-IL-13 antibody or fragment thereof, e.g., a composition that includes an IL-13 antibody or fragment thereof, and, optionally (b) informational material. The informational material can be descriptive, instructional, marketing, or other material that relates to the methods described herein and/or the use of an IL-13 antagonist, e.g., anti-IL-13 antibody or fragment thereof, for the methods described herein.

The informational material of the kits is not limited in its form. In one embodiment, the informational material can include information about production of the compound, molecular weight of the compound, concentration, date of expiration, batch, or production site information, and so forth. In one embodiment, the informational material relates to using the ligand to treat, prevent, diagnose, prognose, or monitor a disorder described herein.

In one embodiment, the informational material can include instructions to administer an IL-13 antagonist, e.g., anti-IL-13 antibody or fragment thereof, in a suitable manner to perform the methods described herein, e.g., in a suitable dose, dosage form, or mode of administration (e.g., a dose, dosage form, or mode of administration described herein). In another embodiment, the informational material can include instructions to administer an IL-13 antagonist, e.g., anti-IL-13 antibody or fragment thereof, to a suitable subject, e.g., a human, e.g., a human having, or at risk for, allergic asthma, non-allergic asthma, or an IL-13 mediated disorder, e.g., an allergic and/or inflammatory disorder, or HTLV-1 infection. IL-13 production has been correlated with HTLV-1 infection (Chung et al., (2003) *Blood* 102: 4130-36).

For example, the material can include instructions to administer an IL-13 antagonist, e.g., anti-IL-13 antibody or fragment thereof, to a patient, a patient with or at risk for allergic asthma, non-allergic asthma, or an IL-13 mediated disorder, e.g., an allergic and/or inflammatory disorder, or HTLV-1 infection.

The kit can include one or more containers for the composition containing an IL-13 antagonist, e.g., anti-IL-13 antibody or fragment thereof. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial, or syringe that has attached thereto the informational material in the form of a label. In some embodiments, the kit includes a plurality (e.g., a pack) of individual containers, each containing one or more unit dosage forms (e.g., a dosage form described herein) of an IL-13 antagonist, e.g., anti-IL-13 antibody or fragment thereof. For example, the kit includes a plurality of syringes, ampules, foil packets, atomizers, or inhalation devices, each containing a single unit dose of an IL-13 antagonist, e.g., anti-IL-13 antibody or fragment thereof, or multiple unit doses.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is an implantable device that dispenses metered doses of the ligand.

The Examples which follow are set forth to aid in the understanding of the inventions but are not intended to, and should not be construed to, limit its scope in any way.

EXAMPLE 1

Generation of a Murine Monoclonal Antibody Specific for Human IL-13

EXAMPLE 1.1

Isolation of a Murine Monoclonal Antibody that Binds to Human IL-13 (mAb13.2)

Polyclonal antisera were prepared by immunization of female BALB/c mice with recombinant human IL-13 (R&D Systems, Minneapolis, Minn.). Sera were screened for binding to human IL-13 by ELISA. Splenocytes from a mouse demonstrating high serum antibody titers were fused with the P3X63_AG8.653 myeloma (ATCC), and plated in selective media. Fusions were isolated with 3 rounds of subcloning by limiting dilution and screened for the production of antibodies that had a binding affinity to human IL-13. Three monoclonal antibodies were capable of binding IL-13, interfering with the formation of a functional IL-13 signaling complex and neutralizing and/or inhibiting one or more IL-13-associated activities; antibody mAb13.2 (IgG1 kappa) was chosen for further study.

EXAMPLE 1.2

Figure 1:
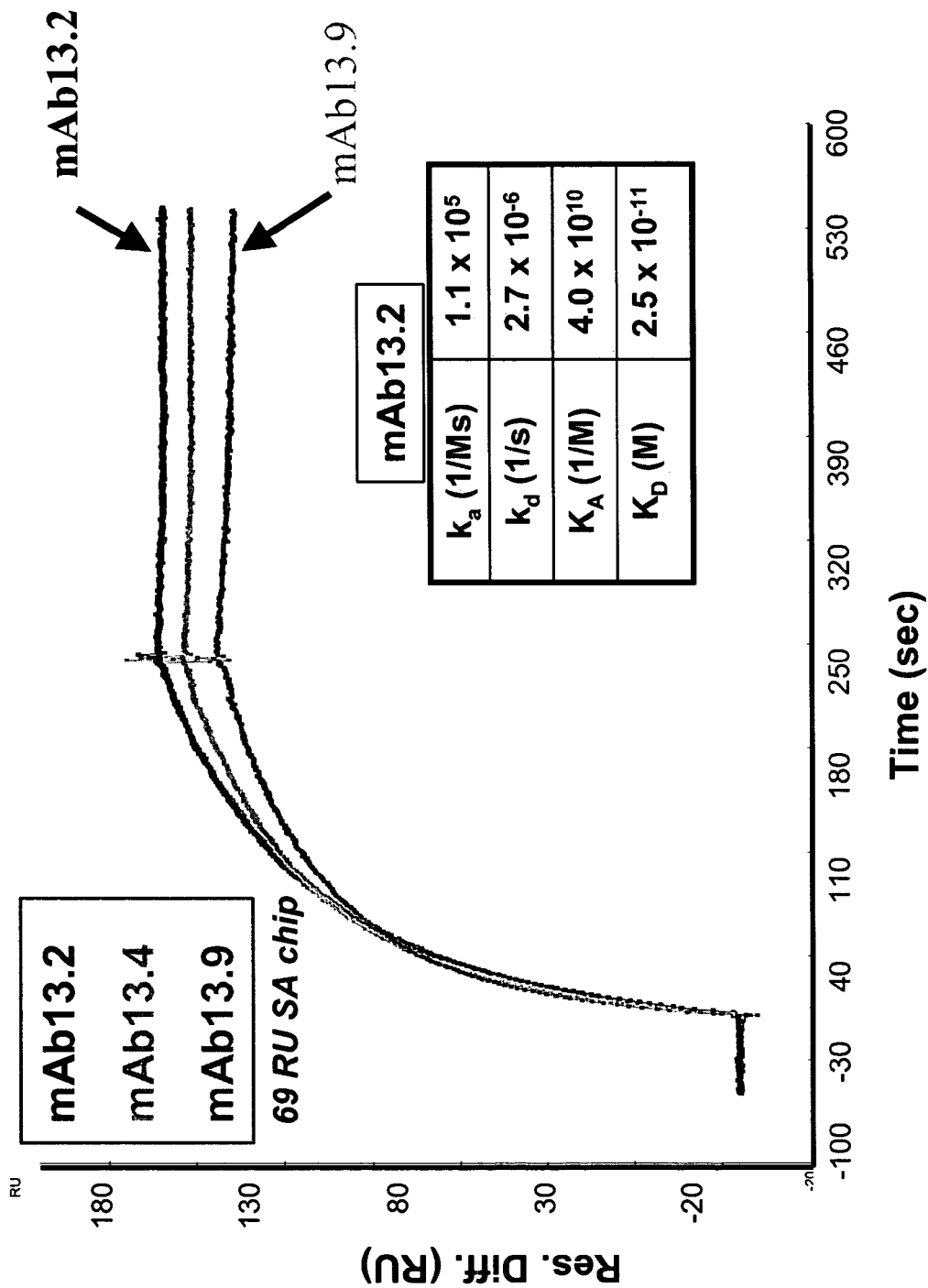
FIG. 1: Kinetic parameters of mAb13.2 binding to human IL 13. The binding interactions between biotinylated IL-13 immobilized to a 69 RU streptavidin chip and monoclonal antibody mAb13.2, monoclonal antibody mAb13.4, or monoclonal antibody mAb13.9 are depicted as resonance units (RU; y-axis) over time (x-axis). Kinetic constants for mAb13.2 also are shown.
Figure 2:
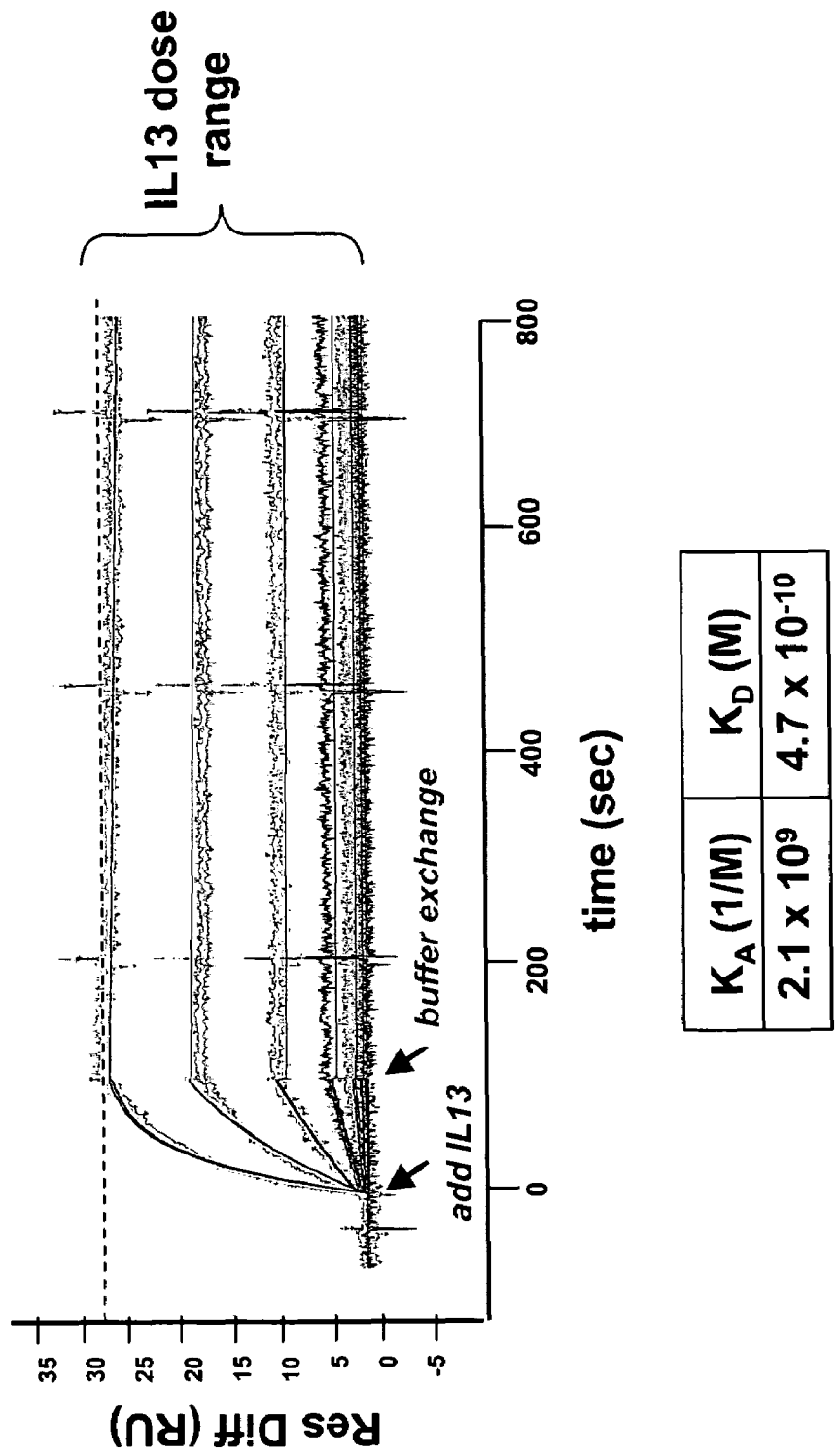
FIG. 2: Kinetic parameters of mAb13.2 binding to IL-13. The binding interaction between various doses of human IL-13 and monoclonal antibody mAb13.2 immobilized to a BIACORE™ chip is depicted as resonance difference (RU; y-axis) over time (x-axis). Kinetic constants for mAb13.2 also are shown.
Figure 3:
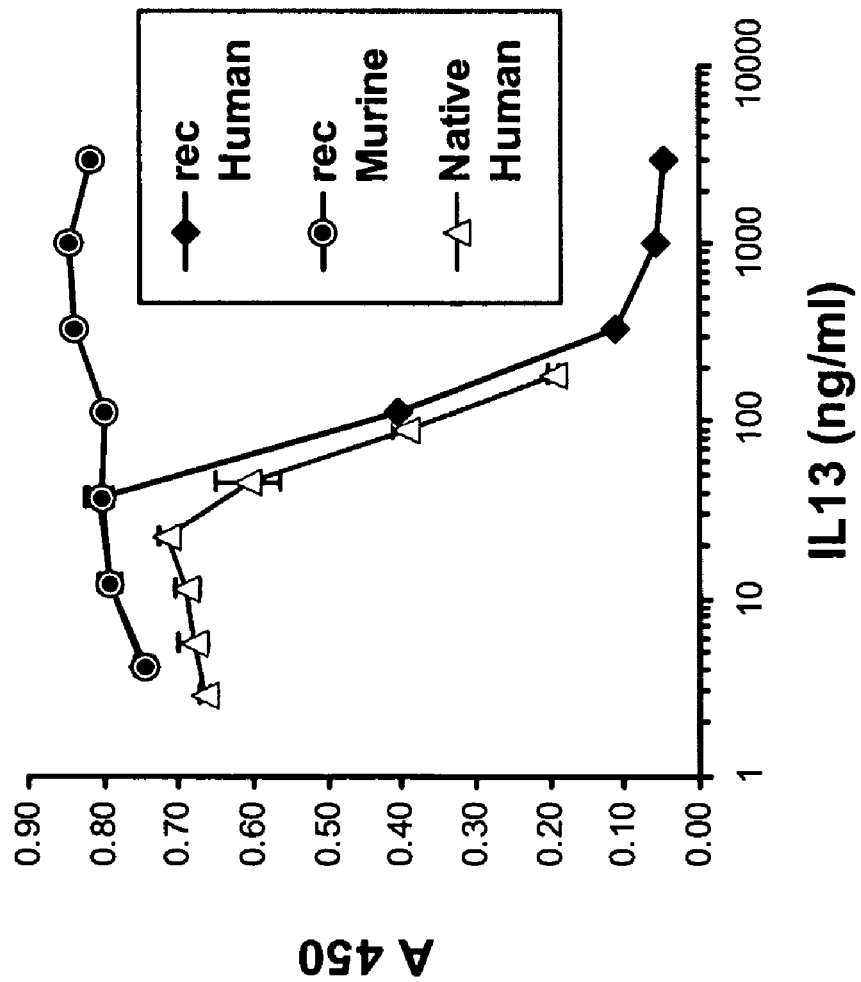
FIG. 3: Monoclonal antibody mAb13.2 binds to native human IL-13. The figure shows the average absorbance value ($A_{450}$; y-axis) of biotinylated mAb13.2 bound to FLAG-human IL-13 in the presence of increasing concentrations (x-axis) of recombinant human IL-13 (◆), recombinant murine IL-13 (●), or native human IL-13 (Δ) isolated from mitogen-activated, Th2-skewed, cord blood mononuclear cells.
Figure 4B:
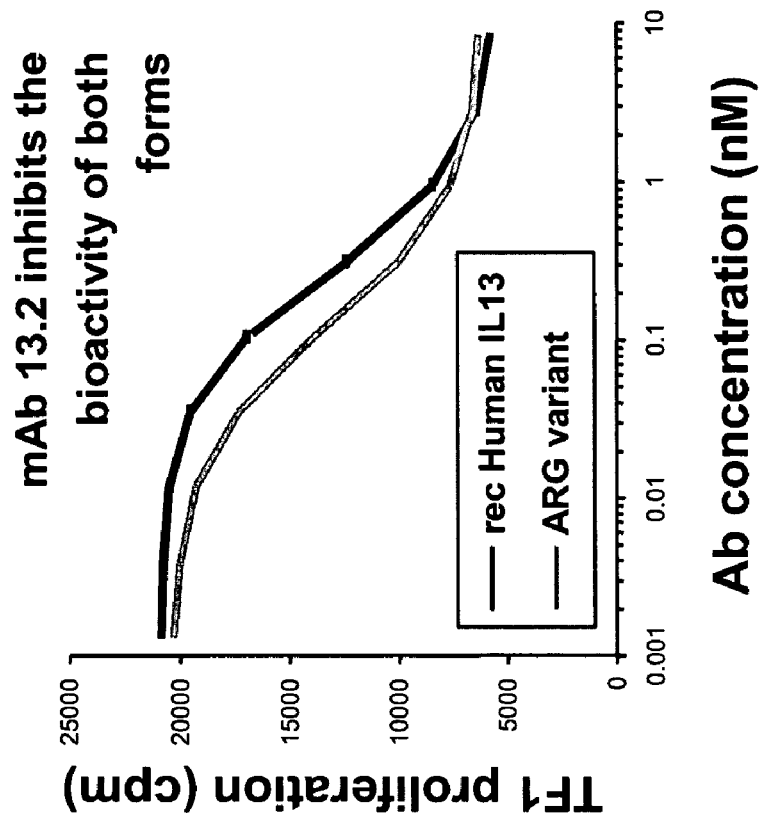
FIG. 4: Monoclonal antibody mAb13.2 binds to and neutralizes the ARG-variant form of human IL-13. (A) The response (y-axis) of human IL-13 or a recombinantly expressed ARG-variant of IL-13 passed over biotinylated mAb13.2 immobilized to a BIACORE™ chip is shown as a function of time (x-axis). (B) The proliferation of TF1 cells (y-axis) incubated with increasing concentrations of mAb13.2 (x-axis) and either recombinant human IL-13 or a recombinantly expressed ARG-variant of IL-13 is shown.
Figure 4A:
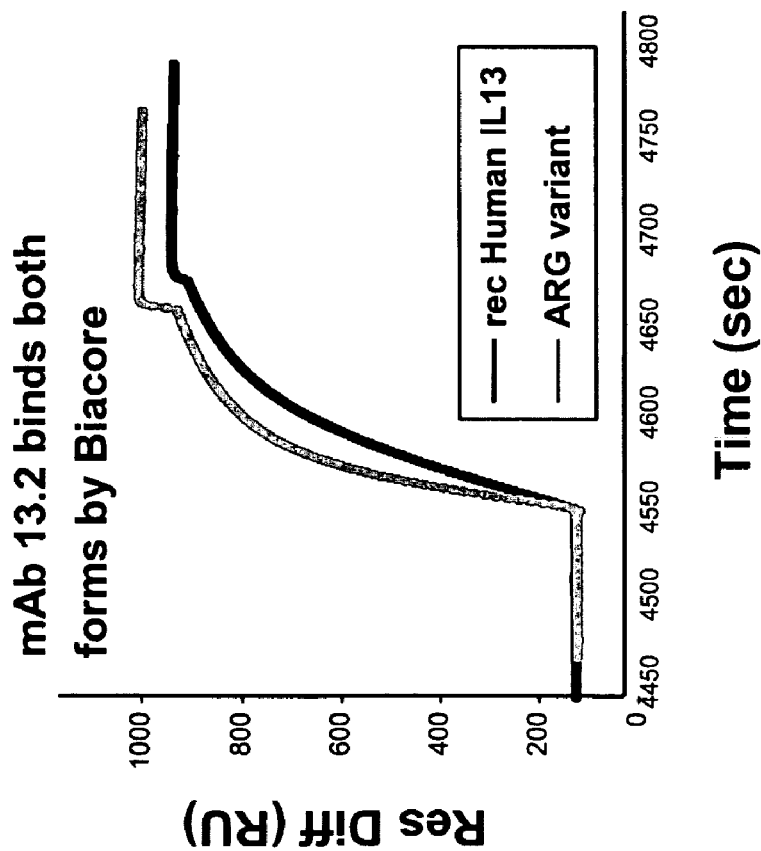

Murine Monoclonal Antibody, mAb13.2, Binds Human IL-13 with High Affinity and Specificity Several measures were taken to confirm that the murine monoclonal antibody isolated in Example 1.1, i.e., mAb13.2, binds with high affinity and specificity to human IL-13. First, BIACORE™ analyses of three monoclonal antibodies to human IL-13 (mAb13.2, mAb13.4, and mAb13.9) were performed using a 69 RU streptavidin chip to which biotinylated IL-13 had been immobilized. The three antibodies were individually passed over the chip and each showed rapid binding (FIG. 1). Upon buffer exchange, dissociation was slow (FIG. 1). Second, BIACORE™ analysis of mAb13.2 was performed using a Biacore chip to which mAb13.2 had been immobilized. Different concentrations of IL-13 were passed over the chip. Again, rapid binding and slow dissociation was shown (FIG. 2). Third, analysis by ELISA determined that mAb13.2 bound to all forms of human IL-13 tested, including native IL-13 derived from cord blood T cells (FIG. 3). Plates were coated with anti-FLAG™ M2 antibody. The binding of FLAG™-human IL-13 was detected with biotinylated mAb13.2 and streptavidin-peroxidase. ELISA demonstrated that the binding between mAb13.2 and IL-13 could be competed with native human IL-13 isolated from mitogen-activated, Th2-skewed, cord blood mononuclear cells and recombinant human IL-13 (FIG. 3). There was no detectable binding of mAb13.2 to recombinant murine IL-13 (FIG. 3). To confirm the results found by ELISA, the monoclonal antibody, mAb13.2, was coated onto a Biacore chip, and solutions containing recombinant human IL-13 or a polymorphic form of IL-13 (ARG variant), which is expressed at high frequency in patients suffering from asthma (Heinzmann et al. (2000) *Hum. Mol. Genet.* 9:594), were passed over the chip. Both forms showed rapid binding and undetectable dissociation from the antibody (FIG. 4A). Finally, during a preliminary cross-reactivity study performed under GLP (good laboratory practice) conditions, mAb13.2 demonstrated no significant cross-reactivity when screened against a panel of 37 normal human tissues obtained at autopsy or biopsy, i.e., a tissue panel that included all the tissues on the "suggested list of human tissues to be used for immunohistochemical investigations of cross-reactivity" in Annex II of the DC CPMP Guideline III/5271/94 Draft 5, "Production and quality control of monoclonal antibodies" and all the tissues recommended in Table 2 of the 1997 US FDA/CBER "Points to Consider in the Manufacture and Testing of Monoclonal Antibody Products for Human Use".

EXAMPLE 1.3

Figure 5:
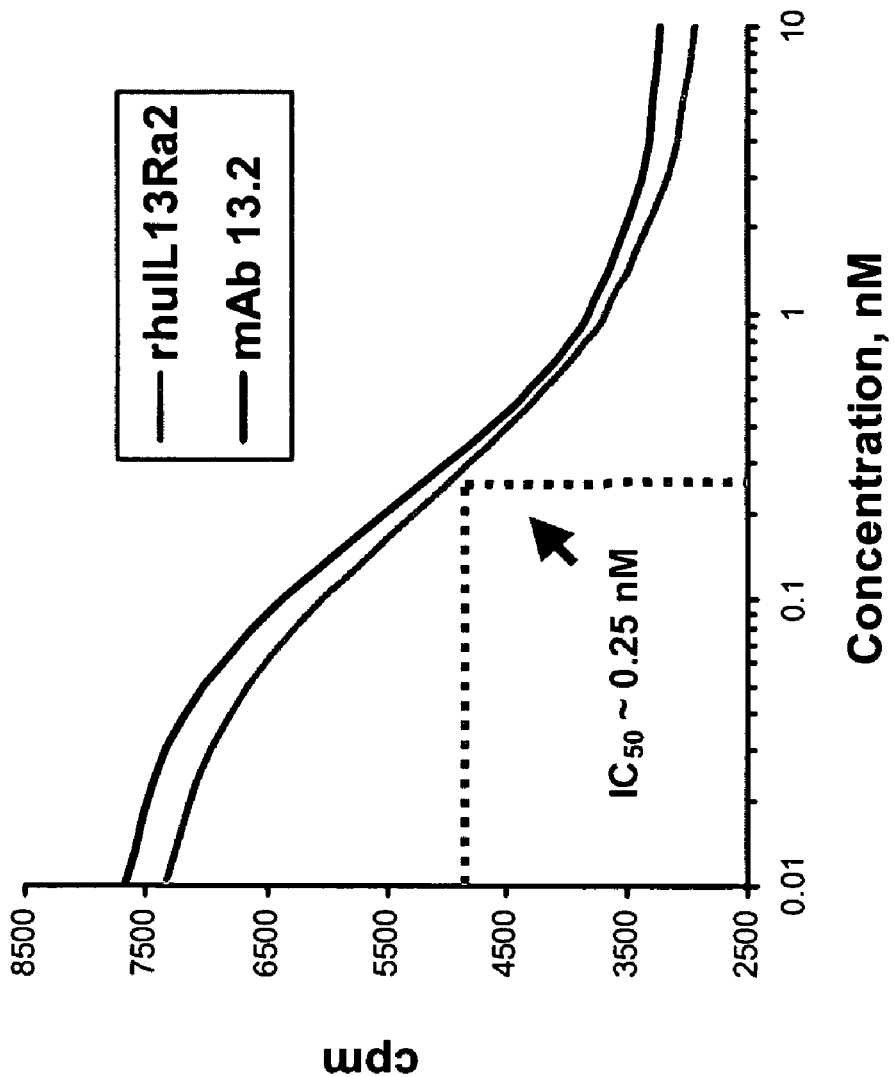
FIG. 5: Monoclonal antibody mAb13.2 inhibits the bioactivity of human IL-13 with an IC50 comparable to that of a soluble IL-13 receptor. The proliferation of the IL-13-dependent TF1 cell line, as determined by $^{3}$H-thymidine incorporation, is measured as cpm (y-axis) after 3 days of incubation with IL-13 and increasing concentrations (x-axis) of either mAb13.2 or soluble IL-13 receptor (rhuIL-13Rα2).

Murine Monoclonal Antibody mAb13.2 Neutralizes IL-13-Associated Activities In Vitro The ability of mAb13.2 to neutralize one or more IL-13-associated activities in vitro was confirmed using the TF1 bioassay, human peripheral blood monocytes, and human peripheral blood B cells. Under appropriate conditions, proliferation of the human TF1 erythroleukemia cell line can be made dependent on IL-13. It was first determined whether proliferation of the cytokine-depending TF1 cell line induced with suboptimal concentrations of either recombinant human IL-13 or the ARG-variant form of human IL-13 could be inhibited by mAb13.2. FIG. 4B demonstrates that mAB13.2 inhibited the abilities of both recombinant human IL-13 and the ARG-variant form of human IL-13 to stimulate TF1 proliferation. Second, the TF1 cell line was starved for IL-13, then exposed to a suboptimal concentration of recombinant human IL-13 to induce proliferation in the presence of either purified mouse mAb13.2 or soluble IL-13 receptor (rhuIL-13Rα2). Cells were incubated for 3 days, and $^3$H-thymidine incorporation over the final 4 hours was determined by liquid scintillation counting. At suboptimal IL-13 concentrations, mAb13.2 caused a dose-dependent inhibition of TF1 proliferation (FIG. 5). The $IC_{50}$ for this effect, 250 pM, is highly comparable to that of soluble rhuIL-13Rα2 (FIG. 5). Exemplary antibodies have an $IC_{50}$ for this effect between about 50-500 pM, or 120-300 pM, or 240-350 pM.

Figure 6:
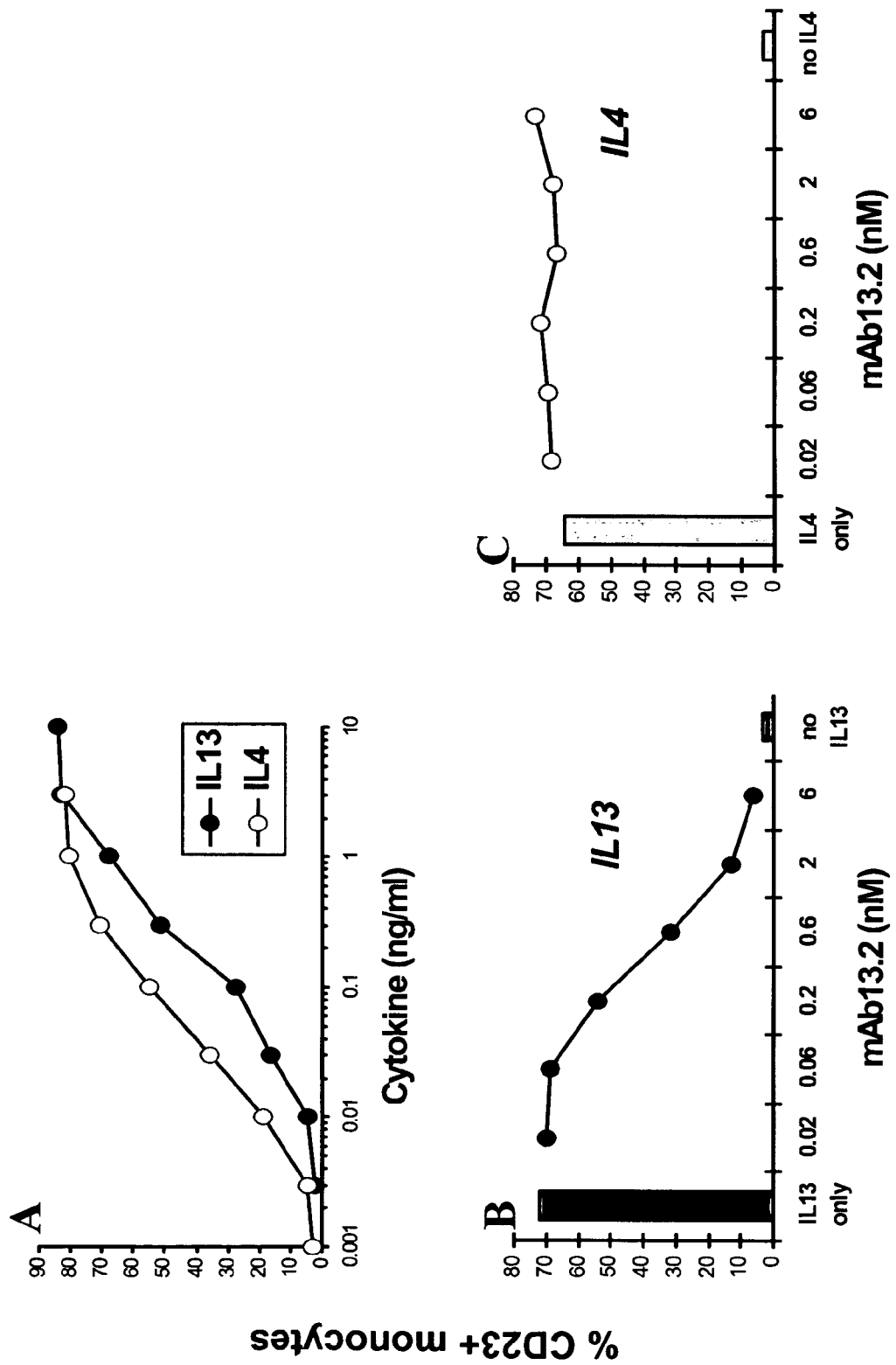
FIG. 6: Monoclonal antibody mAb13.2 inhibits IL 13-mediated CD23 expression, but not IL 4-mediated CD23 expression, on normal human monocytes. (A) The percentage of monocytes that expressed cell surface CD23 (y-axis) after peripheral blood mononuclear cells (PBMCs) isolated from a healthy donor were treated overnight with the indicated concentration (x-axis) of recombinant human IL-13 (●) or IL-4 (o) is shown. (B) The percentage of monocytes that expressed cell surface CD23 (y-axis) after PBMCs isolated from a healthy donor were treated with IL-13 and indicated concentrations of purified mouse mAb13.2 (x-axis) is shown. (C) The percentage of monocytes that expressed cell surface CD23 (y-axis) after PBMCs isolated from a healthy donor were treated overnight with IL-4 and the indicated concentrations of purified mouse mAb13.2 (x-axis) is shown.

Since human peripheral blood monocytes respond in a dose-dependent manner to IL-13 or IL-4 by increasing cell-surface expression of low affinity IgE receptor (CD23) (FIG. 6A), human monocytes were used to confirm the ability of mAb13.2 to neutralize this IL-13-associated activity. To determine whether mAb13.2 could neutralize IL-13-mediated CD23 cell surface expression by monocytes, peripheral blood mononuclear cells were isolated from a healthy donor and incubated with increasing amounts of IL-13 only, increasing amounts of IL-4 only, 1 ng/ml IL-13 and increasing amounts of mAb13.2, or 0.3 ng/ml IL-4 and increasing amounts of mAb13.2. The next day, cells were harvested, and stained with CYCHROME™-labeled anti-CD11b (monocyte marker) and PE-labeled anti-CD23. Gated CD11b$^+$ monocytes were assayed for CD23 expression by flow cytometry. As expected, mAb13.2 inhibited IL-13-mediated CD23 expression (FIG. 6B) but did not inhibit IL-4-induced CD23 expression (FIG. 6C).

Figure 7:
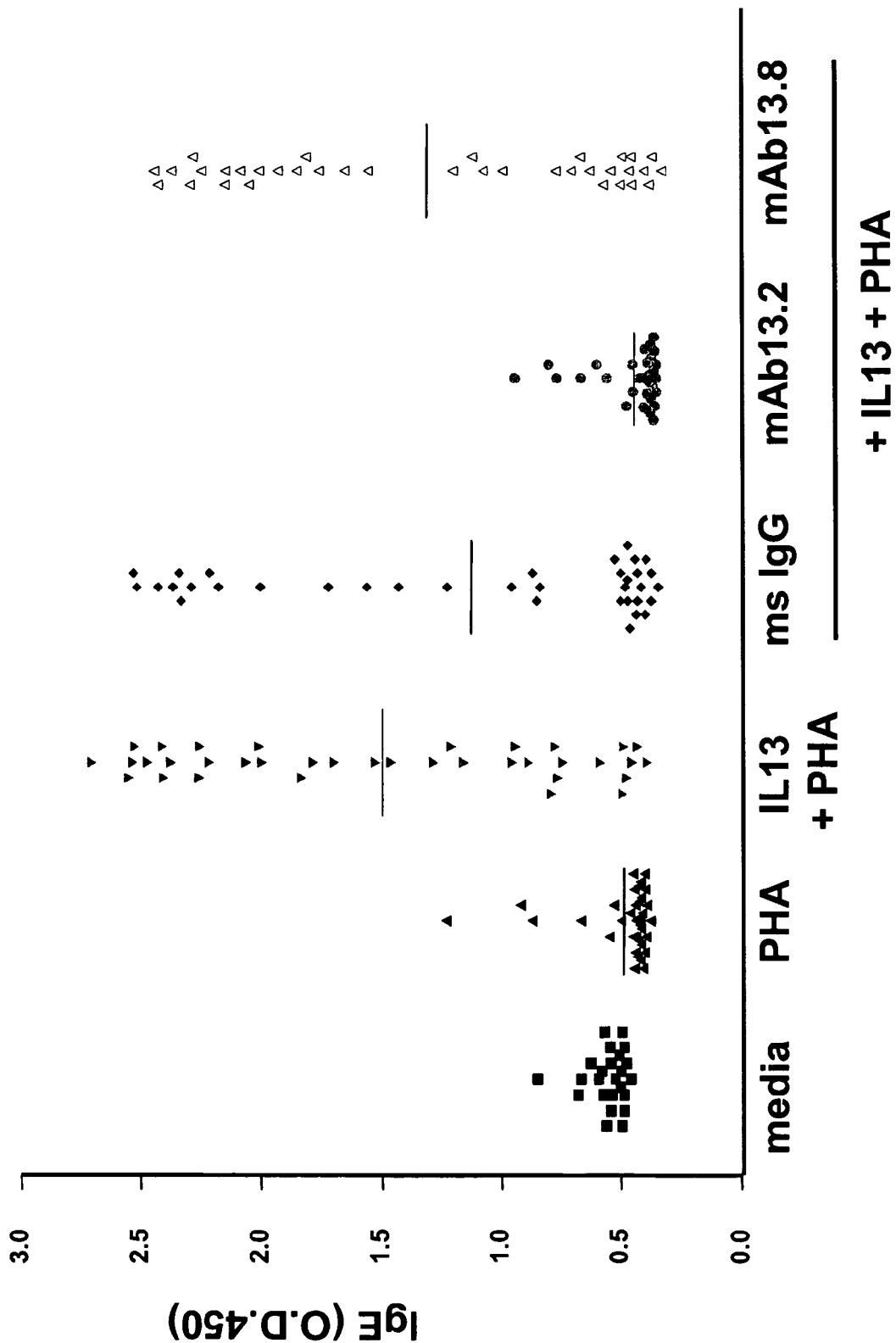
FIG. 7: Monoclonal antibody mAb13.2 inhibits IL 13-dependent IgE production by human B cells. The concentration of IgE in supernatant isolated from PBMCs cultured in media alone or various combinations of PHA, IL-13, control antibody (ms IgG), mAb13.2, and mAb13.8 (x-axis) is shown as the absorbance at 450 nm (IgE (O.D.450); y-axis).

The effects of mAb13.2 were also tested in a model of IL-13-mediated IgE production by human peripheral blood B cells. In response to IL-13 and the T cell mitogen, PHA, human B cells undergo an Ig isotype switch recombination to IgE, resulting in higher IgE levels in culture. This effect can be seen as an increased frequency of IgE-producing B cells. PBMCs from a healthy donor were cultured in microtiter wells in the presence of autologous irradiated PBMCs as feeders, and stimulated with PHA and IL-13. After 3 weeks, each well was assayed for IgE concentrations by ELISA. PHA+IL-13 increased the frequency of IgE-producing B cell clones (FIG. 7). This effect was inhibited by mAb13.2, but not by an IL-13-specific nonneutralizing antibody (mAb13.8) or by control mouse IgG (msIgG) (FIG. 7), demonstrating that mAb13.2 efficiently blocked IL-13-mediated IgE isotype switching by cultured B cells.

Finally, the ability of mAb13.2 to block an early cellular response to IL-13 was tested by examining its effects on signal transducer and activator of transcription (STAT) 6 phosphorylation. Upon IL-13 interaction with its cell surface receptor, STAT6 dimerizes, becomes phosphorylated, and translocates from the cytoplasm to the nucleus, where it activates transcription of cytokine-responsive genes (Murata et al. (1995) *J. Biol. Chem.* 270:30829-36). Specific antibodies to phosphorylated STAT6 can detect this activation by Western blot and/or flow cytometric analysis within 30 minutes of IL-13 exposure.

Figure 8:
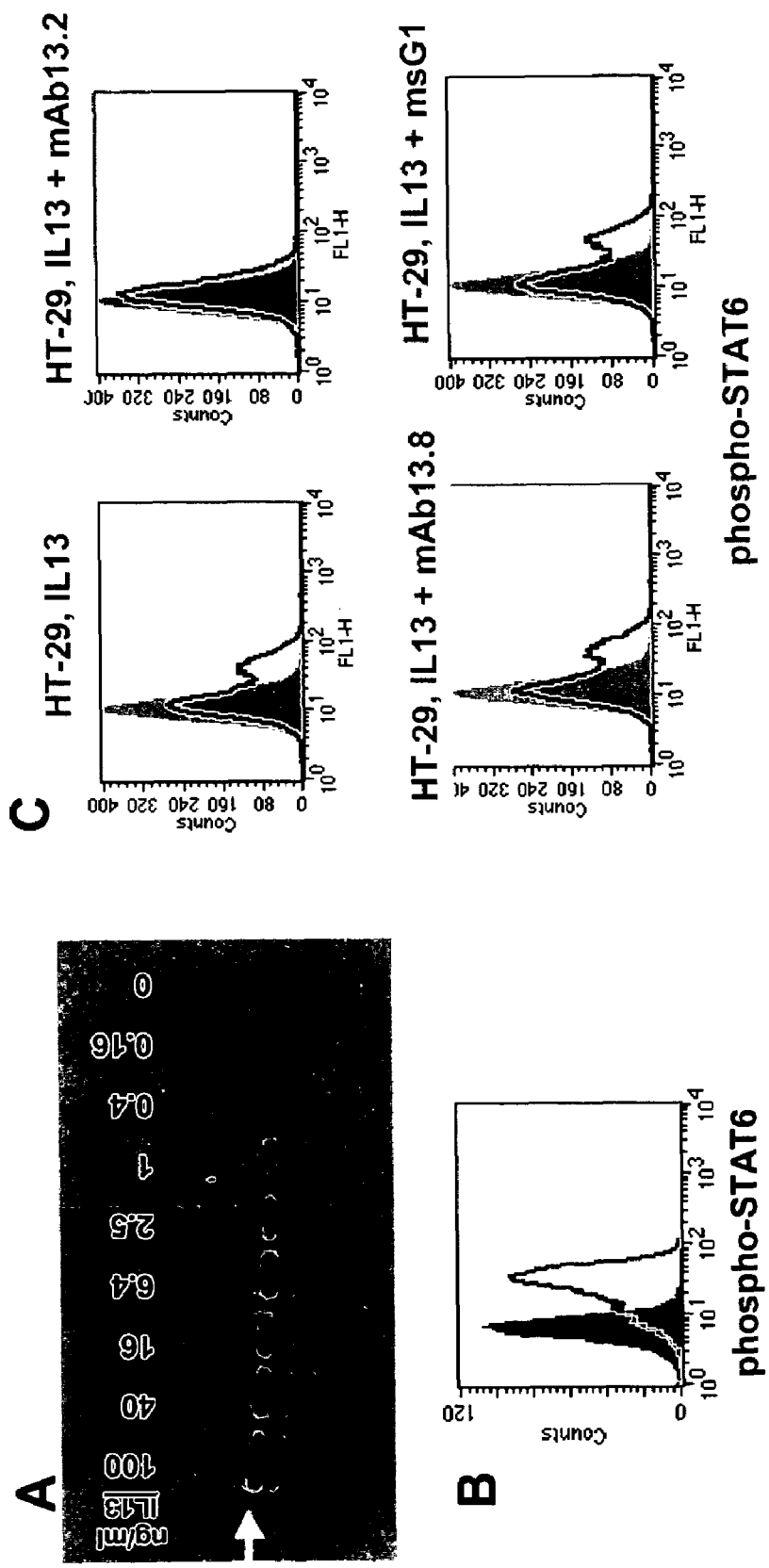
FIG. 8: Monoclonal antibody mAb13.2 inhibits IL 13-mediated STAT6 phosphorylation by human epithelial cells. (A) Western blot analysis for phosphorylated STAT6 in cell lysates isolated from HT-29 cells treated with the indicated concentration of IL-13 is shown. (B) The graph demonstrates the number of HT-29 cells as determined by flow cytometric analysis (counts; y-axis), that demonstrated fluorescence (phospho-STAT6; x-axis) after the cells were untreated (filled histogram) or treated (unfilled histogram) with IL-13 and stained with ALEXA™ Fluor 488-labeled monoclonal antibody to phosphorylated STAT6. (C) The graphs demonstrate the number of HT-29 cells as determined by flow cytometric analysis (counts; y-axis), that demonstrated fluorescence (phospho-STAT6) after the cells remained untreated (filled histograms); or were treated (unfilled histograms) with IL-13 (upper left graph), IL-13 and mAb13.8 (lower left graph), IL-13 and mAb13.2 (upper right graph), or IL-13 and control antibody (msG1) (lower right graph) and stained with ALEXA™ Fluor 488.

The HT-29 human epithelial cell line was used to assay STAT6 phosphorylation. HT-29 cells were incubated in increasing concentrations of IL-13 for 30 minutes at 37° C. Western blot analysis of cell lysates demonstrated dose-dependent IL-13-mediated phosphorylation of STAT6 (FIG. 8A). Similarly, flow cytometric analysis demonstrated phosphorylated STAT6 in HT-29 cells that were treated with a saturating concentration of IL-13 for 30 minutes at 37° C., fixed, permeabilized, and stained with an ALEXA™ Fluor 488-labeled mAb to phospho-STAT6 (FIG. 8B). Treated cells stained with an isotype control antibody did not demonstrate fluorescence. Finally, when cells were treated with a suboptimal concentration of IL-13 alone, IL-13 and mAb13.8, IL-13 and mAB13.2, or IL-13 and a control msIgG1 antibody, flow cytometric analysis demonstrated complete abrogation of STAT6 phosphorylation only when cells were treated in the presence of mAb13.2, i.e., whereas mAb13.2 blocked STAT6 phosphorylation, an IL-13-specific normeutralizing antibody (mAb13.8) and a control mouse IgG1 had no effect (FIG. 8C). These studies demonstrated that mAb13.2 inhibited IL-13-mediated STAT6 phosphorylation.

EXAMPLE 1.4

Figure 9:
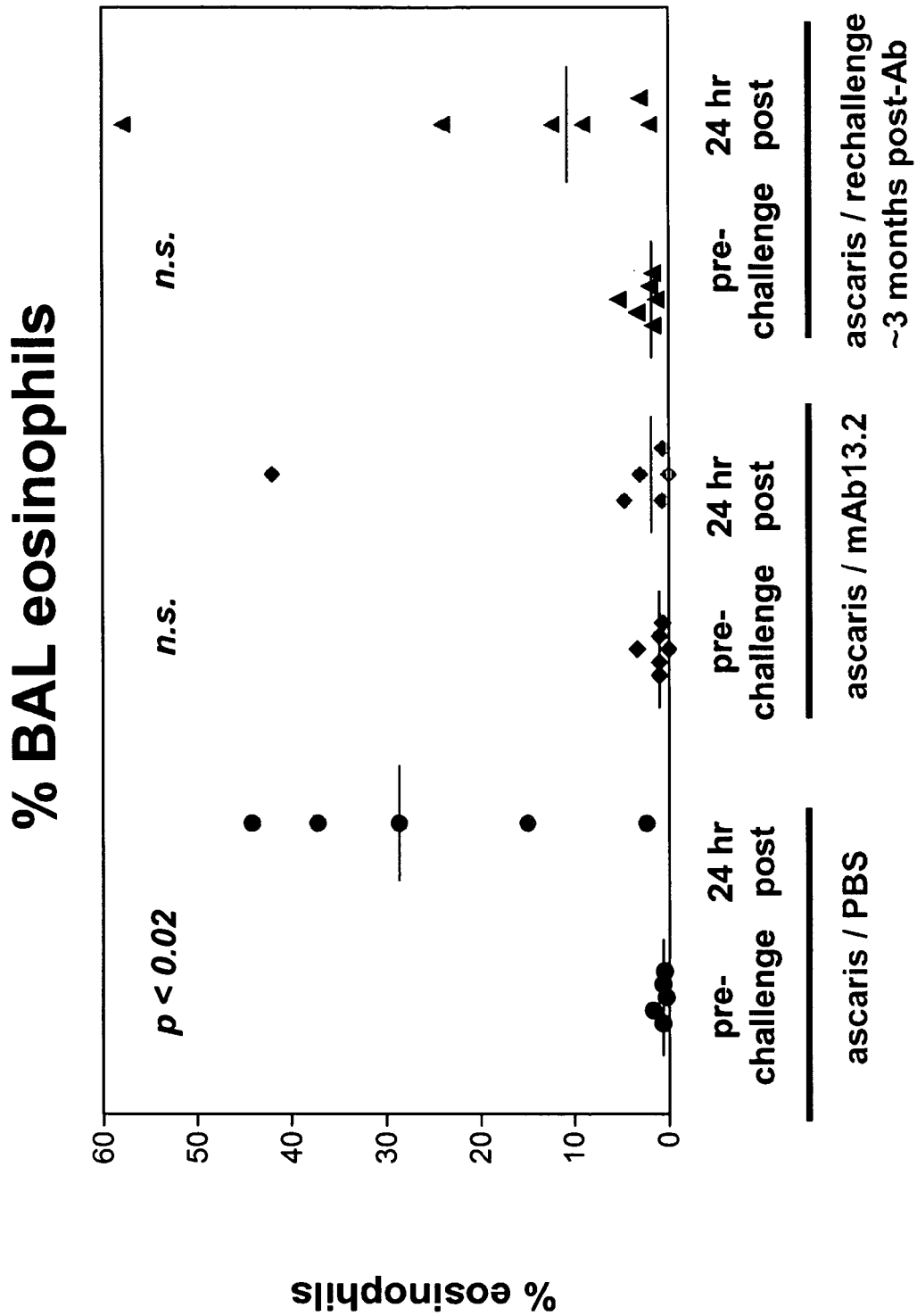
FIG. 9: Monoclonal antibody mAb13.2 prevents *Ascaris*-induced lung eosinophilia in vivo. The figure demonstrates the percentage of eosinophils found in bronchoalveolar lavage (BAL) samples (y-axis) taken from untreated cynomolgus monkeys (*ascaris*/PBS) (●,●), cynomolgus monkeys pretreated with mAb13.2 (*ascaris*/mAb13.2) (♦,♦) or cynomolgus monkeys previously treated with mAb13.2 and challenged with *Ascaris suum* antigen (*ascaris*/rechallenge ~3 months post-Ab) (▲,▲), prior to challenge (dark symbols) or 24 hours post-challenge or rechallenge (light symbols) with *Ascaris suum* antigen.

Murine Monoclonal Antibody mAb13.2 Neutralizes IL-13-Associated Activities In Vivo The efficacy of mouse mAb13.2 to neutralize one or more IL-13-associated activities in vivo was tested using a model of antigen-induced airway inflammation in cynomolgus monkeys naturally allergic to *Ascaris suum*. In this model, challenge of an allergic monkey with *Ascaris suum* antigen results in an influx of inflammatory cells, especially eosinophils, into the airways. To test the ability of mAb13.2 to prevent this influx of cells, the antibody was administered 24 hours prior to challenge with *Ascaris suum* antigen. On the day of challenge, a baseline bronchoalveolar lavage (BAL) sample was taken from the left lung. The antigen was then instilled intratracheally into the right lung. Twenty-four hours later, the right lung was lavaged, and the BAL fluid from animals treated intravenously with 8 mg/kg ascites-purified mAb13.2 was compared to BAL fluid from untreated animals. Eosinophil counts increased in 4 of 5 untreated animals following challenge, as compared to 1 of 6 animals treated with mAb13.2 (FIG. 9). The percent BAL eosinophils was significantly increased for the untreated group (p<0.02), but not for the antibody-treated group. These results confirm that mAb13.2 effectively prevents airway eosinophilia in allergic animals challenged with an allergen.

The average serum half-life of mouse mAb13.2 was less than one week in the monkeys. At the 3-month time point, when all traces of mAb13.2 would have been gone from the serum, mAb13.2-treated animals were rechallenged with *Ascaris suum* to confirm the *Ascaris*-responsiveness of those individuals. Two of six monkeys in the treated group were found to be nonresponders.

EXAMPLE 1.5

Murine Monoclonal Antibody mAb13.2 Binds to a Region of IL-13 that Normally Binds to IL-4Rα

IL-13-associated activities are presumably mediated through a receptor complex consisting of the IL-13Rα1 and IL-4Rα chains. The cytokine first undergoes a relatively low affinity interaction with IL-13Rα1 on the surface of cells. The IL-13/IL-13Rα1 complex then recruits IL-4Rα to form the complete IL-13 receptor, which is bound to its ligand (IL-13) with high affinity (Zurawski et al. (1993) *EMBO J.* 12:2663; Zurawski et al. (1995) *J. Biol. Chem.* 270:23869). The binding of IL-13 with the high affinity receptor then sends downstream signals through the IL-4Rα chain involving the Janus kinase-signal transducer and activator of transcription (JAK-STAT) pathway, e.g., via phosphorylation of STAT6, which can be monitored as one of the earliest cellular responses to IL-13 (Murata et al., supra). Several approaches, such as epitope mapping, x-ray crystallography, and further BIA-CORE™ analysis, were used to elucidate the interaction between murine mAb13.2 antibody and human IL-13 and further examine the basis underlying the ability of mAb13.2 to modulate one or more IL-13-associated activities.

Figure 10:
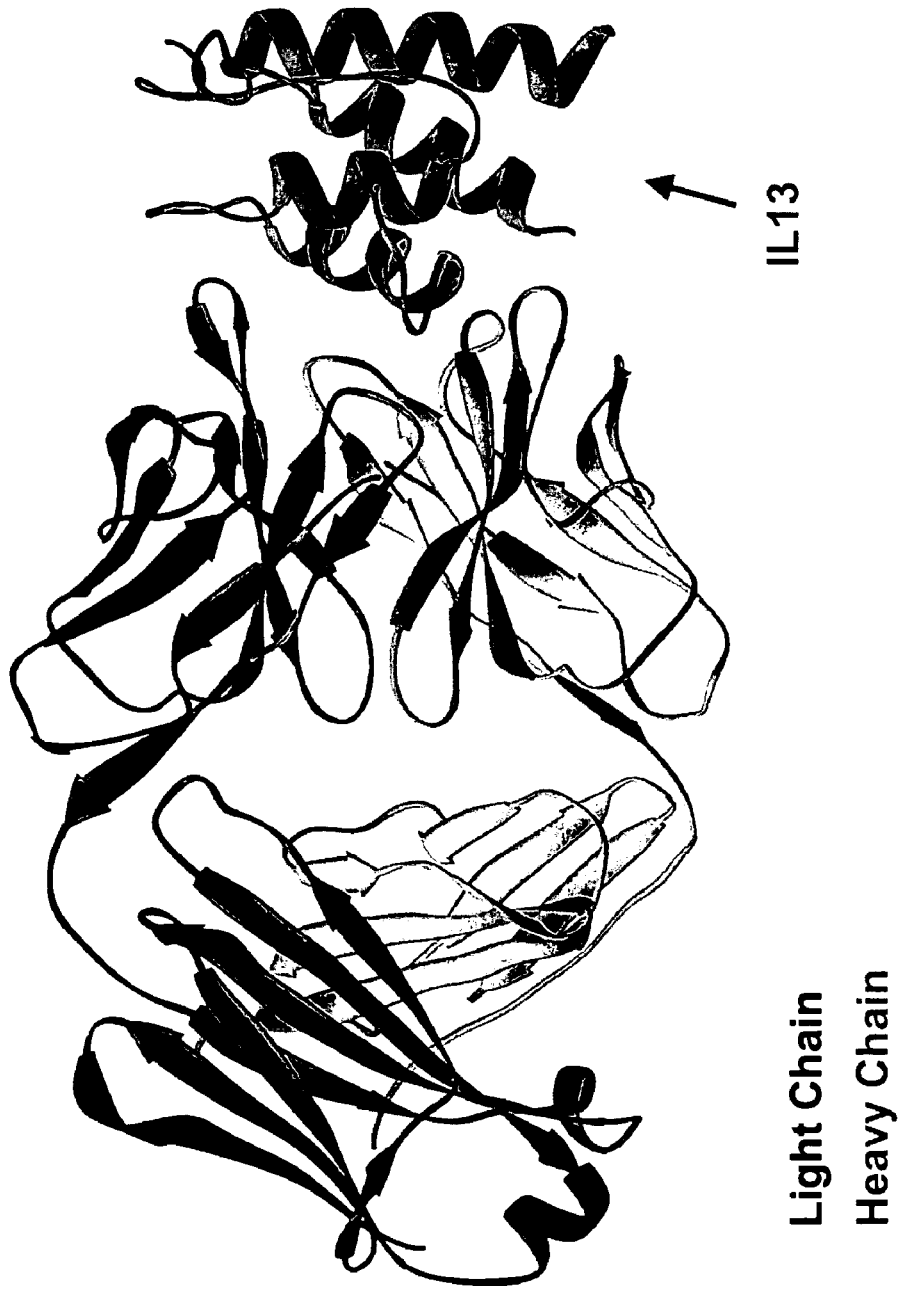
FIG. 10: Cocrystal structure of mAb13.2 Fab fragment with human IL-13. X-ray crystallography of the mAb13.2 Fab fragment reveals the light chain with dark shading, and the heavy chain in lighter shading. Also shown is the IL-13 structure (at right). The figure also depicts interaction of the C-alpha helix of IL-13 with the CDR loops of the antibody.

The interaction between mAb13.2 and IL-13 was studied by x-ray crystallography. Total IgG from ascites was isolated over a protein A column and digested with papain to generate mAb13.2 Fab fragments, which were then highly purified. The Fab fragments themselves were crystallized, and structural analyses were obtained at 2.8 Å resolution using synchrotron radiation. In addition, mAb13.2 Fab fragments were cocrystallized with human IL-13, and this crystal structure resolved to 1.8 Å resolution. The major contact sites between mAb13.2 and IL-13 were identified as clustered mainly at the CDR loops of the antibody and the C-terminal region of the C-helix of IL-13 (FIG. 10). According to the numbering sequence shown in FIG. 11 for the mature IL-13 protein, i.e., the IL-13 protein from which the signal peptide has been cleaved, the major residues of IL-13 that contact mAb13.2 are GLU49, ASN53, GLY69, PRO72, HIS73, LYS74, and ARG86 of SEQ ID NO:32.

Figures 12A, 12B:
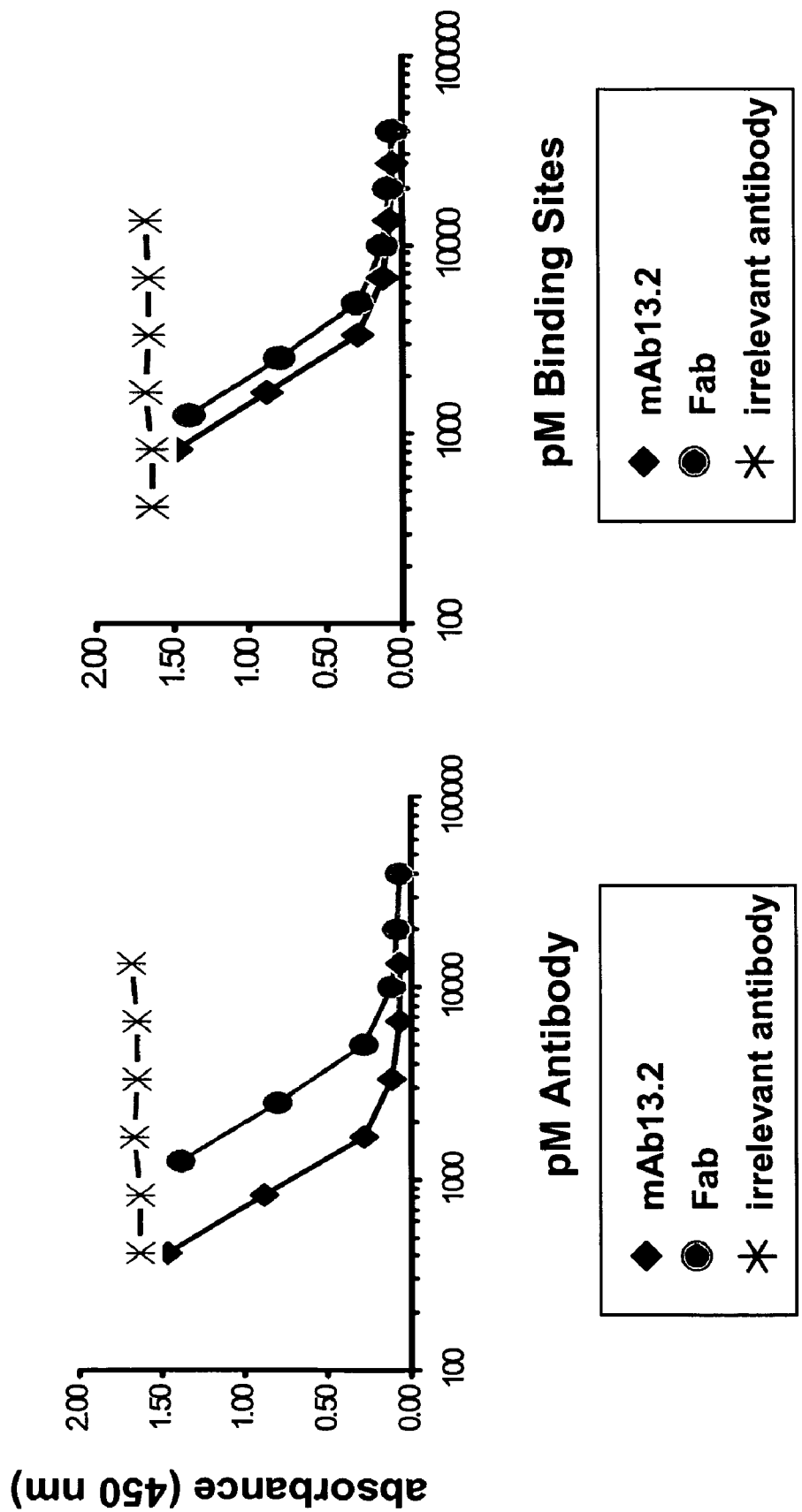
FIG. 12: Fab fragments of mAb13.2 bind to human IL-13. The figure shows the average absorbance value (450 nm; y-axis) of biotinylated mAb13.2 bound to FLAG-human IL-13 in the presence of competing unlabeled mAb13.2 (♦), mAb13.2 Fab fragments (●), or irrelevant antibody (*) at increasing concentrations (x-axis) expressed as (A) pM antibody or (B) pM binding sites.

The ability of mAb13.2 Fab fragments to bind to human IL-13 was confirmed by ELISA. The binding of FLAG-human IL-13 to ELISA plates that were coated overnight with anti-FLAG M2 antibody was detected using biotinylated mAb13.2. Unlabeled mAb13.2, isolated mAb13.2 Fab fragments, or irrelevant antibody was introduced to compete with biotinylated mAb13.2 binding to FLAG-human IL-13. The data demonstrate that unlabeled mAb13.2 and mAb13.2 Fab fragments were able to compete with biotinylated mAb13.2 for binding to FLAG-human IL-13 (FIG. 12). Additionally, although it appeared that a greater concentration of Fab fragments was required to achieve a similar degree of competition as unlabeled mAb13.2 (FIG. 12A), this discrepancy was resolved when the competition was analyzed as a function of the concentration of binding sites, e.g., assuming one binding site per each isolated Fab fragment and two binding sites per each unlabeled mAb13.2 (FIG. 12B). In contrast to unlabeled mAb13.2 and mAb13.2 Fab fragments, irrelevant antibody was unable to compete with biotinylated mAb13.2 for binding to FLAG-human IL-13 (FIG. 12).

Figures 13A, 13B:
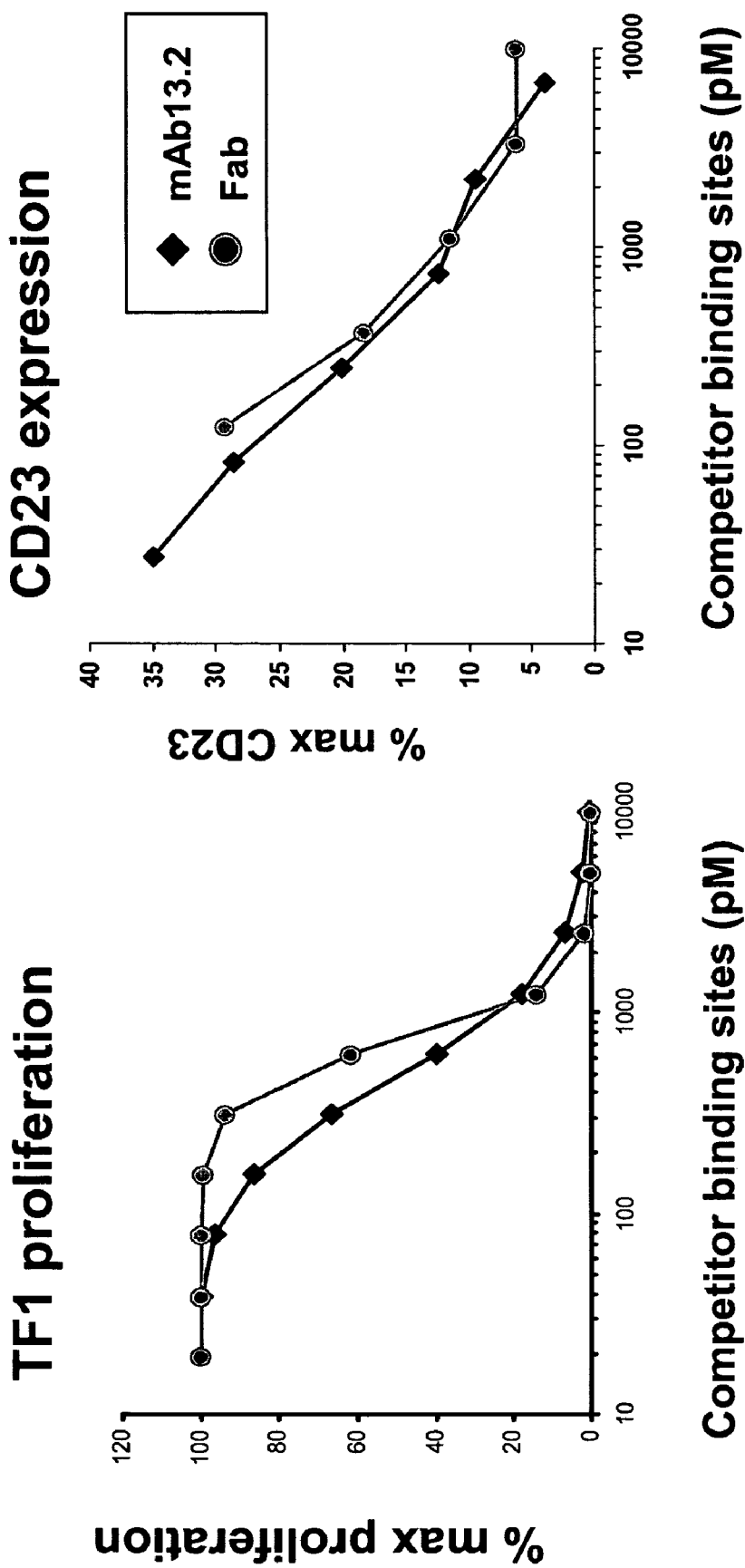
FIG. 13: Fab fragments of mAb13.2 neutralize IL-13-mediated TF1 proliferation and IL-13-mediated CD23 expression by human monocytes. (A) The graph shows the percentage of the maximum proliferation by IL-13-dependent TF1 cell line achieved (y-axis) after 3 days of incubation with IL-13 and increasing concentrations of competitor binding sites (x-axis) provided by either mAb13.2 (♦) or mAb13.2 Fab fragments (●). (B) The figure shows the percentage of the maximum number of monocytes that expressed cell surface CD23 (y-axis) as determined by flow cytometric analysis after peripheral blood mononuclear cells (PBMCs) isolated from a healthy donor were treated overnight with 1 ng/ml IL-13 and indicated concentrations of competitor binding sites (x-axis) provided by either mAb13.2 (♦) or mAb13.2 Fab fragments (●).

The ability of mAb13.2 Fab fragments to neutralize one or more IL-13-associated activities in vitro was confirmed by determining the proliferation of TF1 cells and expression of CD23 by human peripheral blood monocytes, as described above, in the absence or presence of mAb13.2 Fab fragments. FIG. 13A demonstrates that mAB13.2 Fab fragments, similar to mAb13.2, inhibited the ability of recombinant human IL-13 to stimulate TF1 proliferation in a binding site concentration-dependent manner. Additionally, mAb13.2 Fab fragments, similar to mAb13.2, inhibited IL-13-mediated expression of CD23 in a binding site concentration-dependent manner (FIG. 13B).

The x-ray crystallography, epitope mapping, ELISA, TF1 proliferation, and CD23 expression analyses described above indicated that mAb13.2 binds to the C-terminal region of IL-13 helix, i.e., the IL-4R binding region. To confirm this analysis, the interaction between mAb13.2 and IL-13 was analyzed with a BIACORE™ chip. This analysis was done in several formats. First, IL-4R was bound to the BIACORE™ chip, and a complex of IL-13 prebound to IL-13Rα1 was flowed over the chip. In absence of mAb13.2, formation of a trimolecular complex was demonstrated. However, addition of mAb13.2 to the mixture of IL-13 prebound to IL-13Rα1 prevented binding to IL-4R on the chip. Second, mAb13.2 was immobilized on the chip and bound IL-13 was added in solution phase. Although IL-13Rα1 was detected to interact with the bound IL-13, no interaction of IL-4R with bound IL-13 was detected. Third, it was demonstrated that mAb13.2 could bind to IL-13 that was bound to IL-13Rα1-Fc or IL-13Rα1 monomer immobilized on the chip. These observations support the hypothesis that mAb13.2 does not inhibit IL-13 interaction with IL-13Rα1 but disrupts the interaction of IL-13Rα1 with IL-4Rα. This disruption is thought to interfere with the formation of a functional IL-13 signaling complex. These observations provide a theoretical model for the neutralizing activity of this antibody.

The in vitro demonstration of a complex of mAb13.2 with IL-13 and IL-13Rα1 suggests that mAb13.2 could potentially be bound to receptor-associated IL-13 at the cell surface. In order to determine whether cell-bound mAb13.2 could be detected under conditions of saturating receptor-bound IL-13, the HT-29 human epithelial cell line was treated with various concentrations of IL-13 at 4° C. followed by addition of monoclonal antibody mAb13.2, mAb13.8 or control mouse IgG1. Binding was detected by flow cytometric analysis using biotinylated anti-mouse IgG1 and PE-streptavidin. Although HT-29 cells express IL-13Rα1, binding of mAb13.2 to cell surface-bound IL-13 was not detected at concentrations of mAb13.2 up to 2 mg/ml. This observation, together with the demonstration that mAb13.2 is a potent neutralizer of one or more IL-13-associated activities, indicates that normal functioning of the IL-13 signaling complex, i.e., the IL-13 receptor, is disrupted by mAb13.2.

The findings described above confirm that murine monoclonal antibody mAb13.2, binds with high affinity and specificity to IL-13, and exhibits potent neutralization activity, i.e., mAb13.2 efficiently blocks every IL-13-associated activity that was tested. These observations are correlated with the finding that mAb13.2 may interact with the IL-4Rα binding site, and not the IL-13Rα1 binding site, of human IL-13.

EXAMPLE 2

Generation of a Chimeric mAb13.2 Antibody (ch13.2)

EXAMPLE 2.1

Isolation of a Chimeric mAb13.2 Antibody (ch13.2)

The variable heavy (VH) and variable light (VL) genes encoding mAb13.2 were cloned and sequenced from mRNA isolated from the hybridoma producing the antibody. The VH sequence was subcloned into the pED6 huIgG1_mut expression vector, which encodes human IgG1 containing two point mutations (L234A and G237A) to reduce binding to human Fc receptors and complement components (SEQ ID NO:17; Morgan et al. (1995) *Immunology* 86:319-24; Shields et al (2001) *J. Biol. Chem.* 276:6591-604). The VL sequence of mAb13.2 was subcloned into the pED6 Kappa expression vector. The expression vectors containing the mAb13.2 VH and VL sequences were cotransfected into COS-1 cells and the chimeric mAb13.2 antibody (ch13.2) was purified from conditioned medium.

EXAMPLE 2.2

Figure 14B:
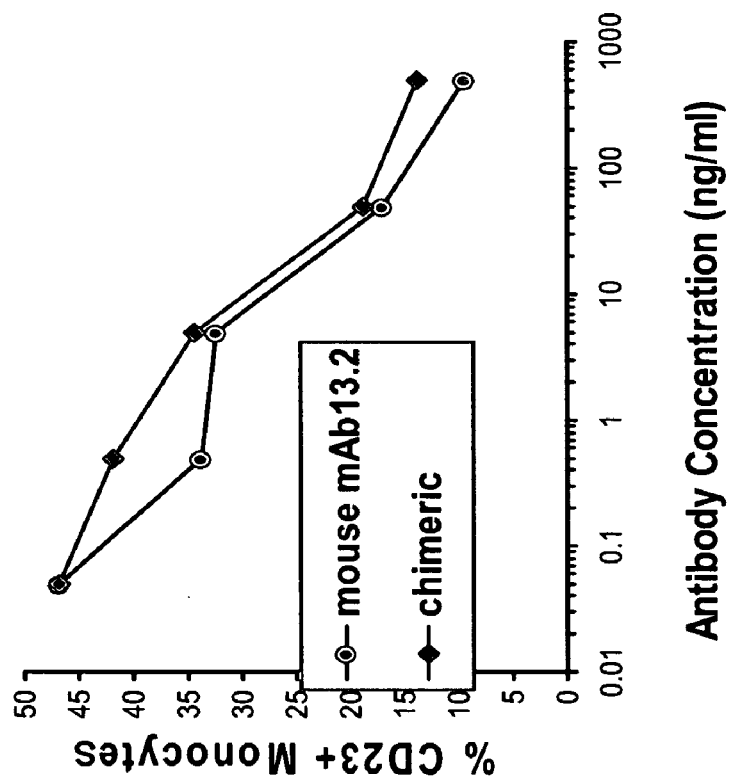
FIG. 14: Chimeric version (ch13.2) of the mouse monoclonal antibody mAb13.2 binds to and neutralizes IL-13. (A) Shown is the absorbance at 450 nm ($A_{450}$; y-axis) of samples containing IL-13-FLAG and biotinylated mAb13.2 only (- -) and samples containing IL-13-FLAG, biotinylated mAB13.2 and increasing concentrations (x-axis) of mAb13.8 (●), mAb13.2 (o), or chimeric mAb13.2 (ch13.2; ▲) as determined by ELISA. (B) Shown is the percentage of monocytes that expressed cell surface CD23 (y-axis) after PBMCs isolated from a healthy donor were treated overnight with 1 ng/ml IL-13 and indicated concentrations (x-axis) of purified mouse mAb13.2 (●) or chimeric mAb13.2 (ch13.2; ♦).
Figure 14A:
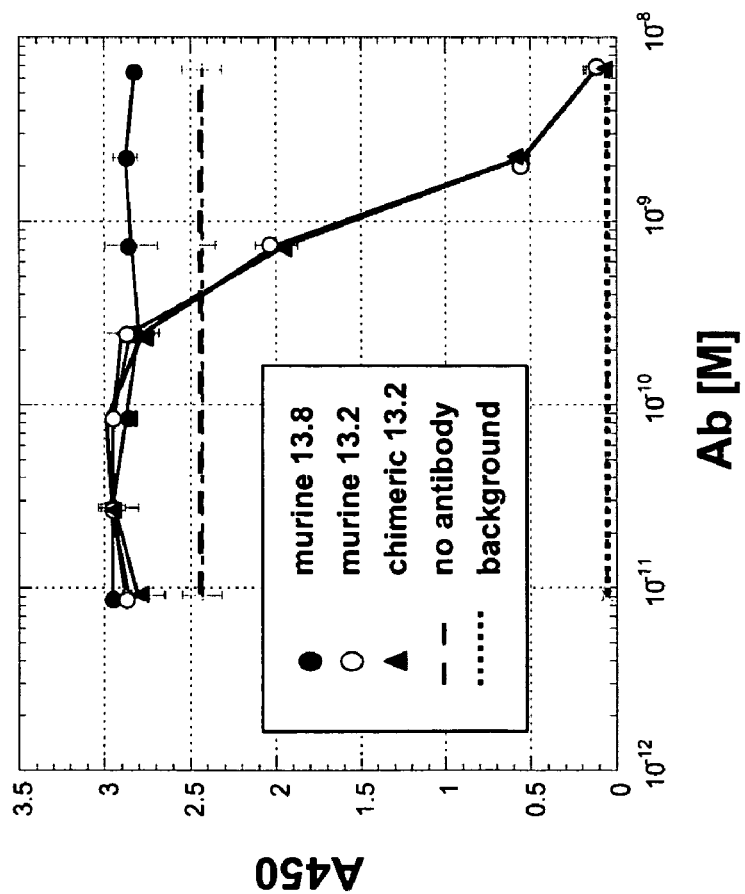

Chimeric mAb13.2 Antibody (ch13.2) Neutralizes IL-13-Associated Activities In Vitro The chimeric antibody, ch13.2, was tested for IL-13 binding. Monoclonal antibody mAb13.2, the chimeric form of mAb13.2 (ch13.2), and a control antibody (13.8) were tested for their abilities to compete with biotinylated mouse mAb13.2 for binding to human IL-13-FLAG immobilized on an ELISA plate with anti-FLAG antibody. Chimeric antibody, ch13.2, was able to competitively bind to IL-13 similarly to mAb13.2 (FIG. 14A). In another test, human peripheral blood monocytes were treated overnight with IL-13 to induce CD23 expression in the presence of various concentrations of mouse mAb13.2 or ch13.2. As shown in FIG. 14B, ch13.2 prevented IL-13-mediated CD23 expression by monocytes to the same degree as mAb13.2.

EXAMPLE 3

Generation of Partially and Fully Humanized mAb13.2 Antibodies (h13.2v1 and h13.2v2)

EXAMPLE 3.1

Isolation of a Partially Humanized mAb13.2 Antibody (h13.2v1)

Humanization of mAb13.2 was based on amino acid sequence homology, CDR cluster analysis, frequency of use among expressed human antibodies, and available information on the crystal structures of human antibodies. Humanization was based on the human DP-54 variable heavy (VH) and DPK-9 variable light (VL) germline genes (shown, e.g., in FIGS. 16 and 17, respectively). Taking into account possible effects on antibody binding, VH-VL pairing, and other factors, murine residues were mutated to human residues where murine and human framework residues were different, with a few exceptions. A comparison of the ch13.2 VH chain amino acid sequence to the predicted amino acid sequence of the human DP-54 germline gene and the resulting partially humanized h13.2v1 VH chain amino acid sequence is shown in FIG. 15. A comparison of the ch13.2 VL chain amino acid sequence to the predicted amino acid sequence of human DPK-9 and the resulting partially humanized h13.2v1 VL chain is shown in FIG. 16. As can be seen in FIGS. 16 and 17, the h13.2v1 VH and VL chains retained the complementarity determining regions (CDR), or antigen-binding regions, of ch13.2 VH and VL chains, respectively. Additionally, only one residue in the VH framework and two in the VL framework were kept murine to reduce the risk of drastically changing the antigen-binding region and the VH-VL pairing (FIGS. 16 and 17).

Partial humanization of mAb13.2 was achieved by mutating the nucleotide sequence encoding (murine) mAb13.2 such that amino acids corresponding to the human germline gene would be substituted at the indicated framework positions. For each amino acid change to be introduced, appropriate nucleotide substitutions were devised, with codons optimized for expression in CHO cells. Humanization of VH was done by a process of PCR mutagenesis, in which oligonucleotide primers incorporating mutations for one or two amino acids at a time were used to amplify the murine template gene sequence. Several rounds of PCR mutagenesis were required to achieve partial humanization. Humanization of VL was done by PCR using a panel of nine overlapping oligonucleotides corresponding to the murine VL sequence with appropriate nucleotide substitutions. The overlapping regions served as templates, and PCR was used to fill in the gaps between primers on the sense and antisense strands. The resulting partially humanized antibody was named h13.2v1. The nucleotide sequences encoding the VL and VH of h13.2v1 are designated SEQ ID NO:3 and SEQ ID NO:7, respectively.

EXAMPLE 3.2

Isolation of Fully Humanized mAb13.2 (h13.2v2)

As indicated in FIG. 15 and FIG. 16, h13.2v1 retained 3 murine residues in the framework regions: one in the VH chain and two in the VL chain. Preliminary work and analysis of the cocrystal structure of mAb13.2 Fab with human IL-13 confirmed that all 3 residues could be mutated to human. These were residue #3 in the VH chain (K in mouse, Q in human), residue #4 in the VL chain (L in mouse, M in human) and residue #72 in the VL chain (#68 in germline; R in mouse, G in human). Therefore, to produce the fully humanized version of mAb13.2, h13.2v2, PCR mutagenesis was used to introduce the mutations K3Q in the VH chain of h13.2v1, and L4M and R72G in the VL chain of h13.2v1. The final VH and VL sequences of h13.2v2 are shown in FIG. 17 and FIG. 18, respectively. Nucleotide sequences encoding the VL and VH of h13.2v2 are designated SEQ ID NO:4 and SEQ ID NO:8, respectively.

According to the sequence shown in FIG. 29 (using the linear numbering scheme), it was determined that the major residues of the mAb13.2 heavy chain that make hydrogen bond contacts with IL-13 are SER50 (CDR2), SER53 (CDR2), TYR101 (CDR3), and TYR102 (CDR3). Additionally, the major residues of the mAb13.2 heavy chain that make Van der Waals contacts with IL-13 are ILE30, SER31 (CDR1), ALA33 (CDR1), TRP47, SER50 (CDR2), SER52 (CDR2), SER53 (CDR2), TYR58 (CDR2), LEU98 (CDR3), ASP99 (CDR3), GLY100 (CDR3), TYR101 (CDR3), TYR102 (CDR3), and PHE103 (CDR3) (based on FIG. 29 using the linear numbering scheme).

According to the sequence shown in FIG. 30 (using the linear numbering scheme), it was determined that the major residues of mAb13.2 light chain that make hydrogen bond contacts with IL-13 are ASN31 (CDR1), TYR32 (CDR1), LYS34 (CDR1), ASN96 (CDR3), and ASP98 (CDR3). The major residues of the mAb13.2 light chain that make Van der Waals contacts with IL-13 are ASN31 (CDR1), TYR32 (CDR1), LYS34 (CDR1), ARG54 (CDR2), ASN96 (CDR3), ASP98 (CDR3), and TRP100 (CDR3) (based on FIG. 30 using the linear numbering scheme).

EXAMPLE 3.3

Fully Humanized mAb13.2 (h13.2v2) Retains Full Binding Activity to IL-13

Figure 19A:
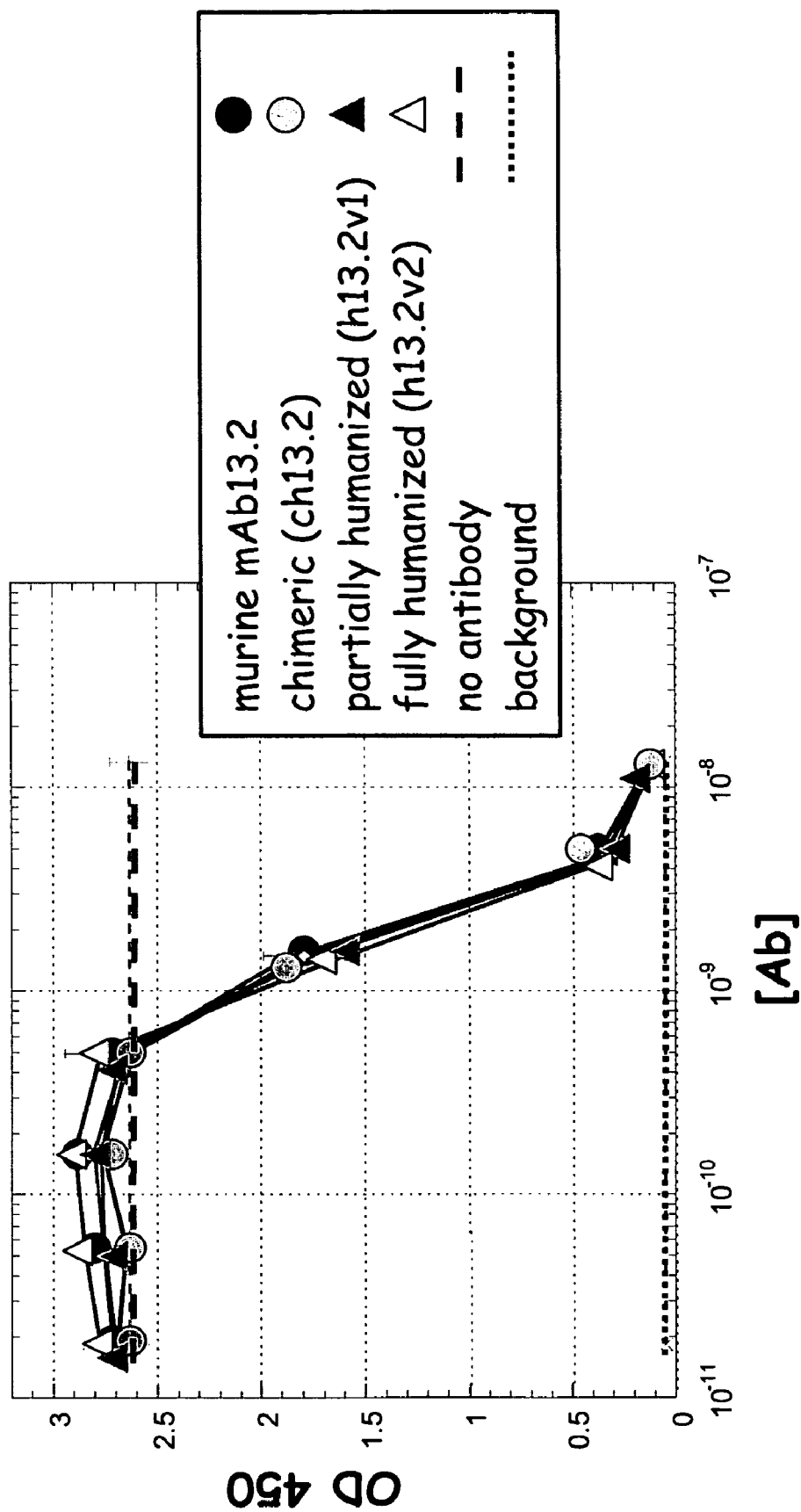
FIG. 19: Fully humanized mAb13.2 (h13.2v2) retains full binding activity to IL-13. (A) Shown is the absorbance at 450 nm (A$_{450}$; y-axis), as determined by ELISA, of samples containing IL-13-FLAG and biotinylated mAb13.2 only (- -) and samples containing IL-13-FLAG, biotinylated mAb13.2 and increasing concentrations (x-axis) of mAb13.2 (●), chimeric mAb13.2 (ch13.2; ●), partially humanized mAb13.2 (h13.2v1; ▲) or fully humanized mAB13.2 (h13.2v2; Δ). (B) The binding interaction between human IL-13 at different dose ranges and fully humanized mAb13.2 (h13.2v2) immobilized to a Biacore™ chip is depicted as resonance difference (RU; y-axis) over time (x-axis). Kinetic constants for h13.2v2 also are shown.
Figure 19B:
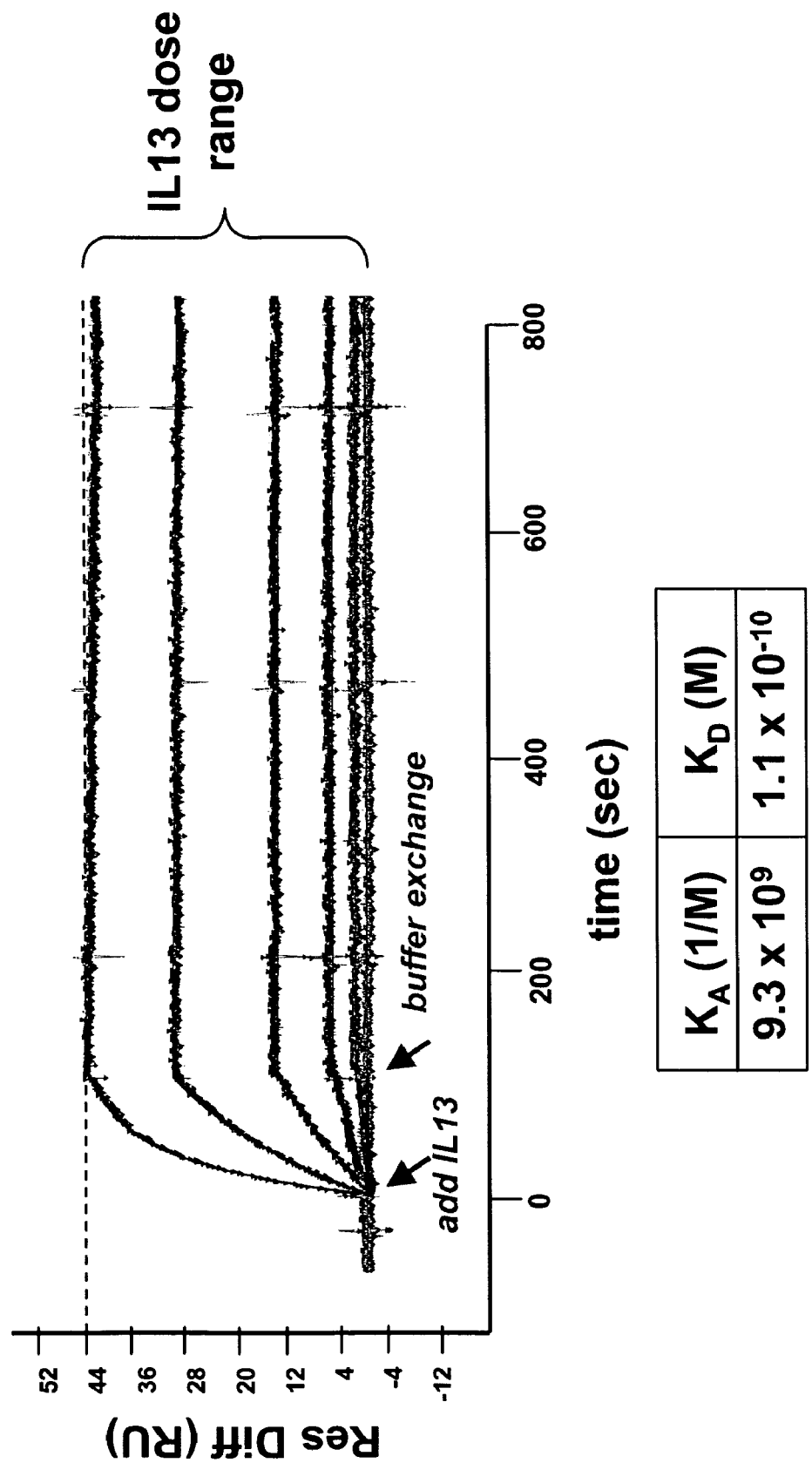

The ability of fully humanized mAb13.2 (h13.2v2) to compete with biotinylated mAb13.2 for binding to IL-13-FLAG was determined by ELISA as described in Example 2. The data demonstrated that the chimeric (ch13.2), partially humanized (h13.2v1) and fully humanized versions of mAb13.2 were capable of competing with biotinylated mAb13.2 for binding to FLAG-human IL-13 to similar degrees (FIG. 19A). BIACORE analysis also confirmed that IL-13 had rapid binding to and slow dissociation to immobilized h13.2v2 (FIG. 19B).

EXAMPLE 3.4

Figure 20B:
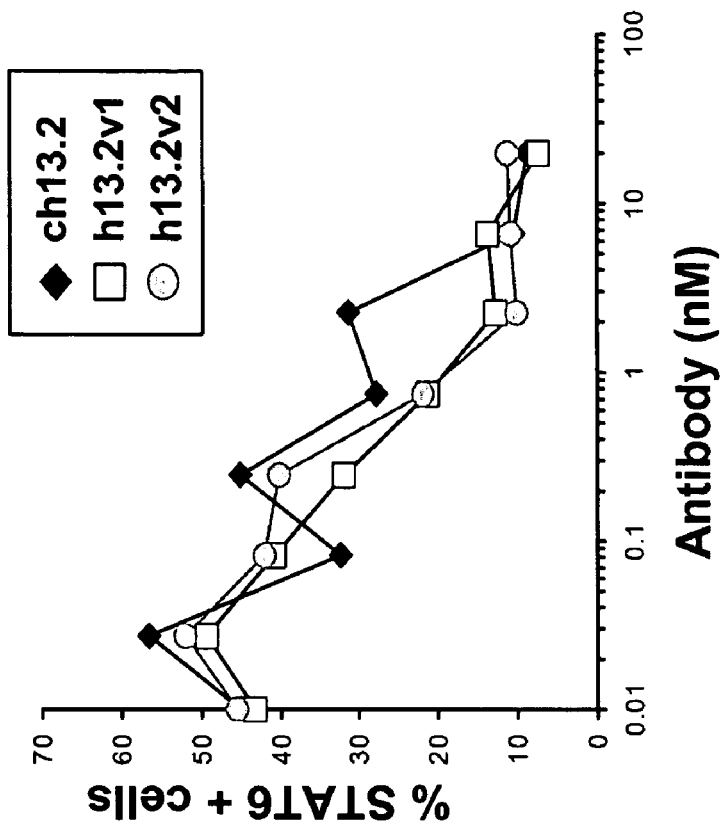
Figure 20A:
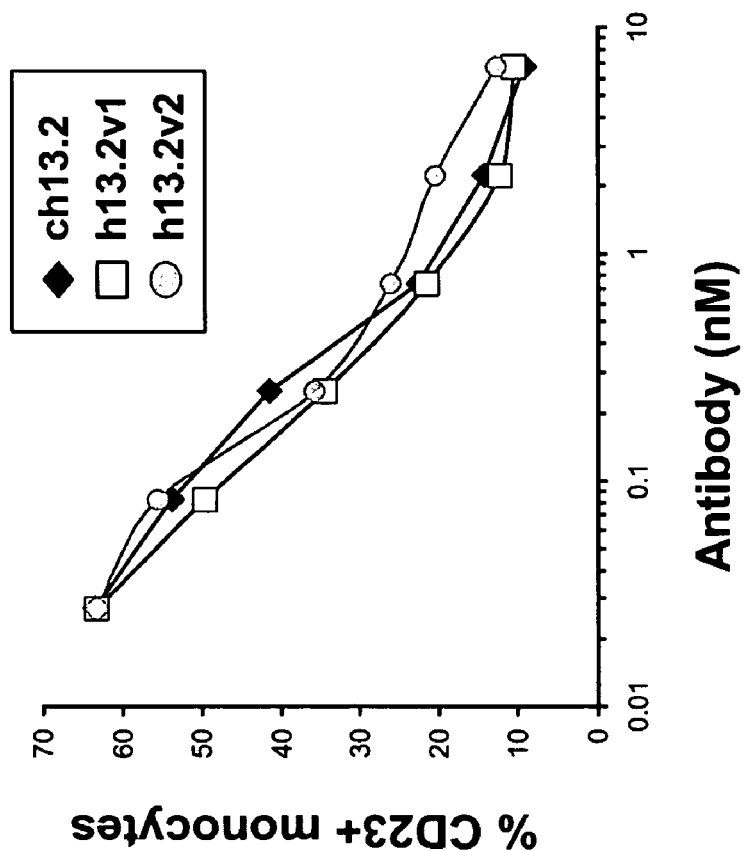

Fully Humanized mAb13.2 (h13.2v2) Neutralizes IL-13-Associated Activities In Vitro Additionally, the ability of the chimeric (ch13.2), partially humanized (h13.2v1) and fully humanized (h13.2v2) versions of mAb13.2 to inhibit IL-13-mediated cell surface expression of CD23 by human monocytes and reduce IL-13-induced STAT6 phosphorylation in HT-29 cells was determined by flow cytometric analysis, as described in Example 1.3. Briefly, human peripheral blood monocytes were incubated overnight with a suboptimal concentration of recombinant human IL-13 in the presence of increasing concentrations of ch13.2, h13.2v1 or h13.2v2. Monocytes were gated and assayed for CD23 expression as an indication of IL-13 responsiveness. Flow cytometric analysis demonstrated that all three versions of mAb13.2, i.e., ch13.2, h13.2v1, and h13.2v2, were capable of mitigating IL-13-mediated CD23 expression by monocytes in a dose dependent manner (FIG. 20A).

To test for STAT6 phosphorylation, the HT-29 human epithelial cell line was incubated for 30 minutes at 37° C. with a suboptimal dose of recombinant human IL-13 and increasing concentrations of ch13.2, h13.2v1, or h13.2v2, then assayed for phosphorylated STAT6 expression using ALEXA™ Fluor 488-labeled monoclonal antibody to phosphorylated STAT6. Flow cytometric analysis demonstrated that all three versions of mAb13.2, i.e., ch13.2, h13.2v1, and h13.2v2, were capable of mitigating IL-13-mediated STAT6 phosphorylation (FIG. 20B).

Since h13.2v2 was capable of inhibiting recombinant IL-13-associated and native human IL-13-associated activities in vitro (FIG. 21), it was tested for its ability to inhibit IL-13-associated disorders in animal models. In preparation for testing fully humanized mAb13.2, h13.2v2, in nonhuman primate (NHP) and sheep models of respiratory disease, the antibody's ability to neutralize recombinant IL-13 from cynomolgus monkeys or from sheep was assayed. IL-13 was cloned from cynomolgus monkeys or from sheep. The NHP IL-13 was expressed in E. coli, purified and refolded as for recombinant human IL-13. In contrast, the recombinant sheep IL-13 was expressed in Chinese Hamster Ovary (CHO) cells. The ability of mAb13.2 or h13.2v2 to inhibit one or more activities associated with the recombinant NHP cynomolgus monkey form of IL-13 or the recombinant sheep form of IL-13 was tested in vitro. FIG. 22 demonstrates that h13.2v2 strongly neutralized the ability of cynomolgus monkey NHP IL-13 to induce cell surface expression of CD23 by human monocytes. However, h13.2v2 only weakly neutralized sheep IL-13, as neutralization of sheep IL-13-associated activity required much higher concentrations of antibody (FIG. 22).

EXAMPLE 3.5

Fully Humanized mAb13.2 (h13.2v2) Neutralizes IL 13 Activities in a Sheep Model of Asthma Despite its relatively low potency in neutralizing the bioactivity of the sheep form of IL-13, h13.2v2 was tested for efficacy in a sheep model of Ascaris-induced airway hyperreactivity. Sheep were sensitized to the roundworm parasite, Ascaris suum, by natural exposure. When given a lung challenge with the Ascaris antigen, the animals undergo bronchoconstriction similar to the response of asthmatic humans to antigen challenge. The response consists of an immediate reaction followed by a late-phase response, beginning 4-5 hours post-challenge. The early phase is thought to be a smooth muscle response, while the late phase is an inflammatory reaction.

To test the ability of h13.2v2 to reduce Ascaris-induced bronchoconstriction, sheep were administered 20 mg/kg, 5 mg/kg, or 2 mg/kg antibody by intravenous (i.v.) infusion. Twenty-four hours post-infusion, the animals were given an intratracheal challenge with Ascaris suum antigen. Results indicated that h13.2v2 at 20 mg/kg or 5 mg/kg attenuated the late-phase response to antigen (FIG. 23). h13.2v2 at 2 mg/kg had no significant effect on the antigen response compared to the control, presumably due to the weak neutralization activity of h13.2v2 on sheep IL-13.

In addition, the ability of h13.2v2 to reduce airway hyperreactivity induced by airway challenge with the cholinergic agonist, carbachol, in sheep was tested. Carbachol elicits bronchoconstriction, measured as a decrease in forced expiratory volume (FEV), and the dose of stimulus required to elicit a given magnitude of response (PC400) is typically lower for asthmatics than for healthy subjects. Sheep remained untreated or were administered 20 mg/kg, 5 mg/kg, or 2 mg/kg of h13.2v2 intravenously 24 hours prior to carbachol-inhalation challenge, and PC400 was determined in the sheep pre- and post-challenge with Ascaris suum. The data demonstrates that h13.2v2 at 20 mg/kg or 5 mg/kg prevented the drop in PC400 induced by challenge with Ascaris suum (FIG. 24). Similar to results of the antigen response experiment, h13.2v2 at 2 mg/kg had no significant effect on PC400 compared to the control.

EXAMPLE 3.6

Fully Humanized mAb13.2 (h13.2v2) Neutralizes IL-13 Activities in a Nonhuman Primate Model of Asthma To test the ability of h13.2v2 to prevent Ascaris-induced lung inflammation in nonhuman primates, control cynomolgus monkeys were treated with saline, 8 mg/kg irrelevant human IgG (IVIG), or 2 mg/kg dexamethasone intramuscularly (as a positive control). Test cynomolgus monkeys were administered 10 mg/kg h13.2v2 intravenously. The next day, prechallenged BAL samples were collected from the left lung, and animals were challenged with Ascaris suum antigen intratracheally in the right lung. Twenty-four hours post-challenge, BAL samples were collected from the right lung and assayed for cellular infiltrate. Results showed that pretreatment of animals with h13.2v2 prevented airway inflammation induced by the *Ascaris suum* allergen (FIG. 25). In a parallel experiment, IL-5 and eotaxin were induced in BAL following *Ascaris* challenge. Pretreatment of animals with h13.2v2 reduced the level of induction of both IL-5 and eotaxin.

Figures 31A, 31B:
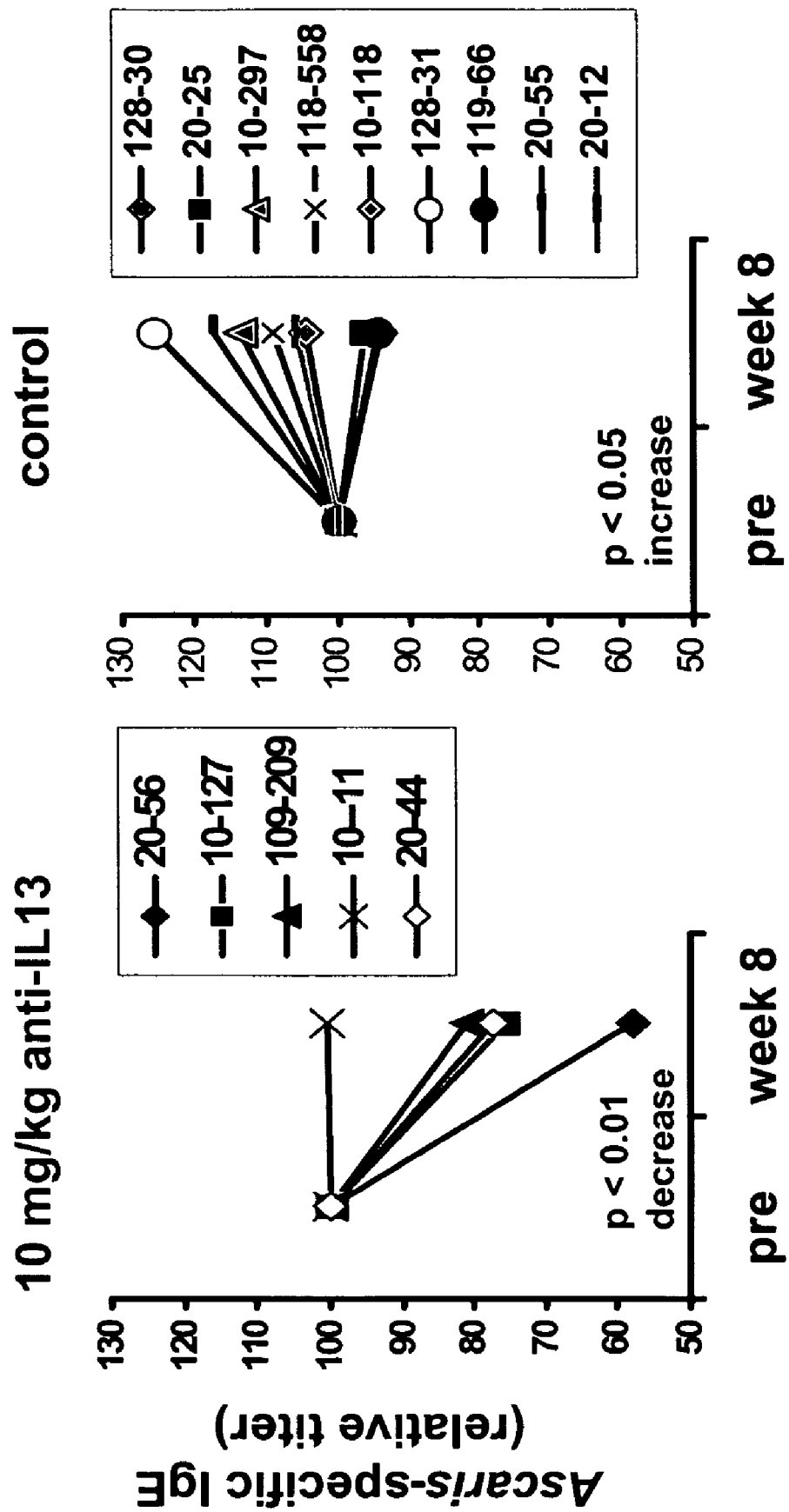

Non-human primates sensitized to *Ascaris suum* develop IgE to *Ascaris* antigen. This IgE binds to FcεRI on circulating basophils, such that in vitro challenge of peripheral blood basophils with *Ascaris* antigen induces degranulation and release of histamine. Repeated antigen exposure boosts basophil sensitization, resulting in enhanced histamine release responses. To test the effects of h13.2v2 on this process, cynomolgus monkeys dosed with h13.2v2 or saline or IVIG controls as described were bled at 8 weeks post-*Ascaris* challenge, and levels of total and *Ascaris*-specific IgE in plasma were determined by ELISA. The levels of *Ascaris*-specific IgE were increased at 8 weeks post-challenge in control animals treated with saline or IVIG (FIG. 31B). In contrast, animals treated with h13.2v2 showed a significant reduction in levels of circulating IgE specific for *Ascaris* (FIG. 31A). There were no significant change in total IgE titer for any of the treatment groups.

Figure 32A:
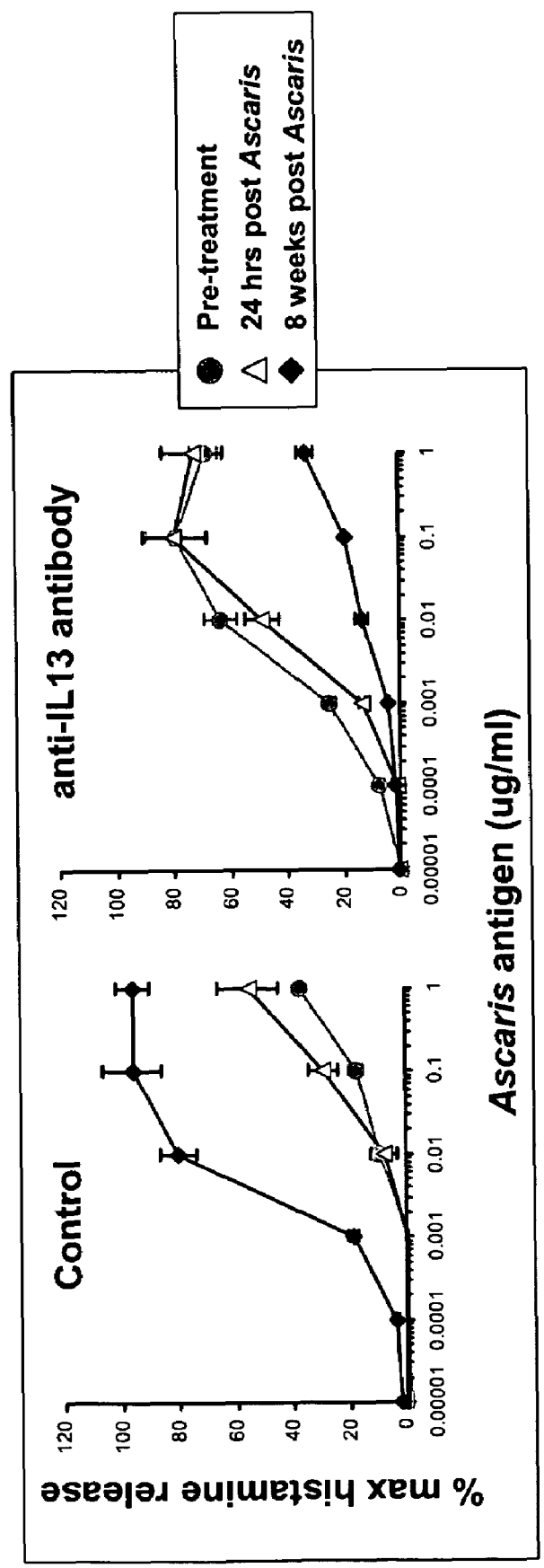
Figure 32B:
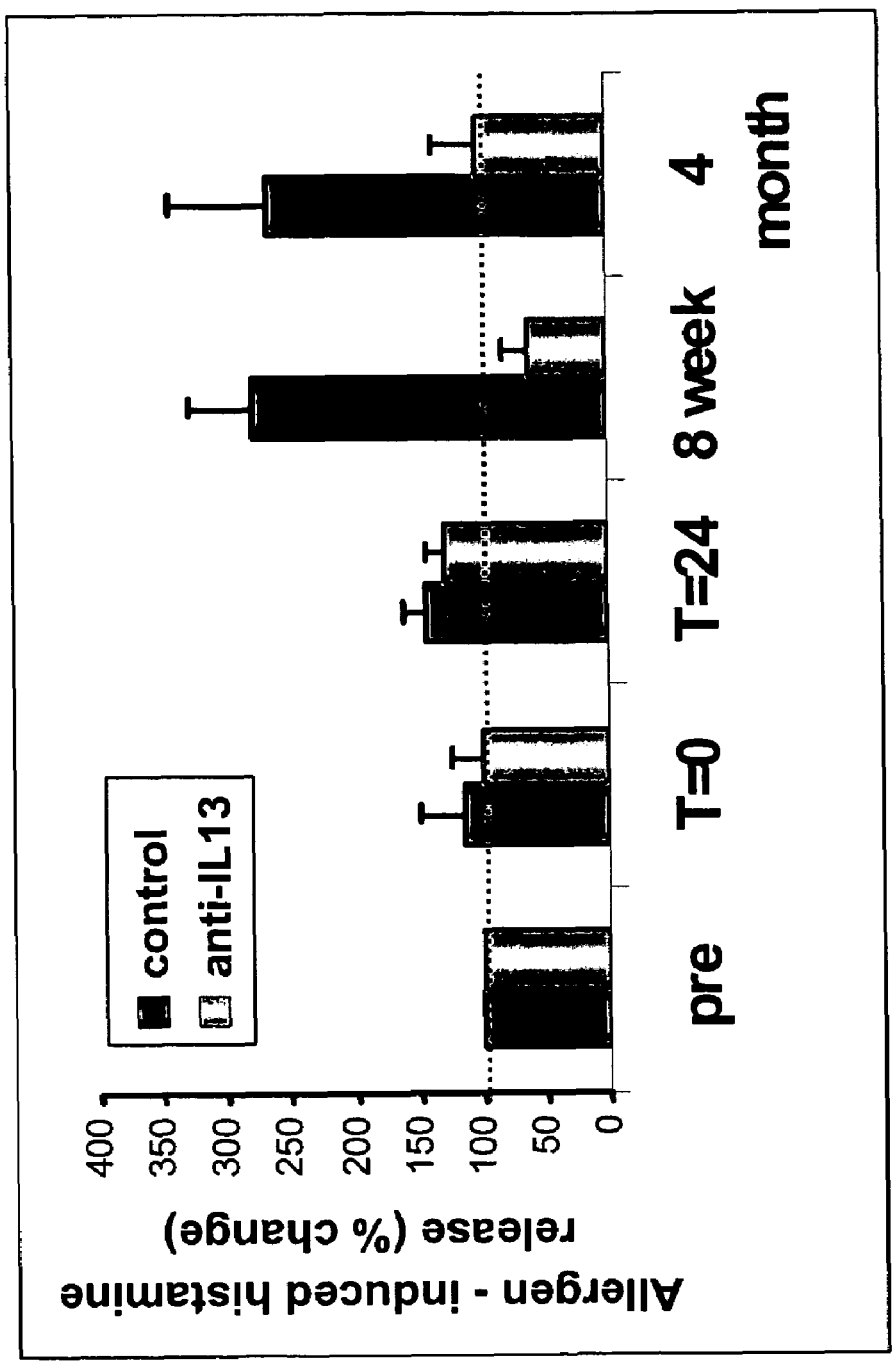

To evaluate effects on basophil histamine release, the animals were bled at 24 hours, 8 weeks, and 4 months post-*Ascaris* challenge. Whole blood was challenged with *Ascaris* antigen for 30 minutes at 37° C., and histamine released into the supernatant was quantitated by ELISA (Beckman Coulter, Fullerton, Calif.). As shown in FIG. 32A, these sensitized animals demonstrated some level of *Ascaris*-induced basophil histamine release even before the segmental antigen challenge. Following challenge, the control animals showed the expected increase in basophil responsiveness. In contrast, the animals treated with h13.2v2 failed to undergo this increase in basophil sensitization, such that at 2-4 months post-challenge, they had a significantly lower in vitro histamine release response to *Ascaris* (FIG. 32B). Thus, a single administration of h13.2v2 had long-term disease-modifying activity in this model.

EXAMPLE 4

Humanization of mAb13.2 Based on Various Human Germline Genes

Example 3 provided a method and result for humanizing mAb13.2 based on the DP-54 and DPK9 germline genes; in this Example, the humanization of mAb13.2 based on other germline genes is briefly detailed.

Additional humanization strategies were designed based on an analysis of human germline antibody sequences, or a subgroup thereof, that possessed a high degree of homology, i.e., sequence similarity, to the actual amino acid sequence of the murine antibody variable regions. For example, the VH group 3 of V-BASE showed a high degree of sequence similarity to mAb13.2. It was determined that the CDRs of heavy chain variable region of mAb13.2 could be transferred into any one of a subgroup of germline genes within VH group 3, i.e., 3-53 (DP-42), 3-48 (DP-51), 3-09 (DP-31), 3-13 (DP-48), 3-15 (DP-38), 3-20 (DP-32), 3-21 (DP-77), 3-23 (DP-47), 3-30 and 3-30.5 (DP-49), 3-64 (DP-45), 3-66 (DP-86), and 3-73 (YAC-9) (FIG. 26). Also shown in FIG. 26 is the sequence for DP-61, which may also be used to humanize mAb13.2. It was determined that the following common amino acid substitutions could be introduced into mAb13.2 to convert its VH framework into any of the proposed human germlined frameworks: K3Q, K13Q or K13R, K19R, T40A, E42G, R44G, R75K, I77S or I77T, S83N, S87A or S87D, M92V or M92L, and T113L. The individual amino acid substitutions for humanization based on a particular germline gene were also delineated, e.g., humanization based on DP-47 may involve the additional mutations of V5L, A49S, and A74S; humanization based on DP-42 may involve the additional mutations of V12I, A49S, and A74S; humanization based on DP-51 may involve the additional mutation of A49S; humanization based on DP-48 may involve the additional mutations of P41T, D72E, and E88G; humanization based on DP-53 may involve the additional mutations of E46V and A49S; humanization based on DP-32 may involve the additional mutations of L11V, A49S, and Y94H; humanization based on DP-38 may involve the additional mutations of A49G, A74D, R75S, N76K, R86K, and S87T; humanization based on DP-31 may involve the additional mutations of G16R, A49S, and R97K; humanization based on DP-61 may involve the additional mutations of W47Y, A49S, A74S, and T90M; and humanization based on DP-45 may involve the additional mutations of E6Q, A24G, A49S, and T90M. For example, when humanization of mAb13.2 is based on the human germline gene DP-47, which has 79% sequence identity, the following mutations, K3Q, V5L, K13Q, K19R, T40A, E42G, R44G, A49S, A74S, R75K, I77T, S83N, S87A, M92V, and T113L, can be introduced into mAb13.2. Introduction of the common amino acid substitutions alone, or in combination with the individual amino acid substitutions based on a particular human germline gene, into mAb13.2 during humanization should result in an active antibody. For example, an active antibody, h13.2v3, resulted when humanization of mAb13.2 was based on 3-21 (DP-77), as described below.

An alternative humanization of mAb13.2 was based on the germline genes DP-77 and B1. The alignment between the predicted amino acid sequence of DP-77, the variable heavy chain amino acid sequence of ch13.2, and the heavy chain amino acid sequence of fully humanized mAb13.2 antibody (h13.2v3) is shown in FIG. 27. The alignment between the predicted amino acid sequence of B1, the variable light chain amino acid sequence of ch13.2, and the variable light chain amino acid sequence of h13.2v3 is shown in FIG. 28. The predicted amino acid sequences of DP-77 and B1 demonstrated 80.4% amino acid identity with the variable heavy chain of mAb13.2 and 77.5% amino acid identity with the variable light chain of mAb13.2, respectively. Although amino acid differences between DP-77 and the heavy chain of mAb13.2 (and the heavy chain of ch13.2, as well), and between B1 and the light chain of mAb13.2 (and the light chain of ch13.2, as well), were found in both the framework and complementarity determining regions, the differences in the CDRs remained unchanged. In contrast, where an amino acid found in the framework region of the heavy chain mAb13.2 differed from the amino acid in the same position in DP-77, the amino acid of the variable heavy region of mAb13.2 was changed to the amino acid in DP-77. Similarly, where an amino acid found in the framework region of the light chain of mAb13.2 differed from the amino acid in the same position in B1, the amino acid in the variable light chain of mAb13.2 was changed to the amino acid in B1. Two rounds of PCR mutagenesis, as described above, introduced the changes. After the first round of changes in the heavy and light chains, ELISA was performed, as described in Example 2, to ensure that the changes did not affect the ability of the antibody to bind to IL-13. After the second round of changes, the amino acid sequences of the framework regions within the heavy and light chains of mAb13.2 were identical to the amino acid sequences of the framework regions of DP-77 and B1, respectively.

The humanized mAb13.2 antibody, h13.2v3, was also capable of inhibiting IL-13-associated activities in vitro. h13.2v3 was tested by ELISA and the TF1 proliferation assay to determine its ability to bind and inhibit one or more IL-13-associated activities. It was demonstrated that h13.2v3 could similarly compete with mAb13.2 for binding to IL-13 when compared to ch13.2 and h13.2v1. Additionally, h13.2v3 was capable of inhibiting TF1 proliferation to the same degree as mAb 13.2 and h13.2v1.

EXAMPLE 5

Effector Activity Mediated by the Wild-Type Fc Revertant of h13.2v2

The cell signaling form of the IL-13 receptor, which includes the IL-13Rα1 and IL-4Rα polypeptides, is found on the surface of cell types that respond to the cytokine. IL-13Rα2 is not typically expressed on the surface of IL-13-responsive cells, but has been reported on tumors of the brain, head, and neck (Kawakami et al. (2003) Clin. Cancer Res. 9:6381-8; Mintz et al. (2002) Neoplasia 4:388-99; Liu et al. (2000) Cancer Immunol. Immunother. 49:319-24). IL-13Rα2 expression may also be induced on IFNγ-treated primary human monocytes (Daines et al. (2002) J. Biol. Chem. 277: 10387-93), or TNFα- or IL-13-treated primary human fibroblasts (Yoshikawa et al. (2003) Biochem. Biophys. Res. Commun. 312:1248-55). This receptor is not competent to mediate signaling responses to IL-13 (Kawakami et al. (2001) Blood 97:2673-9), but instead appears to act as a decoy receptor, competing for productive IL-13 interactions with IL-13Rα1 (Feng et al. (1998) Lab. Invest. 78:591-602). IL-13Rα2 has a high affinity for IL-13 (Andrews et al. (2002) J. Biol. Chem. 277:46073-8), and appears to interact primarily with the C-terminal region of the cytokine (Madhankumar et al. (2002) J. Biol. Chem. 277:43194-205), which is not predicted to include the h13.2v2 binding site. Therefore, it was examined whether h13.2v2 could interact with IL-13 captured by IL-13Rα2 on the cell surface. A375 is a human melanoma cell line that expresses IL-13Rα2. Recombinant human IL-13 (3 ng/ml) was contacted to these cells at 4° C. for 20 minutes. The cells were washed, and tested for binding of biotinylated h13.2v2. Results showed a dose-dependent binding of the antibody in to these cells in the presence of IL-13, indicating that h13.2v2 bound to IL-13 that was bound to its receptor (FIG. 33).

In order to determine whether h13.2v2 could promote Fc-dependent effector function, the mutated Fc residues of h13.2v2 (L234A/G237A; residues 116 and 119 of SEQ ID NO:17) were reverted to wild-type, and the antibodies expressing wild-type or mutated Fc were expressed and purified. Effector function was tested in an antibody-dependent cellular cytotoxicity assay (ADCC) using IL-13-loaded A375 cells as targets. A375 target cells were labeled with Chromium-51 and incubated with 10 ng/ml recombinant human IL-13. Human PBMC enriched for natural killer (NK) cells by treatment with ROSETTESEP® Human NK Enrichment Cocktail (StemCell Technologies, Seattle, Wash.) were used as effectors. Effector and target cells were incubated together in the presence of increasing concentrations of h13.2v2 or its wild-type Fc revertant for 5 hours at 37° C. Cytotoxicity was measured as the release of Chromium-51 into the supernatant, and expressed as a percentage of the maximum release, determined by lysing the A375 target cells with TRITON® X-100.

Figure 34B:
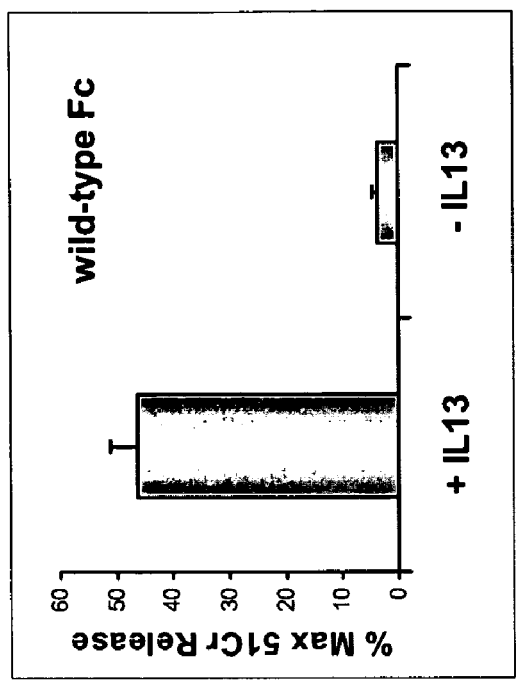
Figure 34A:
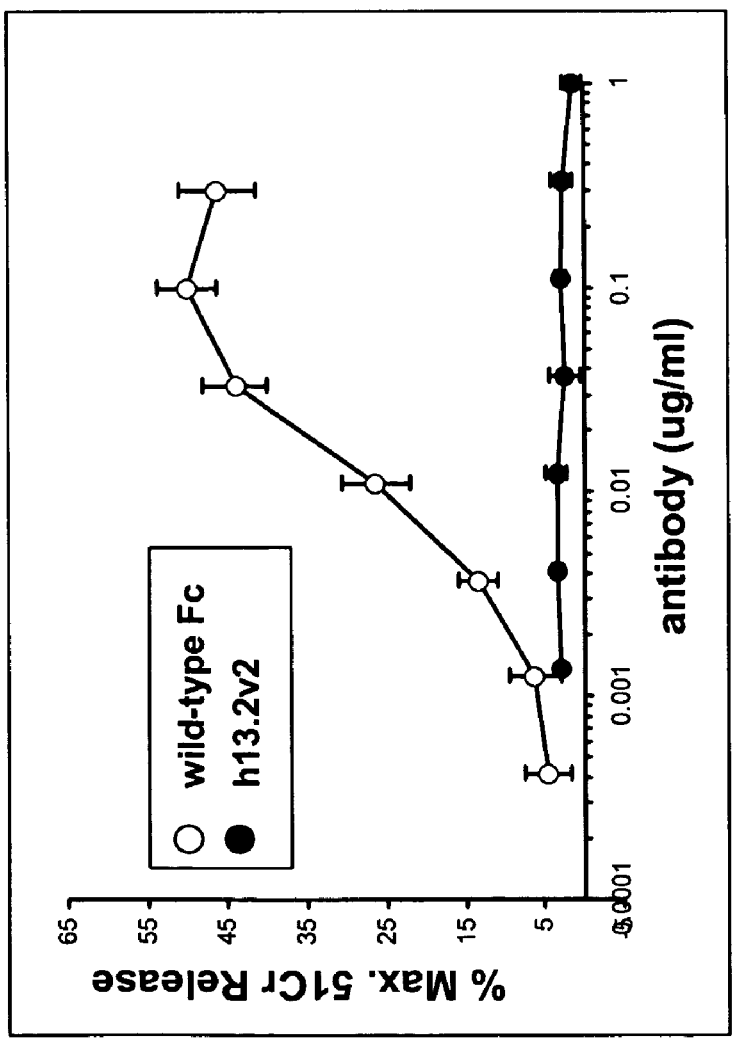

Results showed that the wild-type Fc revertant was able to mediate ADCC of the IL-13-loaded A375 target cells, whereas h13.2v2 was not (FIG. 34A). No cytotoxicity was observed in the absence of IL-13 (FIG. 34B). Similar results were seen using effector cells from three different donors. These results indicate that, due to the presence of the L234A and G237A Fc mutations, h13.2v2 is unable to mediate ADCC, even under optimal in vitro conditions.

Taken together, these observations indicate that h13.2v2 can bind to cells expressing IL-13Rα2 (FIG. 33), but not to those expressing IL-13Rα1. Experiments were done to test whether the h13.2v2 wild-type revertant could mediate ADCC of the IL-13Rα1-expressing HT-29 cells, even in the absence of detectable binding. HT-29 cells were used as targets in an ADCC assay performed as described above. Results showed that under conditions leading to cytolysis of the IL-13Rα2-expressing A375 cells, the IL-13Rα1-expressing HT-29 cells were not lysed (FIG. 35). These results also demonstrate that, whereas antibodies that include the L234A and G237A Fc mutations do not induce ADCC, antibodies with wild-type Fc effector function can be useful for the treatment of certain cancers that express IL-13Rα2.

EXAMPLE 6

Expression of Humanized 13.2 Antibody in COS Cells

In order to evaluate the expression of humanized anti-IL13 antibodies in the mammalian recombinant system the variable regions of mouse 13.2 (SEQ ID NO:9 and SEQ ID NO:13), hu13.2 V1 (SEQ ID NO:11 and SEQ ID NO:15), and hu13.2 V2 (SEQ ID NO:12 and SEQ ID NO:16) were subcloned into a pED6 expression vector containing human kappa and IgG1mut constant regions. Monkey kidney COS-1 cells were grown in DME media (Gibco) containing 10% of heat-inactivated fetal bovine serum, 1 mM of glutamine and 0.1 mg/ml of Penicillin/Streptomycin. Transfection of COS cells was performed using TRANSITIT®-LT1 Transfection reagent (Mirus Bio Corp., Madison, Wis.) according to the protocol suggested by supplier. Transfected COS cells were incubated for 24 hours at 37° C. in the presence of 10% CO2, washed with sterile PBS and then grown in serum-free media R1CD1 (Gibco) for 48 hours to allow the secretion of the antibody and its accumulation in the conditioned media. The expression of 13.2 antibody was quantified by total human IgG ELISA using purified human IgG1/kappa antibody as a standard. The chimeric 13.2 antibody as well as both humanized versions expressed well in COS cells.

TABLE 5

Transient expression of humanized 13.2 antibodies in COS cells.

| N | Construct | Expression µg/ml, 48 hours |
| --- | --- | --- |
| 1 | Chimeric 13.2 | 14.5 |
| 2 | Partially humanized 13.2(V1) | 13.2 |
| 3 | Fully humanized 13.2.2 (V2) | 14.9 |

What is claimed is:

1. A purified antibody, or antigen-binding fragment thereof, comprising a heavy chain immunoglobulin variable domain and a light chain immunoglobulin variable domain that binds to IL-13 with a $K_D$ of less than $10^{-7}$ M as determined by surface plasmon resonance (SPR), wherein the light chain immunoglobulin variable domain comprises the amino acid sequence of:
   (i) KASESVDNYGKSLMH (SEQ ID NO:19), in CDR1,
   (ii) RASNLES (SEQ ID NO:20), in CDR2, and
   (iii) QQSNEDPWT (SEQ ID NO:21), in CDR3;
   and wherein the heavy chain immunoglobulin variable domain comprises the amino acid sequence of:
   (i) SYAMS (SEQ ID NO:22), in CDR1,
   (ii) SISSGGNTYYPDSVKG (SEQ ID NO:23), in CDR2, and
   (iii) LDGYYFGFAY (SEQ ID NO:24), in CDR3,
   or an amino acid sequence that differs by fewer than three conservative amino acid substitutions from the amino acid sequence of any of SEQ ID NO:19-24; and
wherein the light chain immunoglobulin variable domain, with or without said conservative amino substitutions, contacts IL-13 with residues ASN31 (CDR1), TYR32 (CDR1), LYS34 (CDR1), ARG54 (CDR2), ASN96 (CDR3), ASP98 (CDR3), and TRP100 (CDR3), of SEQ ID NO:11, 12, or 35, and the heavy chain immunoglobulin variable domain, with or without said conservative amino substitutions, contacts IL-13 with residues ILE30, SER31 (CDR1), ALA33 (CDR1), TRP47, SER50 (CDR2), SER52 (CDR2), SER53 (CDR2), TYR58 (CDR2), LEU98 (CDR3), ASP99 (CDR3), GLY100 (CDR3), TYR101 (CDR3), TYR102 (CDR3), and PHE103 (CDR3), of SEQ ID NO:15, 16 or 36.

2. The antibody, or antigen-binding fragment thereof, of claim 1 that has one or more of the following properties:
   (a) the heavy chain immunoglobulin variable region comprises a heavy chain CDR3 of mAb13.2 (SEQ ID NO:24);
   (b) the light chain immunoglobulin variable region comprises a light chain CDR1 of mAb13.2 (SEQ ID NO:19);
   (c) the heavy chain immunoglobulin variable region comprises an amino acid sequence encoded by a nucleic acid that hybridizes under high stringency conditions to the complement of a nucleic acid encoding a heavy chain variable domain comprising the amino acid sequence of SEQ ID NO:15, 16, or 36;
   (d) the heavy chain immunoglobulin variable region comprises an amino acid sequence encoded by a nucleic acid that hybridizes under high stringency conditions to the complement of a nucleic acid comprising the nucleotide sequence of SEQ ID NO:7, 8, or 34;
   (e) the light chain immunoglobulin variable region comprises an amino acid sequence encoded by a nucleic acid that hybridizes under high stringency conditions to the complement of a nucleic acid encoding a light chain variable domain comprising the amino acid sequence of SEQ ID NO:11, 12, or 35;
   (f) the light chain immunoglobulin variable region comprises an amino acid sequence encoded by a nucleic acid that hybridizes under high stringency conditions to the complement of a nucleic acid comprising the nucleotide sequence of SEQ ID NO:3, 4, or 33;
   (g) the heavy chain immunoglobulin variable region comprises an amino acid sequence that is at least 90% identical to the amino acid sequence of the heavy chain variable domain of SEQ ID NO:15, 16, or 36;
   (h) the light chain immunoglobulin variable region comprises an amino acid sequence that is at least 90% identical to the amino acid sequence of the light chain variable domain of SEQ ID NO:11, 12, or 35;
   (i) the antibody, or antigen-binding fragment thereof, competes for binding to human IL-13 with an antibody comprising a light chain immunoglobulin variable region comprising the amino acid sequence of SEQ ID NO:9 and a heavy chain immunoglobulin variable region comprising the amino acid sequence of SEQ ID NO:13;

(j) the antibody, or antigen-binding fragment thereof, contacts one or more amino acid residues from IL-13 selected from the group consisting of residues 68, 72, 88, 91, 92, 93, and 105 of SEQ ID NO:31;

(k) the heavy chain variable region has the same canonical structure as an antibody comprising a light chain immunoglobulin variable region comprising the amino acid sequence of SEQ ID NO:9 and a heavy chain immunoglobulin variable region comprising the amino acid sequence of SEQ ID NO:13;

(l) the light chain variable region has the same canonical structure as an antibody comprising a light chain immunoglobulin variable region comprising the amino acid sequence of SEQ ID NO:9 and a heavy chain immunoglobulin variable region comprising the amino acid sequence of SEQ ID NO:13;

(m) the heavy chain variable region or the light chain variable region has FR1, FR2, and FR3 framework regions from VH FR1, FR2 and FR3 framework regions encoded by germline genes DP-54 or DPK-9, or a sequence at least 95% identical to the VH FR1, FR2 and FR3 framework regions encoded by germline genes DP-54 or DPK-9; or (n) confers a post-injection protective effect against exposure to *Ascaris* antigen in a sheep model at least 6 weeks after injection.

3. The antibody, or antigen-binding fragment thereof, of claim 2 or 1 that is recombinant.

4. The antibody, or antigen-binding fragment thereof, of claim 2 or 1 that is a recombinant, full length IgG.

5. The antibody, or antigen-binding fragment thereof, of claim 2 or 1 that is a Fab, a F(ab')$_2$, or a scFv.

6. The antibody, or antigen-binding fragment thereof, of claim 2 or 1 that comprises framework regions from VH FR1, FR2 and FR3 framework regions encoded by germline gene DP-54 or DPK-9, or an amino acid sequence at least 95% identical to the VH FR1, FR2 and FR3 framework regions encoded by the germline gene DP-54 or DPK-9.

7. The antibody, or antigen-binding fragment thereof, of claim 2 or 1 that comprises human framework regions, a human Fc region, or both.

8. The antibody, or antigen-binding fragment thereof, of claim 2 or 1, wherein the heavy chain immunoglobulin variable domain makes hydrogen bond contacts with IL-13 at amino acids SER50 (CDR2), SER53 (CDR2), TYR101 (CDR3) and TYR102 (CDR3) of SEQ ID NO:15, 16 or 36; and the light chain immunoglobulin variable domain makes hydrogen bond contacts with IL-13 at residues ASN31 (CDR1), TYR32(CDR1), LYS34(CDR1), ASN96(CDR3) and ASP98(CDR3) of SEQ ID NO:11, 12, or 35.

9. The antibody, or antigen-binding fragment thereof, of claim 2 or 1 that binds to human IL-13 with a $K_D$ of between 90 and 120 pM as determined by surface plasmon resonance (SPR).

10. The antibody, or antigen-binding fragment thereof, of claim 2 or 1 that binds to human IL-13 with a $k_{off}$ of less than $1 \times 10^{-4} s^{-1}$ as determined by surface plasmon resonance (SPR).

11. The antibody, or antigen-binding fragment thereof, of claim 2 or 1 that binds to human IL-13 with a $k_{on}$ of between $5 \times 10^4$ and $8 \times 10^5$ $M^{-1}s^{-1}$ as determined by surface plasmon resonance (SPR).

12. The antibody, or antigen-binding fragment thereof, of claim 2 or 1 that reduces the ability of IL-13 to bind to IL-4Rα.

13. The antibody, or antigen-binding fragment thereof, of claim 2 or 1 that binds to IL-13 that is in an in vitro complex with IL-13Rα1.

14. An isolated, recombinant IgG antibody that comprises two immunoglobulin chains: a light chain that comprises SEQ ID NO:9, 10, 11, 12, or 35 and a heavy chain that comprises SEQ ID NO:13, 14, 15, 16, or 36.

15. The isolated, recombinant IgG antibody of claim 14 wherein the heavy chain further comprises SEQ ID NO:17 and the light chain further comprises SEQ ID NO:18.

16. The antibody, or antigen-binding fragment thereof, of claim 2 or 1 that has one or more of the following properties:

(a) it specifically binds to an epitope of human IL-13 comprising one or more of the following amino acid residues: Glutamate at position 49, Asparagine at position 53, Glycine at position 69, Proline at position 72, Histidine at position 73, Lysine at position 74, and Arginine at position 86 of SEQ ID NO:32, or a conservative amino acid substitution thereof;

(b) it binds to a complex of IL-13 and IL13Rα1;

(c) it interferes with a binding interaction between IL-13 and IL-4Rα;

(d) it interferes with a binding interaction between IL-13/IL-13Rα1 and IL-4Rα;

(e) it binds specifically to human IL-13 and competitively inhibits the binding of a second antibody to said human IL-13, wherein said second antibody is chosen from mAb13.2, ch13.2, h13.2v1, h13.2v2, or h13.2v3;

(f) it reduces cell surface expression of the low affinity IgE receptor (CD23) in peripheral blood monocytes;

(g) it reduces IL-13-mediated IgE isotype switch in cultured B cells;

(h) it reduces IL-13-dependent phosphorylation of STAT6; or (i) it neutralizes the influx of eosinophils in a cynomolgus monkey having antigen-induced airway inflammation.

17. The antibody, or antigen-binding fragment thereof, of claim 2 or 1 having a constant region mutated to decrease one or more of: Fc receptor binding, antibody glycosylation, the number of cysteine residues, effector cell function, or complement function.

18. The antibody, or antigen-binding fragment thereof, of claim 17, further comprising a human IgG1 constant region mutated at one or more residues 116 or 119 of SEQ ID NO:17.

19. The antibody, or antigen-binding fragment thereof, of claim 18, further comprising a human kappa light chain.

20. The antibody, or antigen-binding fragment thereof, of claim 16, wherein at least one complementarity determining region comprises an amino acid sequence selected from the group consisting of the amino acid sequence of SEQ ID NO:19, the amino acid sequence of SEQ ID NO:20, the amino acid sequence of SEQ ID NO:21, the amino acid sequence of SEQ ID NO:22, the amino acid sequence of SEQ ID NO:23, the amino acid sequence of SEQ ID NO:24.

21. The antibody, or antigen-binding fragment thereof, of claim 16, wherein the fragment is an scFv, Fab, a F(ab')$_2$, fragment.

22. The antibody, or antigen-binding fragment thereof, of claim 16, further comprising a light chain comprising a human kappa constant region, or an active fragment thereof, and a heavy chain comprising a human IgG constant region, or an active fragment thereof.

23. The antibody, or antigen-binding fragment thereof, of claim 22, wherein the human kappa constant region of said light chain comprises the amino acid sequence of SEQ ID NO:18, or an active fragment thereof.

24. The antibody, or antigen-binding fragment thereof, of claim 22, wherein the human IgG constant region of said heavy chain is mutated to reduce FcR and complement binding.

25. The antibody, or antigen-binding fragment thereof, of claim 24, wherein the mutated human IgG constant region of said heavy chain comprises the amino acid sequence of SEQ ID NO:17, or an active fragment thereof.

26. A pharmaceutical composition comprising the antibody, or antigen-binding fragment thereof, of any of claims 2 or 1 and a pharmaceutically acceptable carrier.

27. The pharmaceutical composition of claim 26 that is adapted for subcutaneous, inhalation, or topical administration.

28. The antibody, or antigen-binding fragment thereof, of claim 1, wherein the amino acid sequence of the heavy chain immunoglobulin variable domain is at least 95% identical to SEQ ID NO:15, 16, or 36.

29. The antibody, or antigen-binding fragment thereof, of claim 1 or 28, wherein the amino acid sequence of the light chain immunoglobulin variable domain is at least 95% identical to SEQ ID NO:11, 12, or 35.

30. The antibody, or antigen-binding fragment thereof, of claim 1, wherein the heavy chain immunoglobulin variable domain comprises the amino acid sequence of SEQ ID NO:15, 16, or 36.

31. The antibody, or antigen-binding fragment thereof, of claim 1 or 30, wherein the light chain immunoglobulin variable domain comprises the amino acid sequence of SEQ ID NO:11, 12, or 35.

32. The antibody, or antigen-binding fragment thereof, of claim 1, further comprising a heavy chain constant region that is at least 95% identical to the amino acid sequence of SEQ ID NO:17.

33. The antibody, or antigen-binding fragment thereof, of claim 1 or 32, further comprising a light chain constant region that is at least 95% identical to the amino acid sequence of SEQ ID NO:18.

34. The antibody, or antigen-binding fragment thereof, of claim 1, further comprising a heavy chain constant region that comprises the amino acid sequence of SEQ ID NO:17.

35. The antibody, or antigen-binding fragment thereof, of claim 1 or 34, further comprising a light chain constant region that comprises the amino acid sequence of SEQ ID NO:18.

36. The antibody, or antigen-binding fragment thereof, of claim 8, wherein the light chain immunoglobulin variable domain makes Van der Waals contacts with IL-13 at residues ASN31(CDR1), TYR32(CDR1), LYS34(CDR1), ARG54 (CDR2), ASN96(CDR3), ASP98(CDR3), and TRP100 (CDR3), of SEQ ID NO:11, 12, or 35, and the heavy chain immunoglobulin variable domain makes Van der Waals contacts with IL-13 at residues ILE30, SER31(CDR1), ALA33(CDR1), TRP47, SER50 (CDR2), SER52(CDR2), SER53(CDR2), TYR58 (CDR2), LEU98(CDR3), ASP99(CDR3), GLY100 (CDR3), TYR101(CDR3), TYR102(CDR3), and PHE103(CDR3), of SEQ ID NO:15, 16 or 36.

37. A pharmaceutical composition comprising an antibody, or an antigen-binding fragment thereof, of claim 1, comprising a heavy chain immunoglobulin variable domain sequence and a light chain immunoglobulin variable domain sequence that binds to IL-13 with a $K_D$ of less than $10^{-7}$ M as determined by surface plasmon resonance (SPR) and a pharmaceutically acceptable carrier, co-formulated with one or more additional therapeutic agents selected from the group consisting of:

inhaled steroids; beta-agonists; antagonists of leukotrienes or leukotriene receptors; IgE inhibitors; phosphodiesterase inhibitors; xanthines; anticholinergic drugs; mast cell-stabilizing agents; IL-4 inhibitors; IL-5 inhibitors; eotaxin/CCR3 inhibitors; antihistamines; TNF antagonists; TNF enzyme antagonists; TGFβ antagonists; interferon gamma; perfenidone; chemotherapeutic agents; NSAIDs; immunomodulators; p38 inhibitors; and NFKB inhibitors.

38. The antibody, or antigen-binding fragment thereof, of claim 1, which contacts IL-13 at residues GLU49, ASN53, GLY69, PRO72, HIS73, LYS74, and ARG86 of SEQ ID NO:32.

39. The antibody, or antigen-binding fragment thereof, of claim 1, wherein the heavy chain immunoglobulin variable region comprises an amino acid sequence encoded by a nucleic acid that hybridizes under high stringency conditions to the complement of a nucleic acid encoding a heavy chain variable domain comprising the amino acid sequence of SEQ ID NO:15, 16, or 36, or to the complement of a nucleic acid comprising the nucleotide sequence of SEQ ID NO:7, 8, or 34.

40. The antibody, or antigen-binding fragment thereof, of claim 39, wherein the light chain immunoglobulin variable region comprises an amino acid sequence encoded by a nucleic acid that hybridizes under high stringency conditions to the complement of a nucleic acid encoding a light chain variable domain comprising the amino acid sequence of SEQ ID NO:11, 12, or 35, or to the complement of a nucleic acid comprising the nucleotide sequence of SEQ ID NO:3, 4, or 33.

41. The antibody, or antigen-binding fragment thereof, of claim 1, wherein the heavy chain immunoglobulin variable region comprises an amino acid sequence encoded by the nucleic acid comprising the nucleotide sequence of SEQ ID NO:7, 8, or 34.

42. The antibody, or antigen fragment thereof, of claim 41, wherein the light chain immunoglobulin variable region comprises an amino acid sequence encoded by the nucleic acid comprising the nucleotide sequence of SEQ ID NO:3, 4, or 33.

43. A purified antibody, or antigen-binding fragment thereof, comprising a heavy chain immunoglobulin variable domain and a light chain immunoglobulin variable domain that binds to IL-13 with a $K_D$ of less than $10^{-7}$ M as determined by surface plasmon resonance (SPR), wherein the light chain immunoglobulin variable domain comprises the amino acid sequence of:
(i) KASESVDNYGKSLMH (SEQ ID NO:19), in CDR1,
(ii) RASNLES (SEQ ID NO:20), in CDR2, and
(iii) QQSNEDPWT (SEQ ID NO:21), in CDR3;
and wherein the heavy chain immunoglobulin variable domain comprises the amino acid sequence of:
(i) SYAMS (SEQ ID NO:22), in CDR1,
(ii) SISSGGNTYYPDSVKG (SEQ ID NO:23), in CDR2, and
(iii) LDGYYFGFAY (SEQ ID NO:24), in CDR3.

44. The antibody, or antigen-binding fragment thereof, of claim 43, wherein the heavy chain immunoglobulin variable domain comprises the amino acid sequence of SEQ ID NO:16, and the light chain immunoglobulin variable domain comprises the amino acid sequence of SEQ ID NO:12.

45. The antibody, or antigen-binding fragment thereof, of claim 43, wherein the heavy chain immunoglobulin variable domain comprises the amino acid sequence of SEQ ID NO:15, and the light chain immunoglobulin variable domain comprises the amino acid sequence of SEQ ID NO:11.

46. The antibody, or antigen-binding fragment thereof, of claim 43, wherein the heavy chain immunoglobulin variable domain comprises the amino acid sequence of SEQ ID NO:36, and the light chain immunoglobulin variable domain comprises the amino acid sequence of SEQ ID NO:35.

47. The antibody, or antigen-binding fragment thereof, of any of claims 43, 44, 45, or 46, wherein the heavy chain immunoglobulin variable domain further comprises a human IgG constant region comprising the amino acid sequence of SEQ ID NO:17.

48. The antibody, or antigen-binding fragment thereof, of claim 47, wherein the light chain immunoglobulin variable domain comprises a human kappa constant region comprising the amino acid sequence of SEQ ID NO:18.

49. The antibody, or antigen-binding fragment thereof, of claim 43, wherein the antibody, or antigen-binding fragment thereof, is linked to another antibody, a toxin, a radioisotope, a cytotoxic agent or a cytostatic agent.

50. The antibody, or antigen-binding fragment thereof, of claim 49, which is a bispecific antibody.

51. The antibody, or antigen-binding fragment thereof, of claim 43 that has one or more of the following properties:
   (a) the heavy chain immunoglobulin variable region comprises an amino acid sequence encoded by a nucleic acid that hybridizes under high stringency conditions to the complement of a nucleic acid encoding a heavy chain variable domain comprising the amino acid sequence of SEQ ID NO:15, 16, or 36;
   (b) the heavy chain immunoglobulin variable region comprises an amino acid sequence encoded by a nucleic acid that hybridizes under high stringency conditions to the complement of a nucleic acid comprising the nucleotide sequence of SEQ ID NO:7, 8, or 34;
   (c) the light chain immunoglobulin variable region comprises an amino acid sequence encoded by a nucleic acid that hybridizes under high stringency conditions to the complement of a nucleic acid encoding a light chain variable domain comprising the amino acid sequence of SEQ ID NO:11, 12, or 35;
   (d) the light chain immunoglobulin variable region comprises an amino acid sequence encoded by a nucleic acid that hybridizes under high stringency conditions to the complement of a nucleic acid comprising the nucleotide sequence of SEQ ID NO:3, 4, or 33;
   (e) the heavy chain immunoglobulin variable region comprises an amino acid sequence that is at least 90% identical to the amino acid sequence of the heavy chain variable domain of SEQ ID NO:15, 16, or 36;
   (f) the light chain immunoglobulin variable region comprises an amino acid sequence that is at least 90% identical to the amino acid sequence of the light chain variable domain of SEQ ID NO:11, 12, or 35;
   (g) the antibody, or antigen-binding fragment thereof, competes for binding to human IL-13 with an antibody comprising a light chain immunoglobulin variable region comprising the amino acid sequence of SEQ ID NO:9 and a heavy chain immunoglobulin variable region comprising the amino acid sequence of SEQ ID NO:13;
   (h) the antibody, or antigen-binding fragment thereof, contacts one or more amino acid residues from IL-13 selected from the group consisting of residues 68, 72, 88, 91, 92, 93, and 105 of SEQ ID NO:31;
   (i) the heavy chain variable region contacts IL-13 with one or more of amino acids Ser50, Ser53, Tyr101 or Tyr102 of SEQ ID NO:15, 16 or 36;
   (j) the light chain variable region contacts IL-13 with one or more of amino acids Asn31, Tyr32, Lys34, Asn96 or Asn98 of SEQ ID NO:11, 12 or 35;
   (k) the heavy chain variable region has the same canonical structure as an antibody comprising a light chain immunoglobulin variable region comprising the amino acid sequence of SEQ ID NO:9 and a heavy chain immunoglobulin variable region comprising the amino acid sequence of SEQ ID NO:13;
   (l) the light chain variable region has the same canonical structure as an antibody comprising a light chain immunoglobulin variable region comprising the amino acid sequence of SEQ ID NO:9 and a heavy chain immunoglobulin variable region comprising the amino acid sequence of SEQ ID NO:13;
   (m) the heavy chain variable region or the light chain variable region has FR1, FR2, and FR3 framework regions from VH FR1, FR2 and FR3 framework regions encoded by germline genes DP-54 or DPK-9, or a sequence at least 95% identical to the VH FR1, FR2 and FR3 framework regions encoded by germline genes DP-54 or DPK-9; or
   (n) confers a post-injection protective effect against exposure to *Ascaris* antigen in a sheep model at least 6 weeks after injection.

52. The antibody, or antigen-binding fragment thereof, of claim 43 that is recombinant.

53. The antibody, or antigen-binding fragment thereof, of claim 43 that is a recombinant, full length IgG.

54. The antibody, or antigen-binding fragment thereof, of claim 43 that is a Fab, a F(ab')$_2$, or a scFv.

55. The antibody, or antigen-binding fragment thereof, of claim 43 that binds to human IL-13 with a $K_D$ of between 90 and 120 pM as determined by surface plasmon resonance (SPR).

56. The antibody, or antigen-binding fragment thereof, of claim 43 that binds to human IL-13 with a $k_{off}$ of less than $1\times10^{-4}$ s$^{-1}$ as determined by surface plasmon resonance (SPR).

57. The antibody, or antigen-binding fragment thereof, of claim 43 that binds to human IL-13 with a $k_{on}$ between $5\times10^4$ and $8\times10^5$ M$^{-1}$s$^{-1}$ as determined by surface plasmon resonance (SPR).

58. The antibody, or antigen-binding fragment thereof, of claim 43 that reduces the ability of IL-13 to bind to IL-4Rα.

59. The antibody, or antigen-binding fragment thereof, of claim 43 that binds to IL-13 that is in an in vitro complex with IL-13Rα1.

60. The antibody, or antigen-binding fragment thereof, of claim 43 that has one or more of the following properties:
   (a) it specifically binds to an epitope of human IL-13 comprising one or more of the following amino acid residues: Glutamate at position 49, Asparagine at position 53, Glycine at position 69, Proline at position 72, Histidine at position 73, Lysine at position 74, and Arginine at position 86 of SEQ ID NO:32, or a conservative amino acid substitution thereof;
   (b) it binds to a complex of IL-13 and IL13Rα1;
   (c) it interferes with a binding interaction between IL-13 and IL-4Rα;
   (d) it interferes with a binding interaction between IL-13/IL-13Rα1 and IL-4Rα;
   (e) it binds specifically to human IL-13 and competitively inhibits the binding of a second antibody to said human IL-13, wherein said second antibody is chosen from mAb13.2, ch13.2, h13.2v1, h13.2v2, or h13.2v3;

(f) it reduces cell surface expression of the low affinity IgE receptor (CD23) in peripheral blood monocytes;

(g) it reduces IL-13-mediated IgE isotype switch in cultured B cells;

(h) it reduces IL-13-dependent phosphorylation of STAT6; or (i) it neutralizes the influx of eosinophils in a cynomolgus monkey having antigen-induced airway inflammation.

61. The antibody, or antigen-binding fragment thereof, of claim 43, wherein the light chain immunoglobulin variable domain contacts IL-13 with residues ASN31 (CDR1), TYR32(CDR1), LYS34(CDR1), ARG54(CDR2), ASN96 (CDR3) and ASP98(CDR3), and TRP100 (CDR3), of SEQ ID NO:11, 12, or 35, and the heavy chain immunoglobulin variable domain contacts IL-13 with residues ILE30, SER31 (CDR1), ALA33(CDR1), TRP47, SER50(CDR2), SER52 (CDR2), SER 53 (CDR2), TYR58(CDR2), LEU98(CDR3), ASP99(CDR3), GLY100(CDR3), TYR101(CDR3), TYR102(CDR3), and PHE103(CDR3), of SEQ ID NO:15, 16 or 36.

62. The antibody, or antigen-binding fragment thereof, of claim 43, wherein the heavy chain immunoglobulin variable domain makes hydrogen bond contacts with IL-13 at amino acids SER50 (CDR2), SER 53 (CDR2), TYR101(CDR3) and TYR102(CDR3) of SEQ ID NO:15, 16 or 36; and the light chain immunoglobulin variable domain makes hydrogen bond contacts with IL-13 at residues ASN31(CDR1), TYR32 (CDR1), LYS34(CDR1), ASN96(CDR3) and ASP98(CDR3) of SEQ ID NO:11, 12, or 35.

63. The antibody, or antigen-binding fragment thereof, of claim 43, wherein the light chain immunoglobulin variable domain makes Van der Waals contacts with IL-13 at residues ASN31(CDR1), TYR32(CDR1), LYS34(CDR1), ARG54 (CDR2), ASN96(CDR3), ASP98(CDR3), and TRP100 (CDR3), of SEQ ID NO:11, 12, or 35, and the heavy chain immunoglobulin variable domain makes Van der Waals contacts with IL-13 at residues ILE30, SER31(CDR1), ALA33 (CDR1), TRP47, SER50(CDR2), SER52(CDR2), SER53 (CDR2), TYR58(CDR2), LEU98(CDR3), ASP99(CDR3), GLY100(CDR3), TYR101(CDR3), TYR102(CDR3), and PHE103(CDR3), of SEQ ID NO:15, 16 or 36.

64. The antibody, or antigen-binding fragment thereof, of claim 43 that comprises framework regions from VH FR1, FR2 and FR3 framework regions encoded by germline gene DP-54 or DPK-9, or an amino acid sequence at least 95% identical to the VH FR1, FR2 and FR3 framework regions encoded by the germline gene DP-54 or DPK-9.

65. The antibody, or antigen-binding fragment thereof, of claim 43 having a constant region mutated to decrease one or more of: Fc receptor binding, antibody glycosylation, the number of cysteine residues, effector cell function, or complement function.

66. The antibody, or antigen-binding fragment thereof, of claim 65, further comprising a human IgG1 constant region mutated at one or more residues 116 or 119 of SEQ ID NO:17.

67. The antibody, or antigen-binding fragment thereof, of claim 66, further comprising a human kappa light chain.

68. The antibody, or antigen-binding fragment thereof, of claim 63, further comprising a light chain comprising a human kappa constant region, or an active fragment thereof, and a heavy chain comprising a human IgG constant region, or an active fragment thereof.

69. The antibody, or antigen-binding fragment thereof, of claim 68, wherein the human kappa constant region of said light chain comprises the amino acid sequence of SEQ ID NO:18, or an active fragment thereof.

70. The antibody, or antigen-binding fragment thereof, of claim 69, wherein the human IgG constant region of said heavy chain is mutated to reduce FcR and complement binding.

71. The antibody, or antigen-binding fragment thereof, of claim 70, wherein the mutated human IgG constant region of said heavy chain comprises the amino acid sequence of SEQ ID NO:17, or an active fragment thereof.

72. The antibody, or antigen-binding fragment thereof, of claim 43, wherein the amino acid sequence of the heavy chain immunoglobulin variable domain is at least 95% identical to SEQ ID NO:15, 16, or 36.

73. The antibody, or antigen-binding fragment thereof, of claim 43, wherein the amino acid sequence of the light chain immunoglobulin variable domain is at least 95% identical to SEQ ID NO:11, 12, or 35.

74. The antibody, or antigen-binding fragment thereof, of claim 43, further comprising a heavy chain constant region that is at least 95% identical to the amino acid sequence of SEQ ID NO:17.

75. The antibody, or antigen-binding fragment thereof, of claim 43 or 74, further comprising a light chain constant region that is at least 95% identical to the amino acid sequence of SEQ ID NO:18.

76. A pharmaceutical composition comprising the antibody, or antigen-binding fragment thereof, of claim 43 and a pharmaceutically acceptable carrier.

77. The pharmaceutical composition of claim 76 that is adapted for subcutaneous, inhalation, or topical administration.

78. A pharmaceutical composition comprising an antibody, or an antigen-binding fragment thereof, of claim 43, comprising a heavy chain immunoglobulin variable domain sequence and a light chain immunoglobulin variable domain sequence that binds to IL-13 with a $K_D$ of less than $10^{-7}$ M as determined by surface plasmon resonance (SPR) and a pharmaceutically acceptable carrier, co-formulated with one or more additional therapeutic agents selected from the group consisting of:

inhaled steroids; beta-agonists; antagonists of leukotrienes or leukotriene receptors; IgE inhibitors; phosphodiesterase inhibitors; xanthines; anticholinergic drugs; mast cell-stabilizing agents; IL-4 inhibitors; IL-5 inhibitors; eotaxin/CCR3 inhibitors; antihistamines; TNF antagonists; TNF enzyme antagonists; TGFβ antagonists; interferon gamma; perfenidone; chemotherapeutic agents; NSAIDs; immunomodulators; p38 inhibitors; and NFKB inhibitors.

79. The antibody, or antigen-binding fragment thereof, of claim 43, which contacts IL-13 at residues GLU49, ASN53, GLY69, PRO72, HIS73, LYS74, and ARG86 of SEQ ID NO:32.

80. The antibody, or antigen-binding fragment thereof, of claim 43, wherein the heavy chain immunoglobulin variable region comprises an amino acid sequence encoded by a nucleic acid that hybridizes under high stringency conditions to the complement of a nucleic acid encoding a heavy chain variable domain comprising the amino acid sequence of SEQ ID NO:15, 16, or 36, or to the complement of a nucleic acid comprising the nucleotide sequence of SEQ ID NO:7, 8, or 34.

81. The antibody, or antigen-binding fragment thereof, of claim 80, wherein the light chain immunoglobulin variable region comprises an amino acid sequence encoded by a nucleic acid that hybridizes under high stringency conditions to the complement of a nucleic acid encoding a light chain variable domain comprising the amino acid sequence of SEQ ID NO:11, 12, or 35, or to the complement of a nucleic acid comprising the nucleotide sequence of SEQ ID NO:3, 4, or 33.

82. The antibody, or antigen-binding fragment thereof, of claim 43, wherein the heavy chain immunoglobulin variable region comprises an amino acid sequence encoded by the nucleic acid comprising the nucleotide sequence of SEQ ID NO:7, 8, or 34.

83. The antibody, or antigen fragment thereof, of claim 82, wherein the light chain immunoglobulin variable region comprises an amino acid sequence encoded by the nucleic acid comprising the nucleotide sequence of SEQ ID NO:3, 4, or 33.

84. An isolated, recombinant IgG antibody that comprises two immunoglobulin chains: a light chain that comprises SEQ ID NO:12 and a heavy chain that comprises SEQ ID NO:16.

85. The isolated, recombinant IgG antibody of claim 84, wherein the heavy chain further comprises SEQ ID NO:17 and the light chain further comprises SEQ ID NO:18.

* * * * *

UNITED STATES PATENT AND TRADEMARK OFFICE
CERTIFICATE OF CORRECTION

| | | |
|---|---|---|
| PATENT NO. | : 7,615,213 B2 | Page 1 of 1 |
| APPLICATION NO. | : 11/149309 | |
| DATED | : November 10, 2009 | |
| INVENTOR(S) | : Marion T. Kasaian et al. | |

It is certified that error appears in the above-identified patent and that said Letters Patent is hereby corrected as shown below:

On the Title page,

[*] Notice: Subject to any disclaimer, the term of this patent is extended or adjusted under 35 U.S.C. 154(b) by 404 days.

Delete the phrase "by 404 days" and insert -- by 825 days --

Signed and Sealed this

Twenty-seventh Day of July, 2010

David J. Kappos
*Director of the United States Patent and Trademark Office*